(12) United States Patent
Guerin et al.

(10) Patent No.: US 8,097,044 B2
(45) Date of Patent: Jan. 17, 2012

(54) HAIR COMPOSITIONS COMPRISING AT LEAST ONE DISULFIDE DIRECT DYE AND AT LEAST ONE ALKALINE HYDROXIDE AGENT AND SIMULTANEOUS HAIR SHAPING AND DYEING PROCESSES

(75) Inventors: Frédéric Guerin, Paris (FR); Maxime de Boni, Paris (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 12/219,616

(22) Filed: Jul. 24, 2008

(65) Prior Publication Data
US 2009/0126755 A1    May 21, 2009

Related U.S. Application Data

(60) Provisional application No. 60/997,000, filed on Dec. 13, 2007.

(30) Foreign Application Priority Data

Jul. 24, 2007   (FR) ...................................... 07 56706

(51) Int. Cl.
*A61Q 5/10* (2006.01)
(52) U.S. Cl. ............. 8/405; 8/426; 8/432; 8/437; 8/565; 8/566; 8/567; 8/568; 8/570; 132/202; 132/208
(58) Field of Classification Search ............... 8/405, 426, 8/432, 437, 565, 566, 567, 568, 570; 132/202, 132/208
See application file for complete search history.

(56) References Cited

U.S. PATENT DOCUMENTS

| | | | |
|---|---|---|---|
| 3,971,391 A | 7/1976 | Bore et al. | |
| 5,094,662 A | 3/1992 | Schultz et al. | |
| 7,488,354 B2 | 2/2009 | Daubress et al. | |
| 2002/0192175 A1 | 12/2002 | Patel et al. | |
| 2006/0080791 A1* | 4/2006 | Daubresse et al. | ................ 8/405 |
| 2007/0033744 A1* | 2/2007 | Kravtchenko | ................... 8/405 |

FOREIGN PATENT DOCUMENTS

| | | |
|---|---|---|
| FR | 2 220 244 | 10/1974 |
| FR | 2 876 576 | 4/2006 |
| GB | 0 833 809 | 4/1960 |
| WO | WO 2005/097051 | 10/2005 |
| WO | WO 2007/110542 | 10/2007 |

OTHER PUBLICATIONS

STIC Search Report dated Sep. 30, 2010.*
English language Abstract of WO 2007/110542, dated Oct. 4, 2007.
French Search Report for FR 07/56706, dated Mar. 18, 2008.
Examination Guidelines Update: Developments in the Obviousness Inquiry After KSR v.Teleflex, Federal Register, vol. 75, No. 169, Wednesday, Sep. 1, 2010, Notices, pp. 53643-53660.

* cited by examiner

*Primary Examiner* — Eisa Elhilo
(74) *Attorney, Agent, or Firm* — Finnegan, Henderson, Farabow, Garrett & Dunner, LLP

(57) ABSTRACT

Disclosed herein are compositions for simultaneous shaping, dyeing, and/or lightening of keratin fibers comprising at least one disulfide direct dye and at least one organic or mineral hydroxide alkaline agent. Also disclosed herein are processes for simultaneous shaping, dyeing, and/or lightening of keratin fibers using said compositions and compartmentalized devices comprising said compositions. The compositions disclosed herein may make it possible to obtain a long-lasting dyeing effect, while limiting the degradation of the keratin fibers.

40 Claims, No Drawings

HAIR COMPOSITIONS COMPRISING AT LEAST ONE DISULFIDE DIRECT DYE AND AT LEAST ONE ALKALINE HYDROXIDE AGENT AND SIMULTANEOUS HAIR SHAPING AND DYEING PROCESSES

This application claims benefit of U.S. Provisional Application No. 60/997,000, filed Dec. 13, 2007, the contents of which are incorporated herein by reference. This application also claims benefit of priority under 35 U.S.C. §119 to French Patent Application No. FR 0756706, filed Jul. 24, 2007, the contents of which are also incorporated herein by reference.

One subject of the present disclosure is a hair composition for dyeing and shaping keratin fibers comprising a disulfide direct dye and an alkaline hydroxide agent.

There are various treatments applied to human keratin fibers for the purpose of changing the appearance thereof. As examples of the process that makes it possible to change the color, mention may be made of the bleaching or dyeing of the fibers. As an example of the process that makes it possible to modify the shape of the fibers, mention may be made of relaxing or straightening or smoothing.

As regards the dyeing, two types of processes are known, oxidation dyeing and direct dyeing.

Oxidation dyeing consists in using, in the presence of an oxidizer, oxidation bases (such as, for example, ortho- or para-phenylenediamines, ortho- or para-aminophenols and heterocyclic compounds), optionally combined with couplers (in particular such as aromatic meta-diamines, meta-aminophenols, meta-diphenols and certain heterocyclic compounds).

Direct or semi-permanent dyeing consists in applying direct dyes, which are colored and coloring molecules that have an affinity for the fibers, in leaving them to enable the colored molecules to penetrate via diffusion inside the fiber, then in rinsing them. It is possible to use, for example, nitrobenzene, anthraquinone, nitropyridine, azo, xanthene, acridine, azine or triarylmethane direct dyes.

It is also possible to dye the keratin fibers using disulfide dyes. Such dyes are, for example, described in document FR 2876576.

Bleaching is obtained using an oxidizer which, depending on its nature, makes it possible to bleach the fiber or simply to lighten it. Thus, by using hydrogen peroxide or one of its precursors in a generally alkaline medium, the lightening of the fiber is somewhat slight, and by using compounds of the type of peroxy salts (persulfate or perborate of alkaline metals or of ammonia), in combination with hydrogen peroxide in an alkaline medium, the fiber is more strongly bleached.

It is also possible to observe an optical lightening of dark hair via application of fluorescent dyes. This optical lightening does not use an oxidizer. Such an effect is described, for example, in Patent Application EP 1 432 390.

The shaping of the hair may be carried out according to several methods. One of these methods consists in bringing the fibers into contact with a very strongly alkaline composition, comprising hydroxides, and which has the result of converting the disulfide bridges via lanthionization. This type of process may be used to relax the hair.

Although no problems may be encountered when using a single one of the aforementioned treatments, separately, it is not the same when it is desired to combine a hair shaping operation with a change in the color. This is because the steps of permanent hair shaping, and more particularly of relaxing, are processes that weaken the fibers and it is often difficult to envisage subsequently, placed together, carrying out a dyeing step, and optionally a lightening step, without risking significant degradation of the fiber.

US 2002/192175 describes a hair relaxing and dyeing process starting from cationic dyes, a hair relaxer, an emulsifier, a moisturizer, and a conditioner. The coloring results obtained are not satisfactory and the dyes described do not make it possible to obtain a simultaneous lightening of dark hair.

EP-A-1 464 318 describes a dyeing process with a lightening effect of keratin fibers that have undergone a permanent shaping operation, which consists in applying to the previously shaped fibers, a composition comprising a soluble fluorescent dye. Since this process requires two steps, it is restrictive and time-consuming. The coloring results are not always satisfactory, for example in terms of intensity.

It is thus desirable to be able to simultaneously shape and color the keratin fibers, and optionally obtain a lightening of dark hair, while limiting the degradation of the keratin fibers.

One aspect of the present disclosure is thus a composition for treating keratin fibers, in particular the simultaneous shaping, dyeing and/or lightening of keratin fibers, comprising in a cosmetically acceptable medium:
 at least one disulfide direct dye; and
 at least one alkaline agent of mineral or organic hydroxide type in amount such that the pH of the composition is between 10 and 14.

Another aspect of the present disclosure is a process for simultaneous shaping and dyeing and/or lightening of keratin fibers, in which a dyeing composition according to the present disclosure is applied to the keratin fibers for a sufficient time to develop the desired shaping, dyeing and/or lightening, then the keratin fibers are optionally rinsed, and they are washed with shampoo.

The disclosure also relates to a multi-compartment device having at least a first compartment comprising one or more alkaline agents of mineral or organic hydroxide type, and at least a second compartment comprising a composition containing one or more disulfide direct dyes, the pH of the mixture of the contents of the various compartments being between 10 and 14.

The disclosure also relates to a multi-compartment device having at least a first compartment comprising guanidine carbonate and one or more disulfide direct dyes, and at least a second compartment comprising one or more alkaline agents of alkali metal or alkaline-earth metal hydroxide type, the pH of the mixture of the contents of the various compartments being between 10 and 14.

The disclosure finally relates to a multi-compartment device having at least a first compartment comprising guanidine carbonate, at least a second compartment comprising one or more alkaline agents of alkali metal or alkaline-earth metal hydroxide type, and at least a third compartment comprising one or more disulfide direct dyes, the pH of the mixture of the contents of the various compartments being between 10 and 14. Compositions according to the present disclosure may make it possible to simultaneously obtain a shaping of the hair, for example a relaxing, and dyeing without supplementary degradation of the keratin fibers. When this process is carried out on dark hair, it may also be possible to observe, when the disulfide direct dye is fluorescent, a simultaneous shaping and lightening of the hair without having to use an oxidant in order to obtain this lightening effect. In one embodiment, compositions according to the present disclosure may comprise an oxidant.

It may thus be possible to carry out a simultaneous shaping of the hair, such as a relaxing operation, and a dyeing and/or a lightening operation, using a single composition that is applied in a single step.

Furthermore, it has been observed that the presence of the alkaline agent having a high pH value enabled a better uptake of the disulfide direct dye on the keratin fiber and a better unison, for example due to swelling of the fibers due to said alkaline agent.

According to one embodiment of the present disclosure, the compositions may be applied to dark keratin fibers. For example, the dark keratin fibers may be artificially pigmented or colored fibers, the tone level of which is less than or equal to 6, such as less than or equal to 4.

It should be remembered that the notion of "tone" is based on the classification of natural shades, one tone separating each shade from that which immediately follows or precedes it. This definition and the classification of natural shades are known to hairstyling professionals and are described, for example, in the work "The Science of Hair Care" by Charles ZVIAK, 1988, published by Masson, pp. 215 and 278. The tone levels are graded from 1 (black) to 10 (light light blond), one unit corresponding to one tone; the higher the number, the lighter the shade.

Compositions according to the present disclosure may be suitable for treating keratin fibers, whatever their coloring before treatment and whether this coloring is natural or obtained artificially.

The dyeing and/or lightening effect may be long-lasting, for example with regard to shampooing operations.

As used herein, and unless a different explanation is given:

the term "disulfide direct dye" is understood to mean a compound comprising one or more chromophores such as defined below, and comprising one or more S—S disulfide bonds between two carbon atoms, directly or indirectly connected to the chromophore(s) of the compound, the bond optionally being capable of being reduced in a cosmetically acceptable medium;

the "aryl" or "heteroaryl" radicals or the aryl or heteroaryl part of a radical may be substituted by at least one substituent borne by a carbon atom, chosen from:

a $C_1$-$C_{16}$, for example $C_1$-$C_8$, alkyl radical optionally substituted with one or more radicals chosen from the radicals hydroxyl, $C_1$-$C_2$ alkoxy, (poly)hydroxy($C_2$-$C_4$)alkoxy, acylamino, amino substituted with two $C_1$-$C_4$ alkyl radicals, which are identical or different, optionally bearing at least one hydroxyl group, or it being possible for the two radicals to form, with the nitrogen atom to which they are attached, an optionally substituted, saturated or unsaturated heterocycle comprising from 5 to 7 ring members, for example 5 or 6 ring members, optionally comprising another heteroatom which is identical to or different from nitrogen;

a halogen atom such as chlorine, fluorine or bromine;

a hydroxyl group;

a $C_1$-$C_2$ alkoxy radical; a (poly)hydroxy($C_2$-$C_4$)alkoxy radical;

an amino radical;

a heterocycloalkyl radical having 5 or 6 ring members;

an optionally cationic, for example imidazolium, heteroaryl radical having 5 or 6 ring members, optionally substituted with a ($C_1$-$C_4$) alkyl radical, for example a methyl radical;

an amino radical substituted with one or two $C_1$-$C_6$ alkyl radicals, which are identical or different, optionally bearing at least:

i) one hydroxyl group;

ii) one amino group with two optionally substituted $C_1$-$C_3$ alkyl radicals, it being possible for said alkyl radicals to form, with the nitrogen atom to which they are attached, an optionally substituted, saturated or unsaturated heterocycle comprising from 5 to 7 ring members, optionally comprising at least one other heteroatom different from or identical to nitrogen;

iii) a quaternary ammonium —N$^+$R'R"R'", M$^-$ group for which R', R" and R'", which are identical or different, represent a hydrogen atom or a $C_1$-$C_4$ alkyl group; and M$^-$ represents the counterion of the organic or mineral acid or of the corresponding halide; or iv) an optionally cationic, for example imidazolium, heteroaryl radical having 5 or 6 ring members, optionally substituted with a ($C_1$-$C_4$) alkyl radical, for example a methyl radical;

an acylamino (—NR—COR') radical in which the radical R is a hydrogen atom, a $C_1$-$C_4$ alkyl radical optionally bearing at least one hydroxyl group and the radical R' is a $C_1$-$C_2$ alkyl radical; a carbamoyl ((R)$_2$N—CO—) radical in which the radicals R, which are identical or different, represent a hydrogen atom, a $C_1$-$C_4$ alkyl radical optionally bearing at least one hydroxyl group; an alkylsulfonylamino (R'SO$_2$—NR—) radical in which the radical R represents a hydrogen atom, a $C_1$-$C_4$ alkyl radical optionally bearing at least one hydroxyl group and the radical R' represents a $C_1$-$C_4$ alkyl radical, a phenyl radical; an aminosulfonyl ((R)$_2$N—SO$_2$—) radical in which the radicals R, which are identical or different, represent a hydrogen atom, a $C_1$-$C_4$ alkyl radical optionally bearing at least one hydroxyl group, a carboxyl radical in acid form or salified form, for example salified with an alkali metal or substituted or unsubstituted ammonium;

a nitro radical;

a cyano (CN) group;

a polyhaloalkyl group, for example a trifluoromethyl (CF$_3$) group;

the cyclic or heterocyclic part of a non-aromatic radical may be substituted with at least one substituent borne by a carbon atom chosen from the groups:

hydroxyl, $C_1$-$C_4$ alkoxy, (poly)hydroxy$C_2$-$C_4$alkoxy, alkylcarbonylamino (RCO—NR'—) in which the radical R' is a hydrogen atom, a $C_1$-$C_4$ alkyl radical optionally bearing at least one hydroxyl group and the radical R is a $C_1$-$C_2$ alkyl radical, an amino radical substituted with two $C_1$-$C_4$ alkyl groups which are identical or different, optionally bearing at least one hydroxyl group, it being possible for said alkyl radicals to form, with the nitrogen atom to which they are attached, an optionally substituted, saturated or unsaturated heterocycle comprising from 5 to 7 ring members, optionally comprising at least one other heteroatom different from or identical to nitrogen;

alkylcarbonyloxy (RCO—O—) in which the radical R is a $C_1$-$C_4$ alkyl radical, an amino radical substituted with two $C_1$-$C_4$ alkyl groups which are identical or different, optionally bearing at least one hydroxyl group, it being possible for said alkyl radicals to form, with the nitrogen atom to which they are attached, an optionally substituted, saturated or unsaturated heterocycle comprising from 5 to 7 ring members, optionally comprising at least one other heteroatom different from or identical to nitrogen;

alkoxycarbonyl (RO—CO—) in which the radical R is a C$_1$-C$_4$ alkyl radical, an amino radical substituted with two C$_1$-C$_4$ alkyl groups which are identical or different, optionally bearing at least one hydroxyl group, it being possible for said alkyl radicals to form, with the nitrogen atom to which they are attached, an optionally substituted, saturated or unsaturated heterocycle comprising from 5 to 7 ring members, optionally comprising at least one other heteroatom different from or identical to nitrogen;

a cyclic or heterocyclic radical, or a non-aromatic part of an aryl or heteroaryl radical, may also be substituted with one or more oxo groups;

a hydrocarbon chain is unsaturated when it comprises one or more double bonds and/or one or more triple bonds;

the term "aryl" radical is understood to mean a fused or unfused monocyclic or polycyclic group comprising from 6 to 22 carbon atoms, and of which at least one ring is aromatic; for example phenyl, biphenyl, naphthyl, indenyl, anthracenyl, and tetrahydronaphthyl radicals;

the term "heteroaromatic or heteroaryl radical" is understood to mean an optionally cationic, fused or unfused, monocyclic or polycyclic group comprising from 5 to 22 ring members, from 1 to 6 heteroatoms chosen from nitrogen, oxygen, sulfur and selenium atoms, and of which at least one ring is aromatic; for example a heteroaryl radical chosen from acridinyl, benzimidazolyl, benzobistriazolyl, benzopyrazolyl, benzopyridazinyl, benzoquinolyl, benzothiazolyl, benzotriazolyl, benzoxazolyl, pyridinyl, tetrazolyl, dihydrothiazolyl, imidazopyridinyl, imidazolyl, indolyl, isoquinolyl, naphthoimidazolyl, naphthooxazolyl, naphthopyrazolyl, oxadiazolyl, oxazolyl, oxazolopyridyl, phenazinyl, phenooxazolyl, pyrazinyl, pyrazolyl, pyrilyl, pyrazoyltriazyl, pyridyl, pyridinoimidazolyl, pyrrolyl, quinolyl, tetrazolyl, thiadiazolyl, thiazolyl, thiazolopyridinyl, thiazoylimidazolyl, thiopyrylyl, triazolyl, xanthylyl and its ammonium salt;

the term "cyclic radical" is understood to mean a fused or unfused, monocyclic or polycyclic, non-aromatic cycloalkyl radical containing from 5 to 22 carbon atoms, which may optionally comprise 1 or more unsaturations;

the term "heterocyclic radical" is understood to mean a fused or unfused, monocyclic or polycyclic, non-aromatic radical containing from 5 to 22 ring members, comprising from 1 to 6 heteroatoms chosen from nitrogen, oxygen, sulfur and selenium atoms;

the term "alkyl radical" is understood to mean a linear or branched, C$_1$-C$_{16}$, for example C$_1$-C$_8$, hydrocarbon radical;

the term "optionally substituted" attributed to an alkyl radical is understood to mean that said alkyl radical may be substituted with one or more radicals chosen from the radicals i) hydroxy, ii) C$_1$-C$_4$ alkoxy, iii) acylamino, iv) amino optionally substituted with one or two C$_1$-C$_4$ alkyl radicals, which are identical or different, it being possible for said alkyl radicals to form, with the nitrogen atom which bears them, a heterocycle comprising from 5 to 7 ring members, optionally comprising one other heteroatom different from or identical to nitrogen; v) or a quaternary ammonium group —N$^+$R'R''R''',M$^-$ for which R', R'', R''', which are identical or different, represent a hydrogen atom, or a C$_1$-C$_4$ alkyl group or else —N$^+$R'R''R''' forms a heteroaryl such as imidazolium optionally substituted by a C$_1$-C$_4$ alkyl group, and M$^-$ represents the counterion of the organic or mineral acid, or of the corresponding halide;

the term "alkoxy radical" is understood to mean an alkyloxy radical for which the alkyl radical is a linear or branched C$_1$-C$_{16}$, for example C$_1$-C$_8$ hydrocarbon radical; when the alkoxy group is described as optionally substituted, this is understood to mean that the alkyl radical of the alkoxy group is optionally substituted as defined above.

Furthermore, unless otherwise indicated, the limits defining the extent of a range of values are included in this range of values. Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

According to the present disclosure, the term "chromophore" is understood to mean a radical derived from a dye, that is to say a radical derived from a molecule that absorbs in the visible radiation field (between 400 and 800 nm).

In particular, the disulfide direct dye may be a fluorescent disulfide direct dye or a non-fluorescent disulfide direct dye.

As used herein, the expression "fluorescent compound" is understood to mean a dye which is a molecule that colors by itself, and therefore absorbs the light from the visible spectrum, and optionally from the ultraviolet spectrum, but which, unlike a conventional dye, converts the energy absorbed into fluorescent light of a larger wavelength emitted in the visible part of the spectrum. Thus, a fluorescent compound is capable of absorbing in the field of UV or visible radiation at a wavelength $\lambda_{abs}$ between 250 and 800 nm and capable of reemitting in the visible field at an emission wavelength $\lambda_{em}$ between 400 and 800 nm.

For example, the fluorescent compounds may be dyes capable of absorbing in the visible range at a wavelength $\lambda_{abs}$ between 400 and 800 nm, and of reemitting in the visible range at a wavelength $\lambda_{em}$ between 400 and 800 nm. For further example, the fluorescent dyes may be dyes capable of absorbing at a wavelength $\lambda_{abs}$ between 420 nm and 550 nm and of reemitting in the visible range at a wavelength $\lambda_{em}$ between 470 and 600 nm.

A fluorescent dye should be differentiated from an optical lightening agent. The optical lightening agents generally known as optical brighteners, or brighteners, or fluorescent brighteners, or fluorescent brightening agents, or fluorescent whitening agents or whiteners or else fluorescent whiteners are colorless transparent compounds, which do not dye because they do not absorb light in the visible region, but only in the ultraviolet region (wavelengths ranging from 200 to 400 nm), and convert the energy absorbed into fluorescent light of longer wavelength emitted in the visible region of the spectrum; the color impression is then generated solely by purely fluorescent light that is predominantly blue (wavelengths ranging from 400 to 500 nm).

A fluorescent dye is different from a fluorescent pigment which itself is insoluble in the medium of the composition.

That is, a fluorescent dye in the context of the present disclosure, optionally neutralized, is soluble in the medium of the composition to at least 0.001 g/l, for example at least 0.5 g/l, for example at least 1 g/l, for example at least 5 g/l at a temperature between 15 and 25° C.

According to one embodiment, the disulfide direct dyes of the present disclosure may be chosen from the compounds of formulae (I), (II) or (III) below:

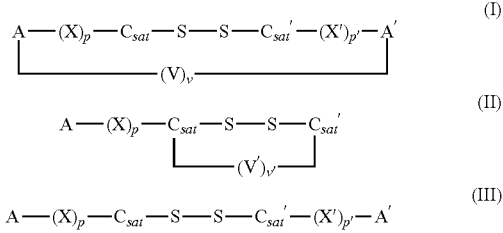

and their salts, optical isomers, geometrical isomers, and solvates such as hydrates, in which formulae:
- A and A' are, independently of one another, chosen from radicals comprising at least one cationic or non-cationic chromophore;
- V and V' are, independently of one another, chosen from bridging groups;
- v and v' are, independently of one another, chosen from 0 and 1;
- X and X' are, independently of one another, chosen from saturated and unsaturated, linear and branched $C_1$-$C_{30}$ hydrocarbon chains optionally interrupted and optionally terminated at one or both of its ends by one or more divalent groups or combinations thereof, chosen from:
  —N(R)—, —N$^+$(R)(R)—, —O—, —S—, —CO—, —SO$_2$— wherein R and R' are, independently of one another, chosen from hydrogen atoms and $C_1$-$C_4$ alkyl, hydroxyalkyl, and aminoalkyl radicals;
  optionally substituted, saturated and unsaturated, fused and non-fused, aromatic and non-aromatic (hetero) cyclic radicals optionally comprising at least one heteroatom;
- p and p' are, independently of one another, chosen from 0 and 1;
- $C_{sat}$ and $C'_{sat}$ are, independently of one another, chosen from optionally substituted, cyclic, linear and branched $C_1$-$C_{18}$ alkylene chains; and
- D is chosen from hydroxyl, hydroxyalkyl, alkoxy, carboxyl, carboxylate, amino, alkylamino, and dialkylamino radicals.

I. Dyes of Formulae (I), (II) and (III).

The radicals A and A' from the formulae (I), (II) and (III) may contain one or more identical or different, fluorescent or non-fluorescent chromophores.

I.1. Chromophores

As used herein, chromophores are said to be different when they differ in their chemical structure. Such chromophores may be chromophores derived from different families or from the same family, on condition that they have different chemical structures. For example, the chromophores may be chosen from the family of azo or polymethine dyes, but differ in the chemical structure of the radicals of which they are composed or in the respective position of these radicals.

Non-limiting examples of chromophores that may be used according to the present disclosure include radicals derived from the following dyes: acridines, acridones, anthranthrones, anthrapyrimidines, anthraquinones, azines, azos, azomethines, benzanthrones, benzimidazoles, benzimidazolones, benzindoles, benzoxazoles, benzopyrans, benzothiazoles, benzoquinones, bisazines, bisisoindolines, carboxanilides, coumarins, cyanins (such as azacarbocyanins, diazacarbocyanins, diazahemicyanins, hemicyanins and tetraazacarbocyanins), diazines, diketopyrrolopyrroles, difluoro-{2-[2H-pyrrol-2-ylidene-kN)methyl]-1H-pyrrolato-kN]-boron complexes (BODIPY®), dioxazines, diphenylamines, diphenylmethanes, dithiazines, flavonoids such as flavanthrones and flavones, fluorindines, formazans, hydrazones, in particular arylhydrazones, hydroxy ketones, indamines, indanthrones, indigoids and pseudo-indigoids, indophenols, indoanilines, isoindolines, isoindolinones, isoviolanthrones, lactones, methines, (poly)methines (for example cyanins and styryls/hemicyanins), naphthalimides, naphthanilides, naphthylamines (such as dansyls), naphtholactams, naphthoquinones, nitro dyes, for example nitro (hetero)aromatic dyes, oxadiazoles, oxazines, perilones, perinones, perylenes, phenazines, phenothiazines, phthalocyanin, polyenes/carotenoids, porphyrins, pyranthrones, pyrazolanthrones, pyrazolones, pyrimidinoanthrones, pyronines, quinacridones, quinolines, quinophthalones, squaranes, stilbenes, tetrazoliums, thiazines, thioindigo, thiopyronines, triarylmethanes and xanthenes.

Non-limiting examples of nitro chromophores that may be used according to the present disclosure include radicals derived from the following dyes:
1,4-diamino-2-nitrobenzene;
1-amino-2-nitro-4-(β-hydroxyethylamino)benzene;
1-amino-2-nitro-4-bis(β-hydroxyethyl)aminobenzene;
1,4-bis(β-hydroxyethylamino)-2-nitrobenzene;
1-β-hydroxyethylamino-2-nitro-4-bis(β-hydroxyethylamino)benzene;
1-β-hydroxyethylamino-2-nitro-4-aminobenzene;
1-β-hydroxyethylamino-2-nitro-4-(ethyl)(β-hydroxyethyl)aminobenzene;
1-amino-3-methyl-4-β-hydroxyethylamino-6-nitrobenzene;
1-amino-2-nitro-4-β-hydroxyethylamino-5-chlorobenzene;
1,2-diamino-4-nitrobenzene;
1-amino-2-β-hydroxyethylamino-5-nitrobenzene;
1,2-bis(β-hydroxyethylamino)-4-nitrobenzene;
1-amino-2-[tris(hydroxymethyl)methylamino]-5-nitrobenzene;
1-hydroxy-2-amino-5-nitrobenzene;
1-hydroxy-2-amino-4-nitrobenzene;
1-hydroxy-3-nitro-4-aminobenzene;
1-hydroxy-2-amino-4,6-dinitrobenzene;
1-β-hydroxyethyloxy-2-β-hydroxyethylamino-5-nitrobenzene;
1-methoxy-2-β-hydroxyethylamino-5-nitrobenzene;
1-β-hydroxyethyloxy-3-methylamino-4-nitrobenzene;
1-β,γ-dihydroxypropyloxy-3-methylamino-4-nitrobenzene;
1-β-hydroxyethylamino-4-β,γ-dihydroxypropyloxy-2-nitrobenzene;
1-β,γ-dihydroxypropylamino-4-trifluoromethyl-2-nitrobenzene;
1-β-hydroxyethylamino-4-trifluoromethyl-2-nitrobenzene;
1-β-hydroxyethylamino-3-methyl-2-nitrobenzene;
1-β-aminoethylamino-5-methoxy-2-nitrobenzene;

1-hydroxy-2-chloro-6-ethylamino-4-nitrobenzene;
1-hydroxy-2-chloro-6-amino-4-nitrobenzene;
1-hydroxy-6-bis(β-hydroxyethyl)amino-3-nitrobenzene;
1-β-hydroxyethylamino-2-nitrobenzene;
1-hydroxy-4-β-hydroxyethylamino-3-nitrobenzene.

Non-limiting examples of azo, azomethine and methine chromophores that may be used according to the present disclosure include radicals derived from the cationic azo, azomethine and methine dyes described in patent applications WO 95/15144, WO 95/01772 and EP-714 954, for example Basic Red 59, Basic Orange and Basic Yellow 87.

Non-limiting examples of azo chromophores also include those described in the Color Index International 3rd edition, for example the following compounds:
Disperse Red 17;
Acid Yellow 9;
Acid Black 1;
Basic Red 22;
Basic Red 76;
Basic Yellow 57;
Basic Brown 16;
Acid Yellow 36;
Acid Orange 7;
Acid Red 33;
Acid Red 35;
Basic Brown 17;
Acid Yellow 23;
Acid Orange 24; and
Disperse Black 9.

Non-limiting examples of chromophores also include 1-(4'-amino-diphenylazo)-2-methyl-4-[bis(β-hydroxyethyl)amino]benzene and 4-hydroxy-3-(2-methoxyphenylazo)-1-naphthalenesulfonic acid.

Non-limiting examples of quinone chromophores that may be used according to the present disclosure include those mentioned in the abovementioned Color Index International, for example radicals derived from the following dyes:
Disperse Red 15;
Solvent Violet 13;
Acid Violet 43;
Disperse Violet 1;
Disperse Violet 4;
Disperse Blue 1;
Disperse Violet 8;
Disperse Blue 3;
Disperse Red 11;
Acid Blue 62;
Disperse Blue 7;
Basic Blue 22;
Disperse Violet 15;
Basic Blue 99;
and also the following compounds:
1-N-methylmorpholiniumpropylamino-4-hydroxyanthraquinone;
1-aminopropylamino-4-methylaminoanthraquinone;
1-aminopropylaminoanthraquinone;
5-β-hydroxyethyl-1,4-diaminoanthraquinone;
2-aminoethylaminoanthraquinone; and
1,4-bis(β,γ-dihydroxypropylamino)anthraquinone.

Non-limiting examples of azine chromophores that may be used according to the present disclosure include those listed in the Color Index International and for example the radicals derived from the following dyes:
Basic Blue 17; and
Basic Red 2.

Non-limiting examples of triarylmethane chromophores that may be used according to the present disclosure include those listed in the Color Index and radicals derived from the following dyes:
Basic Green 1;
Acid Blue 9;
Basic Violet 3;
Basic Violet 14;
Basic Blue 7;
Acid Violet 49;
Basic Blue 26; and
Acid Blue 7.

Non-limiting examples of indoamine chromophores that may be used according to the present disclosure include radicals derived from the following dyes:
2-β-hydroxyethylamino-5-[bis(β-4'-hydroxyethyl)amino]anilino-1,4-benzoquinone;
2-β-hydroxyethylamino-5-(2'-methoxy-4'-amino)anilino-1,4-benzoquinone;
3-N(2'-chloro-4'-hydroxy)phenylacetylamino-6-methoxy-1,4-benzoquinoneimine;
3-N (3'-chloro-4'-methylamino)phenylureido-6-methyl-1,4-benzoquinoneimine; and
3-[4'-N-(ethylcarbamylmethyl)amino]phenylureido-6-methyl-1,4-benzoquinoneimine.

Non-limiting examples of chromophores also include the chromophores described in documents U.S. Pat. No. 5,888,252, EP 1 133 975, WO 03/029359 and EP 860 636, and those mentioned in the encyclopaedia "The chemistry of synthetic dye" by K. Venkataraman, 1952, Academic Press, Vol. 1 to 7, in the "Kirk-Othmer Encyclopaedia of Chemical Technology", in the chapter "Dyes and Dye Intermediate", 1993, Wiley & Sons, and in various chapters of the encyclopaedia "Ullmann's Encyclopedia of Industrial Chemistry" 7th edition, Wiley & Sons.

In one embodiment, in the formulae (I), (II) or (III), A and A' may represent a radical comprising a chromophore chosen from chromophores of the azo, anthraquinone and hydrazone type.

Non-limiting examples of fluorescent dyes also include those described in documents EP 1 133 975, WO 03/029359, EP 860636, WO 95/01772, WO 95/15144, EP 714954 and those mentioned in the encyclopaedia "The chemistry of synthetic dye" by K. Venkataraman, 1952, Academic Press, Vol. 1 to 7, in the "Kirk-Othmer Encyclopaedia of Chemical Technology", in the chapter "Dyes and Dye Intermediate", 1993, Wiley & Sons, and in various chapters of the encyclopaedia "Ullmann's Encyclopedia of Industrial Chemistry" 7th edition, Wiley & Sons in "The Handbook—A Guide to Fluorescent Probes and Labeling Technologies", 10th Ed., Molecular Probes/Invitrogen—Oregon 2005 issued on the Internet or in the preceding printed editions.

In at least one embodiment, the radicals, A and/or A' of formulae (I), (II) or (III) may or may not contain one cationic radical borne by or included in at least one of the chromophores.

For example, the cationic radical may be a quaternary ammonium.

Non-limiting examples of cationic radicals include alkylammonium, acridinium, benzimidazolium, benzobistriazolium, benzopyrazolium, benzopyridazinium, benzoquinolium, benzothiazolium, benzotriazolium, benzoxazolium, bi-pyridinium, bis-tetrazolium, dihydrothiazolium, imidazopyridinium, imidazolium, indolium, isoquinolinium, naphthimidazolium, naphthoxazolium, naphthopyrazolium, oxadiazolium, oxazolium, oxazolopyridinium, oxonium, phenazinium, phenoxazolium, pyrazinium, pyrazolium, pyrazoyltriazolium, pyridinium, pyridinoimidazolium, pyrrolium, pyrylium, quinolium, tetrazolium, thiadiazolium, thiazolium, thiazolopyridinium, thiazoylimidazolium, thiopyrylium, triazolium, or xanthylium radical.

In one embodiment, fluorescent chromophores may be chosen from those derived from dyes of the coumarin, (poly) methine (for example cyanin and styryl/hemicyanin) and naphthalimide type.

In at least one embodiment, the radicals A and/or A' of formulae (I), (II) or (III), which may be identical or different, may be chosen from radicals that contains one or more cationic or non-cationic fluorescent chromophores. For example, the radicals A and/or A', which may be identical or different, may contain a styryl chromophore.

In one embodiment, the radicals A, A' in the formulae (I), (II) or (III) may comprise one or more cationic azo chromophores described for example in EP 850 636, FR 2 788 433, EP 920 856, WO 99/48465, FR 2 757 385, EP 850 637, EP 918 053, WO 97/44004, FR 2 570 946, FR 2 285 851, DE 2 538 363, FR 2 189 006, FR 1 560 664, FR 1 540 423, FR 1 567 219, FR 1 516 943, FR 1 221 122, DE 4 220 388, DE 4 137 005, WO 01/66646, U.S. Pat. No. 5,708,151, WO 95/01772, WO 51/5144, GB 1 195 386, U.S. Pat. No. 3,524, 842, U.S. Pat. No. 5,879,413, EP 1 062 940, EP 1 133 976, GB 738 585, DE 2 527 638, FR 2 275 462, GB 1974-27645, Acta Histochem. (1978), 61(1), 48-52; Tsitologiya (1968), 10(3), 403-5; Zh. Obshch. Khim. (1970), 40(1), 195-202; Ann. Chim. (Rome) (1975), 65(5-6), 305-14; Journal of the Chinese Chemical Society (Taipei) (1998), 45(1), 209-211; Rev. Roum. Chim. (1988), 33(4), 377-83; Text. Res. J. (1984), 54(2), 105-7; Chim. Ind. (Milan) (1974), 56(9), 600-3; Khim. Tekhnol. (1979), 22(5), 548-53; Ger. Monatsh. Chem. (1975), 106(3), 643-8; MRL Bull. Res. Dev. (1992), 6(2), 21-7; Lihua Jianyan, Huaxue Fence (1993), 29(4), 233-4; Dyes Pigm. (1992), 19(1), 69-79; Dyes Pigm. (1989), 11(3), 163-72.

I.2. $C_{sat}$ and $C'_{sat}$:

As indicated above, in formulae (I), (II) or (III), $C_{sat}$ and $C'_{sat}$, independently of each other, represent an optionally substituted, optionally cyclic, linear or branched $C_1$-$C_{18}$ alkylene chain. For example, substituents may be chosen from amino, ($C_1$-$C_4$)alkylamino or ($C_1$-$C_4$)dialkylamino groups, and $R^a$—$Z^a$—$C(Z^b)$-groups (in which $Z^a$ and $Z^b$, which may be identical or different, represent an oxygen or sulfur atom or an $NR^{a'}$ group, and $R^{a'}$ represents an alkali metal, a hydrogen atom or a $C_1$-$C_4$ alkyl group and $R^a$ represents a hydrogen atom or a $C_1$-$C_4$ alkyl group), for example present on the carbon at the beta or gamma position of the sulfur atoms.

For example, in formulae (I) or (III), $C_{sat}$ and $C'_{sat}$ may represent a —$(CH_2)_k$— chain with k being an integer between 1 and 8 inclusive.

For example, in formula (II), $C'_{sat}$ may represent a —$(CH_2)_k$— radical and $C_{sat}$ may represent a

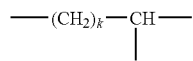

radical, k having the same meaning as above.

I.3. X and X':

In one embodiment of the present disclosure, in formulae (I), (II) or (III), when p and/or p' respectively are equal to 1, X and/or X' may respectively represent a sequence -$(T)_t$-$(Y)_y$—$(Z)_z$—, said sequence being present in Formulae (I), (II), or (III) as follows: A-$(T)_t$-$(Y)_y$—$(Z)_z$—$C_{sat}$ or $C'_{sat}$-$(T)_t$-$(Y)_y$—$(Z)_z$-A' wherein:

i) T is chosen from —$SO_2$—, —O—, —S—, —N(R)—, —$N^+$(R)(R')—, and —CO— radicals, and combinations thereof, wherein R and R' are, independently of one another, chosen from hydrogen atoms, $C_1$-$C_4$ alkyl radicals, and $C_1$-$C_4$ hydroxyalkyl radicals; and the coefficient t is chosen from 0 and 1;

ii) Y is chosen from:
radicals chosen from —$(CH_2)_2$—$SO_2$—, and —$CH_2$—CHR—CO—NR'— radicals, wherein R and R' are, independently of one another, chosen from hydrogen atoms and $C_1$-$C_4$ alkyl radicals;
groups of formula (a), (a'), or (a"):

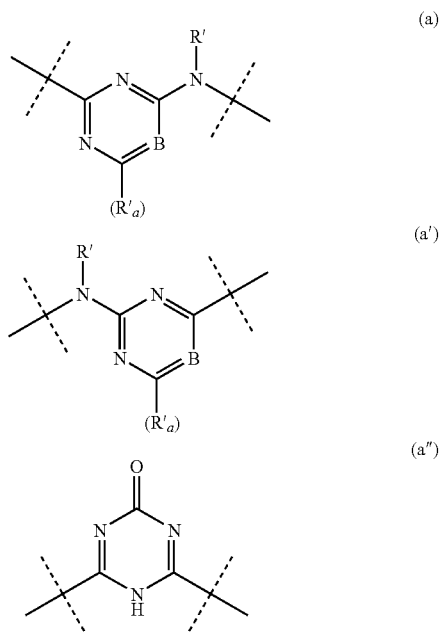

wherein:
B is chosen from —N— and —$CR_a$— radicals, wherein $R_a$ is chosen from
hydrogen atoms,
halogen atoms chosen from chlorine and fluorine,
nitro groups,
optionally substituted pyridinium groups;
R' has the same definition as above;
$R'_a$ is chosen from:
hydrogen atoms;
halogen atoms chosen from chlorine and fluorine;
pyridinium groups, optionally substituted with at least one group $R_c$ chosen from $C_1$-$C_4$ alkyl radicals, halogen atoms, carboxyl groups —COOM (wherein M is chosen from hydrogen atoms, alkali metal atoms, ammonium groups, and ammonium groups substituted with at least one group chosen from linear and branched $C_1$-$C_{18}$ alkyl radicals, optionally bearing at least one hydroxyls), ester groups —$COOR_d$ wherein —$R_d$ is chosen from $C_1$-$C_4$ alkyl radicals; amide groups —$CON(R_d)_2$ wherein the $R_d$ groups are, independently of one another, chosen from hydrogen atoms and $C_1$-$C_4$ alkyl radicals;

hydroxyl groups;

amino, alkylamino, and dialkylamino groups, wherein the alkyl radicals are chosen from linear and branched $C_1$-$C_{18}$ alkyl groups, optionally interrupted by a heteroatom chosen from N and O, and optionally substituted with at least one hydroxyl group;

—NHNHCOR radicals wherein R is chosen from linear and branched $C_1$-$C_{10}$ alkyl groups;

groups of formula (b):

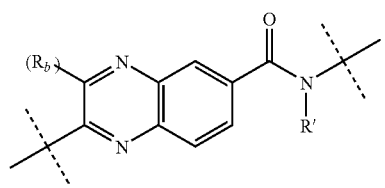

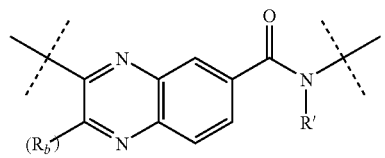

wherein:

R' has the same definition as above;

$R_b$ is chosen from:

chlorine atoms, amino, alkylamino, and dialkylamino groups, wherein the alkyl radicals are chosen from linear and branched $C_1$-$C_{18}$ alkyl groups, optionally interrupted by a heteroatom chosen from N, O, and S, and optionally substituted with at least one hydroxyl, saturated and unsaturated heterocycles comprising at least one nitrogen atom and optionally substituted, and arylamino groups, for example a $C_6$ aryl radical;

and y is chosen from 0 and 1;

iii) Z is chosen from:

—$(CH_2)_m$— radicals wherein m is an integer ranging from 1 to 8

—$(CH_2CH_2O)_q$— and —$(OCH_2CH_2)_q$— radicals wherein q is an integer ranging from 1 to 15, aryl, alkylaryl, and arylalkyl radicals wherein the alkyl radicals are chosen from $C_1$-$C_4$ alkyl radicals and the aryl radicals, for example $C_6$ aryl radicals, are optionally substituted with at least one group —$SO_3M$ wherein M is chosen from hydrogen atoms, alkali metal atoms, and ammonium groups optionally substituted with at least one linear or branched $C_1$-$C_{18}$ alkyl radical optionally bearing at least one hydroxyl;

and z is chosen from 0 and 1.

In at least one embodiment, Y may be chosen from the groups below:

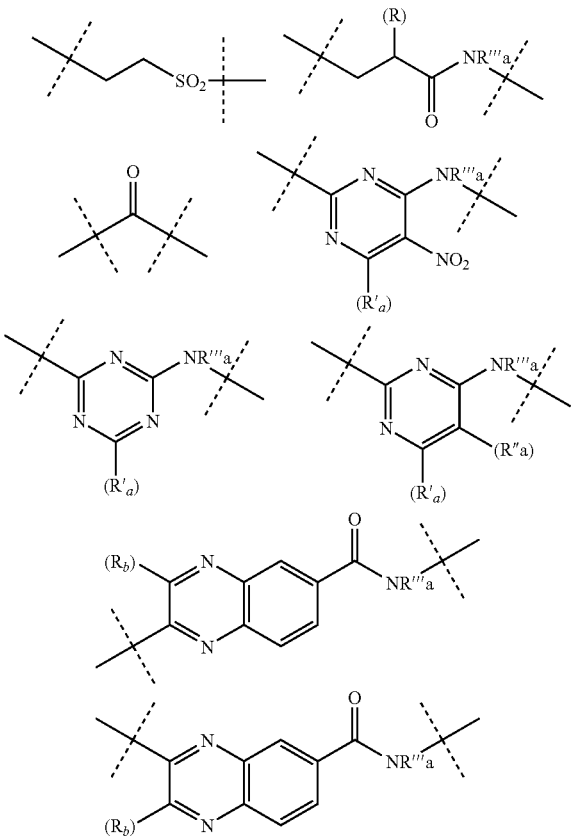

wherein the radicals R, $R'_a$ and $R_b$ are as defined above; $R'''_a$ has the same definition as $R'_a$, independently of each other; $R''''_a$ represents a hydrogen atom or an alkyl radical.

In at least one embodiment, Z may be chosen from the groups below:

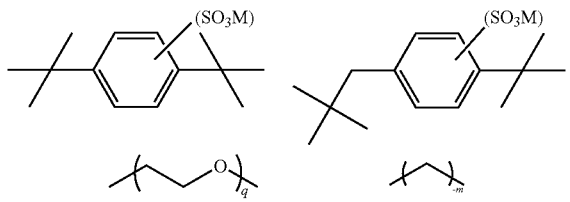

wherein M, q and m having the same meanings as before.

In at least one embodiment, X and X', which may be identical or different, may represent an —N(R)— group, in which R has the meaning indicated above and is for example a hydrogen atom.

I.4. Disulfide Direct Dyes:

As indicated above, in the formulae (I) and (II), V represents a group bridging the two radicals A and A', which may be identical or different, v possibly being equal to 0 or 1, and V' represents a group bridging the two radicals $C_{sat}$ and $C'_{sat}$, which may be identical or different, v' possibly being equal to 0 or 1.

When v or v' is equal to 1, the group V or V' respectively bridging the two chromophores A and A' or the two radicals $C_{sat}$ and $C'_{sat}$, represents a $C_1$-$C_8$ alkyl radical, optionally terminated at one or both of its ends by a group chosen from an amine, amide or ester group.
In one embodiment, the disulfide direct dye of formula (I) is chosen such that v is equal to 0.
For example, the disulfide direct dye may be chosen from:
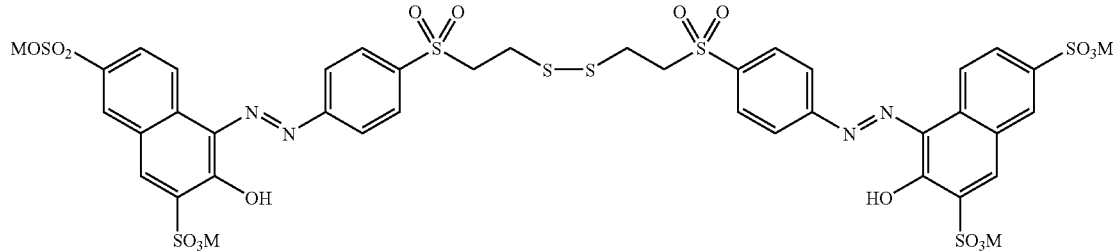
and the following compounds, in acidic, basic or neutralized form:
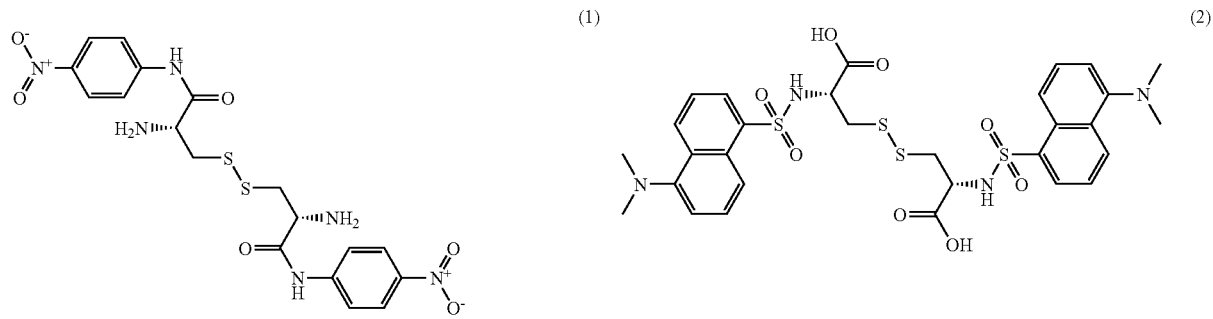
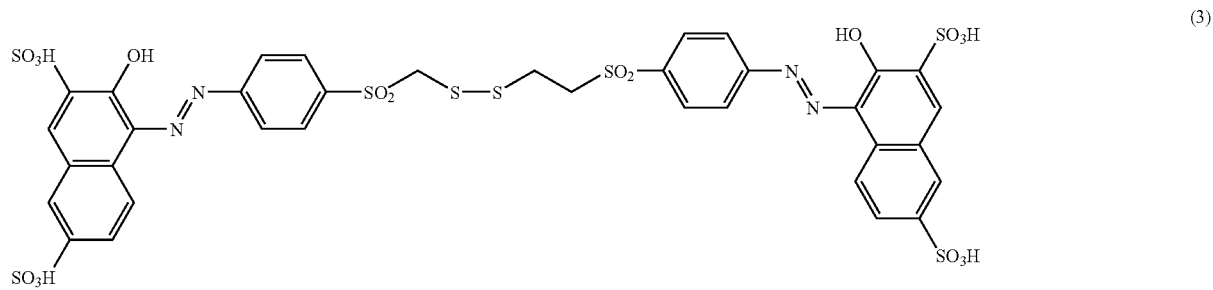
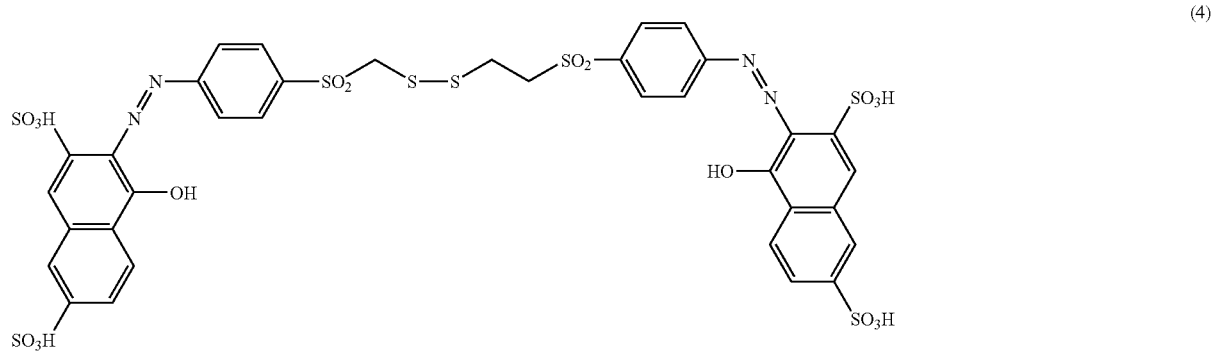

-continued
(5)
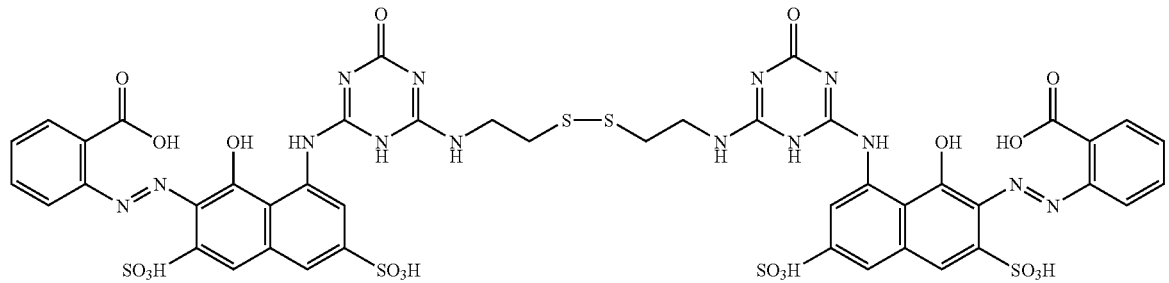
(6)
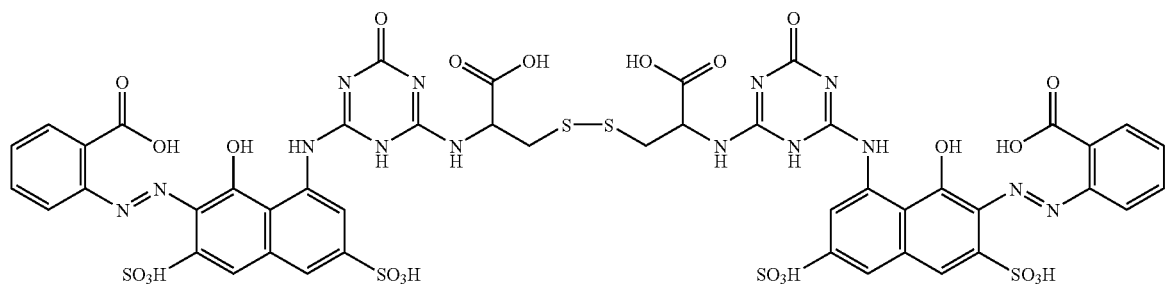
(7)
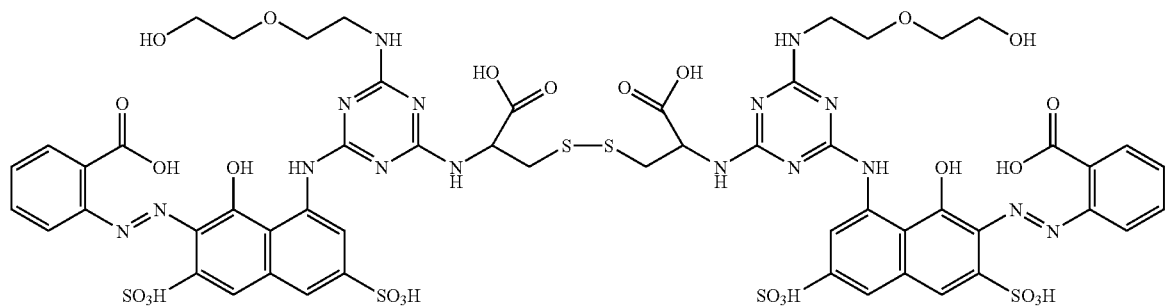
(8)
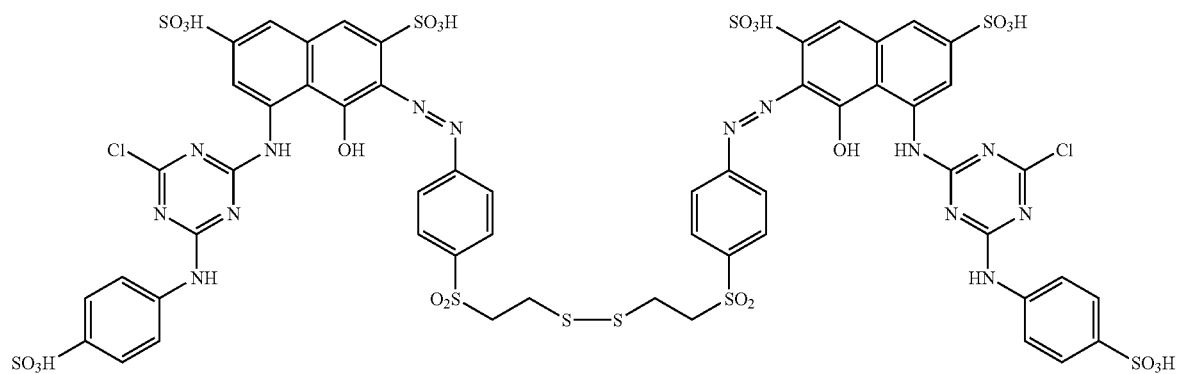
(9)
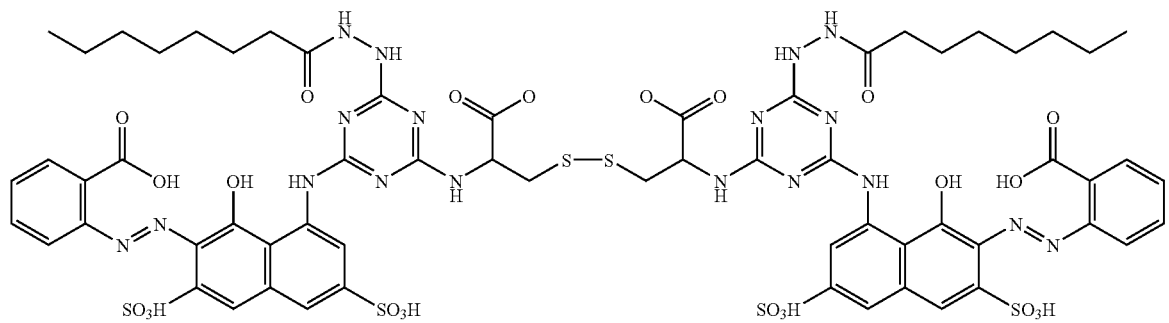

-continued
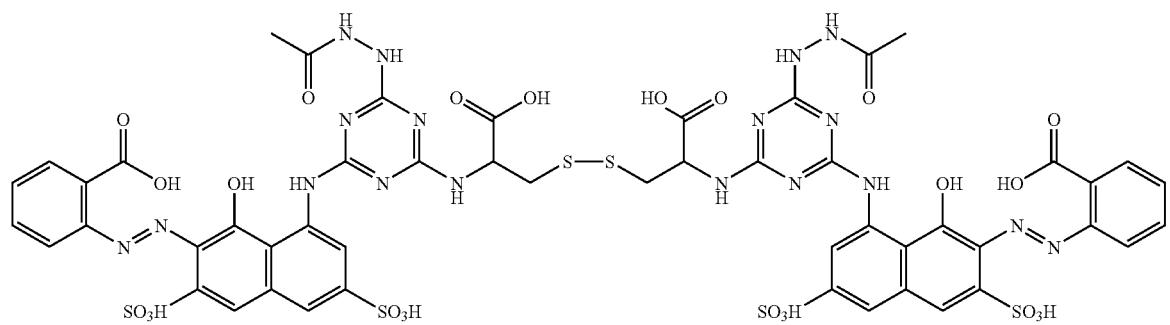
(10)
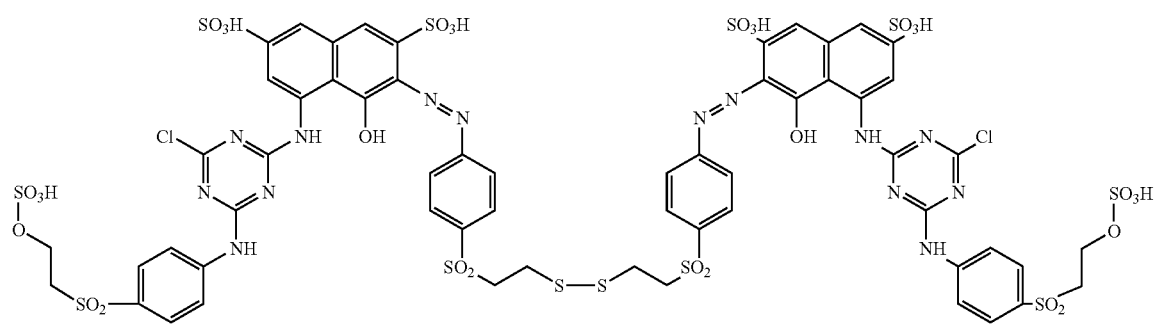
(11)
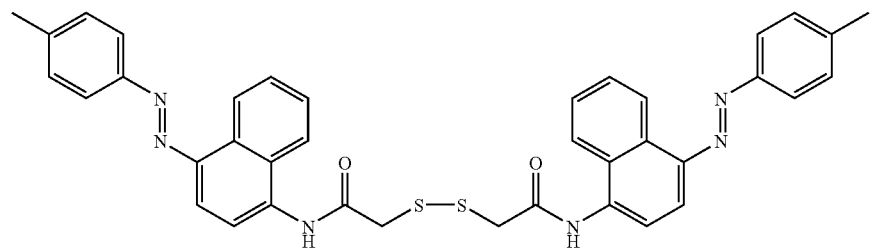
(12)
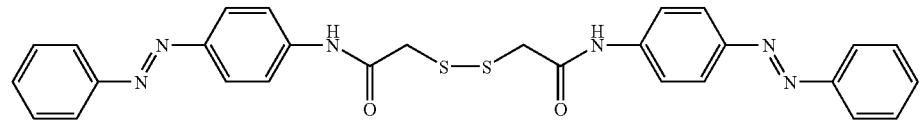
(13)
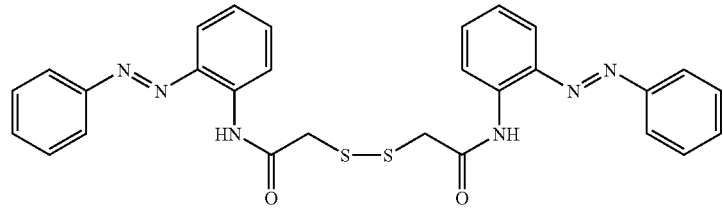
(14)
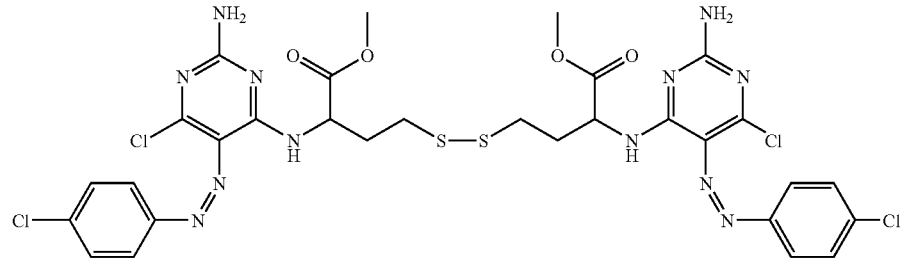
(15)

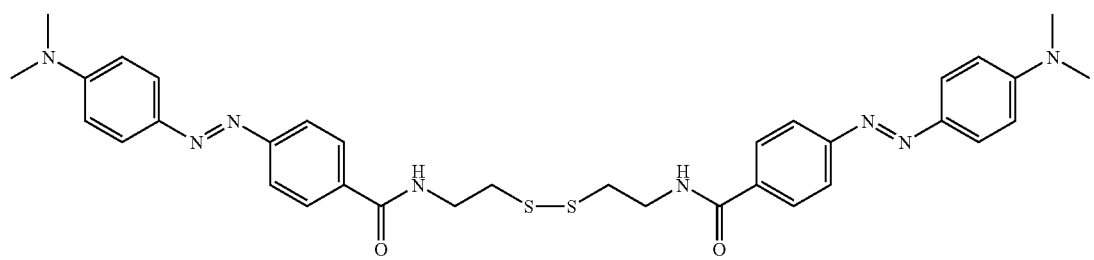
(16)
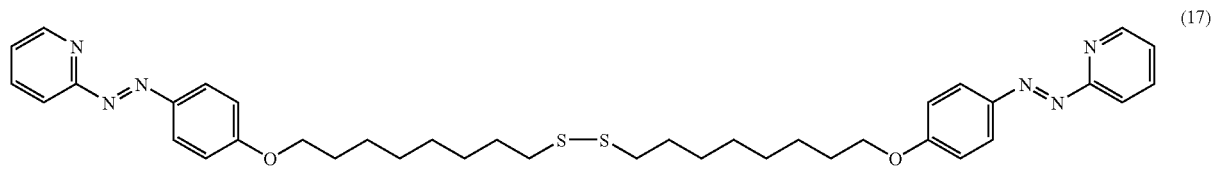
(17)
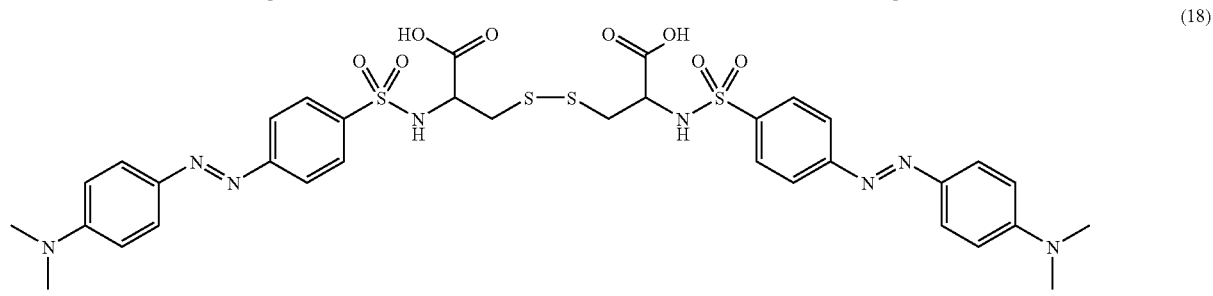
(18)
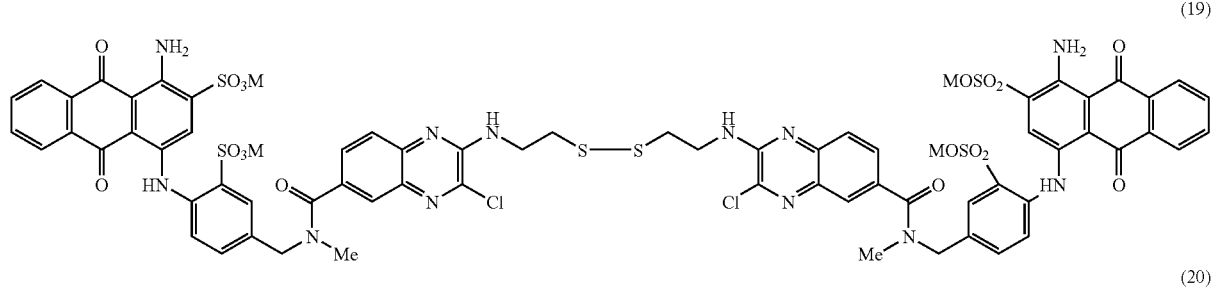
(19)
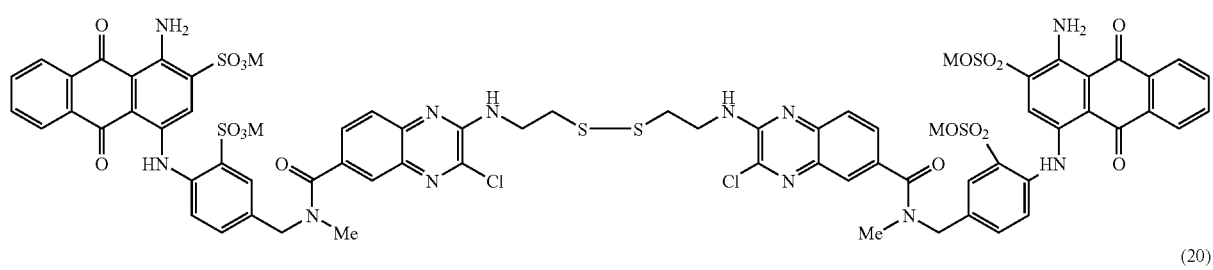
(20)
wherein M is chosen from a hydrogen atom, an alkali metal or an ammonium group or an ammonium group substituted with one or more identical or different, linear or branched $C_1$-$C_{10}$ alkyl radicals optionally bearing at least one hydroxyl;
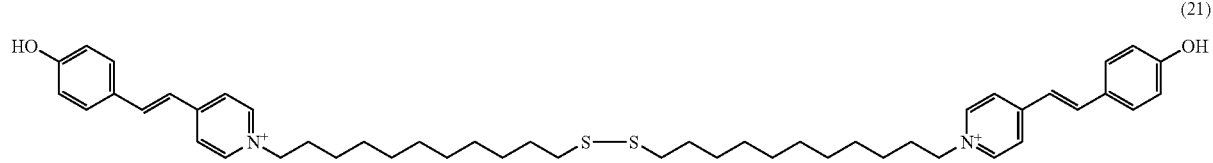
(21)

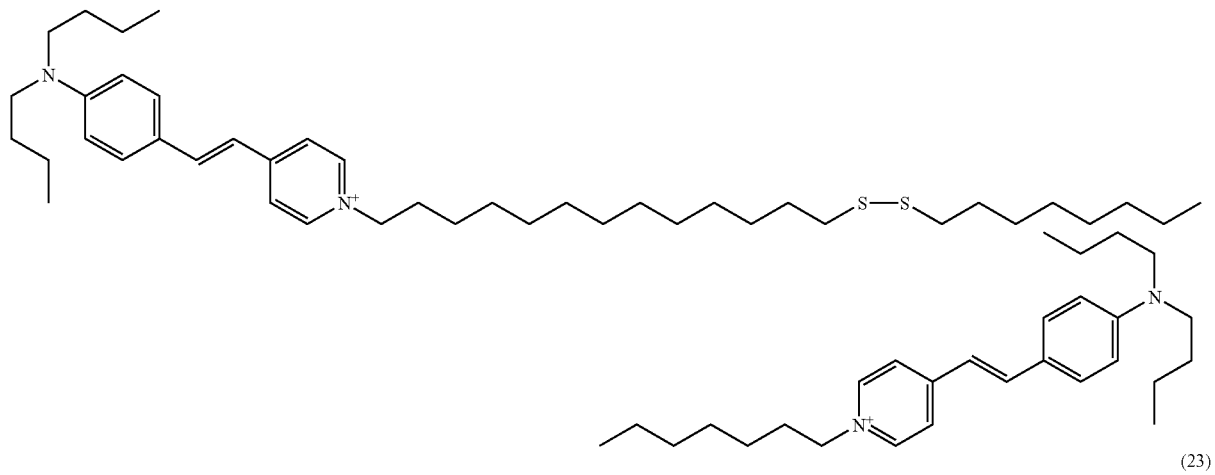

(22)

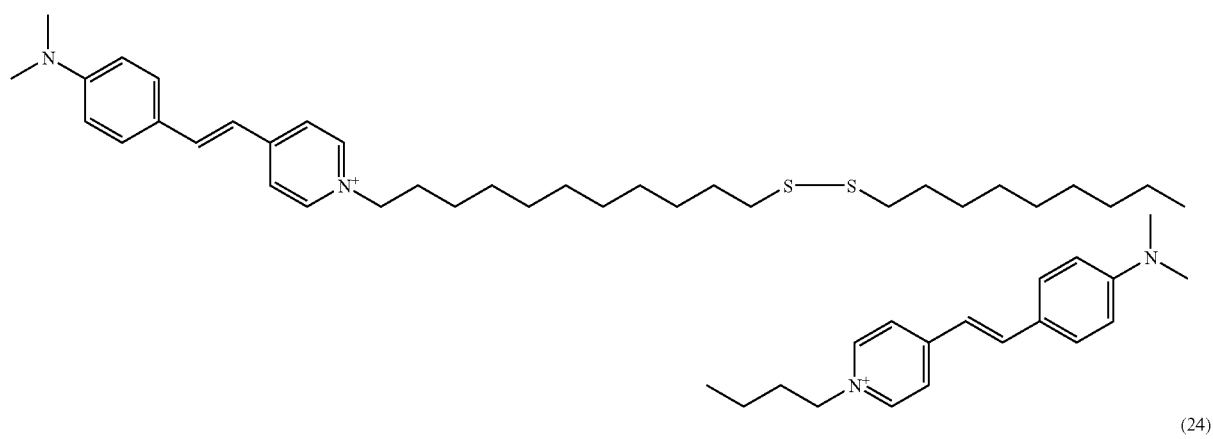

(23)

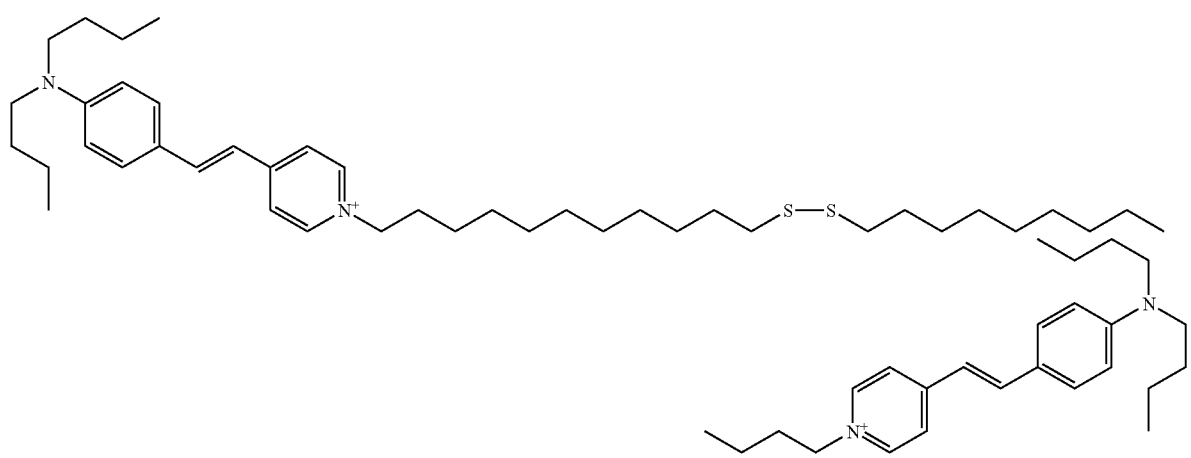

(24)

In at least one embodiment of the present disclosure, in formulae (I), (II) or (III), A and/or A' may comprise a cationic chromophore.

As examples, non-limiting mention may be made of the compounds of formula (21) to (24) above, their salts, hydrates, and solvates.

In at least one embodiment of the present disclosure, the disulfide direct dye is a cationic, fluorescent or non-fluorescent dye, comprising at least one quaternary ammonium radical and is such that, in the formula (I) with p and p' equal to 1:

A and A', which may be identical or different, for example identical, represent W—N=N—Ar— or —W—N=N—Ar or W—C($R^c$)=C($R^d$)—Ar— or —W—C($R^c$)=C($R^d$)—Ar, with W representing a fused or non-fused, aromatic or non-aromatic heterocycle comprising a quaternary ammonium; Ar represents a (hetero)aryl radical having 5 or 6 ring members, or a (hetero)aromatic bicyclic ring of naphthyl, benzopyridinium, indolinyl or benzoindolinyl type, optionally substituted with one or more halogen atoms; with one or more alkyl groups; with one or more hydroxyl groups; with one or more alkoxy groups, with one or more hydroxyalkyl groups, with one or more amino or (di)alkylamino groups, with one or more acylamino groups; with one or more heterocycloalkyl or heteroaryl groups having 5 or 6 ring members; $R^c$ and $R^d$, which are identical or different, represent a hydrogen atom or a $C_1$-$C_4$ alkyl group.

In one embodiment, p=p'=1; y=z=0; t=1 and T represents —N(R)—, for example in the para position on Ar relative to the azo function.

For example, W may be chosen from imidazolium, pyridinium, benzopyridinium, benzimidazolium, quinolinium, pyrazolium or benzothiazolium optionally substituted with one or more identical or different $C_1$-$C_4$ alkyl radicals.

Non-limiting examples of disulfide direct dyes according to the present disclosure include the following compounds:

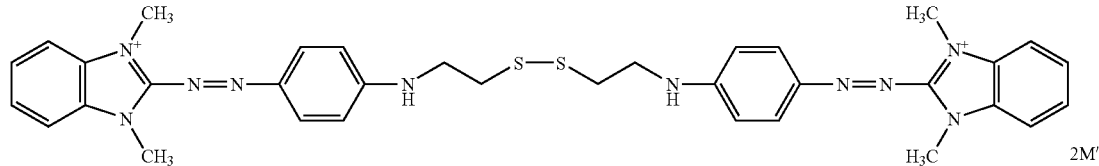

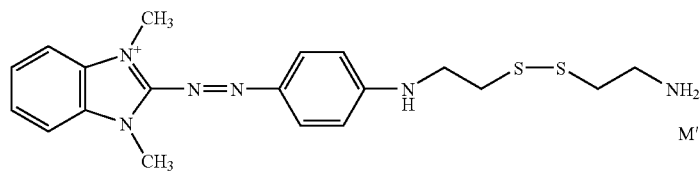

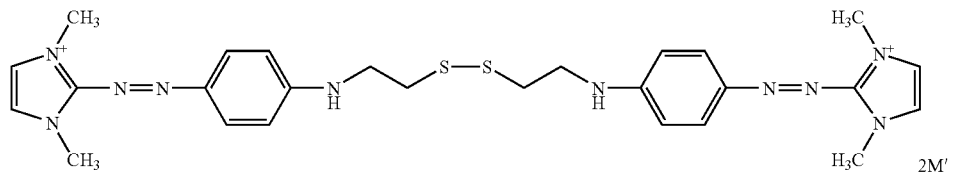

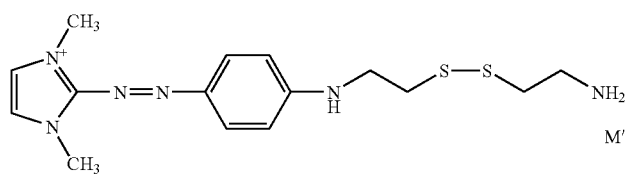

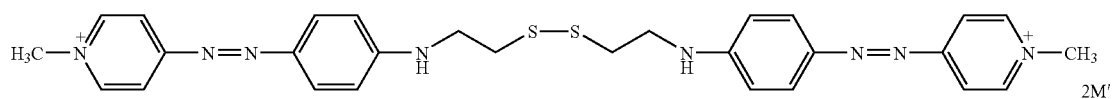

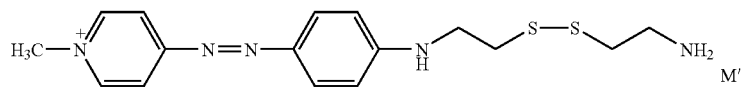

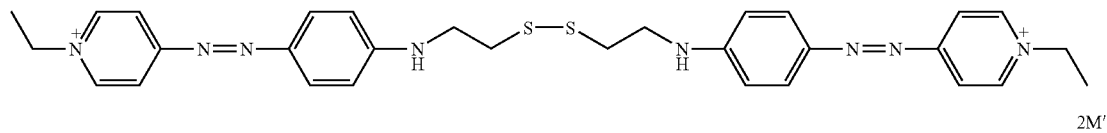

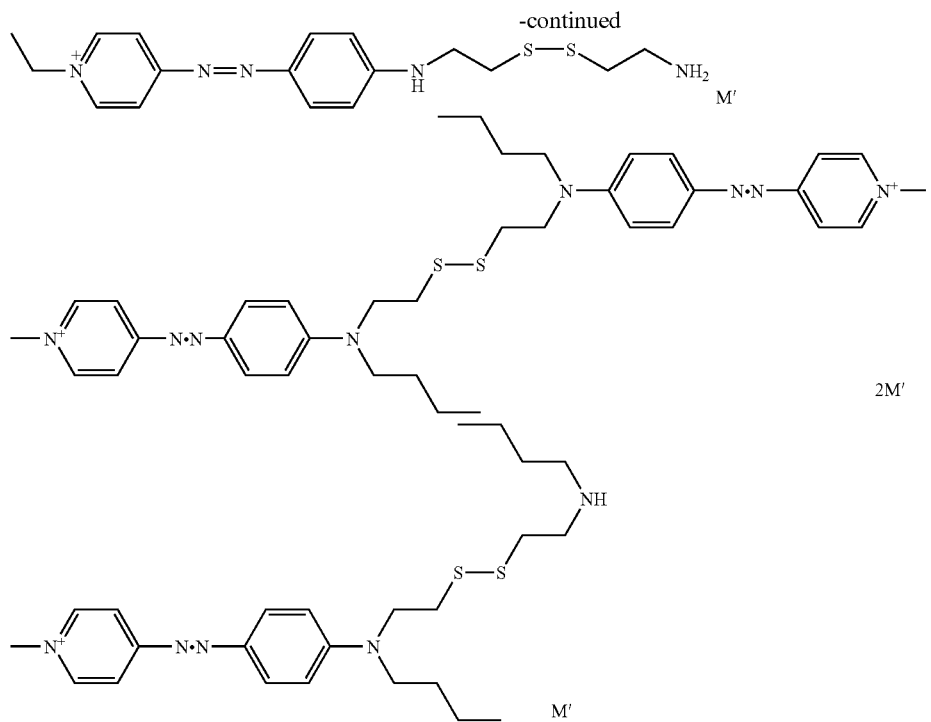

wherein M' represents an organic or mineral acid salt.

In another embodiment, the disulfide direct dye may be a cationic fluorescent dye comprising at least one quaternary ammonium radical and is such that, in the formula (I) with p equal to 1 and v equal to 0, A represents a naphthalimidyl radical of formula:

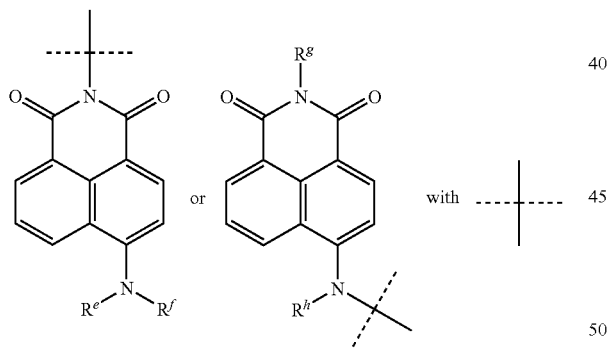

representing the bond between the X or X', $C_{sat}$ or $C'_{sat}$ group wherein $R^e$, $R^f$, $R^g$, and $R^h$, which are identical or different, represent a hydrogen atom or an optionally substituted $C_1$-$C_6$ alkyl group.

In another embodiment, the disulfide direct dye may be a fluorescent dye chosen from:

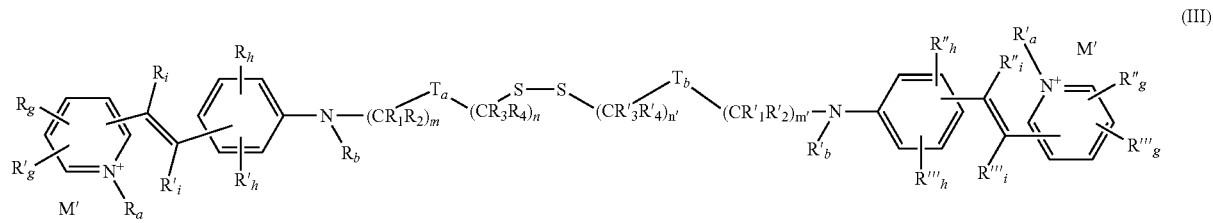

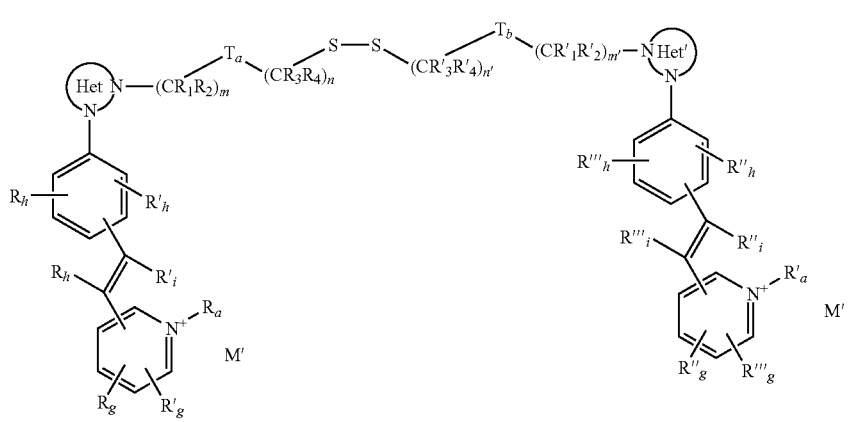
(IV)
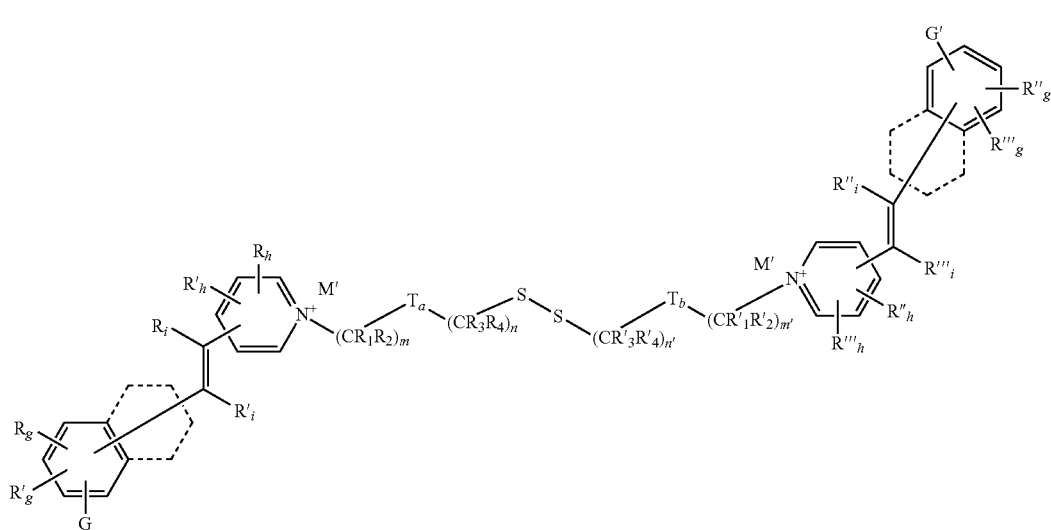
(V)
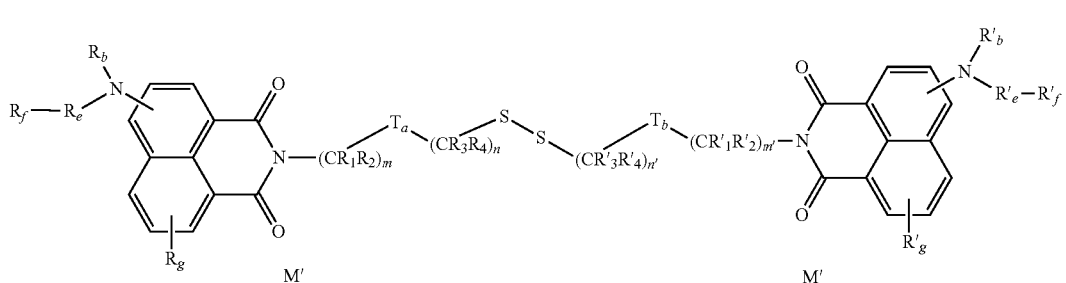
(VI)
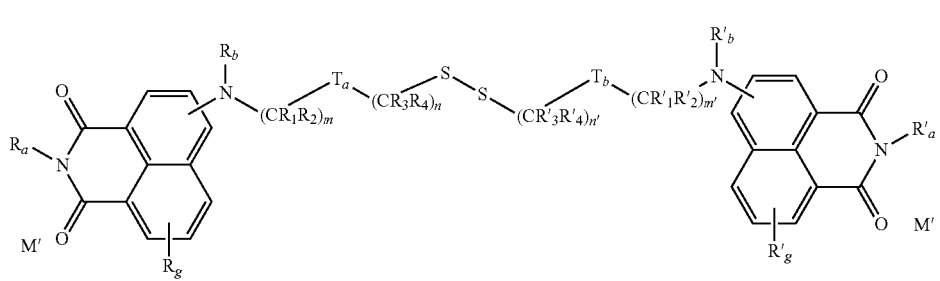
(VII)

-continued
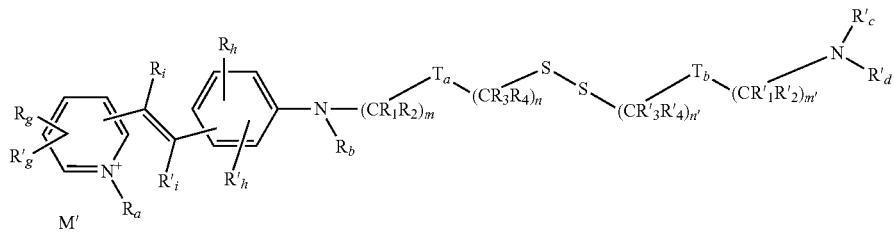
(VIII)
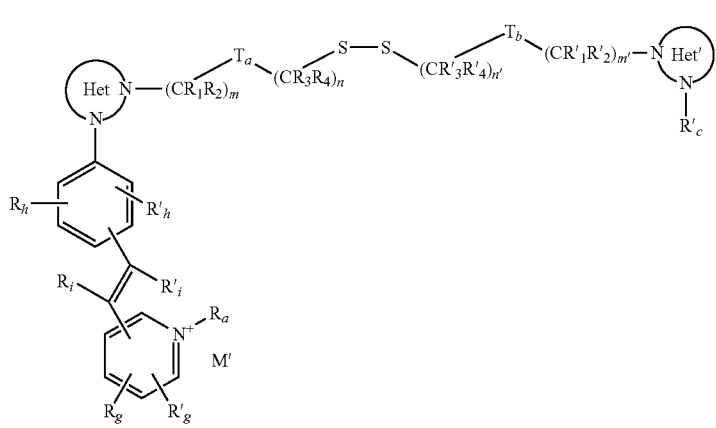
(IX)
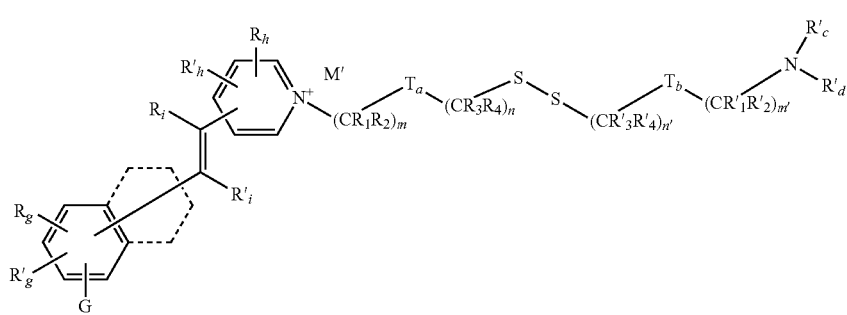
(X)
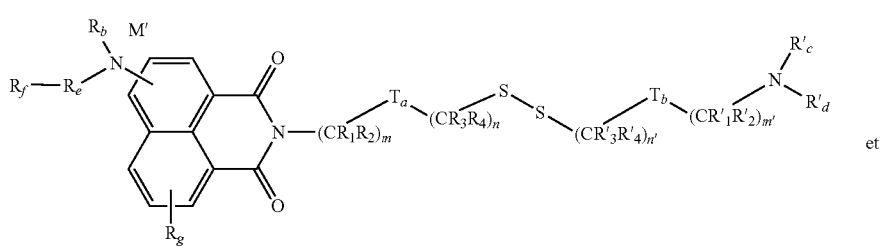
(XI)
et
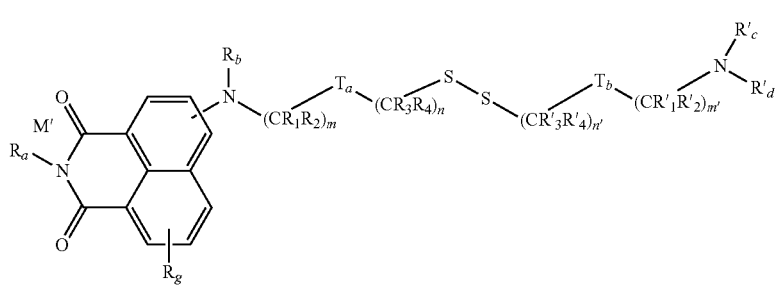
(XII)

wherein:
- G and G', which may be identical or different, represent an optionally substituted, for example unsubstituted —$NR_cR_d$, —$NR'_cR'_d$, or $C_1$-$C_6$ alkoxy group; for example G and G' represent an —$NR_cR_d$ and —$NR'_cR'_d$ group respectively;
- $R_a$ and $R'_a$, which may be identical or different, represent an aryl($C_1$-$C_4$)alkyl group or a $C_1$-$C_6$ alkyl group optionally substituted with a hydroxyl, amino, $C_1$-$C_4$ alkylamino or $C_1$-$C_4$ dialkylamino group, said alkyl radicals possibly forming with the nitrogen atom which bears them, a heterocycle comprising from 5 to 7 ring members, optionally comprising another heteroatom which may or may not be different from nitrogen; for example $R_a$ and $R'_a$ represent a $C_1$-$C_3$ alkyl group optionally substituted with a hydroxyl group, or a benzyl group;
- $R_b$, $R'_b$, which may be identical or different, represent a hydrogen atom, an aryl($C_1$-$C_4$)alkyl group or a $C_1$-$C_6$ alkyl group which is optionally substituted; for example $R_b$ and $R'_b$ represent a hydrogen atom or a $C_1$-$C_3$ alkyl or benzyl group;
- $R_c$, $R'_c$, $R_d$ and $R'_d$, which may be identical or different, represent a hydrogen atom, an aryl($C_1$-$C_4$)alkyl, $C_1$-$C_6$ alkoxy group or an optionally substituted $C_1$-$C_6$ alkyl group; $R_c$, $R'_c$, $R_d$ and $R'_d$ for example represent a hydrogen atom, a hydroxyl, $C_1$-$C_3$ alkoxy, amino or $C_1$-$C_3$ (di)alkylamino group, or a $C_1$-$C_3$ alkyl group optionally substituted with i) a hydroxyl group, ii) an amino group, iii) a $C_1$-$C_3$ (di)alkylamino group, or iv) a quaternary ammonium $(R'')(R''')(R'''')N^+$— group;
  - or else two adjacent radicals $R_c$ and $R_d$, or $R'_c$ and $R'_d$ borne by the same nitrogen atom together form a heterocyclic or heteroaryl group; for example the heterocycle or heteroaryl group is monocyclic and comprises between 5 and 7 ring members; for example, the groups are chosen from imidazolyl and pyrrolidinyl groups;
- $R_e$ and $R'_e$, which may be identical or different, represent an optionally unsaturated, linear or branched, divalent $C_1$-$C_6$ alkylenyl hydrocarbon chain;
- $R_f$ and $R'_f$, which may be identical or different, represent a quaternary ammonium group $(R'')(R''')(R'''')N^+$— where $R''$, $R'''$ and $R''''$, which may be identical or different, represent a hydrogen atom or a $C_1$-$C_4$ alkyl group or else $(R'')(R''')(R'''')N^+$— represents an optionally substituted cationic heteroaryl group, for example an imidazolinium group optionally substituted with a $C_1$-$C_3$ alkyl group;
- $R_g$, $R'_g$, $R''_g$, $R'''_g$, $R_h$, $R'_h$, $R''_h$, and $R'''_h$, which may be identical or different, represent a hydrogen atom, a halogen atom, an amino, $C_1$-$C_4$ alkylamino, $C_1$-$C_4$ dialkylamino, cyano, carboxy, hydroxyl, or trifluoromethyl group, an acylamino, $C_1$-$C_4$ alkoxy, a (poly)hydroxy($C_2$-$C_4$)alkoxy, alkylcarbonyloxy, alkoxycarbonyl or alkylcarbonylamino radical, an acylamino, carbamoyl or alkylsulfonylamino radical, an aminosulfonyl radical, or a $C_1$-$C_{16}$ alkyl radical optionally substituted with a group chosen from $C_1$-$C_{12}$ alkoxy, hydroxy, cyano, carboxy, amino, $C_1$-$C_4$ alkylamino and $C_1$-$C_4$ dialkylamino groups, or else the two alkyl radicals borne by the nitrogen atom of the amino group form a heterocycle comprising from 5 to 7 ring members and optionally comprising another heteroatom which is identical or different to that of the nitrogen atom; for example $R_g$, $R'_g$, $R''_g$, $R'''_g$, $R_h$, $R'_h$, $R''_h$ and $R'''_h$ represent a hydrogen or halogen atom or a $C_1$-$C_3$ alkyl group;
  - or else two groups $R_g$ and $R'_g$; $R''_g$ and $R'''_g$; $R_h$, and $R'_h$; $R''_h$ and $R'''_h$ borne by two adjacent carbon atoms together form a benzo or indeno ring, or a fused heterocyclo alkyl or fused heteroaryl group; the benzo, indeno, heterocycloalkyl or heteroaryl ring optionally being substituted with a halogen atom, an amino, $C_1$-$C_4$ alkylamino, $C_1$-$C_4$ dialkylamino, nitro cyano, carboxy, hydroxyl, or trifluoromethyl group, an acylamino, $C_1$-$C_4$ alkoxy, a (poly)hydroxy($C_2$-$C_4$)alkoxy, alkylcarbonyloxy, alkoxycarbonyl or alkylcarbonylamino radical, an acylamino, carbamoyl or alkylsulfonylamino radical, an aminosulfonyl radical, or a $C_1$-$C_{16}$ alkyl radical optionally substituted with a group chosen from $C_1$-$C_{12}$ alkoxy, hydroxy, cyano, carboxy, amino, $C_1$-$C_4$ alkylamino and $C_1$-$C_4$ dialkylamino groups, or else the two alkyl radicals borne by the nitrogen atom of the amino group form a heterocycle comprising from 5 to 7 ring members and optionally comprising another heteroatom which is identical or different to that of the nitrogen atom; for example $R_g$ and $R'_g$; $R''_g$ and $R'''_g$ together form a benzo group;
  - or else when G represents —$NR_cR_d$ and G' represents —$NR'_cR'_d$, two groups $R_c$ and $R'_g$; $R'_c$ and $R''_g$; $R_d$ and $R_g$; or $R'_d$ and $R'''_g$ together form a saturated heteroaryl or heterocycle, optionally substituted with one or more $C_1$-$C_6$ alkyl groups, for example a heterocycle containing one or two heteroatoms chosen from nitrogen and oxygen and comprising between 5 and 7 ring members; for example the heterocycle is chosen from morpholinyl, piperazinyl, piperidinyl and pyrrolidinyl groups;
- $R_i$, $R'_i$, $R''_i$, and $R'''_i$, which may be identical or different, represent a hydrogen atom or a $C_1$-$C_4$ alkyl group;
- $R_1$, $R_2$, $R_3$, $R_4$, $R'_1$, $R'_2$, $R'_3$ and $R'_4$, which may be identical or different, represent a hydrogen atom or a $C_1$-$C_4$ alkyl, $C_1$-$C_{12}$ alkoxy, hydroxy, cyano, carboxy, amino, $C_1$-$C_4$ alkylamino or $C_1$-$C_4$ dialkylamino group, said alkyl radicals possibly forming with the nitrogen atom that bears them, a heterocycle comprising from 5 to 7 ring members, optionally comprising another heteroatom that may or may not be different from nitrogen; for example $R_1$, $R_2$, $R_3$, $R_4$, $R'_1$, $R'_2$, $R'_3$ and $R'_4$ are hydrogen atoms or an amino group; for example $R_1$, $R_2$, $R_3$, $R_4$, $R'_1$, $R'_2$, $R'_3$ and $R'_4$ represent a hydrogen atom;
- $T_a$ and $T_b$, which may be identical or different, represent i) either a covalent bond a, ii) or one or more radicals or combinations thereof chosen from —$SO_2$—, —O—, —S—, —N(R)—, —$N^+(R)(R^o)$—, —CO—, with R and $R^o$, which may be identical or different, representing a hydrogen atom, a $C_1$-$C_4$ alkyl or $C_1$-$C_4$ hydroxyalkyl radical; or an aryl($C_1$-$C_4$)alkyl radical, for example $T_a$ is identical to $T_b$ and they represent a covalent bond σ, or a group chosen from —N(R)—, —C(O)—N(R)—, —N(R)—C(O)—, —O—C(O)—, —C(O)—O— and —$N^+(R)(R^o)$—, with R and $R^o$, which may be identical or different, representing a hydrogen atom or a $C_1$-$C_4$ alkyl group; for example $T_a$ and $T_b$ represent a σ bond;

iii) or a cationic or non-cationic heterocycloalkyl or heteroaryl radical, for example monocyclic, for example identical, that may contain two heteroatoms (for example two nitrogen atoms) and that may comprise from 5 to 7 ring members such as the imidazolium radical;

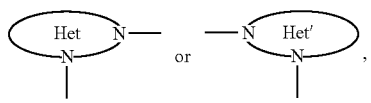

which may be identical or different, represent an optionally substituted heterocyclic group; for example the heterocycles may be identical, monocyclic, saturated and comprise in total two nitrogen atoms and from 5 to 8 ring members;

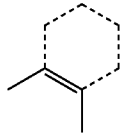

represents an aryl or heteroaryl group fused to the phenyl ring; or else that is lacking the phenyl ring; for example when the ring is present the ring may be a benzo ring;
m, m', n and n', which may be identical or different, represent an integer between 0 and 6 inclusive with m+n and m'+n', which may be identical or different, representing an integer between 1 and 10 inclusive; for example m+n=m'+n'=an integer between 2 and 4 inclusive; for example m+n=m'+n'=an integer equal to 2;
wherein M' represents an organic or mineral acid salt.

Non-limiting examples of fluorescent disulfide direct dyes include the following compounds:

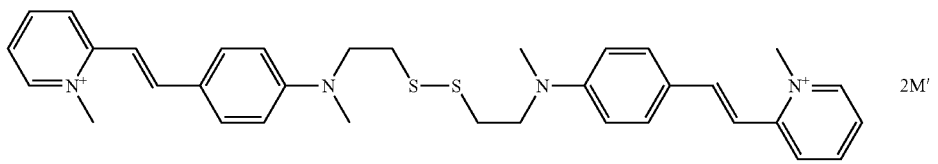

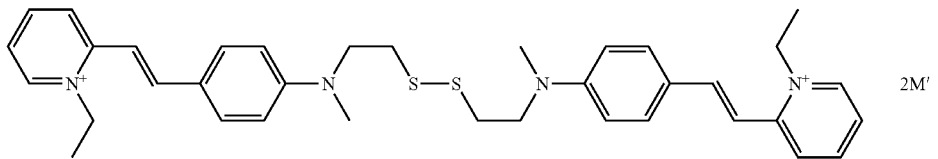

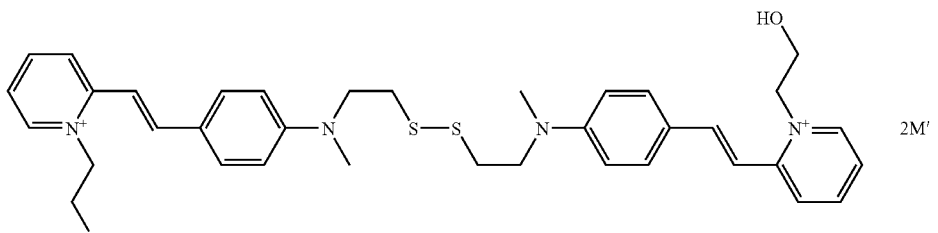

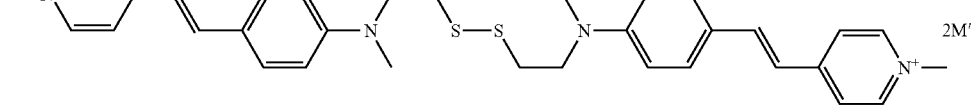

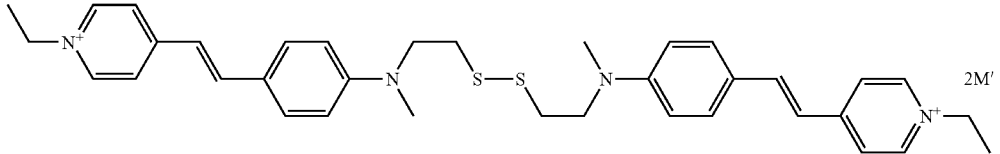

-continued

-continued
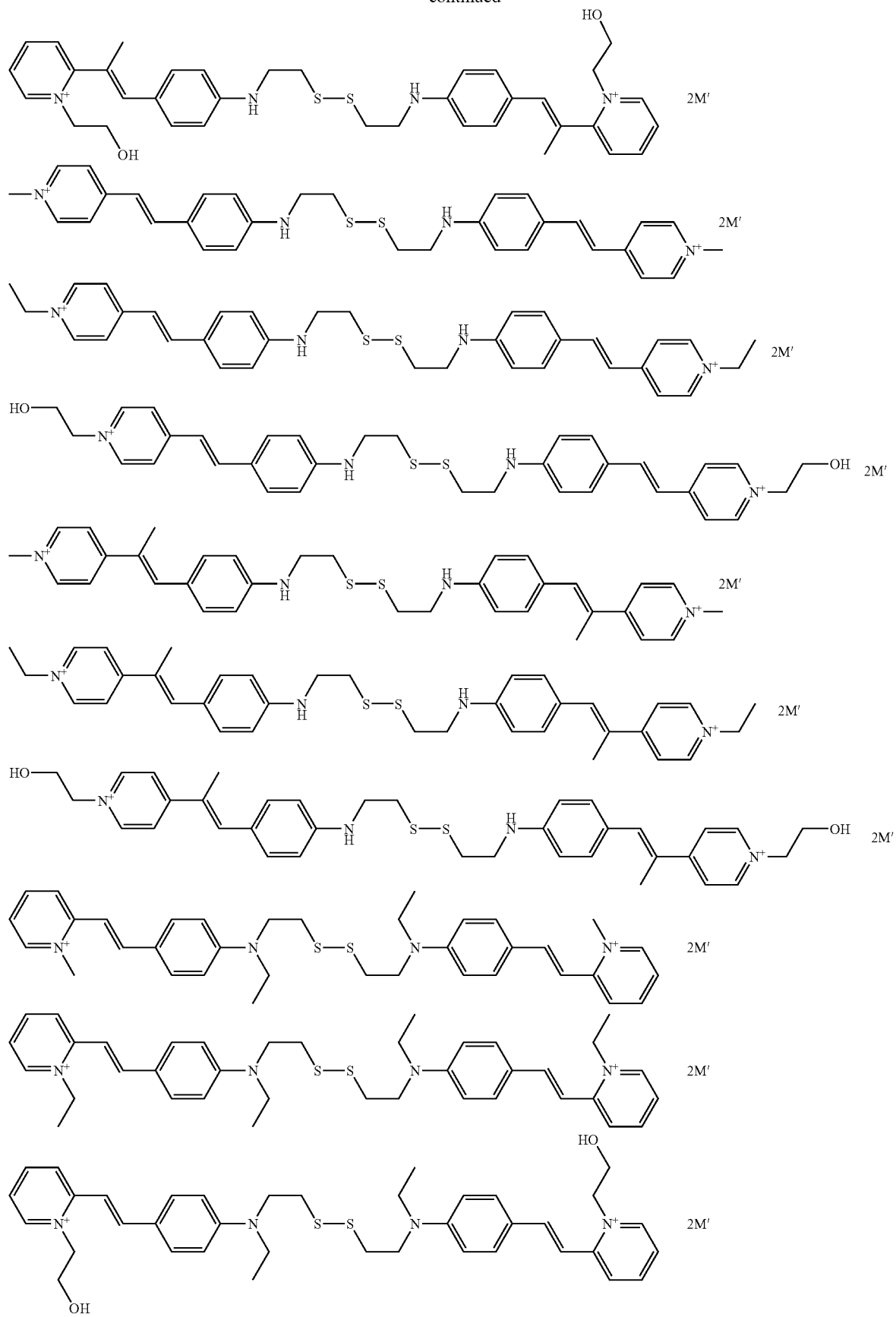

-continued
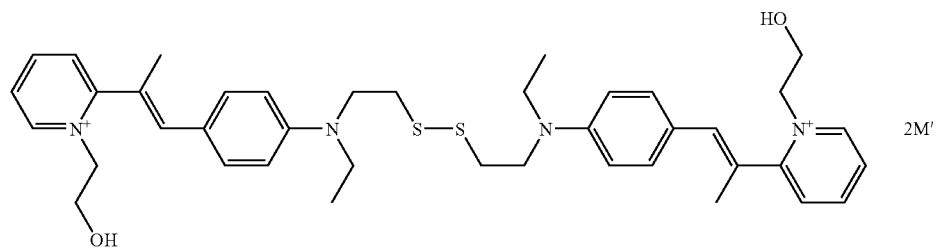 2M'
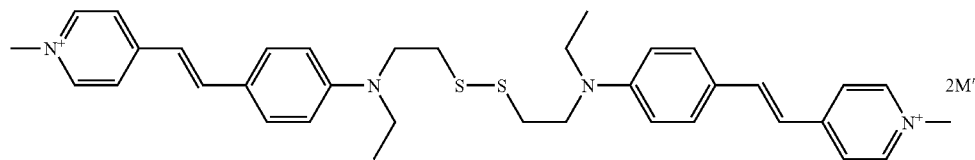 2M'
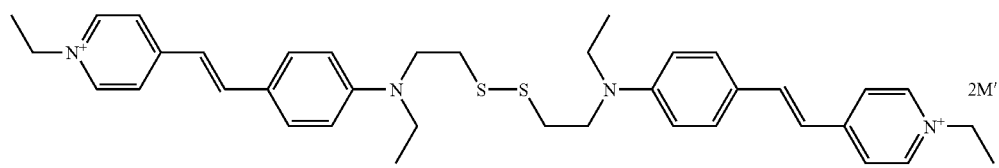 2M'
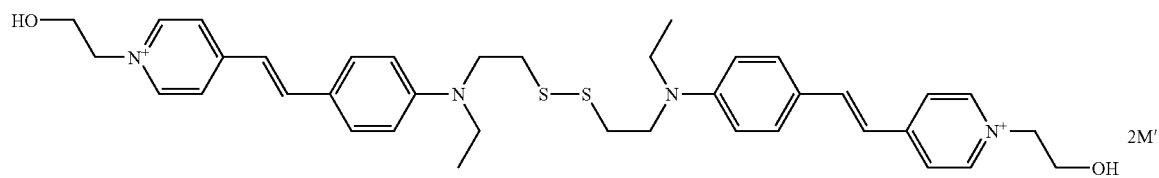 2M'
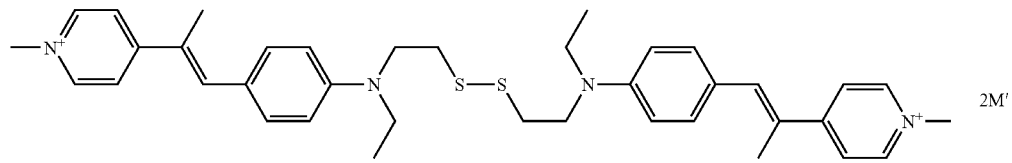 2M'
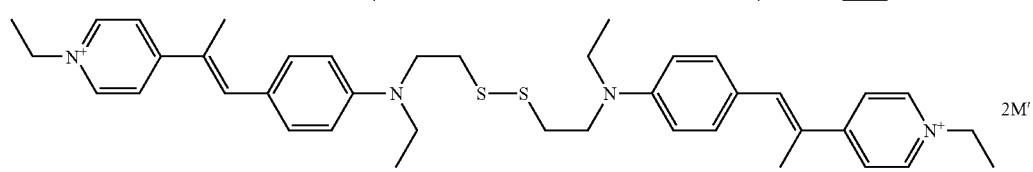 2M'
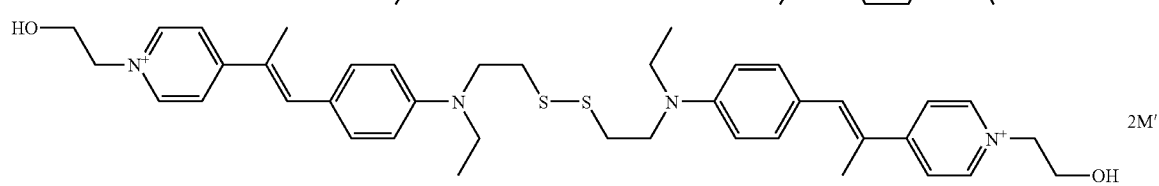 2M'
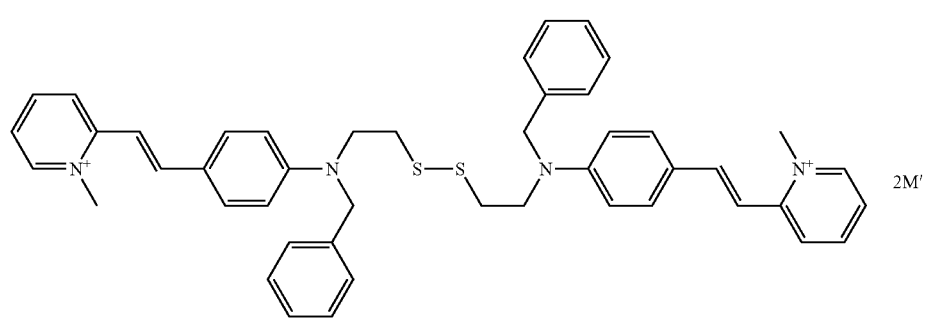 2M'

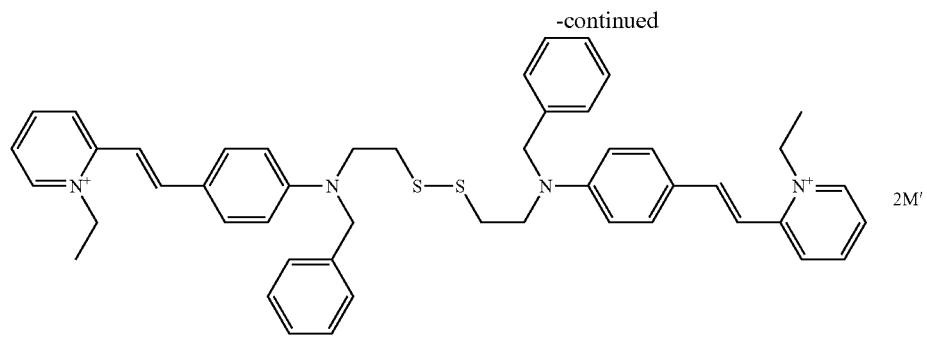
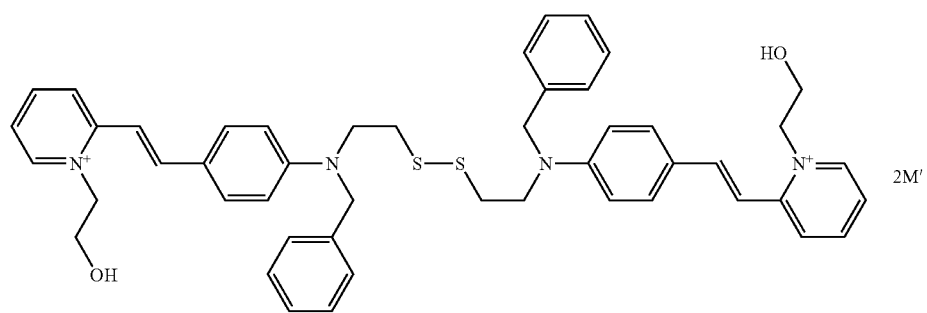
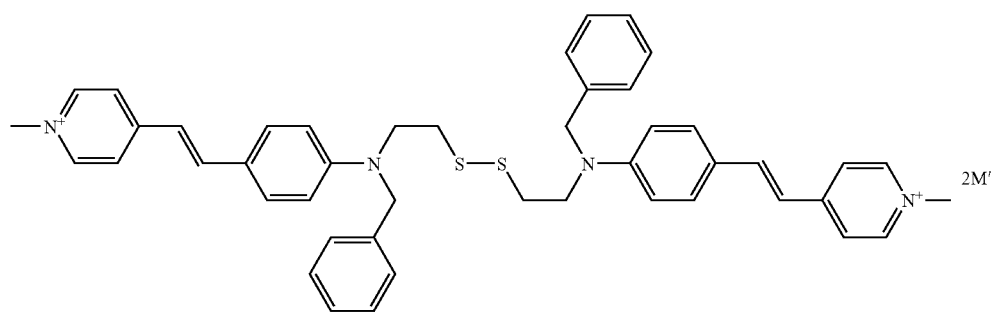
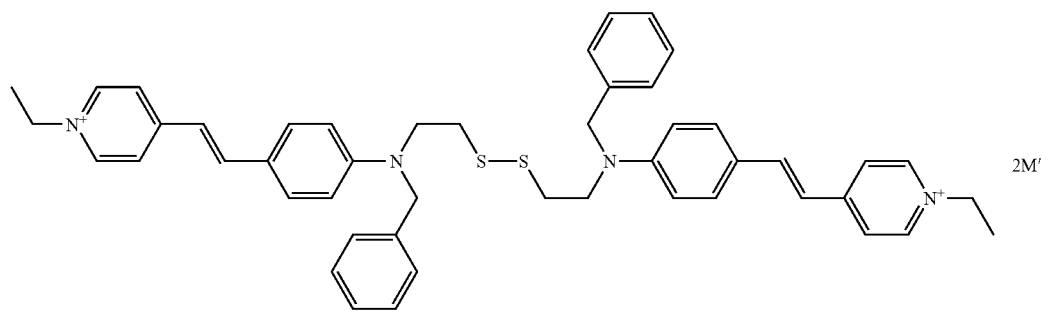
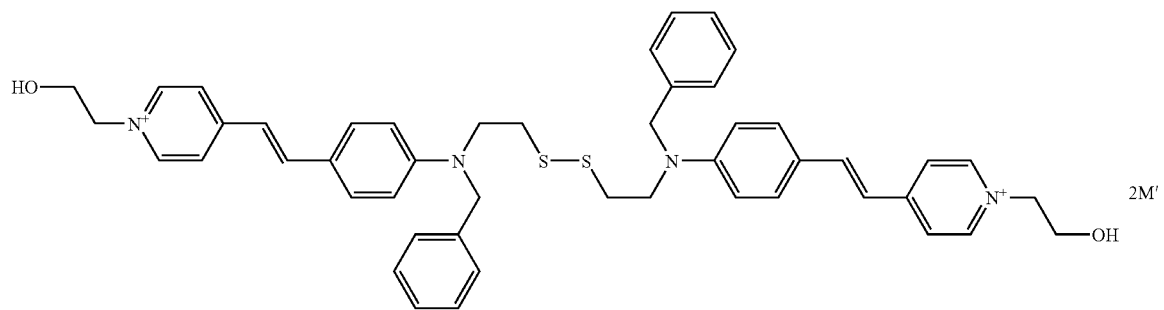

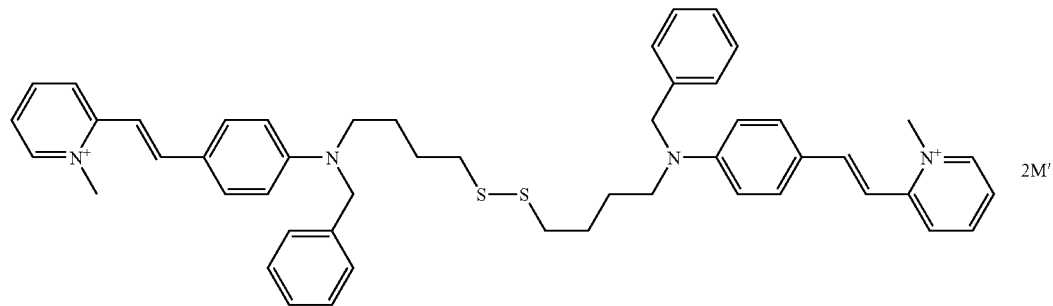
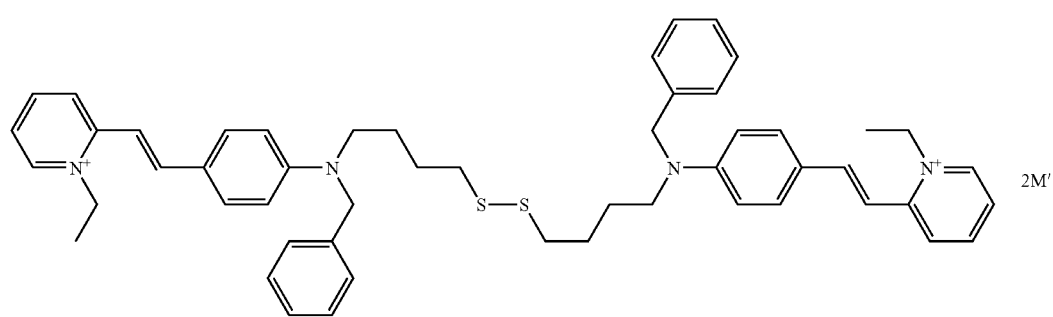
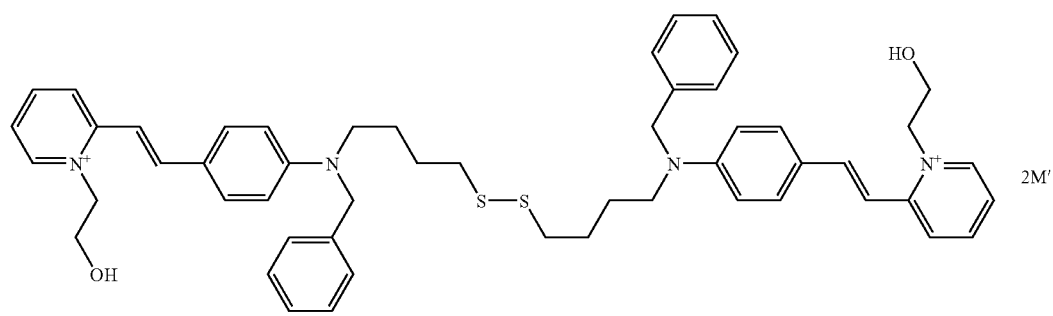
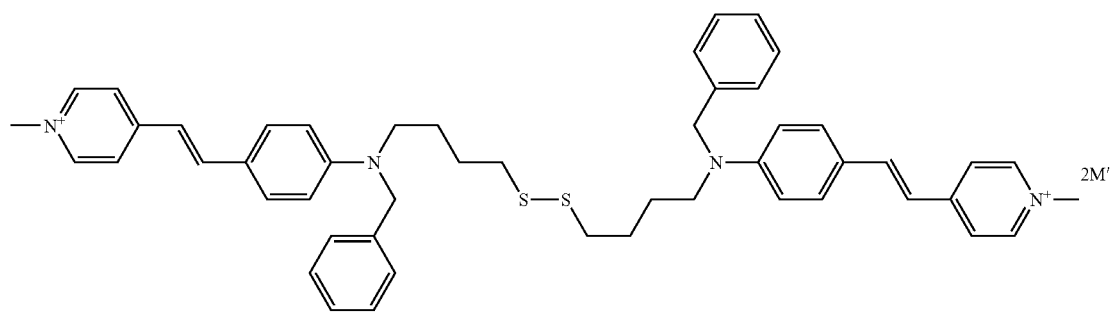
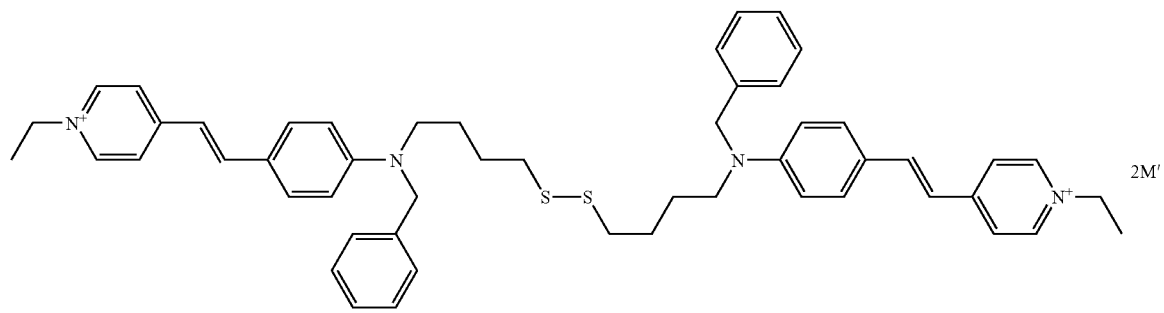

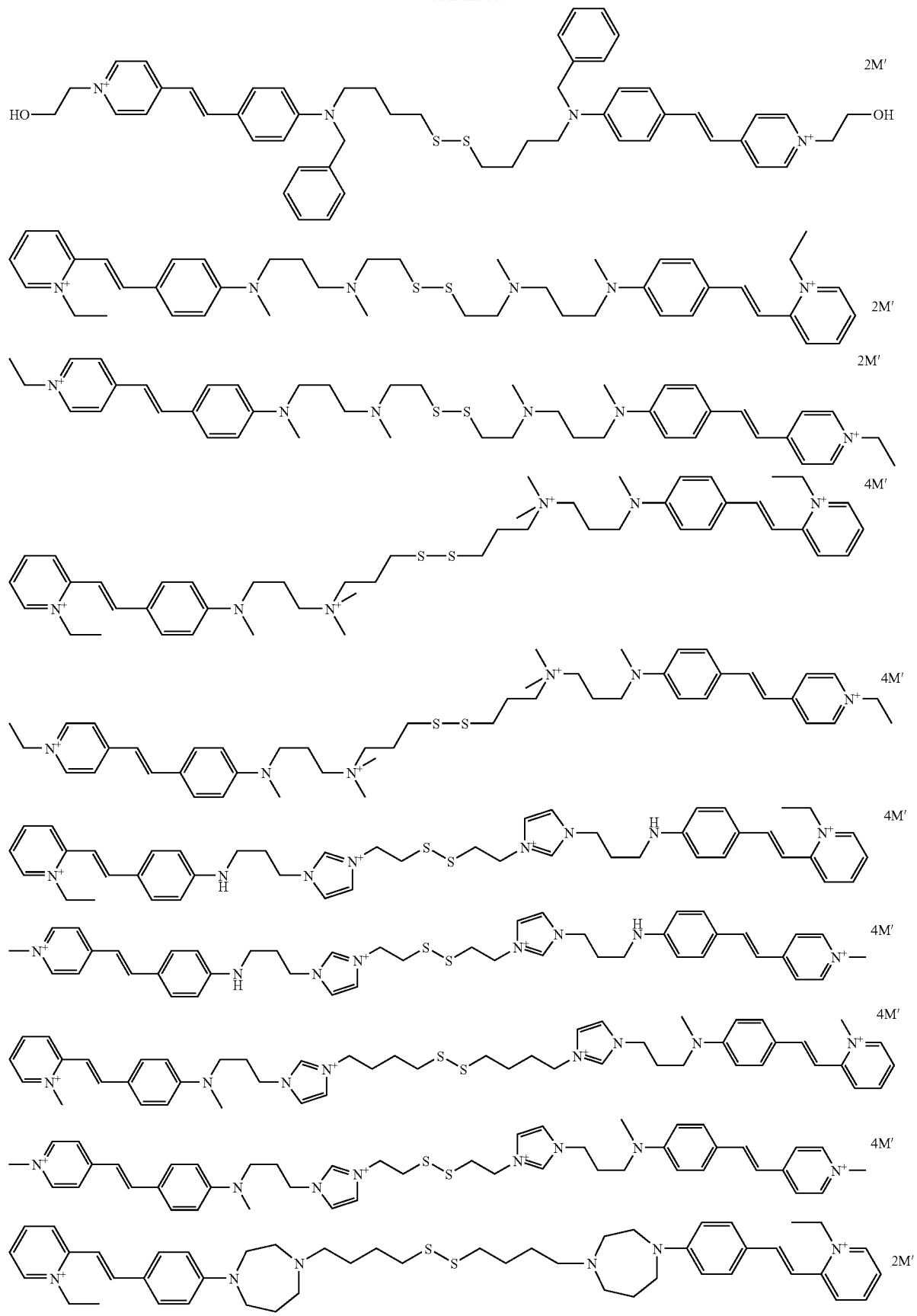

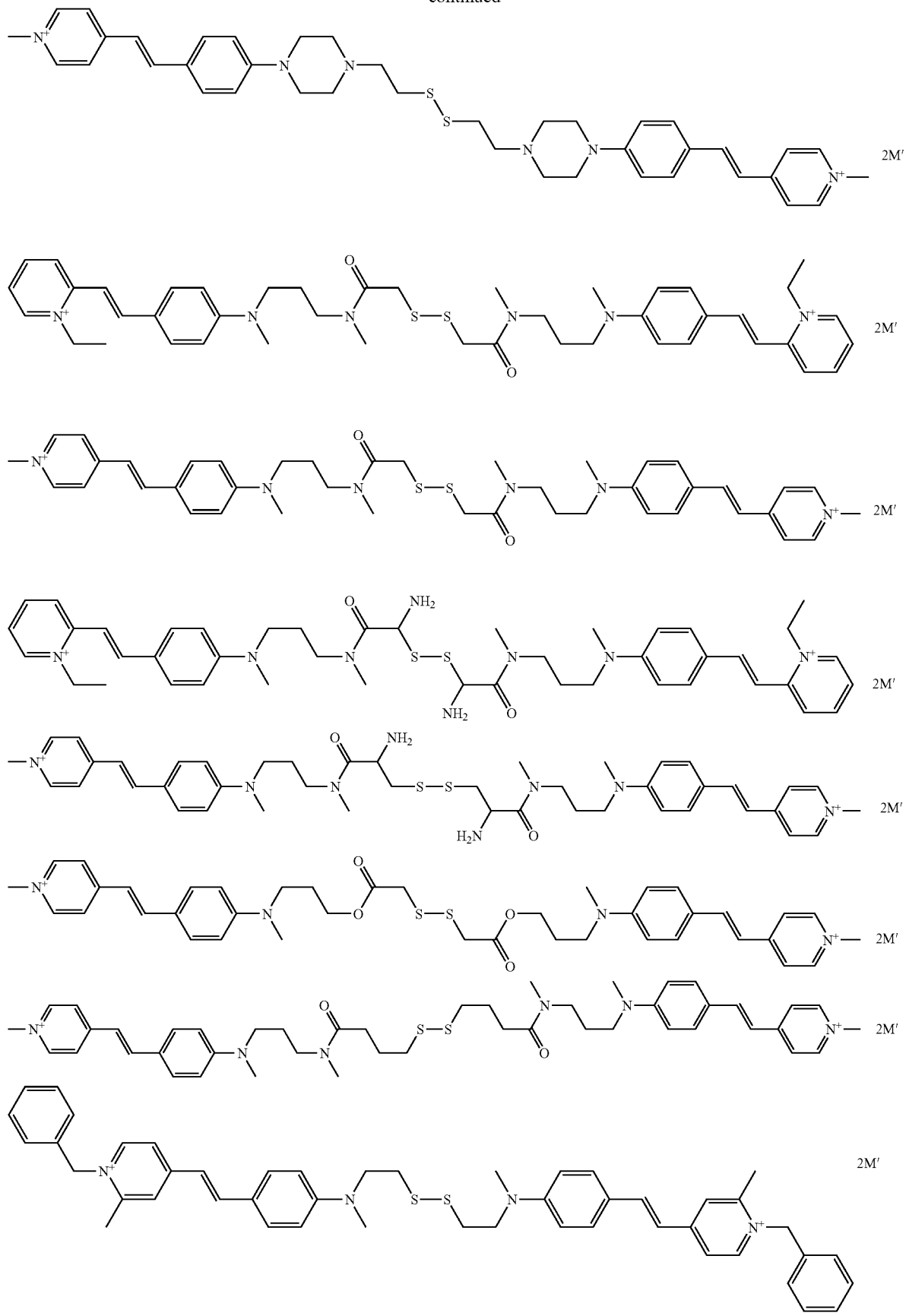

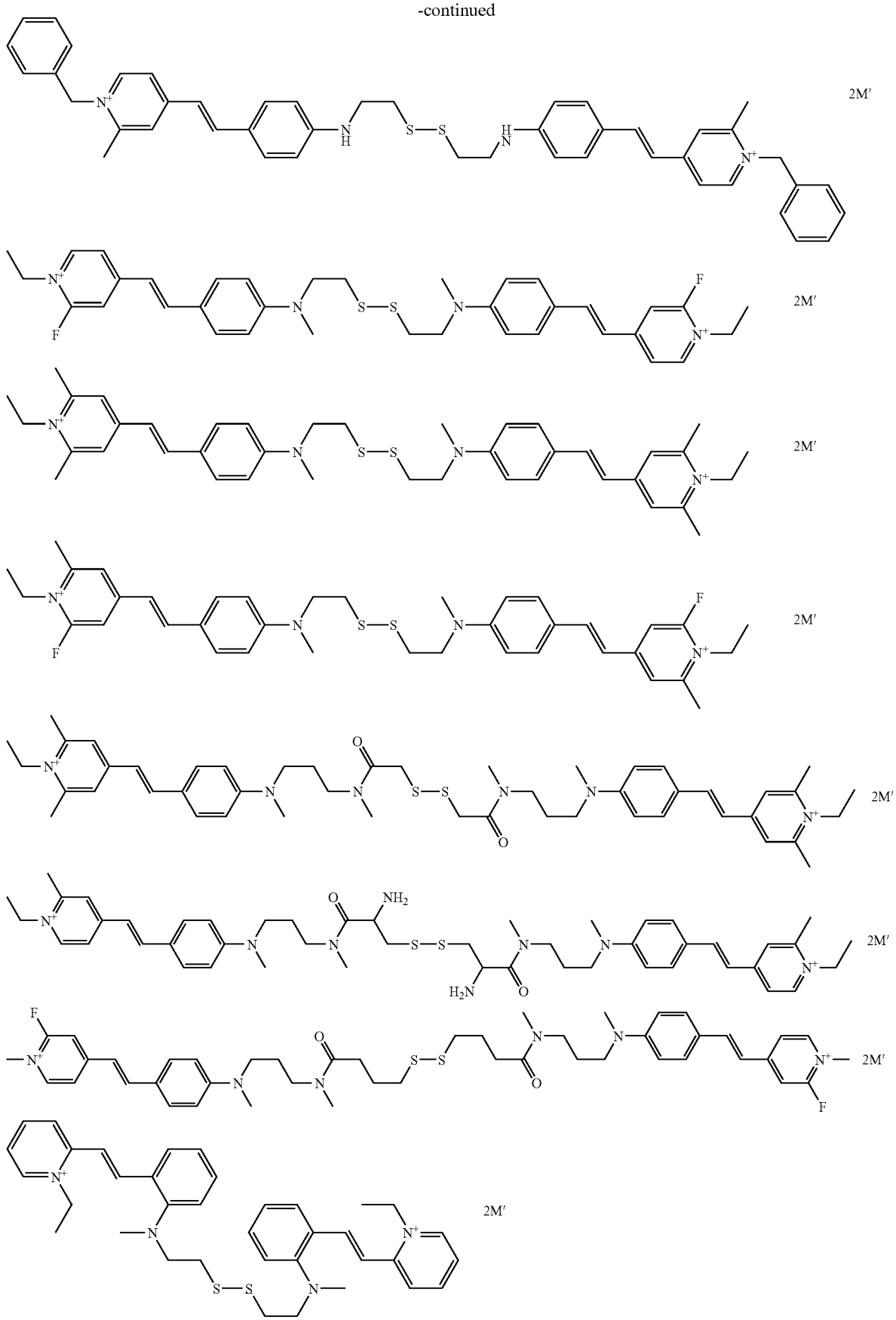

-continued
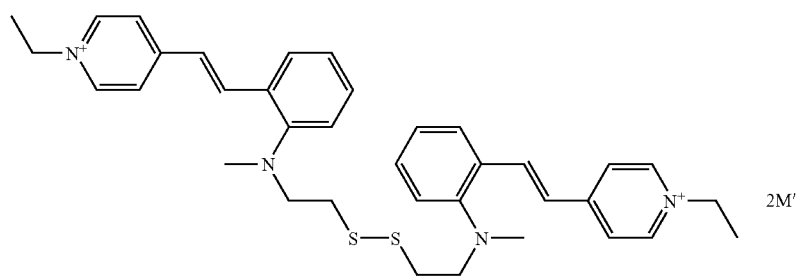 2M'
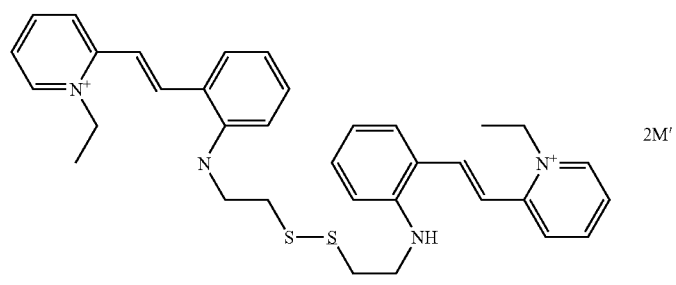 2M'
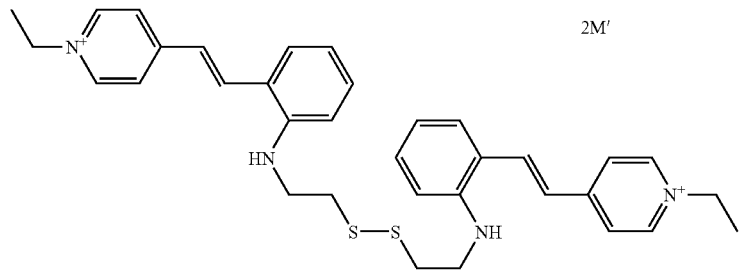 2M'
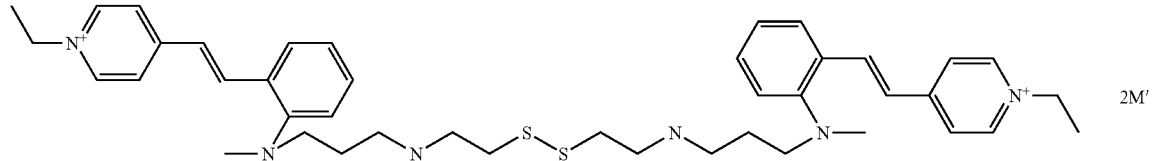 2M'
 4M'
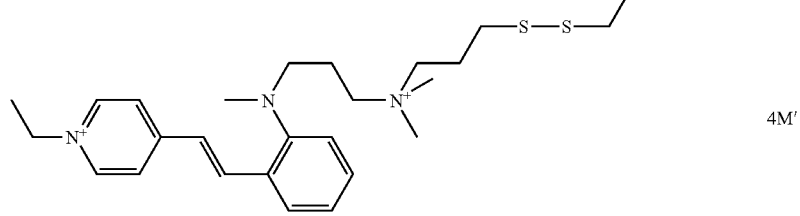 2M'
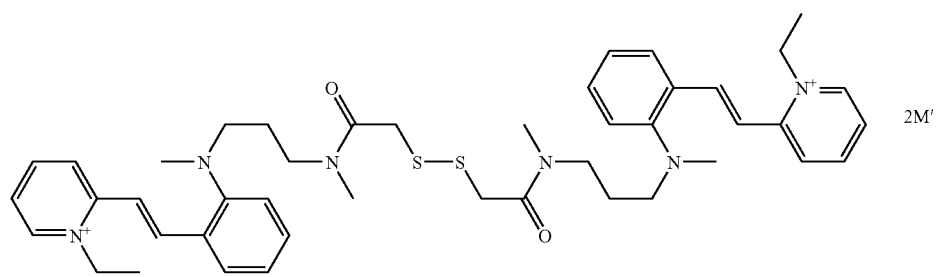

-continued
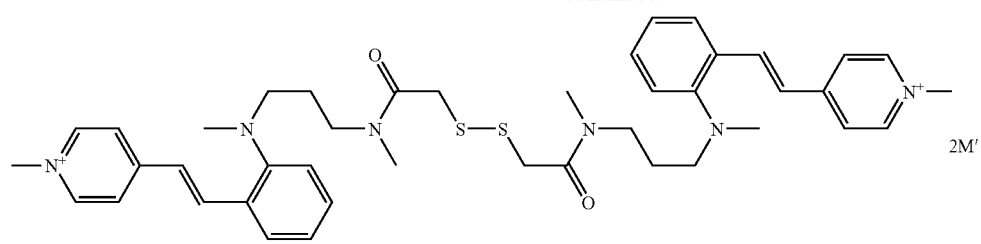
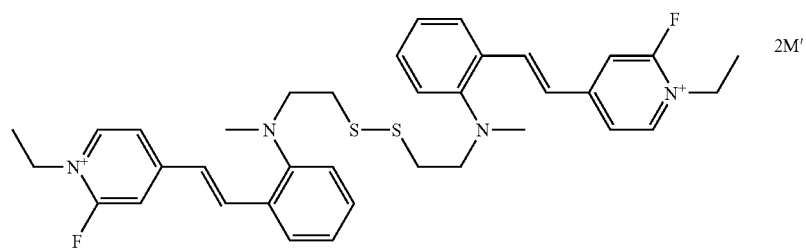
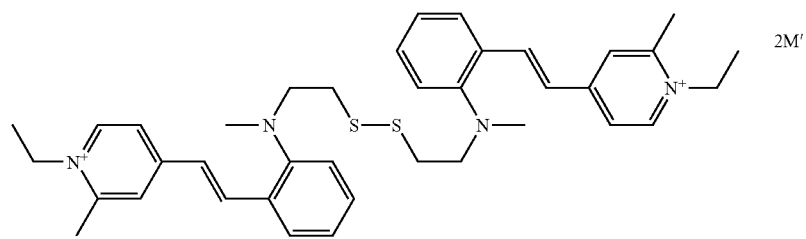
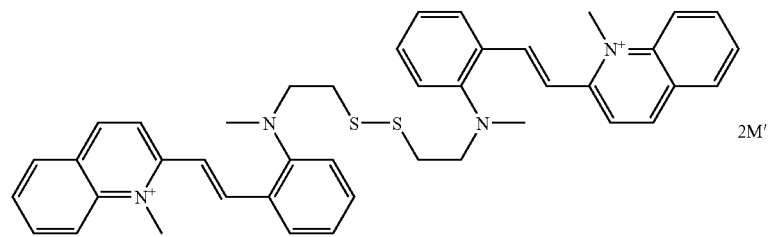
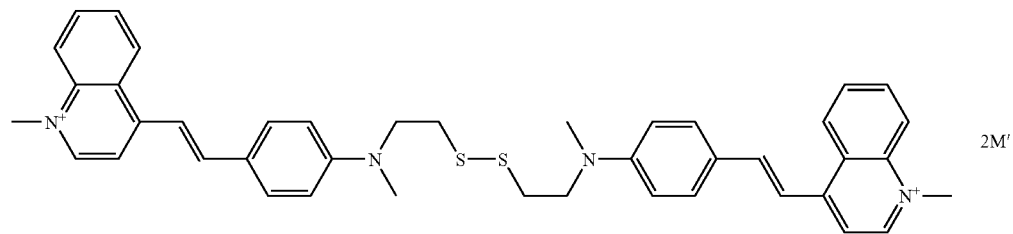
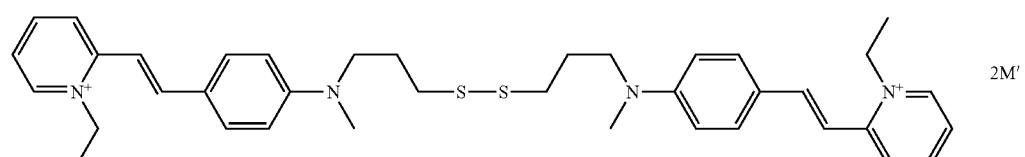
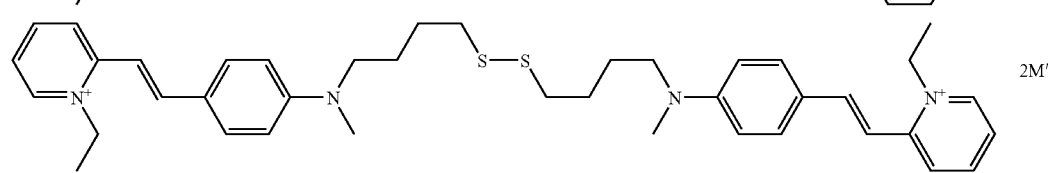
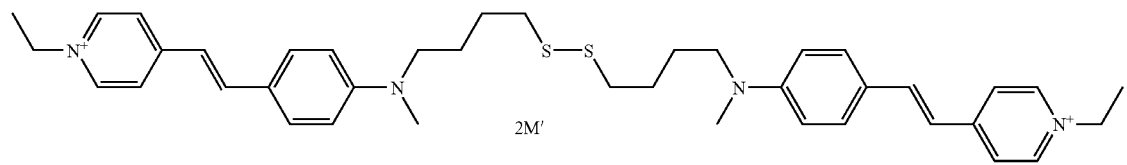

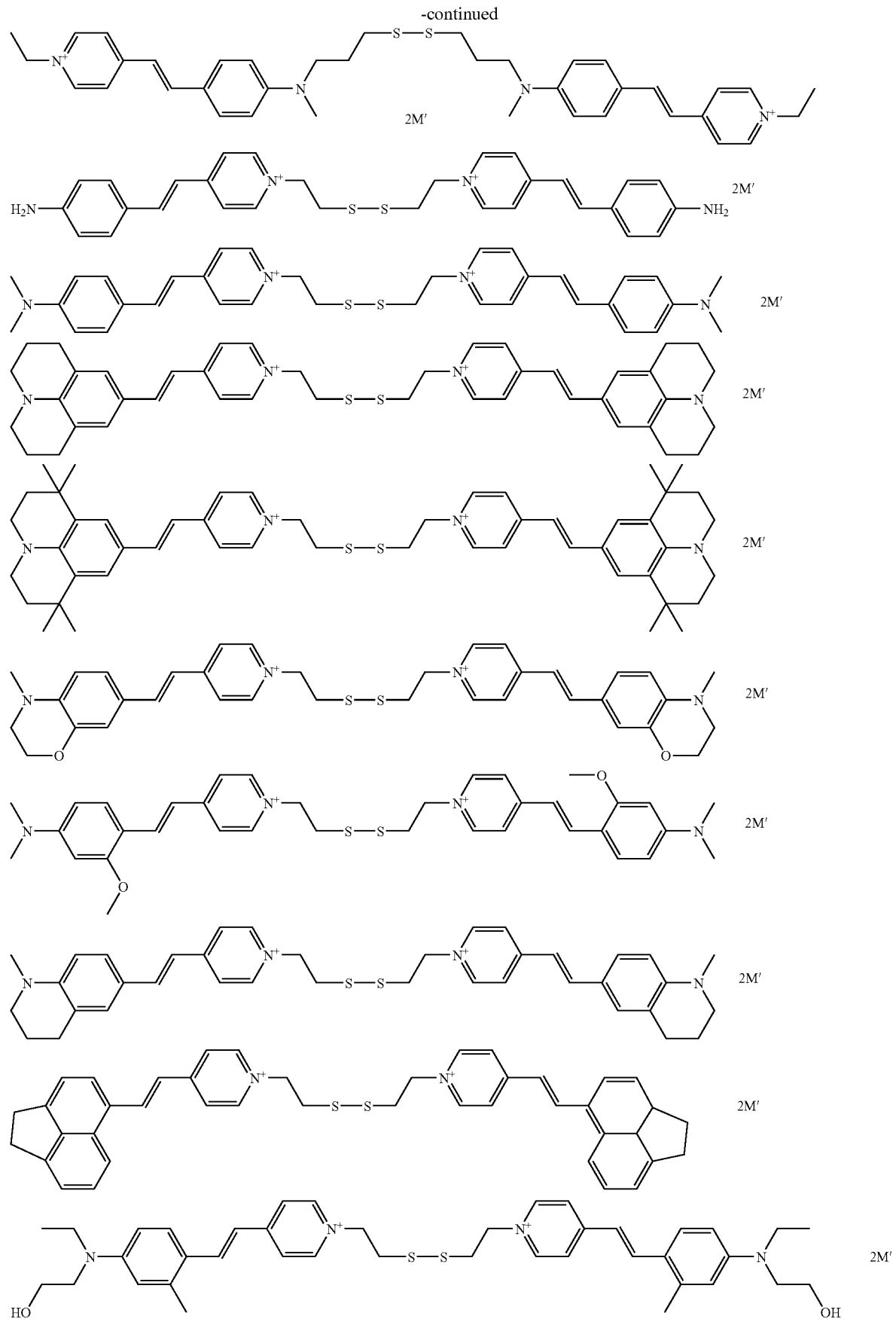

-continued
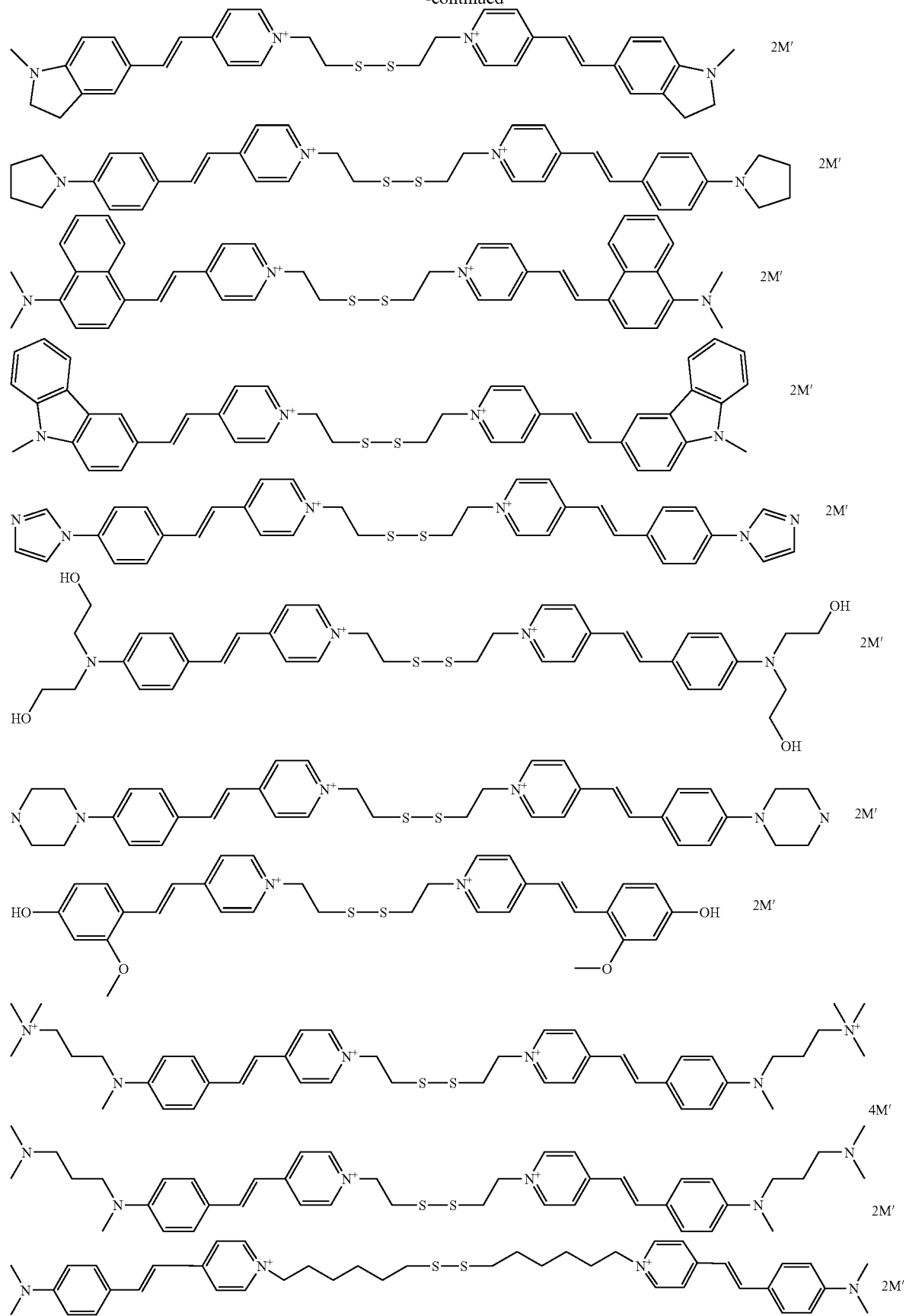

-continued
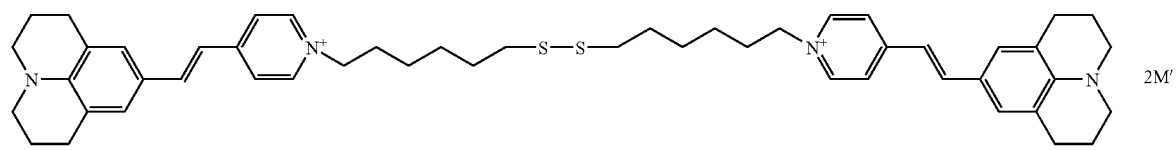
2M'
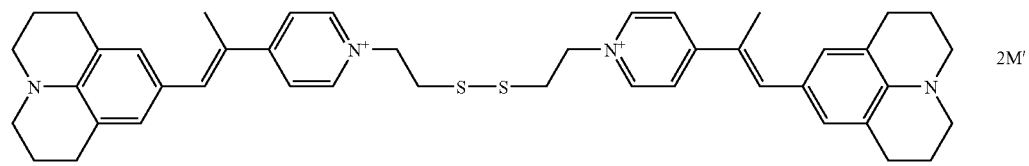
2M'
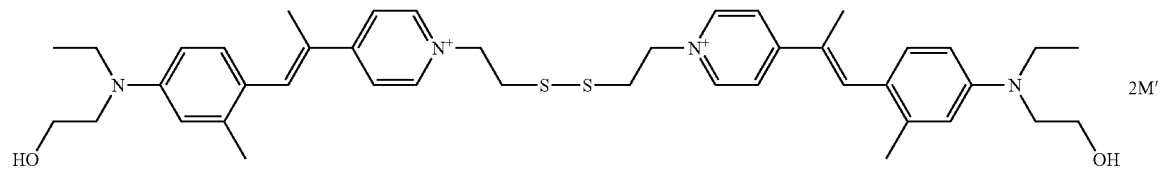
2M'
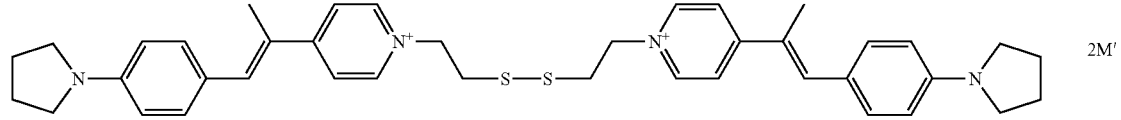
2M'
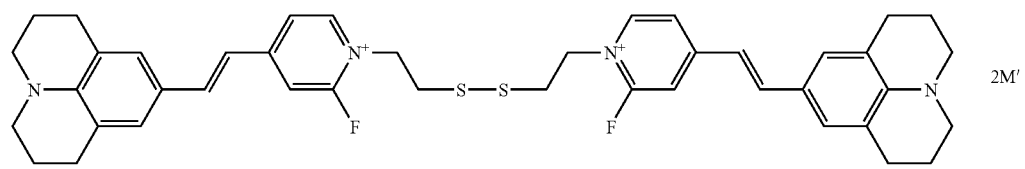
2M'
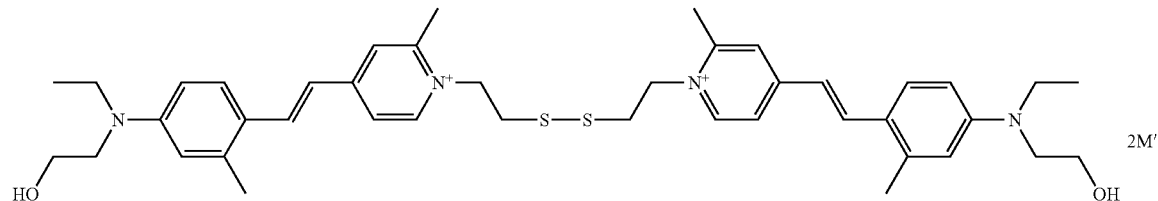
2M'
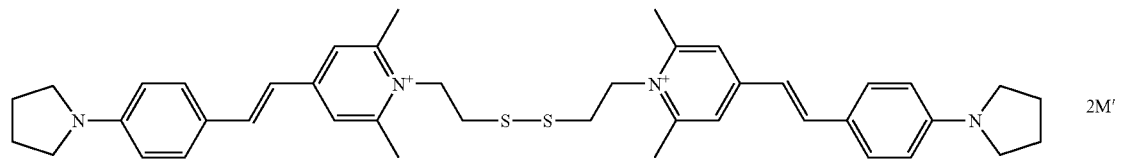
2M'
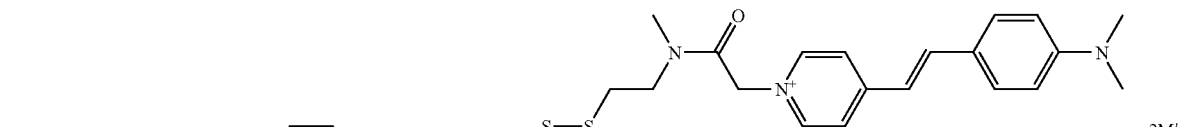
2M'
2M'
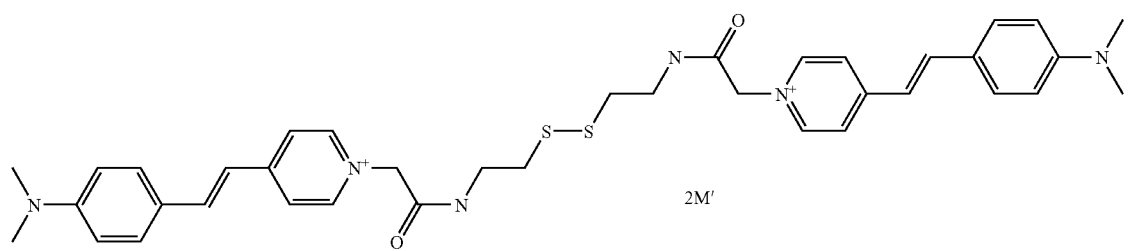
2M'

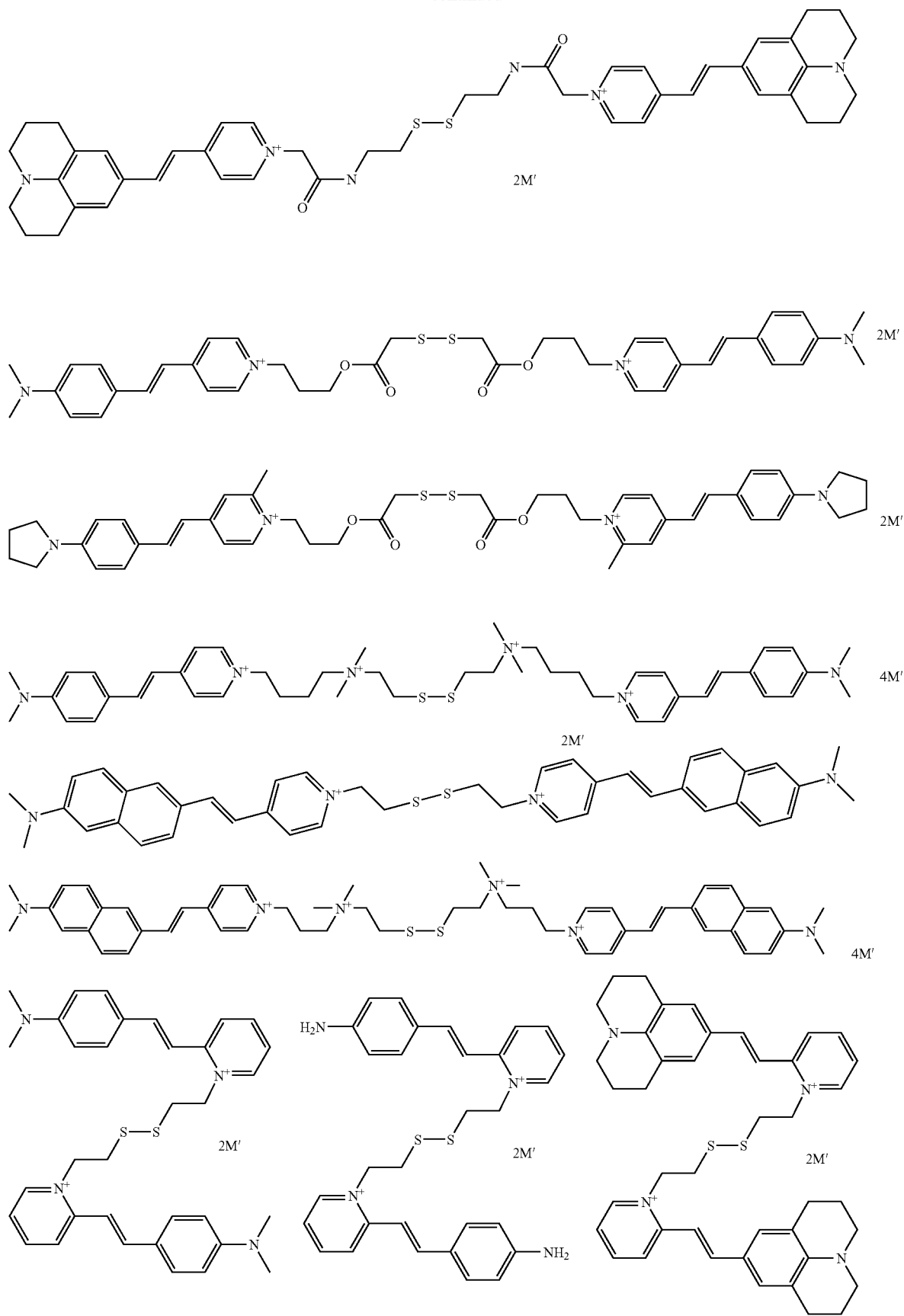

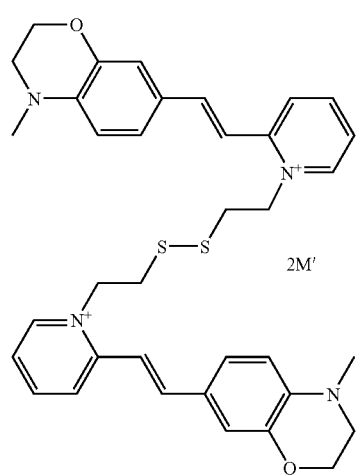 2M'
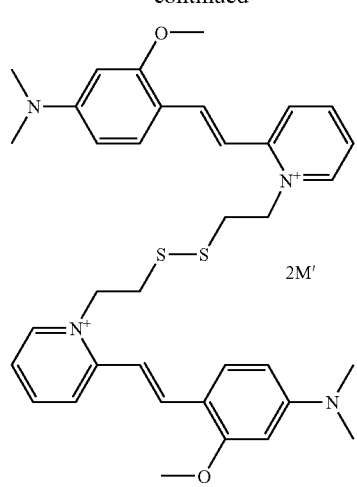 2M'
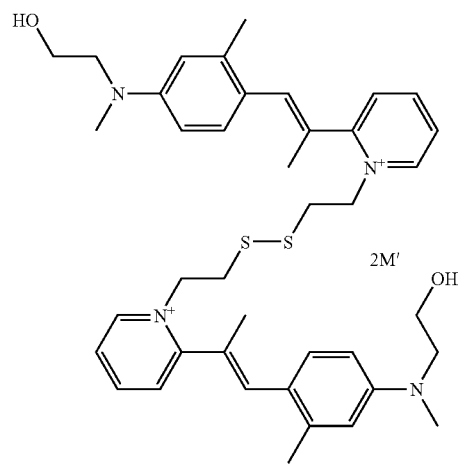 2M'
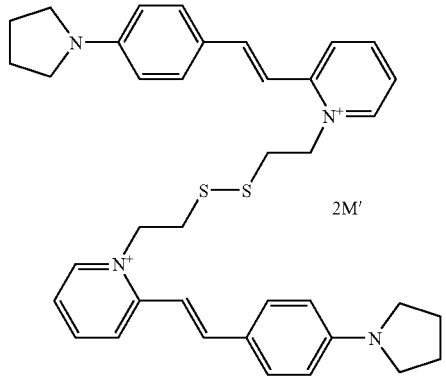 2M'
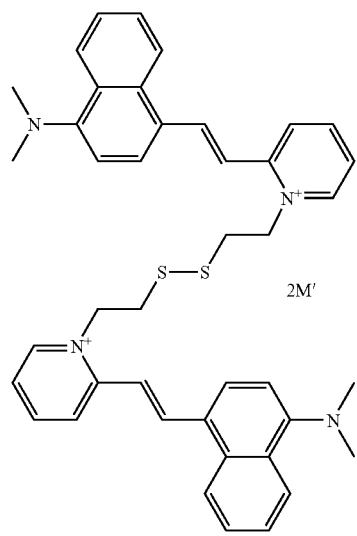 2M'
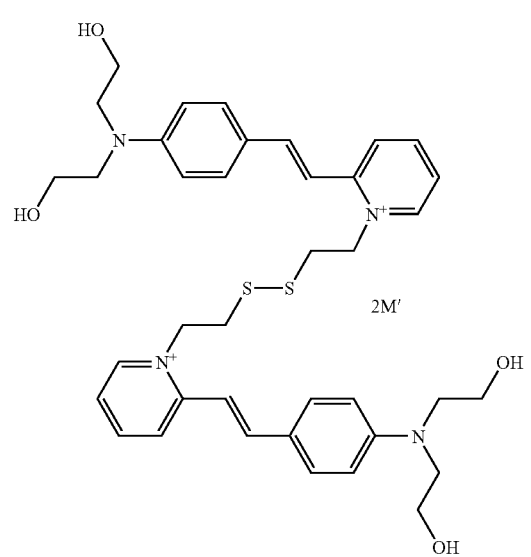 2M'

-continued
67
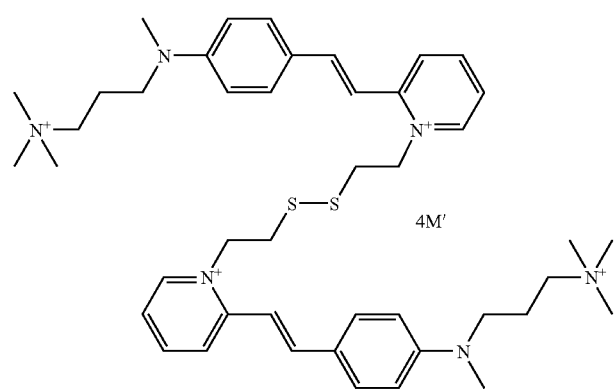
4M′
68
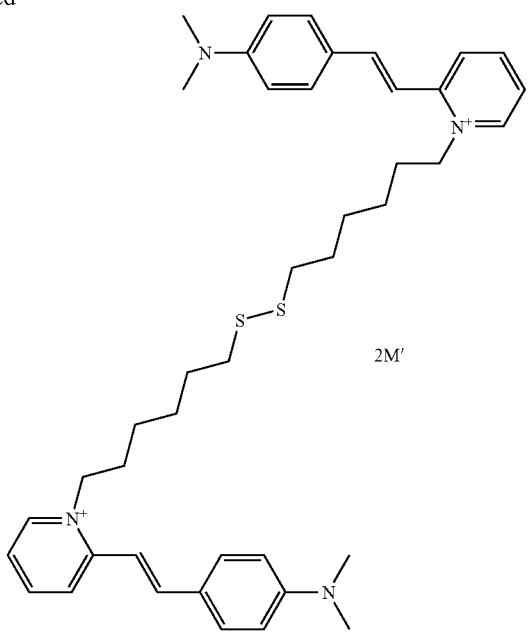
2M′
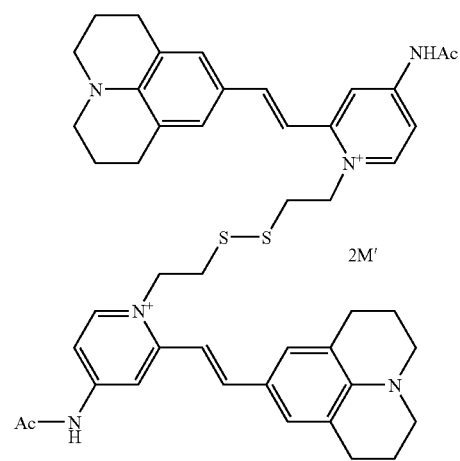
2M′
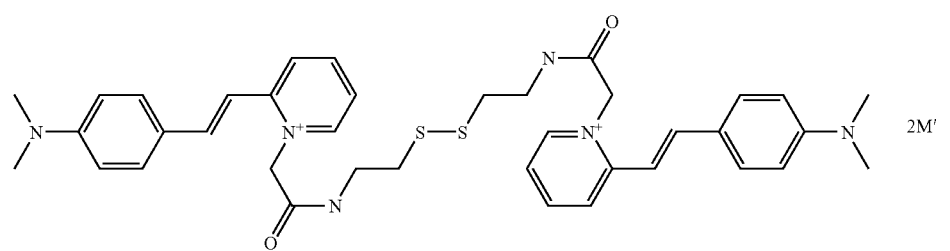
2M′
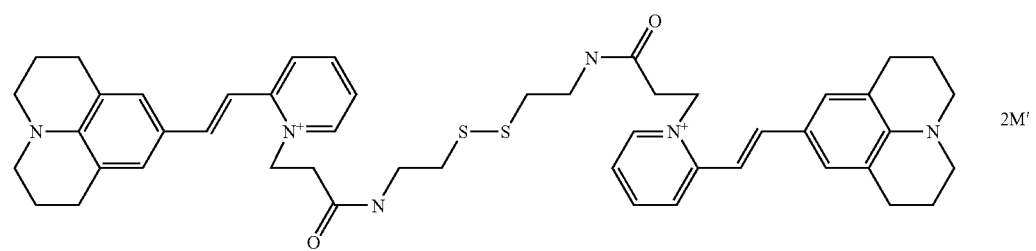
2M′

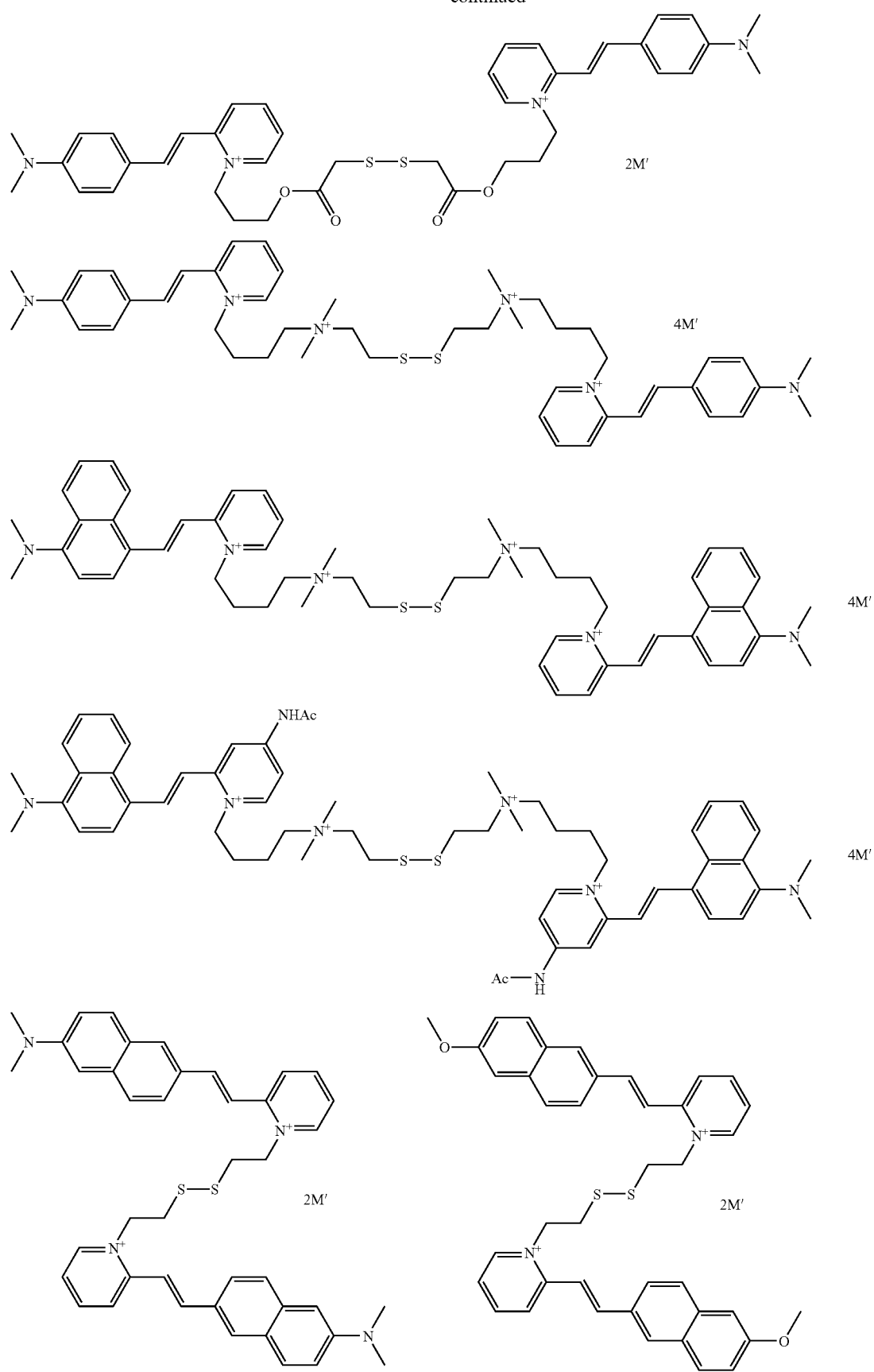

-continued
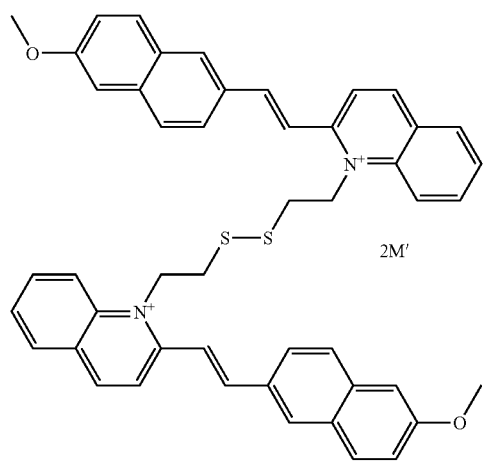
2M'
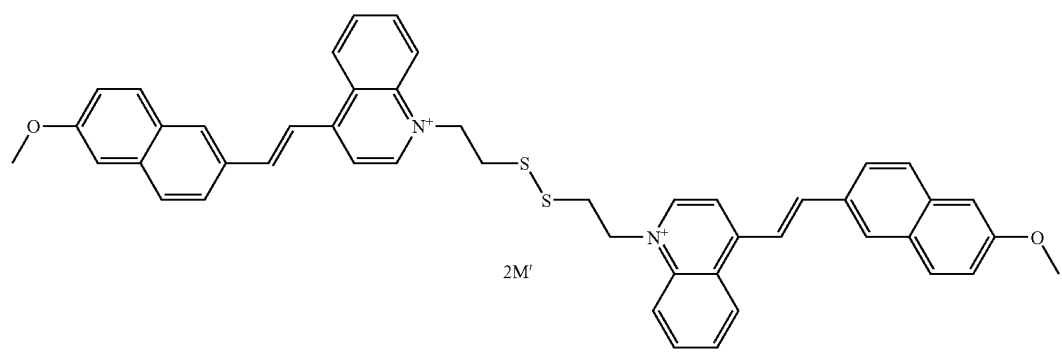
2M'
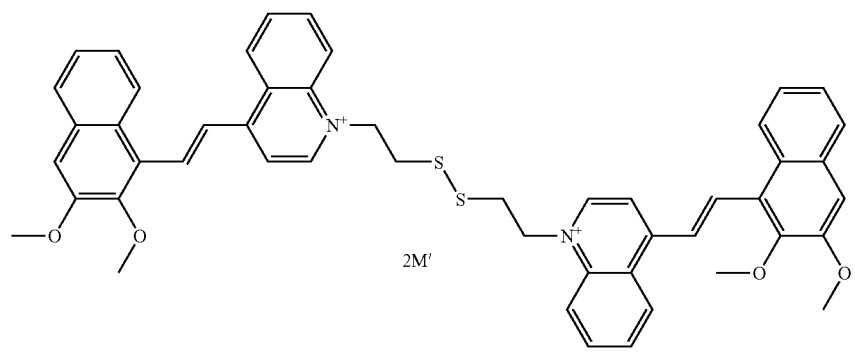
2M'
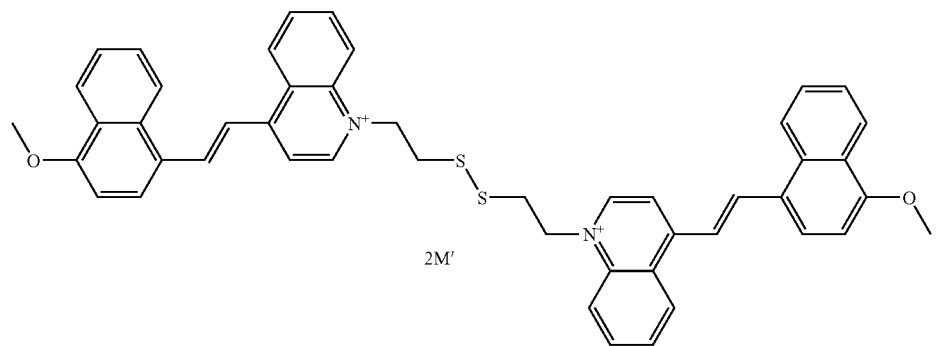
2M'

-continued
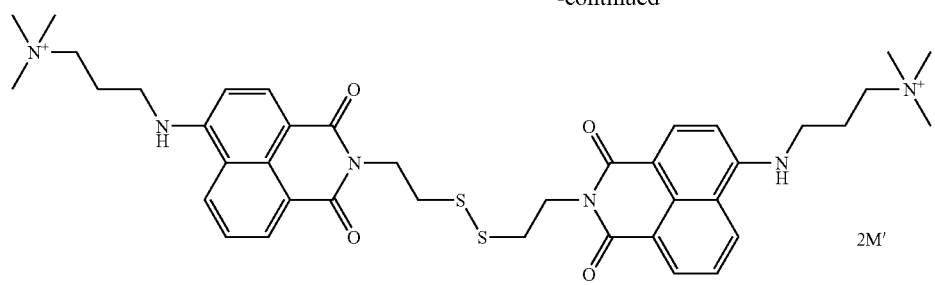
2M'
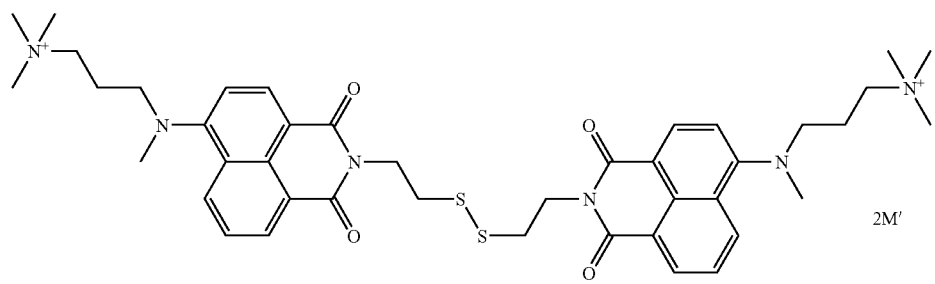
2M'
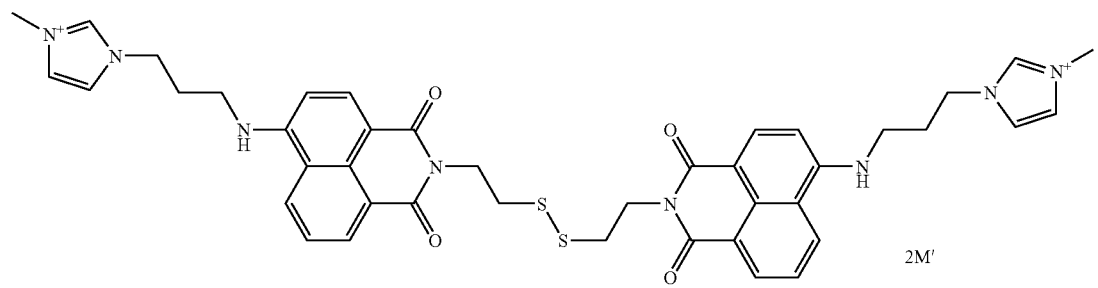
2M'
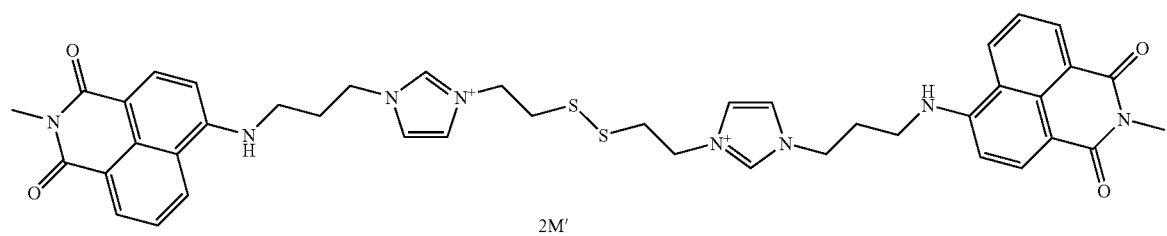
2M'
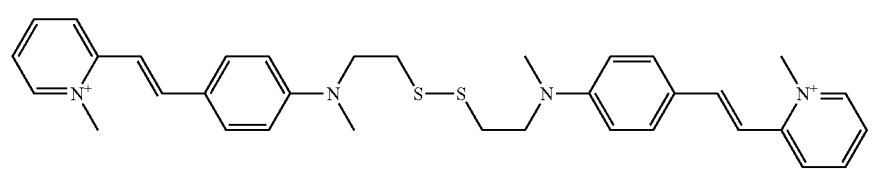
2M'
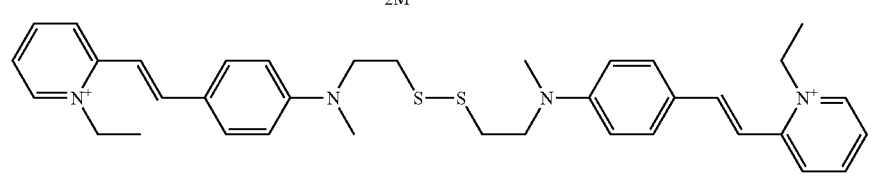
2M'

-continued
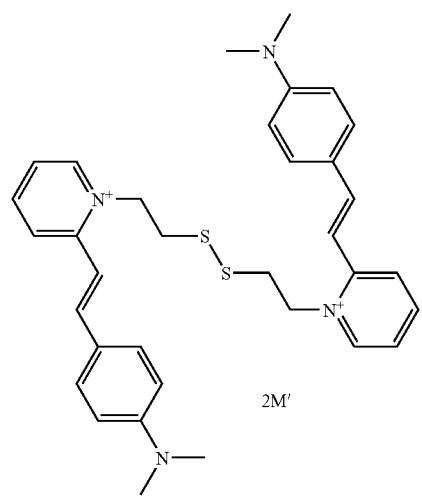
2M'
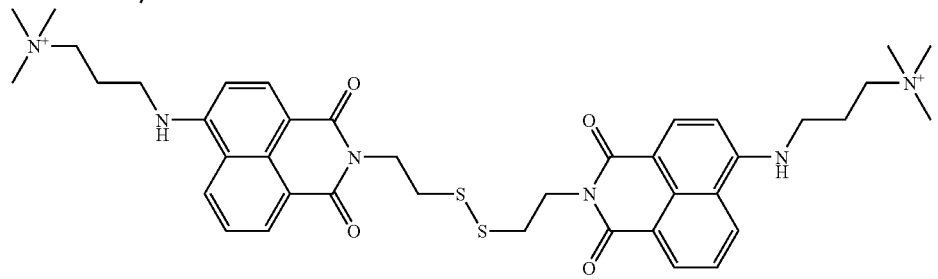
2M'
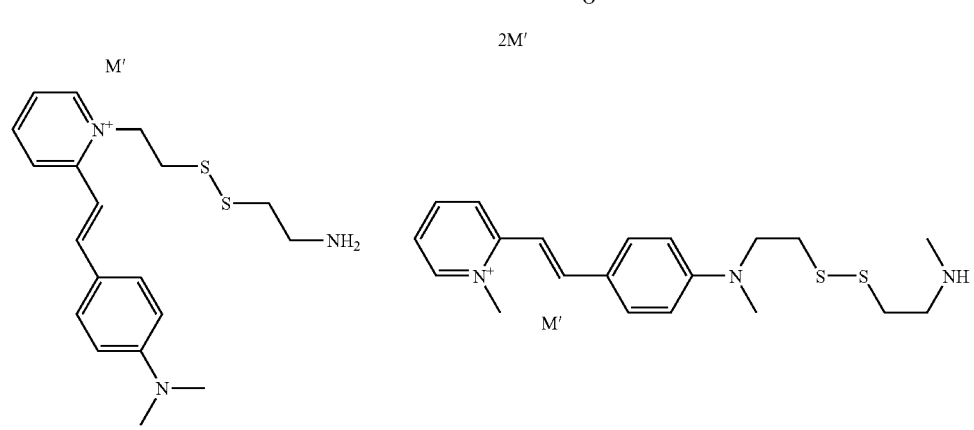
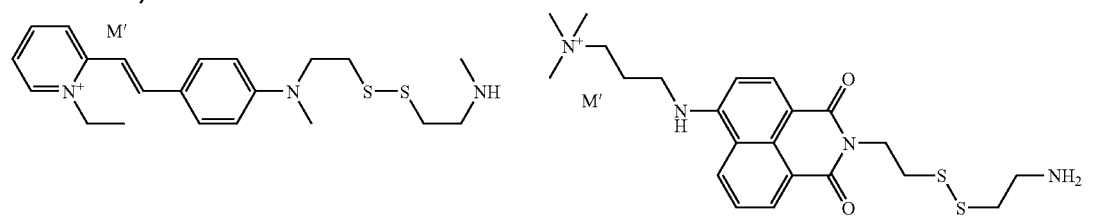
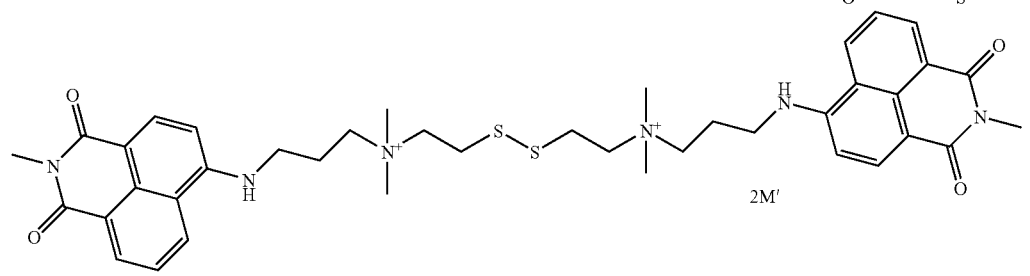
2M'
wherein M' represents an organic or mineral acid salt.

In at least one embodiment, as disulfide direct dyes, it is possible to use those described in Patent Applications GB 2 412 916, WO 05 097051, WO 06 134043, WO 06 134051, WO 06 136516, WO 06 136518, WO 06 136617.

I.5. The Organic or Mineral Acid Salt:

The organic or mineral acid salt may be chosen from, for example, hydrochlorides, hydrobromides, sulfates, including methyl sulfate and ethyl sulfate, citrates, succinates, tartrates, lactates, methosulfates, tosylates, benzenesulfonates, phosphates, acetates, triflates and tetrafluoroborates.

I.6. Preparation of Fluorescent or Non-Fluorescent Disulfide Direct Dyes:

The disulfide direct dyes may be prepared according to methods known to persons skilled in the art.

In one embodiment of the present disclosure, a disulfide compound comprising two amine functional groups, for example chosen from primary and secondary amines, can be reacted with a sufficient quantity of a reactive chromophore, which may be fluorescent or non-fluorescent, or of a compound comprising such a reactive chromophore, in other words comprising an electrophilic functional group.

Non-limiting examples of reactive chromophores according to the present disclosure include reactive dyes containing, for example, a group chosen from vinylsulfone, sulfatoethylsulfone, mono- and dichlorotriazine, mono- and dichloropyrimidine, difluorochloropyrimidine, dichloroquinoxaline, and bromovinylsulfone functional groups.

Further non-limiting examples of reactive chromophores include chromophore compounds comprising at least one group capable of reacting with an amine functional group to give a sulfamide group (—SO$_2$—NR—) or an amide group (—CO—NR—). For example, mention may be made of the —SO$_3$W', —COOW' groups (with W' representing a hydrogen atom, an alkali metal such as sodium or potassium, an ammonium group, an ammonium group substituted with one or more identical or different, linear or branched $C_1$-$C_{10}$ alkyl groups, optionally bearing at least one hydroxyl), which can be activated beforehand according to known methods as —SO$_2$Cl or —COCl groups, respectively.

It is thus possible to envisage using, as reactive chromophores, the acid dyes of the Color Index which are listed as such.

Reference may also be made to the book *Advanced Organic Chemistry*, March, 4th Ed, to have more details on the operating conditions used.

Also in the context of this embodiment, it is possible to use chromophores comprising a labile group which is directly linked or otherwise to the chromophore and which may be substituted with an amine group, such as Cl, Br, F, O-alkyl (for example O-Me), O-aryl, O-alkylaryl (for example O-benzyl).

The disulfide direct dyes may also be obtained, in the context of this possibility, using chromophores possessing an acrylate functional group (—OCO—C=C—) on which an addition reaction is performed.

In accordance with another embodiment, the disulfide direct dyes of the present disclosure may be obtained by reacting a disulfide compound with a compound bearing two carboxylic acid functional groups activated according to conventional methods (for example reaction with a carbodiimide or with thionyl chloride). The resulting product is then reacted with a chromophore bearing a nucleophilic functional group, for example of the primary or secondary amine type, or of the aliphatic or aromatic alcohol type such as phenol.

Here again, reference may be made to the book *Advanced Organic Chemistry*, March, 4th Ed, to have more details on the operating conditions used.

In accordance with yet another embodiment, the disulfide direct dyes of the present disclosure may be obtained by reaction of a compound comprising a disulfide group and two hydroxyl groups activated beforehand as leaving groups (for example mesylate or tosylate groups) with a chromophore bearing a nucleophilic functional group, for example of the primary, secondary, or tertiary amine type, which may be heteroaromatic or not, for example of the pyridine, imidazole, or benzimidazole type.

In accordance with another embodiment, the disulfide direct dyes of the present disclosure may be obtained by controlled oxidation of dyes bearing an —SH functional group.

In accordance with yet another embodiment, for example for the preparation of the compounds corresponding to formulae (II) and (III), the disulfide direct dyes of the present disclosure may be obtained by a variant of possibilities described above, using a molar quantity of disulfide reagent greater than or equal to the molar quantity of reagent containing the chromophore group.

The preparation of the disulfide direct dyes corresponding to the formula (I) for which A and A' are identical may be facilitated by the use of a molar quantity of reagent containing the chromophore group, for example greater than or equal to twice the quantity of disulfide reagents.

In accordance with yet another embodiment, for example for the preparation of compounds corresponding to the formula (I) in which v=0 and the two groups A and A', on the one hand, and X and X', on the other hand, are different, the disulfide compounds may be obtained from disulfide compounds corresponding to formula (III).

II. Dyeing Composition

II.1. Dyes

Dyeing compositions according to the present disclosure may contain one or more disulfide direct dyes, for example present in an amount ranging from 0.001 to 10% by weight, for example ranging from 0.005 to 5% by weight, relative to the total weight of the composition.

The dyeing compositions may also contain additional direct dyes lacking a disulfide bond, and which may be of non-ionic, cationic or anionic nature, or mixtures thereof.

The additional direct dye(s) may be present in the dyeing compositions in a quantity ranging from 0.0005 to 12% by weight, for example ranging from 0.005 to 6% by weight, relative to the total weight of the dyeing composition, As used herein, the term "appropriate medium for dyeing," which may also be called "dye support," is understood to refer to a cosmetic medium which may consist of water or a mixture of water and at least one organic solvent. As organic solvent, non-limiting examples include lower $C_1$-$C_4$ alkanols such as ethanol and isopropanol, and aromatic alcohols such as benzyl alcohol or phenoxyethanol, polyols, or polyol ethers such as, for example, ethylene glycol monomethyl, monoethyl and monobutyl ethers, propylene glycol, or its esters such as, for example, propylene glycol monomethyl ether, butylene glycol, dipropylene glycol and also diethylene glycol alkyl ethers such as, for example, diethylene glycol monoethyl ether or monobutyl ether or else glycerol. It is also possible to use, as solvents, polyethylene glycols and polypropylene glycols, and mixtures of their compounds. It is also possible to use propylene carbonate.

The organic solvents, when they are present, are for example present in proportions ranging from 1 to 40% by weight relative to the total weight of the dyeing composition, for example ranging from 5 to 30% by weight.

II.2. Alkaline Agent:

Compositions according to the present disclosure may further comprise one or more alkaline agents of mineral or organic hydroxide type, for example in an amount such that the pH of the composition ranges from 10 to 14, for example from 12 to 14.

In one embodiment, alkaline agents of mineral or organic hydroxide type may be chosen from the hydroxides of alkali metals, alkaline-earth metals, transition metals, for example metals from groups IIIB, IVB, VB, and VIB, lanthanides and actinides, ammonium and guanidine hydroxides, and mixtures thereof.

Non-limiting examples of such compounds include sodium hydroxide, potassium hydroxide, lithium hydroxide, rubidium hydroxide, cesium hydroxide, francium hydroxide, magnesium hydroxide, calcium hydroxide, strontium hydroxide, barium hydroxide, manganese hydroxide, zinc hydroxide, cerium hydroxide, lanthanium hydroxide, actinium hydroxide, thorium hydroxide, aluminum hydroxide, guanidine hydroxide and quaternary ammonium hydroxides.

It should be noted that certain hydroxides, for example guanidine hydroxide, may be in the form of precursors, that is to say in the form of at least two compounds which when brought together, result, via a chemical reaction, in guanidine hydroxide. By way of example, mention may be made of the combination of an alkaline-earth metal hydroxide, such as calcium hydroxide, with guanidine carbonate.

In at least one embodiment, mineral or organic hydroxide alkaline agents may be chosen from sodium and guanidine hydroxides and mixtures thereof.

In at least one embodiment, the amount of hydroxide alkaline agent may range from 0.5 to 10% by weight, for example from 1 to 8% by weight, relative to the weight of the composition.

II.3. Adjuvants:

Compositions according to the present disclosure may also comprise surfactants chosen from non-ionic, anionic, and cationic surfactants, and mixtures thereof. The surfactants used may comprise a $C_{10}$-$C_{24}$, for example $C_{12}$-$C_{24}$, for example $C_{12}$-$C_{22}$ alkyl or acyl chain, which is optionally monooxyalkylated or polyoxyalkylated or monoglycerolated or polyglycerolated.

Non-limiting examples of anionic surfactants include salts, for example alkaline metal salts, such as sodium salts, ammonium salts, amine salts, amino alcohol salts, and alkaline-earth metal, for example magnesium, salts, of the following compounds, alone and as a mixture:

alkyl sulfates, alkyl ether sulfates, alkylamido ether sulfates, alkylaryl polyether sulfates;
alkyl sulfonates, alkylamide sulfonates, alkylaryl sulfonates;
alkyl sulfosuccinates, alkyl ether sulfosuccinates, alkylamide sulfosuccinates;
alkyl sulfoacetates;
acyl sarcosinates; and acyl glutamates;
alkyl esters of polyglycoside carboxylic acids such as alkyl glucoside citrates, alkyl polyglycoside tartrates and alkyl polyglycoside sulfosuccinates;
alkyl sulfosuccinamates;
acyl isethionates, N-acyl taurates and acyl lactylates;
alkyl-D-galactoside uronic acids;
polyoxyalkylenated alkyl ether carboxylic acids, polyoxyalkylenated alkylaryl ether carboxylic acids, and polyoxyalkylenated alkylamido ether carboxylic acids;

the alkyl or acyl (RCO—) group of these compounds for example comprising from 10 to 24 carbon atoms and the aryl group for example denoting a phenyl or benzyl group; the number of oxyalkylenated, for example oxyethylenated groups, for example ranging from 2 to 50.

Non-limiting examples of non-ionic surfactants include the following compounds, alone and as a mixture:

polyethoxylated, polypropoxylated and polyglycerolated fatty alcohols;
polyethoxylated, polypropoxylated and polyglycerolated α-diols;

the number of ethylene oxide or propylene oxide groups ranging for example from 2 to 50; the number of glycerol groups ranging for example from 2 to 30;

copolymers of ethylene oxide and of propylene oxide;
condensates of ethylene oxide and of propylene oxide with fatty alcohols;
polyethoxylated fatty alkanol amides, for example having from 2 to 30 mol of ethylene oxide;
polyglycerolated fatty amides, for example comprising from 1 to 5 glycerol groups;
ethoxylated sorbitan fatty acid esters, for example having from 2 to 30 mol of ethylene oxide, sucrose fatty acid esters and polyethylene glycerol fatty acid esters; and
alkyl polyglucosides and derivatives of N-alkyl glucamine;

these compounds comprising an alkyl or acyl chain that comprises, for example, from 10 to 24 carbon atoms.

Non-limiting examples of cationic surfactants include the following compounds, alone and as a mixture:

optionally polyoxyalkylenated salts of primary, secondary, and tertiary fatty amines;
quaternary ammonium salts such as the chlorides and bromides of tetraalkylammonium, alkylamidoalkyltrialkylammonium, trialkylbenzylammonium, trialkylhydroxyalkylammonium and alkylpyridinium; and
alkyl imidazoline derivatives;

these compounds comprising at least one alkyl chain that comprises, for example, from 10 to 24 carbon atoms.

Non-limiting examples of amphoteric surfactants include the following compounds, alone and as mixture:

derivatives of secondary and tertiary aliphatic amines, in which the aliphatic group is a linear or branched chain containing, for example, from 10 to 24 carbon atoms and comprising at least one water-solubilizing anionic group such as, for example, a carboxylate, sulfonate, sulfate, phosphate or phosphonate group;
alkyl betaines, sulfobetaines, alkylamidoalkyl($C_6$-$C_8$)betaines, or alkylamidoalkyl($C_6$-$C_8$)sulfobetaines;

these compounds comprising an alkyl chain that comprises, for example, from 10 to 24 carbon atoms.

In one embodiment, surfactants may be chosen from alkyl sulfates, alkylbenzene sulfates, alkyl ether sulfates, alkyl sulfonates, quaternary ammonium salts, alkyl betaines, fatty acid alkanolamides, and oxyethylenated fatty acid esters, alone or as mixtures.

When compositions according to the present disclosure comprise surfactants, the surfactant or surfactants may be present at a concentration ranging from 0.5 to 30% by weight, for example from 0.5 to 10% by weight, relative to the total weight of the composition.

Compositions according to the present disclosure may also comprise one or more treating agents of cationic, anionic, non-ionic or amphoteric nature.

Non-limiting examples of treating agents according to the present disclosure include linear and cyclic, volatile and non-volatile silicones and mixtures thereof, polydimethylsiloxanes, quaternized polyorganosiloxanes such as those described in French Patent Application No. 2 535 730, polyorganosiloxanes containing aminoalkyl groups modified by alkoxycarbonylalkyl groups such as those described in U.S. Pat. No. 4,749,732, polyorganosiloxanes such as the polydimethylsiloxane/polyoxyalkyl copolymer of the Dimethicone Copolyol type, a polydimethylsiloxane containing stearoxy end groups (stearoxydimethicone), a polydimethylsiloxane/dialkylammonium acetate copolymer or a polydimethylsiloxane/poly(alkyl betaine) copolymer described in British Patent No. 2 197 352, polysiloxanes organomodified by mercapto or mercaptoalkyl groups such as those described in French Patent No. 1 530 369 and in European Patent Application No. 295 780, and also silanes such as stearoxytrimethylsilane.

Compositions according to the present disclosure may further comprise additional treating ingredients, which may be chosen, for example, from cationic polymers such as those used in the compositions from French Patents No. 79/32078 (2 472 382) and 80/26421 (2 495 931), cationic polymers of the ionene type such as those used in the compositions from Luxembourg Patent No. 83703, basic amino acids (such as lysine or arginine) or acidic amino acids (such as glutamic acid or aspartic acid), peptides and derivatives thereof, protein hydrolysates, waxes including ceramides, fatty alcohols, and lanolin derivatives.

Compositions according to the present disclosure may also comprise at least one adjuvant chosen from vitamins and provitamins, for example panthenol, silicone-based and non-silicone-based water-soluble and liposoluble sunscreens, pearlescent agents and opacifiers, sequestrants, plasticizers, film-forming agents, ceramides, stabilizers, conditioning agents, mineral and organic thickeners other than carboxyvinyl (co)polymers, antioxidants, penetrating agents, fragrances and preservatives.

Adjuvants may be present in compositions according to the present disclosure in an amount ranging from, for each of them, 0.01 to 20% by weight, relative to the weight of the composition.

Compositions according to the present disclosure may further comprise at least one other additional disulfide compound different from the disulfide direct dyes of the present disclosure. For example, the disulfide may be chosen from compounds comprising at least one fatty chain, for example at least one saturated or unsaturated, linear or branched, $C_5$-$C_{30}$ hydrocarbon chain which is optionally substituted with a heteroatom and optionally interrupted by a neutralized or unneutralized carboxyl group. Non-limiting examples of compounds of this type include dimers of thioglycolic acid and derivatives thereof of the $CH_3$—$(CH_2)_{17}$—S—S—$(CH_2)_{17}$—$CH_3$ or $CH_3$—$(CH_2)$—S—S—$(CH_2)_{10}$—$CH_3$ type.

When it is present, this compound may be present in an amount ranging from 0.001 to 10% by weight relative to the weight of the composition.

A person skilled in the art will be careful to choose any optional additional compounds in such a way that the desired properties intrinsically linked to the hair composition according to the present disclosure are not, or are not substantially, impaired by the envisaged addition or additions.

II.4. Forms of the Composition:

Dyeing compositions according to the present disclosure may be in various forms, for example in the form of a liquid, lotion, cream or gel or in any other form suitable for dyeing keratin fibers, for example hair. They may also be packaged under pressure in an aerosol bottle in the presence of a propellant and form a foam.

In one embodiment, compositions according to the present disclosure may be present in the form of a thick cream that may help keep the hair as straight as possible. Such creams may be produced in the form of "heavy" emulsions, for example based on an inert liquid phase.

Non-limiting examples of inert liquid phases include polydecenes of formula $C_{10n}H_{[(20n)+2]}$ in which n ranges from 3 to 9 for example from 3 to 7, esters, for example esters of fatty alcohols or of fatty acids, sugar esters or diesters of $C_{12}$-$C_{24}$ fatty acids, cyclic esters and cyclic ethers, silicone oils, mineral oils and plant oils, and mixtures thereof.

Compounds of formula $C_{10n}H_{[(20n)+2]}$ in which n ranges from 3 to 9 correspond to the name "polydecene" of the CTFA dictionary, 7th edition, 1997 of the Cosmetic, Toiletry and Fragrance Association, USA, and also to the same INCI name in the USA and in Europe. These may be poly-1-decene hydrogenation products.

Non-limiting examples of polydecene compounds include the product sold under the name Silkflo® 366 NF Polydecene by Amoco Chemical, and those sold under the name Nexbase® 2002 FG, 2004 FG, 2006 FG, and 2008 FG by Fortum.

Non-limiting examples of esters include:
  esters of saturated, linear or branched $C_3$-$C_6$ lower monoalcohols with monofunctional $C_{12}$-$C_{24}$ fatty acids, these fatty acids optionally being linear or branched, saturated or unsaturated and chosen for example from oleates, laurates, palmitates, myristates, behenates, cocoates, stearates, linoleates, linolenates, caprates and arachidonates, or mixtures thereof, and for example oleopalmitates, oleostearates and palmitostearates. For example, such esters may be chosen from isopropyl palmitate, isopropyl myristate, and octyidodecyl stearate;
  esters of linear or branched $C_3$-$C_8$ monoalcohols with difunctional $C_8$-$C_{24}$ fatty acids, these fatty acids optionally being linear or branched, and saturated or unsaturated, for example the isopropyl diester of sebacic acid, which may be known as diisopropyl sebacate;
  esters of linear or branched $C_3$-$C_8$ monoalcohols with difunctional $C_2$-$C_8$ fatty acids, these fatty acids optionally being linear or branched, and saturated or unsaturated, for example dioctyl adipate and dicaprylyl maleate; and
  the ester of a trifunctional acid, for example triethyl citrate.

As used herein with regard to sugar esters and diesters of $C_{12}$-$C_{24}$ fatty acids, the term "sugar" is understood to mean compounds containing several alcohol functional groups, with or without an aldehyde or ketone functional group, and which comprise at least 4 carbon atoms. These sugars may be monosaccharides, oligosaccharides or polysaccharides.

As sugars that may be used according to the present disclosure, non-limiting examples include sucrose (which may be known as saccharose), glucose, galactose, ribose, fucose, maltose, fructose, mannose, arabinose, xylose and lactose, and derivatives thereof, for example alkyl derivatives such as methyl derivatives, for example methylglucose.

In one embodiment, sugar esters of fatty acids that may be used according to the present disclosure may be chosen from the group comprising esters or mixtures of esters of sugars described above and of linear or branched, saturated or unsaturated $C_{12}$-$C_{24}$ fatty acids.

For example, esters may be chosen from mono-, di-, tri- and tetraesters and polyesters, and mixtures thereof.

For example, esters may be chosen from oleates, laurates, palmitates, myristates, behenates, cocoates, stearates, linoleates, linolenates, caprates and arachidonates, and mixtures thereof such as oleopalmitate, oleostearate and palmitostearate mixed esters.

In at least one embodiment, esters may be chosen from monoesters and diesters, for example sucrose, glucose or methylglucose mono- or dioleates, stearates, behenates, oleopalmitates, linoleates, linolenates and oleostearates.

An example that may be mentioned is the product sold under the name Glucate® DO by Amerchol, which is a methylglucose dioleate.

Further non-limiting examples of esters or mixtures of esters of sugar and of fatty acid include:
- the products sold under the names F160, F140, F110, F90, F70 and SL40 by the company Crodesta, respectively denoting sucrose palmitostearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;
- the products sold under the name Ryoto Sugar Esters, for example referenced B370 and corresponding to sucrose behenate formed from 20% monoester and 80% diester, triester and polyester; and
- the sucrose mono-dipalmitostearate sold by Goldschmidt under the name Tegosoft® PSE.

In at least one embodiment, cyclic ethers and cyclic esters may be chosen from γ-butyrolactone, dimethyl isosorbide and diisopropyl isosorbide.

Silicone oils may also be used as inert organic liquid phases.

For example, silicone oils that may be used include liquid, non-volatile silicone fluids with a viscosity of less than or equal to 10,000 mPa·s at 25° C., the viscosity of the silicones being measured according to ASTM 445 standard Appendix C.

Silicone oils are discussed, for example in Walter Noll's "Chemistry and Technology of Silicones" (1968)—Academic Press.

Non-limiting examples of silicone oils that may be used according to the present disclosure include the silicone oils sold under the names DC-200 Fluid—5 mPa·s, DC-200 Fluid—20 mPa·s, DC-200 Fluid—350 mPa·s, DC-200 Fluid—1000 mPa·s and DC-200 Fluid—10 000 mPa·s by the company Dow Corning.

Mineral oils may also be used as inert organic liquid phases, for example liquid paraffins.

Plant oils may also be used as inert organic liquid phases, for example avocado oil, olive oil or liquid jojoba wax.

In one embodiment, the inert organic liquid phase may be chosen from the polydecenes of formula $C_{10n}H_{[(20n)+2]}$ in which n ranges from 3 to 9, for example from 3 to 7, esters of fatty alcohols and of fatty acids, and mixtures thereof.

The inert organic liquid phase may represent from 5 to 60% of the total weight of the composition.

It is also possible to use liquids or gels containing thickeners such as carboxyvinyl polymers or copolymers which fix the hair and keep it in a smooth form during the leave-in time.

III. Dyeing Process:

Another subject of the present disclosure is a hair-shaping process such as the relaxing of keratin fibers comprising the use of cosmetic compositions comprising, in a cosmetically acceptable medium, at least one disulfide direct dye and at least one alkaline agent of organic or mineral hydroxide type as defined previously, said agent or agents being present in the composition in an amount such that the pH of the composition ranges from 10 to 14, for example from 12 to 14.

According to the process of simultaneous shaping and dyeing, and optionally lightening, of keratin fibers, the dyeing composition is applied to the keratin fibers for a sufficient time to obtain the desired shaping and dyeing, and optionally lightening. The keratin fibers are then optionally rinsed and washed with shampoo.

In processes according to the present disclosure, the application time may be less than 40 minutes, for example less than 30 minutes.

According to one embodiment of the process according to the present disclosure, a composition according to the present disclosure is applied to keratin fibers, for example hair, and then the fibers are subjected to a mechanical shaping operation that may give them a new shape, for example via an operation for smoothing the hair, for example with a large-toothed comb, with the back of a comb, or by hand. After a leave-in time, for example from 5 to 60 minutes, for example from 10 to 30 minutes, a new smoothing operation is optionally carried out, and then the hair is rinsed.

Compositions according to the present disclosure, when they contain a fluorescent dye, may be applied to the hair having a tone level less than or equal to 6, for example less than or equal to 4.

The application temperature may range from ambient temperature (15 to 25° C.) to 80° C., for example from 15 to 40° C. Thus, it may be possible, after application of a composition according to the present disclosure, to subject a head of hair to a heat treatment via heating to a temperature between 30 and 60° C. For example, this operation may be carried out by means of a hair-styling hood, a hair dryer, an infrared radiation emitter, and/or other conventional heating equipment.

It is possible to use, both as a means of heating and smoothing the head of hair, heated tongs at a temperature between 60 and 220° C., for example between 120 and 200° C.

According to one embodiment, the keratin fibers may be pigmented and/or artificially colored.

When a composition according to the present disclosure is used to lighten dark keratin fibers, for example brown hair, the lightening obtained may be evaluated by the reflectance measured before and after application. When the reflectance of the hair is measured when it is irradiated with visible light in the wavelength spectrum ranging from 400 to 700 nm, and when the curves of reflectance are compared as a function of the wavelength of hair treated with a composition of the present disclosure and of untreated hair, it may be observed that the reflectance curve corresponding to treated hair, in a wavelength spectrum ranging from 400 to 700 nm, is greater than that corresponding to the untreated hair.

This means that, in the wavelength spectrum ranging from 500 to 700 nm, for example from 540 to 700 nm, there may be at least one range where the reflectance curve corresponding to the treated hair is greater than the reflectance curve corresponding to the untreated hair. As used herein, the term "greater" is understood to mean a difference of at least 0.05% in reflectance, for example of at least 0.1%.

It is also possible for there to be, in the wavelength spectrum ranging from 500 to 700 nm, for example from 540 to 700 nm, one or more ranges where the reflectance curve corresponding to the treated fibers is superposable, or is less than the reflectance curve corresponding to the untreated fibers.

In one embodiment, the wavelength where the difference between the reflectance curve of treated hair and that of untreated hair is at a maximum may lie within the wavelength spectrum ranging from 500 to 650 nm, for example in the wavelength spectrum ranging from 550 to 620 nm.

III. Dyeing Device or "Kit":

Another subject of the present disclosure are multi-compartment devices, which may be referred to as "kits," for dyeing in which at least a first compartment (i) comprises at least one alkaline agent of mineral or organic hydroxide type, and at least a second compartment (ii) comprises a composition containing at least one disulfide direct dye, wherein the pH of the mixture of the contents of the various compartments ranges from 10 to 14.

In one embodiment, when a hydroxide-type alkaline agent is used in the form of a precursor, the precursor components are not stored in the same compartment. Thus, for example in the case of guanidine, guanidine carbonate may be stored in the disulfide direct dye, and the alkali metal or alkaline-earth metal hydroxide in a second compartment. It is also possible to have at least three compartments, the first containing guanidine carbonate, the second an alkali metal or alkaline-earth metal hydroxide, and the third a disulfide direct dye.

According to one embodiment, devices according to the present disclosure comprise, in addition, a supplementary composition (iii) comprising at least one treating agent and/or at least one adjuvant, as described herein.

According to another embodiment, the treating agent(s) and/or adjuvant(s) may be present in one and/or the other of the compartments (i) or (ii), for example in compartment (ii).

At least one of these compartments may also contain at least one additional direct dye.

The compositions of devices according to the present disclosure may be packaged in separate compartments or containers or devices, optionally accompanied by suitable application means, which may be identical or different, such as fine brushes, coarse brushes or sponges. The devices may also be equipped with a means enabling the desired mixture to be delivered to the hair, for example the devices described in Patent FR 2 586 913.

The examples which follow are intended to illustrate the disclosure without, however, being limiting. The fluorescent disulfide dyes from the examples below have been fully characterized by conventional spectroscopic and spectrometric methods.

EXAMPLES

Examples of Synthesis

Example 1

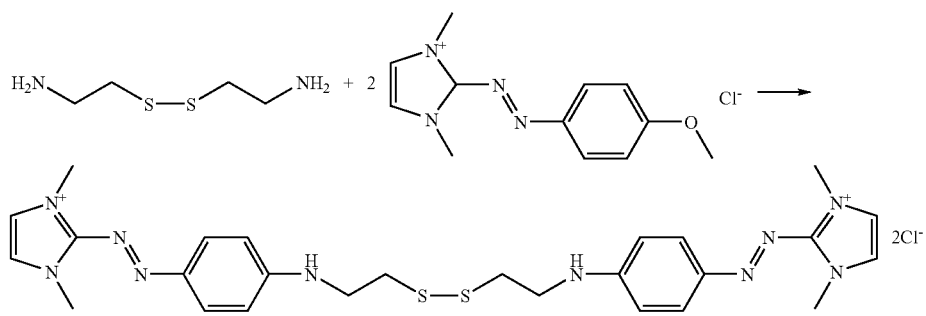

The base cystamine (552.2 mg; 3.62 mmol) obtained from cystamine dihydrochloride by addition of sodium hydroxide and extraction with ethyl acetate, was dissolved in 2 ml of pentanol. 2-[(4-Methoxyphenyl)diazenyl]-1,3-dimethyl-1H-imidazol-3-ium chloride (2.42 mg; 9.1 mmol), in suspension in 80 ml of dichloromethane, was added. The mixture was brought to 50° C. and was kept stirring for 1 hour. It was concentrated under vacuum (removal of dichloromethane), 20 ml of water was added and the reaction mixture was kept at 50° C. for an additional hour. It was then cooled and poured over 50 ml of pentanol; a red precipitate appeared, which was filtered and washed with acetone, then dried under vacuum.

Thus, 1.1 g of dark red powder was obtained which conformed to the above structure.

Example 2

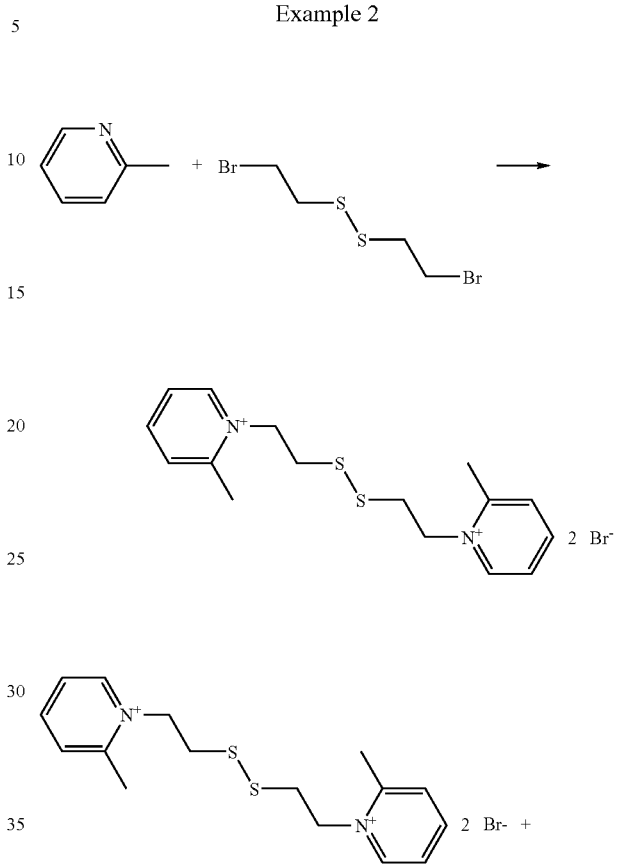

-continued

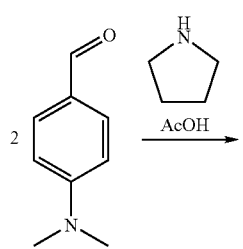

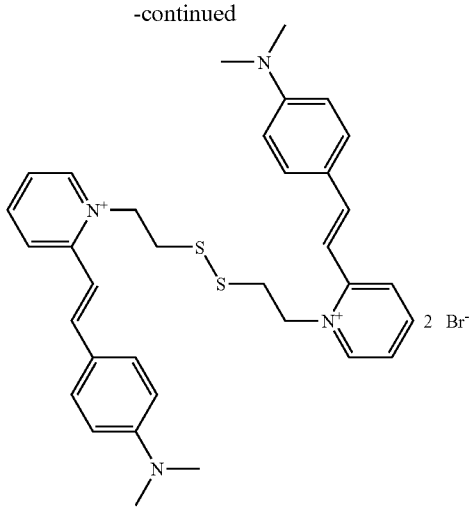

Step 1: 1,1'-(disulfanediyldiethane-2,1-diyl)bis(2-methylpyridinium) dibromide

A mixture of 56 g of 1-bromo-2-[(2-bromoethyl)disulfanyl]ethane and 15 ml of N-methylpyrrolidone (NMP) was poured dropwise over 35 g of 2-picoline with stirring at 80° C. The mixture (white suspension) continued to be stirred for 30 min at 80° C., then 100 ml of acetonitrile were added and the stirring was continued at 80° C. for 90 min. After cooling, the solid obtained was filtered, washed with 100 ml of acetonitrile, then dried. 56.2 g of brown powder were recovered. 45 g of this powder were suspended in 300 ml of isopropanol, under reflux. Once the temperature dropped to 40° C., the solid was filtered, washed with three times 100 ml of isopropanol and dried under vacuum. Thus, 40.56 g of a light beige product was obtained. Analyses were in accordance with the expected structure.

Step 2: 1,1'-(disulfanediyldiethane-2,1-diyl)bis(2-{(E)-2-[4-(dimethylamino)phenyl]vinyl}pyridinium) dibromide 150 mg of pyrrolidine, then 129 mg of acetic acid were added to a solution of 297 mg of 4-dimethylaminobenzaldehyde in 2 ml of methanol.

After stirring at ambient temperature for 18 h, 495 mg of 1'-(disulfanediyldiethane-2,1-diyl)bis(2-methylpyridinium) dibromide were added to the mixture and the stirring was continued at ambient temperature for 7 days. After filtering, washing with methanol and drying under the vacuum, 312 mg of orange powder were recovered. Analyses were in accordance with the expected structure. $^1$H NMR (400 MHz, MeOH-d$_4$): 3.02 (s, 6H), 3.22 (t, 2H), 5 (t, 2H), 6.72 (m, 2H), 7.19 (d, 1H), 7.63 (m, 3H), 7.76 (d, 1H), 8.3 (m, 2H), 8.59 (m, 1H).

Example 3

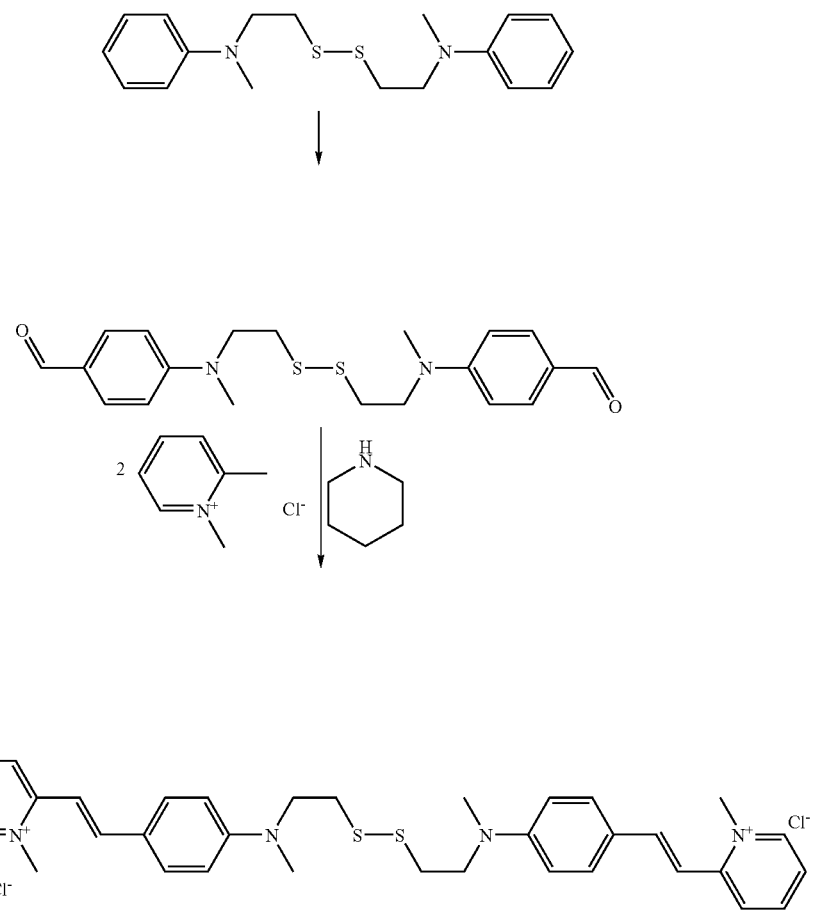

Step 1: 4,4'-{disulfanediylbis[ethane-2,1-diyl(methylimino)]}dibenzaldehyde 82.3 g of phosphorus oxychloride were added to 500 ml of DMF at 0° C. After stirring for 30 min at 0° C., a solution of 47 g of N,N'-(disulphanediyldiethane-2,1-diyl)bis(N-methylaniline) was added dropwise. The mixture was then stirred for 90 min at 0° C., then for 75 min at 10° C. and 105 min at 40° C. It was then poured over 2.5 l of iced water, and 700 ml of 5 N sodium hydroxide were added.

The yellow precipitate obtained was filtered over celite, dissolved in 200 ml of dichloromethane, and the solution obtained was washed with 200 ml of a saturated aqueous sodium chloride solution. After drying over magnesium sulfate and evaporating the dichloromethane, the yellow residue (80 g) was purified by chromatography over silica gel.

After drying, a light yellow powder was recovered. The analyses indicated that the product was in accordance with the expected structure.

Step 2: 2,2'-{disulfanediylbis[ethane-2,1-diyl(methylimino)-4,1-phenylene(E)ethene-2,1-diyl]}bis(1-methylpyridinium) dichloride 25 g of 4,4'-{disulfanediylbis[ethane-2,1-diyl(methylimino)]}dibenzaldehyde and 18.5 g of N-methylpicolinium chloride were dissolved in 300 ml of methanol. 12.7 ml of piperidine were added to the mixture. The resulting mixture was heated, with stirring at 55° C. for 11 h. The methanol was removed under vacuum at 40° C. The solid was mixed with 300 ml of isopropanol. After again drying by evaporation, 200 ml of isopropanol was introduced. The mixture hardened and it was extended by addition of 100 ml of isopropanol and filtered through sintered glass. The solid recovered was washed with isopropanol, then acetone, then dried under vacuum. After drying, 36.7 g of orange powder were recovered. Via recrystallization in isopropanol, 27 g of higher purity orange-red powder were recovered. The analyses indicated that the product conformed to the expected structure and was substantially pure. $^1$H NMR (400 MHz, MeOH-d$_4$) 2.99 (t, 4H), 3.81 (t, 4H), 4.31 (s, 6H), 6.86 (d, 4H), 7.22 (d, 2H), 7.63 (m, 2H), 7.69 (d, 4H), 7.83 (d, 2H), 8.29 (m, 2H), 8.36 (m, 2H), 8.61 (m, 2H).

Example 4

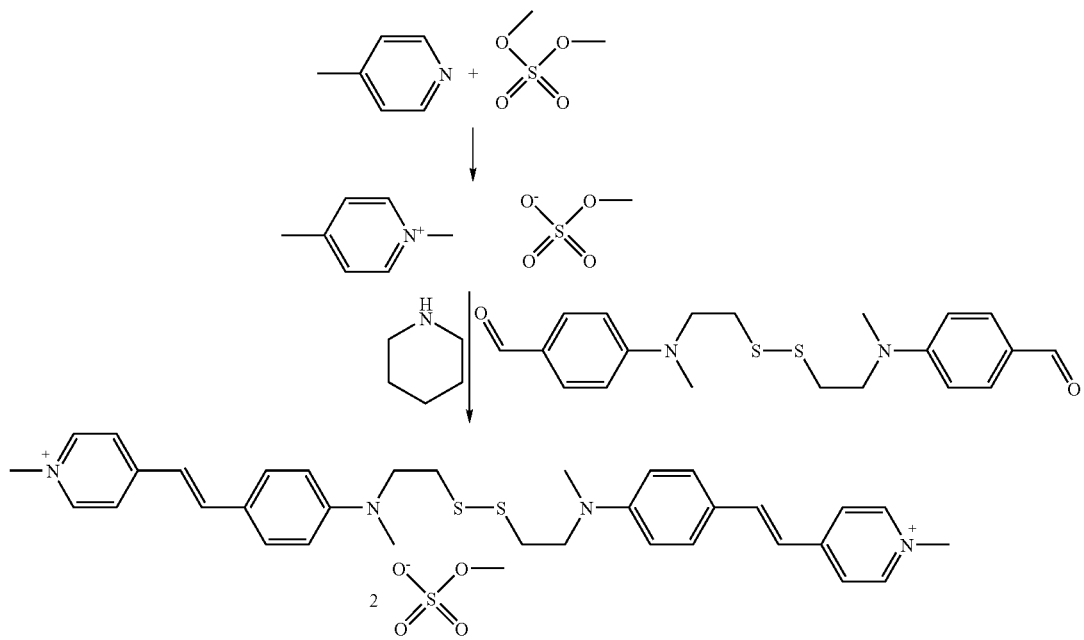

4,4'-{disulfanediylbis[ethane-2,1-diyl(methylimino)-4,1-phenylene(E)ethene-2,1-diyl]}bis(1-methylpyridinium) dimethoxysulfate 2.62 g of 4-picoline were diluted in 25 ml of dichloromethane, 3 ml of dimethyl sulfate were added to the solution, the temperature of which was raised to reflux (40° C.). After stirring for 40 min, 50 ml of isopropanol were added, and the mixture was concentrated by distillation of the dichloromethane (mixture heated at 60° C.). 1.83 g of pyrrolidine were introduced into the mixture, followed by 4.99 g of 4,4'-{disulfanediylbis[ethane-2,1-diyl(methylimino)]}dibenzaldehyde. After stirring for 2 h at 65° C., the reaction mixture was cooled to ambient temperature, the precipitate formed was filtered, and washed with three times 100 ml of isopropanol. The red paste obtained was dispersed in 200 ml of isopropanol, the mixture thus obtained was brought to reflux, then cooled. The red precipitate formed was filtered, then dried. 8.94 g of red powder were recovered. The analyses indicated that the product conformed to the expected structure and was substantially pure. $^1$H NMR (400 MHz, DMSO-d$_6$) 2.96 (t, 4H), 3.02 (s, 6H), 3.36 (s, 6H), 3.72 (t, 4H), 4.16 (s, 6H), 6.81 (d, 4H), 7.15 (d, 2H), 7.57 (d, 4H), 7.87 (d, 2H), 8.02 (d, 4H), 8.66 (d, 4H).

Example 5

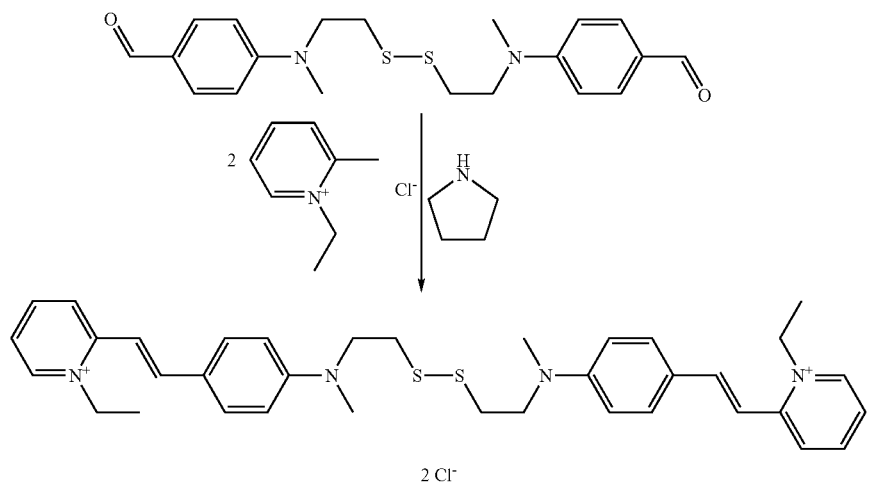

2,2'-{Disulfanediylbis[ethane-2,1-diyl(methylimino)-4,1-phenylene(E)ethene-2,1-diyl]}bis(1-ethylpyridinium) dichloride 10 g of 4,4'-{disulfanediylbis[ethane-2,1-diyl(methylimino)]}dibenzaldehyde and 8.1 g of N-ethylpicolinium chloride were dissolved in 100 ml of isopropanol. 1.3 g of piperidine were added to the mixture. The whole thing was heated, with stirring, under reflux for 5 h. The isopropanol was removed under vacuum at 50° C. The gum obtained was ground with acetone. 18 g of solid were recovered and treated with carbon black. 7.1 g of product were collected and 4 g were purified by liquid-liquid (water/BuOH) chromatography. After drying, 1.65 g of red powder were recovered. The analyses indicated that the product conformed to the expected structure and was substantially pure. $^1$H NMR (400 MHz, MeOH-d$_4$) 1.57 (t, 6H), 2.98 (t, 4H), 3.11 (s, 6H), 3.8 (t, 4H), 4.73 (q, 4H), 6.85 (m, 4H), 7.23 (d, 2H), 7.69 (m, 6H), 7.85 (d, 2H), 8.29 (m, 2H), 8.38 (m, 2H), 8.67 (m, 2H).

Example 6

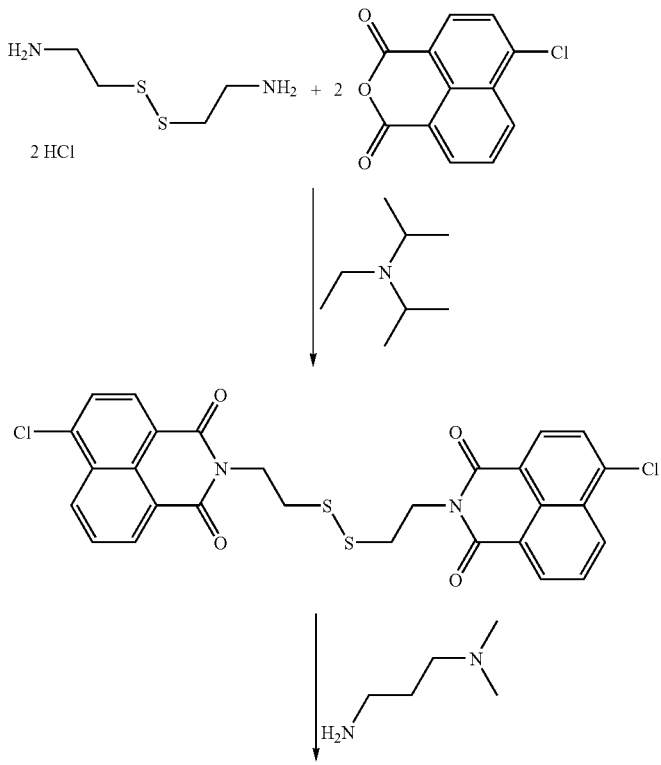

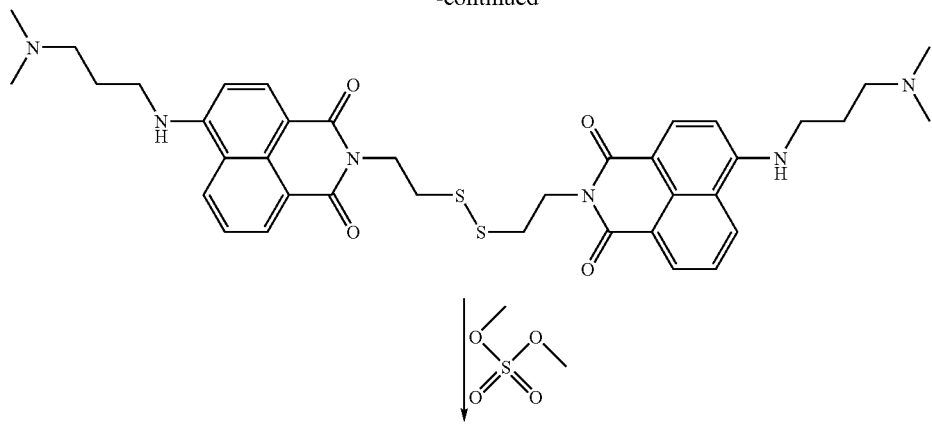

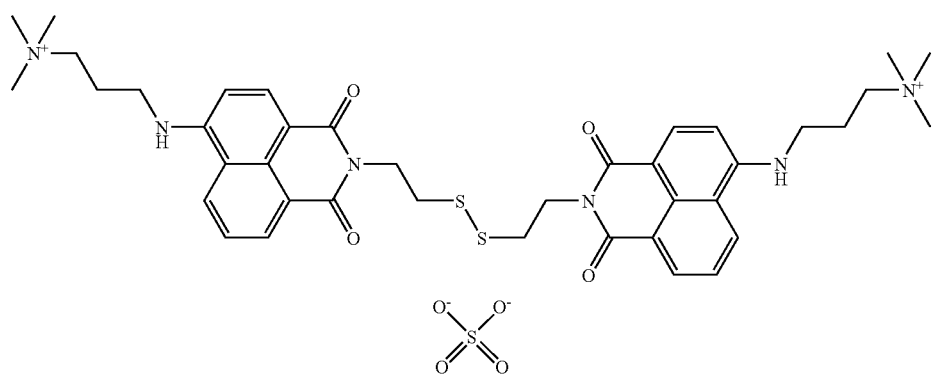

Step 1: 2,2'-(disulfanediyldiethane-2,1-diyl)bis(6-chloro-1H-benzo[de]-isoquinoline-1,3(2H)-dione)

9.30 g of 6-chloro-1H,3H-benzo[de]isochromene-1,3-dione and 4.46 g of cystamine hydrochloride were suspended in 50 ml of N-methylpyrrolidone (NMP). 5.5 g of diisopropylethylamine were added and the mixture was heated, with stirring, at 120° C. After 2 hours, 50 ml of NMP were added and the mixture continued to be stirred at 120° C. for 3 h. After cooling, the precipitated product was recovered, the filtered solution was extended by addition of 200 ml of water and a second precipitate was recovered. The precipitates were washed in water and dried. 11.46 g of white powder were recovered. The analyses showed that the product conformed to the expected structure.

Step 2: 2,2'-(disulfanediyldiethane-2,1-diyl)bis[6-{[3-(dimethylamino)propyl]-amino}-1H-benzo[de]isoquinoline-1,3(2H)-dione]

4 g of (6-chloro-2-(2-{[2-(6-chloro-1,3-dioxo-1H-benzo[de]isoquinolin-2(3H)-yl)ethyl]-disulfanyl}ethyl)-1H-benzo[de]isoquinoline-1,3(2H)-dione were suspended in 40 ml of N,N-dimethylpropane-1,3-diamine. The mixture was heated with stirring at 110° C. for 12 h. After cooling, a yellow precipitate was collected, and 500 ml of a 1/1 ethanol/water mixture were added dropwise to the filtrate. The yellow paste obtained was isolated and ground with 200 ml of acetone. The solids obtained were washed with 300 ml of water and dried. 4.5 g of yellow powder were recovered. The analyses showed that the product conformed to the expected structure.

Step 3: 3,3'-{disulfanediylbis[ethane-2,1-diyl(1,3-dioxo-1H-benzo[de]isoquinoline-2,6(3H)-diyl)imino]}bis(N,N,N-trimethylpropan-1-aminium) sulfate 4 g of 6-{[3-(dimethylamino)propyl]amino}-2-[2-({2-[6-{[3-(dimethylamino)propyl]-amino}-1,3-dioxo-1H-benzo[de]isoquinolin-2(3H)-yl]ethyl}disulfanyl)ethyl]-1H-benzo-[de]isoquinoline-1,3(2H)-dione were suspended in 50 ml of dimethylformamide, and 4 ml of dimethylsulfate were added and the mixture was kept stirring at ambient temperature for 4 h. The reaction mixture was poured into 500 ml of ethyl acetate. The precipitate was filtered, washed with 4 times 100 ml of ethyl acetate and dried under vacuum. 5.9 g of yellow powder were recovered. The analyses indicated that the product conformed to the expected structure. $^1$H NMR (400 MHz, DMSO-$d_6$): 2.13 (m, 4H), 3.06 (m, 4H), 3.09 (s, 18H), 3.46 (m, 4H), 4.36 (m, 4H), 6.85 (d, 2H), 7.71 (m, 2H), 7.82 (t, 2H), 8.28 (d, 2H), 8.29 (dd, 2H), 8.45 (dd, 2H).

Example 7

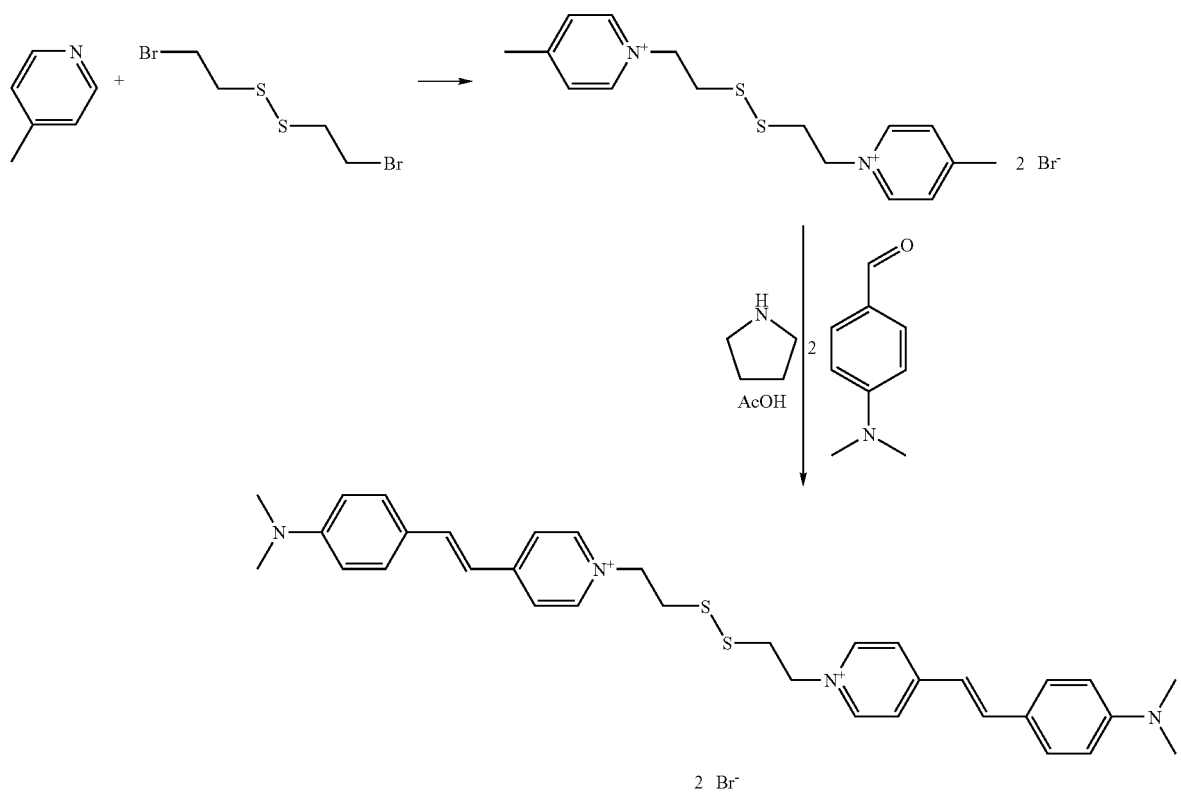

Step 1: 1,1'-(disulfanediyldiethane-2,1-diyl)bis(4-methylpyridinium) dibromide 67 g of 4-picoline were diluted in 100 ml of acetonitrile and the mixture was brought to 80° C. A mixture of 60 g of 1-bromo-2-[(2-bromoethyl)disulphanyl]ethane and 15 ml of N-methylpyrrolidone (NMP) was added over 5 min. After stirring for 4 h at 85° C., the mixture was cooled. The solid obtained was filtered, rinsed with 3×200 ml of acetonitrile then dissolved in 800 ml of isopropanol (under reflux). After cooling, 1 l of ethyl ether was added. The precipitate formed was filtered, rinsed with 3×200 ml of ethyl ether, then dried. The off-white powder obtained (73.77 g) very predominantly contained (>90%) the expected product which was used as such for the following step.

Step 2: 1,1'-(disulfanediyldiethane-2,1-diyl)bis (4-{(E)-2-[4-(dimethylamino)phenyl]vinyl}pyridinium) dibromide 13.2 g of 4-dimethylaminobenzaldehyde were suspended in 100 ml of methanol. 6.2 g of pyrrolidine then 5.3 g of acetic acid diluted in 20 ml of methanol were added to the mixture (final pH: 5 to 6). 20 g of 1,1'-(disulfanediyldiethane-2,1-diyl) bis(4-methylpyridinium) dibromide obtained in the preceding step, dissolved in 80 ml of methanol, were introduced, then the reaction mixture was diluted by addition of 100 ml of methanol. After stirring for 21 h at ambient temperature, a first precipitate was recovered, washed with 3×100 ml of ethanol then 3×200 ml of ethyl acetate and dried (yielding red powder, 7.4 g), then a second precipitate formed in the filtrate was also recovered and dried (red powder, 11.44 g). The analyses indicated that the two fractions conformed to the expected structure. $^1$H NMR (400 MHz, MeOH-$d_4$): 3.02 (s, 12H), 3.42 (t, 4H), 4.74 (t, 4H), 6.77 (d, 4H), 7.19 (d, 2H), 7.6 (d, 4H), 7.97 (d, 2H), 8.1 (d, 4H), 8.79 (d, 4H).

IMPLEMENTATION EXAMPLES

Example 1

The following compositions were prepared (contents expressed in grams of active material):

| Composition (i) | |
| --- | --- |
| Propylene glycol | 50.5 g |
| Silica | 3 g |
| Calcium hydroxide | 45 g |
| Titanium dioxide | 1.5 g |
| Composition (ii) | |
| Disulfide direct dye (*) | 0.62 g |
| Guanidine carbonate | 7 g |
| Mineral oil | 13.5 g |

-continued

| | |
|---|---|
| Liquid paraffin | 16.5 g |
| Cetearyl alcohol, PEG-75 lanolin, behentrimonium methosulfate | 10 g |
| Alkaline agent | qs for pH = 11 |
| Demineralized water | qs for 100 g |

(*) Disulfide direct dye:

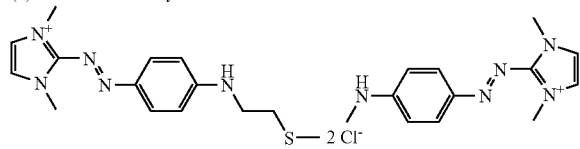

At the moment of use, 30 g of composition (i) and 235 g of composition (ii) were mixed together, then the mixture obtained was applied to curly hair containing 90% white hair for 15 minutes at ambient temperature.

After rinsing, washing with shampoo, rinsing and drying, the hair was smoothed with a comb and dyed a very intense fuchsia red shade. The coloring had very good fastness with respect to washing.

-continued

| | |
|---|---|
| glycol monostearate (23 OE) | |
| Oxyethylenated lanolin alcohol (15 OE) | 1 g |
| Oxyethylenated lanolin | 0.5 g |
| Cetyl alcohol | 1 g |
| Sodium hydroxide | 1.99 g |
| Demineralized water | qs for 100 g |

This composition was applied to curly hair containing 90% white hair for 15 minutes at ambient temperature.

After rinsing, washing with shampoo, rinsing and drying, the hair was smoothed with a comb and dyed a very intense fuchsia red shade. The coloring had very good fastness with respect to washing.

Example 3

The following compositions were prepared (contents expressed in grams of active material):

| | |
|---|---|
| Composition (i) | |
| Propylene glycol | 50.5 g |
| Silica | 3 g |
| Calcium hydroxide | 45 g |
| Titanium dioxide | 1.5 g |
| Composition (ii) | |
| Fluorescent disulfide direct dye (**) | 10 g |
| Demineralized water | qs for 100 g |
| Composition (iii) | |
| Guanidine carbonate | 7 g |
| Mineral oil | 13.5 g |
| Liquid paraffin | 16.5 g |
| Cetearyl alcohol, PEG-75 lanolin, behentrimonium methosulfate | 10 g |
| Alkaline agent | qs for pH = 13 |
| Demineralized water | qs for 100 g |

(**) Fluorescent disulfide direct dye:

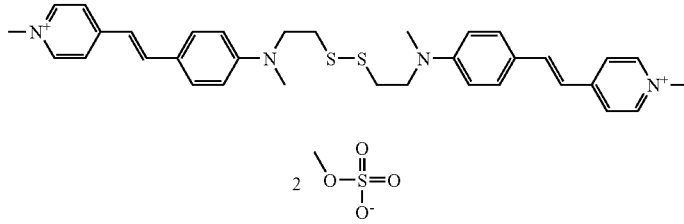

Example 2

The following composition was prepared (contents expressed in grams of active material):

| | |
|---|---|
| Disulfide direct dye (* above) | 0.62 g |
| Propylene glycol | 5.5 g |
| Liquid petroleum jelly | 13.5 g |
| Petroleum jelly | 23 g |
| Cetearyl alcohol/polyethylene | 10 g |

At the moment of use, 30 g of composition (i), 12 g of composition (ii) and 235 g of composition (iii) were mixed together, then the mixture obtained was applied to curly brown (tone level 2) hair for 20 minutes at ambient temperature.

After rinsing, washing with shampoo, rinsing and drying, the hair was smoothed with a comb and dyed a shade with a tone level 4 (chestnut brown) and a very visible mahogany tint. The coloring had very good fastness with respect to washing.

What is claimed is:

1. A composition for simultaneous shaping, dyeing, and/or lightening of keratin fibers comprising, in a cosmetically acceptable medium:
   at least one disulfide direct dye; and
   at least one alkaline agent chosen from mineral and organic hydroxides and present in the composition in an amount such that the pH of the composition ranges from 10 to 14.

2. The composition according to claim 1, wherein the at least one disulfide direct dye is chosen from compounds of Formulae (I), (II), or (III):

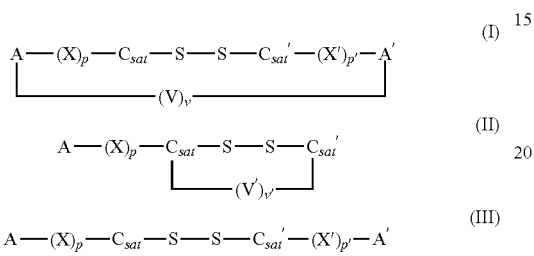

and their salts, optical isomers, geometrical isomers, and solvates, wherein:
A and A' are, independently of one another, chosen from radicals comprising at least one cationic or non-cationic chromophore;
V and V' are, independently of one another, chosen from bridging groups;
v and v are, independently of one another, chosen from 0 and 1;
X and X' are, independently of one another, chosen from:
   1) saturated and unsaturated, linear and branched $C_1$-$C_{30}$ hydrocarbon chains optionally interrupted and optionally terminated at one or both ends by one or more divalent groups or combinations thereof, chosen from:
      —N(R)—, —N⁺(R)(R)—, —O—, —S—, —CO—, and —$SO_2$— wherein R and R' are, independently of one another, chosen from hydrogen atoms and $C_1$-$C_4$ alkyl, hydroxyalkyl and aminoalkyl radicals;
      substituted and unsubstituted, saturated and unsaturated, fused and non-fused, aromatic and non-aromatic (hetero)cyclic radicals optionally comprising at least one heteroatom;
   2) a sequence -(T)$_t$-(Y)$_y$—(Z)$_z$—, said sequence being present in Formulae (I), (II), or (III) as follows:
      A-(T)$_t$-(Y)$_y$—(Z)$_z$-$C_{sat}$ or $C'_{sat}$-(T)$_t$-(Y)$_y$—(Z)$_z$-A', wherein:
      i) T is chosen from —$SO_2$—, —O—, —S—, —N(R)—, —N⁺(R)(R')—, and —CO— radicals, and combinations thereof, wherein R and R' are, independently of one another, chosen from hydrogen atoms, $C_1$-$C_4$ alkyl radicals, and $C_1$-$C_4$ hydroxyalkyl radicals; and the coefficient t is chosen from 0 and 1;
      ii) Y is chosen from:
         radicals chosen from —($CH_2$)—$SO_2$—, —CO—, —($CH_2$)$_2$—$SO_2$—, and —$CH_2$—CHR—CO—NR'— radicals, wherein R and R' are, independently of one another, chosen from hydrogen atoms and $C_1$-$C_4$ alkyl radicals;
   groups of formula (a), (a'), or (a"):

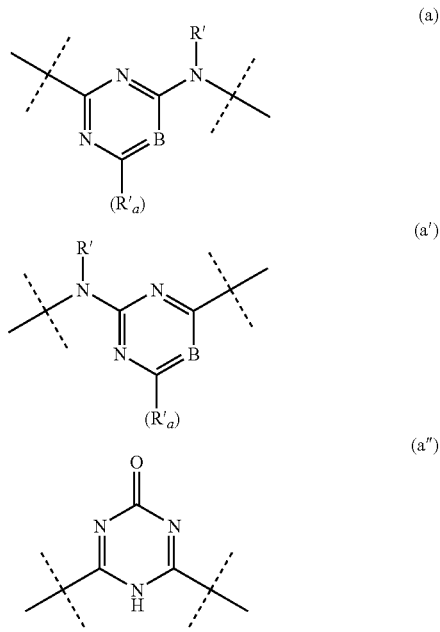

wherein:
B is chosen from —N— and —CR$_a$— radicals, wherein R$_a$ is chosen from
hydrogen atoms,
halogen atoms chosen from chlorine and fluorine,
nitro groups,
optionally substituted pyridinium groups;
hydroxyl groups;
amino, alkylamino and dialkylamino groups, wherein the alkyl radicals are chosen from linear and branched $C_1$-$C_{18}$ alkyl radicals, optionally interrupted by a heteroatom chosen from N and O, and optionally substituted with at least one hydroxyl group;
—NHNHCOR radicals wherein R is chosen from linear and branched $C_1$-$C_{10}$ alkyl radicals;
R' has the same definition as above;
R'$_a$ is chosen from:
hydrogen atoms;
halogen atoms chosen from chlorine and fluorine;
pyridinium groups, optionally substituted with at least one group R$_c$ chosen from $C_1$-$C_4$ alkyl radicals, halogen atoms, carboxyl groups —COOM (wherein M is chosen from hydrogen atoms, alkali metal atoms, ammonium groups, and ammonium groups substituted with at least one group chosen from linear and branched $C_1$-$C_{18}$ alkyl radicals, optionally bearing at least one hydroxyls), ester groups —COOR$_d$ wherein R$_d$ is chosen from $C_1$-$C_4$ alkyl radicals; amide groups —CON(R$_d$)$_2$ wherein the R$_d$ groups are, independently of one another, chosen from hydrogen atoms and $C_1$-$C_4$ alkyl radicals;
hydroxyl groups;
amino, alkylamino, and dialkylamino groups, wherein the alkyl radicals are chosen from linear and branched $C_1$-$C_{18}$ alkyl groups, optionally interrupted by a heteroatom chosen from N and O, and optionally substituted with at least one hydroxyl group;

—NHNHCOR radicals wherein R is chosen from linear and branched $C_1$-$C_{10}$ alkyl groups; groups of formula (b):

(b)

(b)

wherein:
R' has the same definition as above;
$R_b$ is chosen from:
chlorine atoms,
amino, alkylamino, and dialkylamino groups, wherein the alkyl radicals are chosen from linear and branched $C_1$-$C_{18}$ alkyl groups, optionally interrupted by a heteroatom chosen from N, O, and S, and optionally substituted with at least one hydroxyl,
saturated and unsaturated heterocycles comprising at least one nitrogen atom and optionally substituted, and
arylamino groups;
and y is chosen from 0 and 1;

iii) Z is chosen from:
—$(CH_2)_m$— radicals wherein m is an integer ranging from 1 to 8
—$(CH_2CH_2O)_q$— and —$(OCH_2CH_2)_q$— radicals wherein q is an integer ranging from 1 to 15,
aryl, alkylaryl, and arylalkyl radicals wherein the alkyl radicals are chosen from $C_1$-$C_4$ alkyl radicals and the aryl radicals are optionally substituted with at least one group —SOW wherein M is chosen from hydrogen atoms, alkali metal atoms, and ammonium groups optionally substituted with at least one linear or branched $C_1$-$C_{18}$ alkyl radical optionally bearing at least one hydroxyl; and
z is chosen from 0 and 1;

p and p' are, independently of one another, chosen from 0 and 1;

$C_{sat}$ and $C'_{sat}$ are, independently of one another, chosen from optionally substituted cyclic, linear, and branched $C_1$-$C_{18}$ alkylene chains; and D is chosen from hydroxyl, hydroxyalkyl, alkoxy, carboxyl, carboxylate, amino, alkylamino, and dialkylamino radicals.

3. The composition according to claim 2, wherein, in Formulae (I), (II), or (III), when p is equal to 1, X represents the sequence -$(T)_t$-$(Y)_y$—$(Z)_z$—, and when p' is equal to 1, X' represents the sequence -$(T)_t$-$(Y)_y$—$(Z)_z$—, said sequence being present in Formulae (I), (II) or (III) as follows:

A-$(T)_t$-$(Y)_y$—$(Z)_z$-$C_{aat}$ or $C'_{sat}$-$(T)_t$-$(Y)_y$—$(Z)_z$-K,
wherein:

i) T is chosen from —$SO_2$—, —O—, —S—, —N(R)—, —$N^+(R)(R')$, and —CO—, and combinations thereof, wherein R and R" are, independently of one another, chosen from hydrogen atoms, $C_1$-$C_4$ alkyl radicals, and $C_1$-$C_4$ hydroxyalkyl radicals; and the coefficient t is chosen from 0 and 1;

ii) Y is chosen from:
radicals chosen from —$(CH_2)_2$—$SO_2$— and —$CH_2$—CHR—CO—NR'— radicals wherein R and R" are, independently of one another, chosen from hydrogen atoms and $C_1$-$C_4$ alkyl radicals;
groups of formula (a), (a'), or (a"):

(a)

(a')

(a")

wherein:
B is chosen from —N— and —$CR_a$-radicals, wherein $R_1$ is chosen from:
hydrogen atoms,
halogen atoms chosen from chlorine or fluorine,
nitro groups,
optionally substituted pyridinium groups;
hydroxyl groups;
amino, alkylamino, and dialkylamino groups, wherein the alkyl radicals are chosen from linear and branched $C_1$-$C_{18}$ alkyl radicals, optionally interrupted by a heteroatom chosen from N and O, and optionally substituted with at least one hydroxyl groups;
—NHNHCOR radicals wherein R is chosen from linear and branched $C_1$-$C_{10}$ alkyl radicals;
R' has the same definition as above;
$R'_a$ is chosen from:
hydrogen atoms;
halogen atoms chosen from chlorine and fluorine;
pyridinium groups, optionally substituted with at least one group $R_c$ chosen from $C_1$-$C_4$ alkyl radicals, halogen atoms, carboxyl groups —COOM (wherein M is chosen from hydrogen atoms, alkali metal atoms, ammonium groups, and ammonium groups substituted with at least one group chosen from linear and branched $C_1$-$C_{18}$ alkyl radicals, optionally bearing at least one hydroxyl); ester groups —COOR$_d$ wherein R$_d$ is chosen from C$_1$-C$_4$ alkyl radicals; amide groups —CON(R$_d$)$_2$ wherein the R$_d$ groups are, independently of one another, chosen from hydrogen atoms and C$_1$-C$_4$ alkyl radicals;

hydroxyl groups;

amino, alkylamino, and dialkylamino groups, wherein the alkyl radicals are chosen from linear and branched C$_1$-C$_{18}$ alkyl groups, optionally interrupted by a heteroatom chosen from N and O, and optionally substituted with at least one hydroxyl group;

—NHNHCOR radicals wherein R is chosen from linear and branched C$_1$-C$_{10}$ alkyl groups;

groups of formula (b):

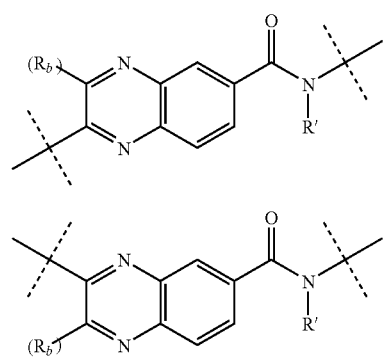

(b)

wherein:
R' has the same definition as above;
R$_b$ is chosen from:
chlorine atoms;
amino, alkylamino, and dialkylamino groups, wherein the alkyl radicals are chosen from linear and branched C$_1$-C$_{18}$ alkyl groups, optionally interrupted by a heteroatom chosen from N, O, and S, and optionally substituted with at least one hydroxyl;
saturated and unsaturated heterocycles comprising at least one nitrogen atom and optionally substituted, and
arylamino groups;
and y is equal to 0 or 1;
iii) Z is chosen from:
—(CH$_2$)$_m$— radicals wherein m is an integer ranging from 1 to 8
—(CH$_2$CH$_2$O)$_q$— and —(OCH$_2$CH$_2$)$_q$— radicals wherein q is an integer ranging from 1 to 15
aryl, alkylaryl, and arylalkyl radicals wherein the alkyl radicals are chosen from C$_1$-C$_4$ alkyl radicals and the aryl radicals are optionally substituted with at least one group —SO$_3$M wherein M is chosen from hydrogen atoms, alkali metal atoms, and ammonium groups optionally substituted with at least one linear or branched C$_1$-C$_{18}$ alkyl radical optionally bearing at least one hydroxyl; and
z is chosen from 0 and 1.

4. The composition according to claim 2, wherein Y is chosen from the groups:

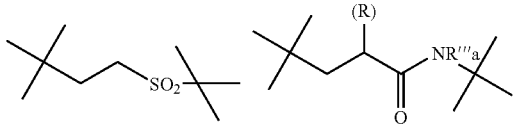

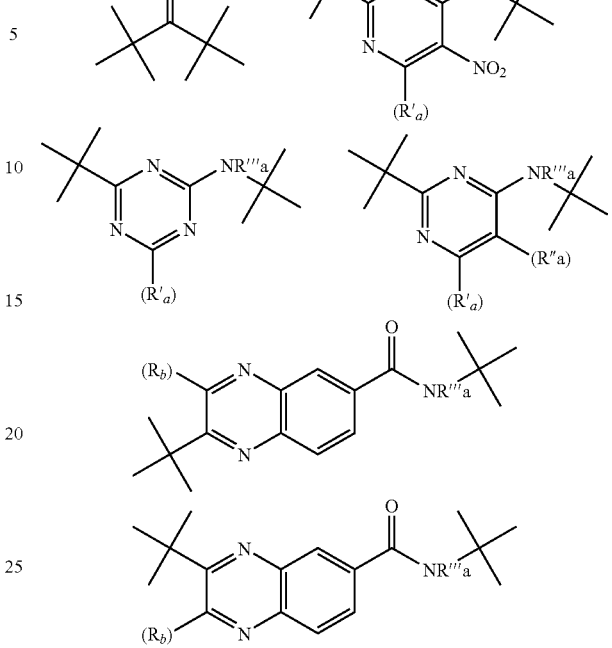

wherein the radicals R, R'$_a$, and R$_b$ have the meanings given in claim 2; R"$_a$ has the same definition as R'$_a$, wherein R"$_a$ and R'$_a$ are chosen independently of each other; and R'''$_a$ is chosen from hydrogen atoms and C$_1$-C$_4$ alkyl radicals.

5. The composition according to claim 2, wherein Z is chosen from:

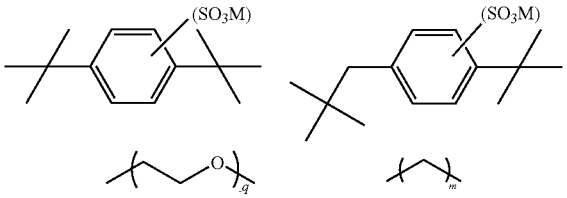

wherein M, q, and m have the meanings given in claim 2.

6. The composition according to claim 2, wherein the at least one disulfide direct dye of formula (I) is chosen such that v is equal to 0.

7. The composition according to claim 2, wherein, in Formulae (I), (II), or (III), A and A' are chosen from radicals comprising at least one chromophore derived from dyes of the following type: acridines, acridones, anthranthrones, anthrapyrimidines, anthraquinones, azines, azos, azomethines, benzanthrones, benzimidazoles, benzimidazolones, benzindoles, benzoxazoles, benzopyrans, benzothiazoles, benzoquinones, bisazines, bisisoindolines, carboxanilides, coumarins, cyanins, diazines, diketopyrrolopyrroles, dioxazines, diphenylamines, diphenylmethanes, dithiazines, flavonoids, fluorindines, formazans, hydrazones, hydroxy ketones, indamines, indanthrones, indigoids and pseudo-indigoids, indophenols, indoanilines, isoindolines, isoindolinones, isoviolanthrones, lactones, methines, naphthalimides, naphthanilides, naphtholactams, naphthoquinones, nitro dyes, oxadiazoles, oxazines, perilones, perinones, perylenes, phenazines, phenothiazines, phthalocyanin, polyenes/carotenoids, porphyrins, pyranthrones, pyrazolanthrones, pyrazolones, pyrimidinoanthrones, pyronines, quinacridones, quinolines, quinophthalones, squaranes, stilbenes, tetrazoliums, thiazines, thioindigo, thiopyronines, triarylmethanes and xanthenes.

8. The composition according to claim 7, wherein, in Formulae (I), (II), or (III), A and A' are chosen from radicals comprising a chromophore chosen from chromophores of the azo, anthraquinone, and hydrazone type.

9. The composition according to claim 1, wherein the at least one disulfide direct dye is chosen from:

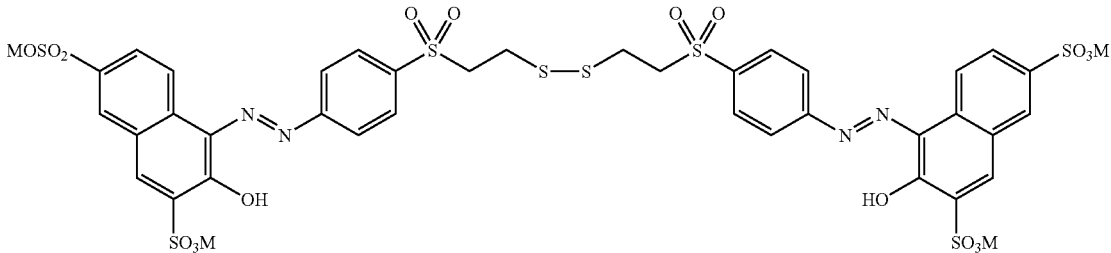

and the following compounds, in acidic, basic or neutralized form:

(1)

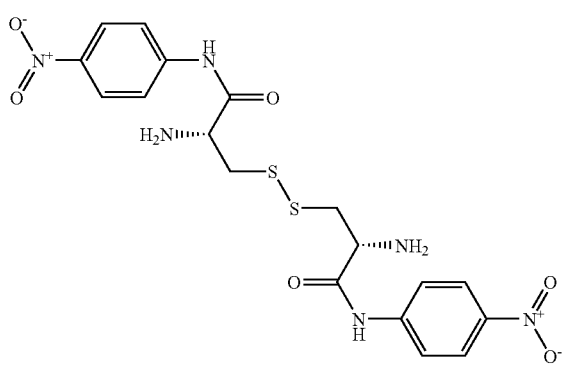

(2)

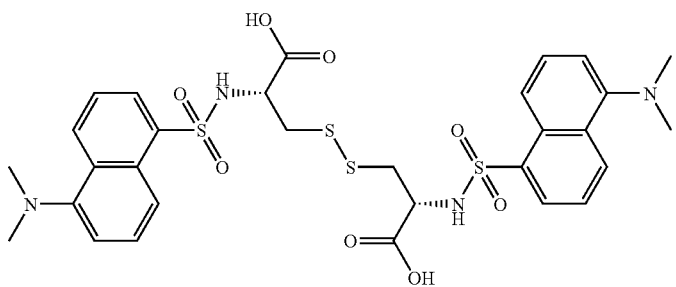

(3)

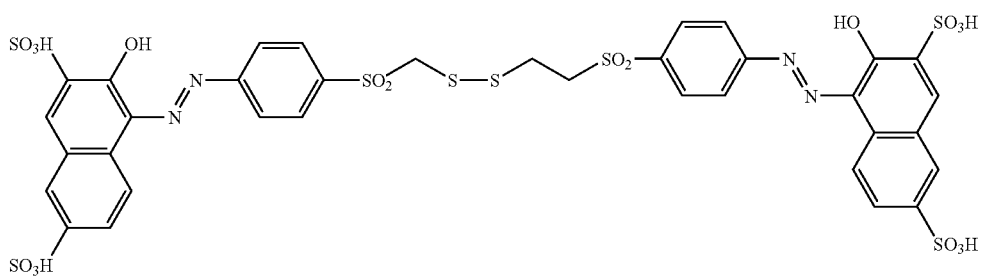

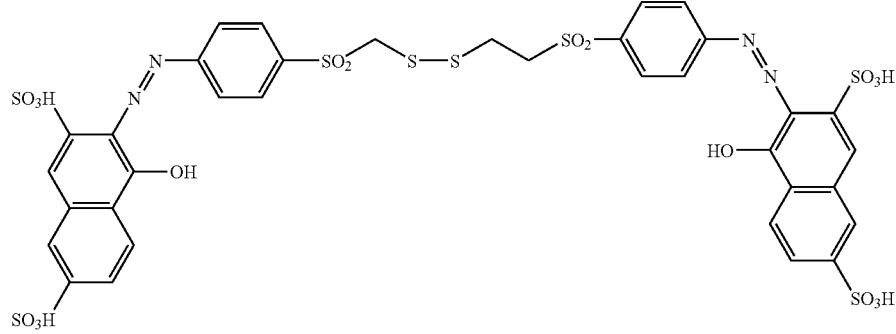
(4)
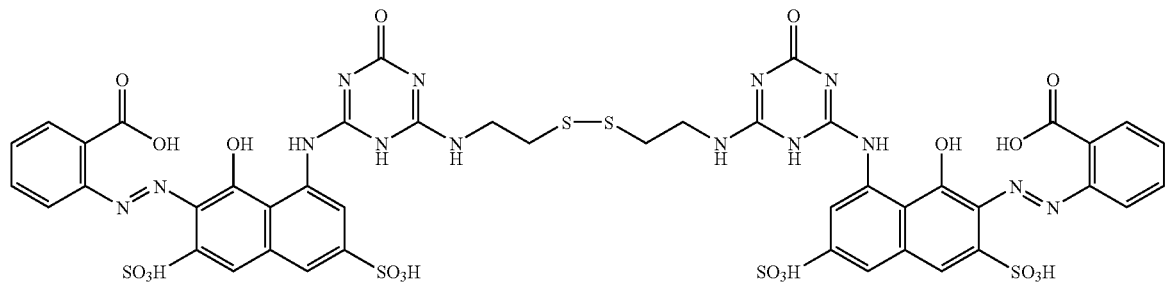
(5)
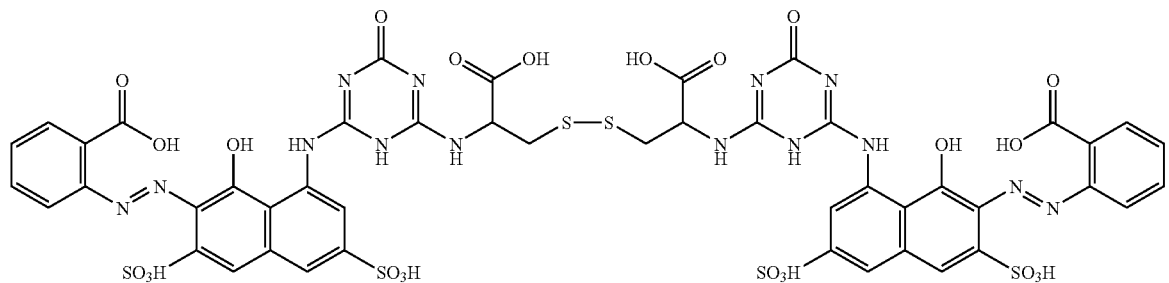
(6)
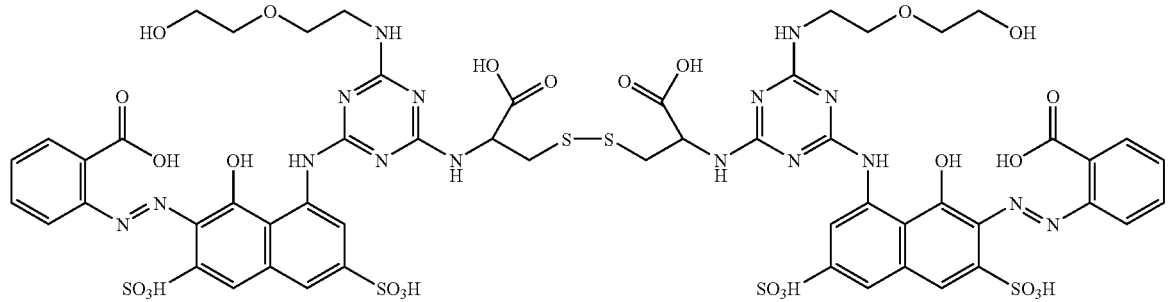
(7)
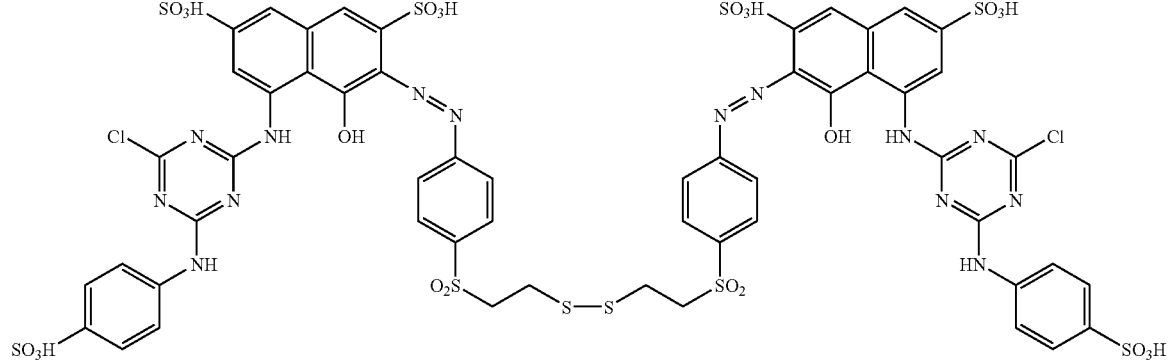
(8)

-continued
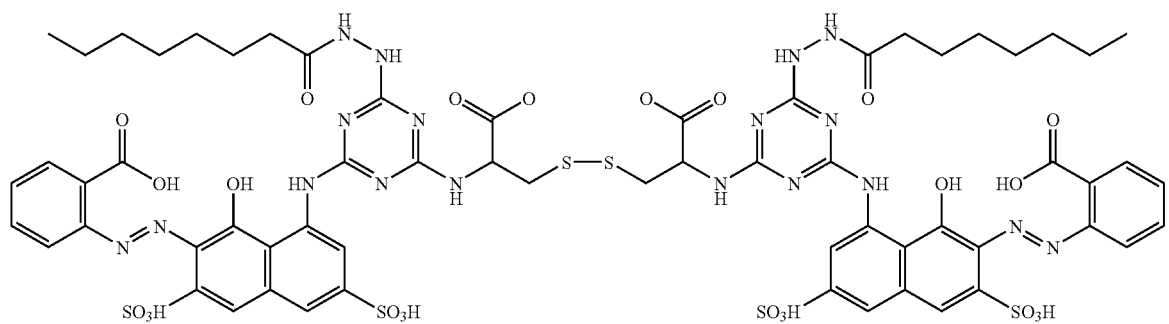
(9)
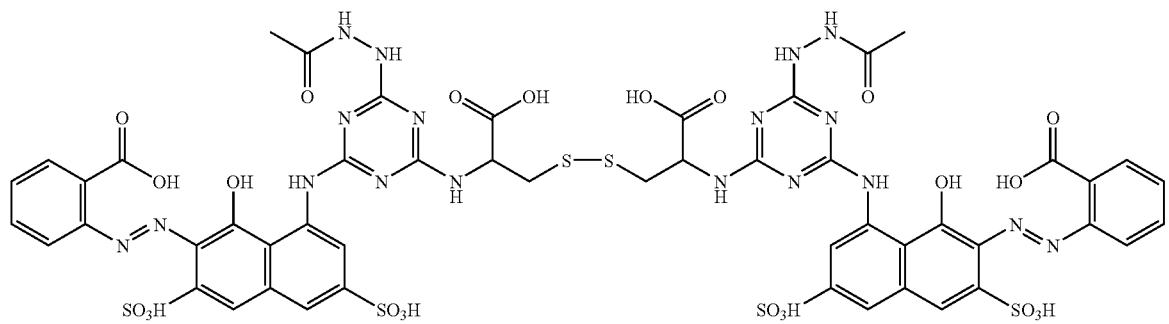
(10)
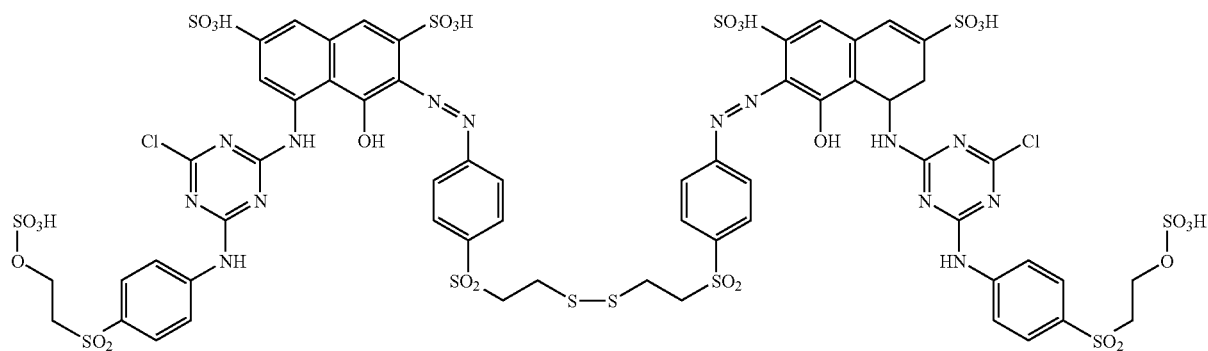
(11)
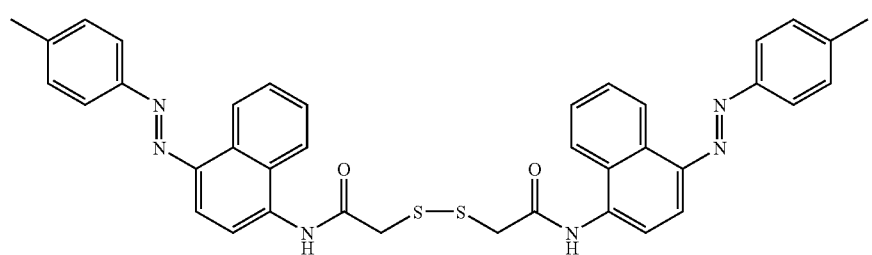
(12)
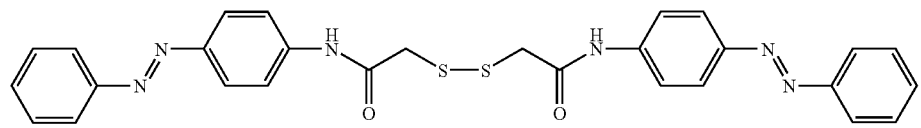
(13)
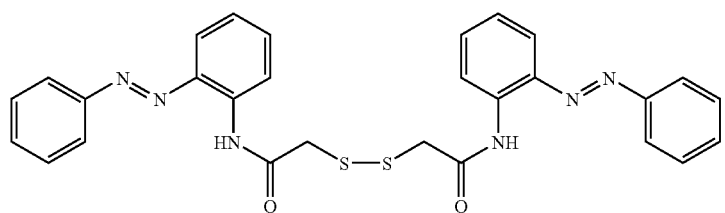
(14)

-continued
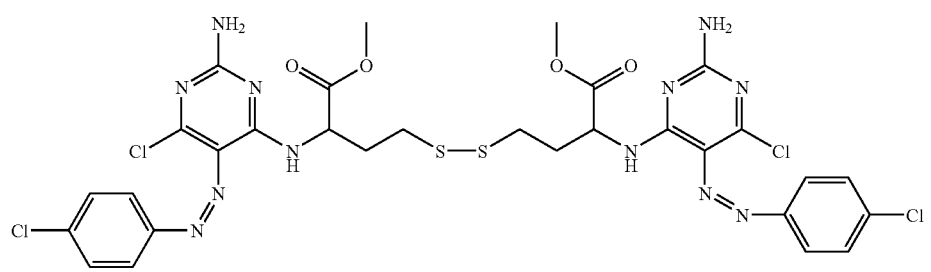
(15)
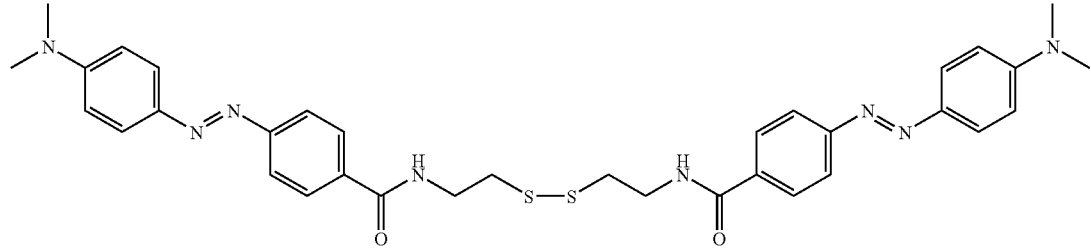
(16)
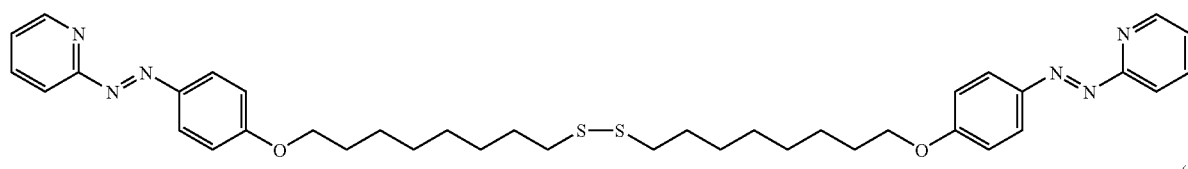
(17)
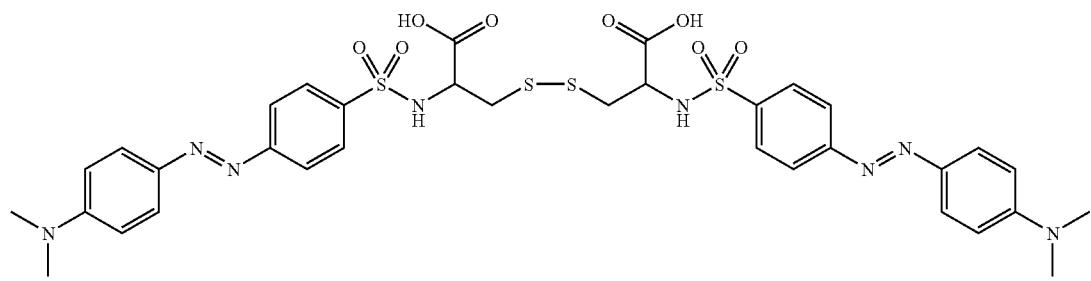
(18)
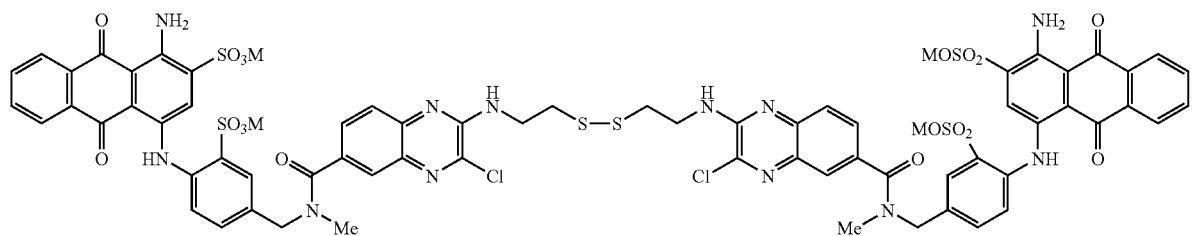
(19)
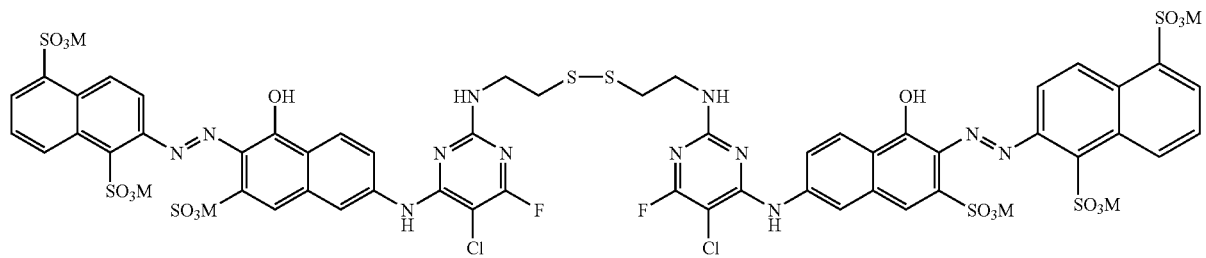
(20)

wherein M is chosen from hydrogen atoms, alkali metal atoms, ammonium groups, and ammonium groups substituted with at least one radical chosen from linear and branched $C_1$-$C_{10}$ alkyl radicals optionally bearing at least one hydroxyl;
and the following compounds, and their salts, hydrates, and solvates:

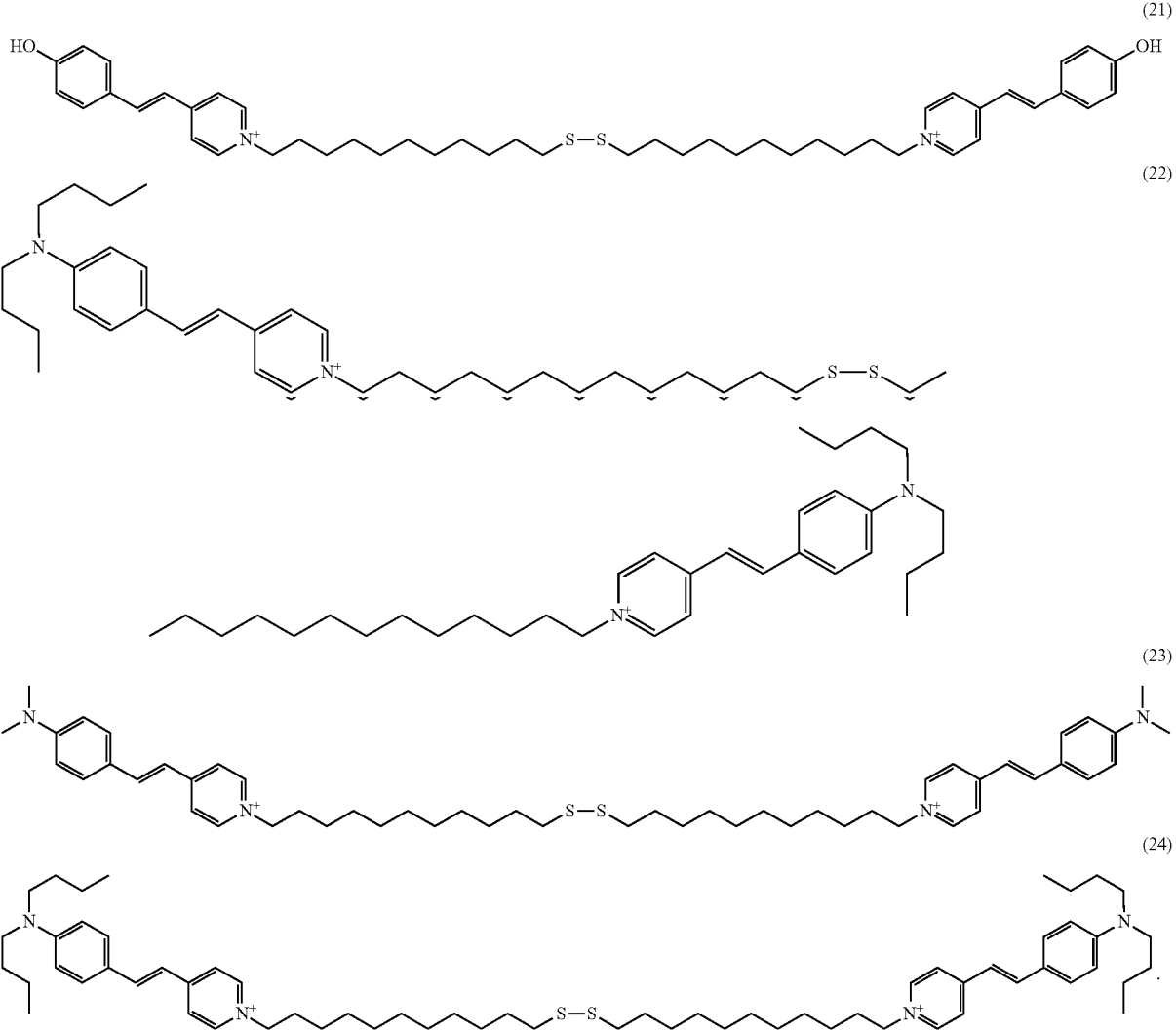

10. The composition according to claim 2, wherein, in Formulae (I), (II), or (III), at least one of A and A' comprises a cationic chromophore.

11. The composition according to claim 10, wherein the cationic chromophore comprises a cationic radical which is a quaternary ammonium.

12. The composition according to claim 2, wherein the at least one disulfide direct dye is a dye of Formula (I), (II), or (III) in which at least one of A and A' is chosen from radicals comprising one or more cationic or non-cationic fluorescent chromophores.

13. The composition according to claim 12, wherein at least one of A and A' comprises a styryl chromophore.

14. The composition according to claim 2, wherein X and X' are, independently of one another, chosen from —N(R)— groups.

15. The composition according to claim 2, wherein the at least one disulfide direct dye is chosen such that v or v' is equal to 0, and A and A' are, independently of one another, chosen from W—N=N—Ar—, —W—N=N—Ar, W—C($R^c$)=C($R^d$)—Ar—, and —W—C($R^c$)=C($R^d$)—Ar groups, wherein W is chosen from fused and non-fused, aromatic and non-aromatic heterocycles comprising a quaternary ammonium; Ar is chosen from (hetero)aryl radicals having from 5 to 6 ring members, and (hetero)aromatic bicyclic rings of naphthyl, benzopyridinium, indolinyl, or benzoindolinyl type, optionally substituted with at least one group chosen from halogen atoms, alkyl groups, hydroxyl groups, alkoxy groups, hydroxyalkyl groups, amino and (di)alkylamino groups, acylamino groups; heterocycloalkyl and heteroaryl groups having from 5 to 6 ring members; and wherein $R^c$ and $R^d$ are, independently of one another, chosen from hydrogen atoms and $C_1$-$C_4$ alkyl groups.

16. The composition according to claim 15, wherein W is chosen from imidazolium, pyridinium, benzopyridinium, benzimidazolium, quinolinium, pyrazolium, and benzothiazolium groups.

17. The composition according to claim 1, wherein the at least one disulfide direct dye is chosen from:

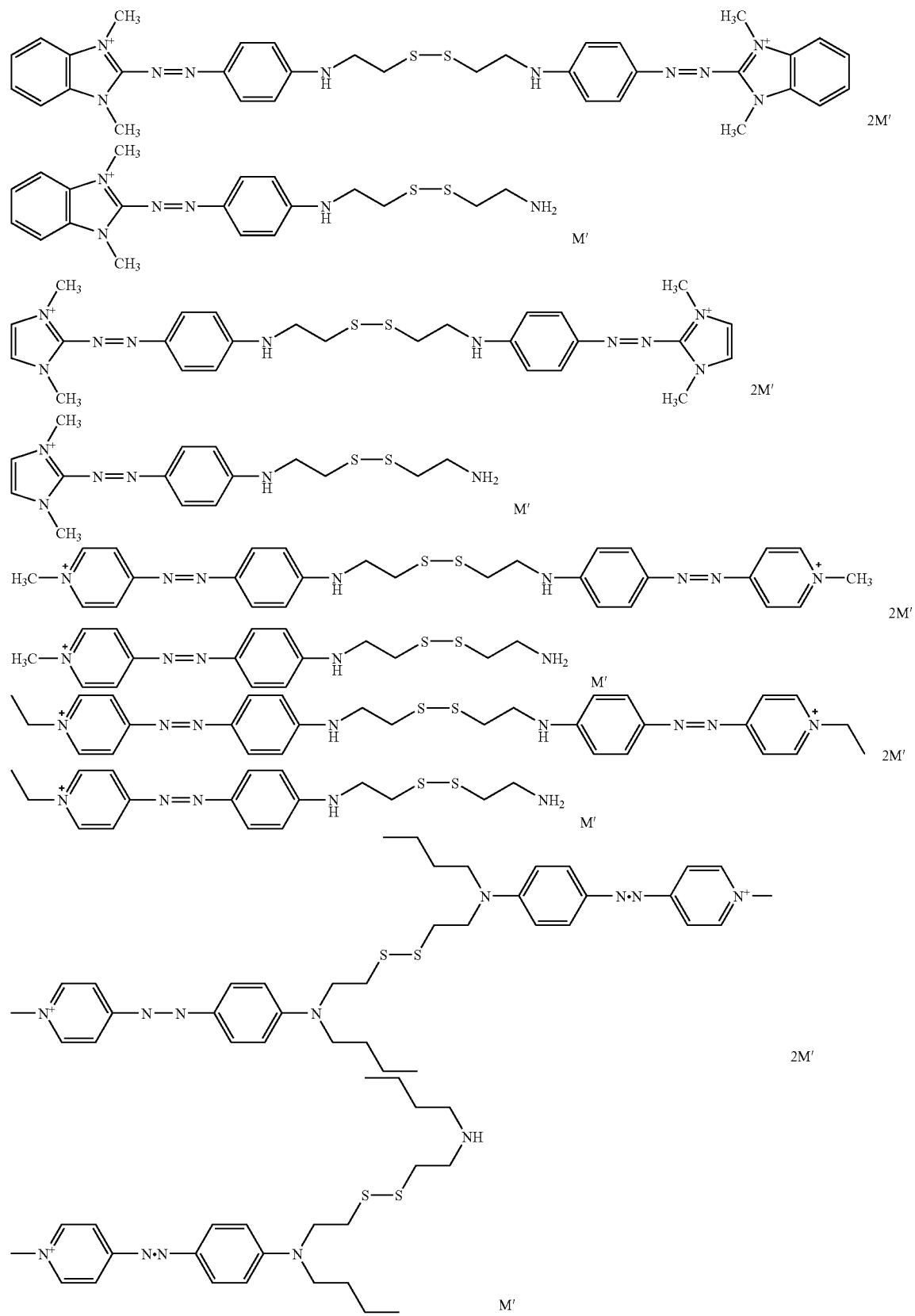
wherein M' is chosen from organic and mineral acid salts.

18. The composition according to claim 1, wherein the at least one disulfide direct dye is chosen from:
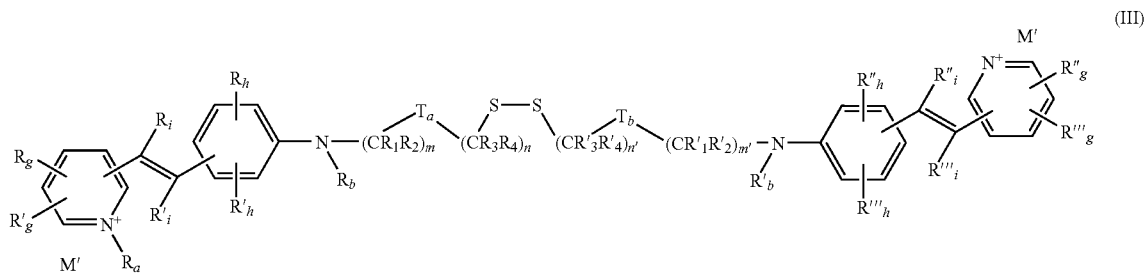
(III)
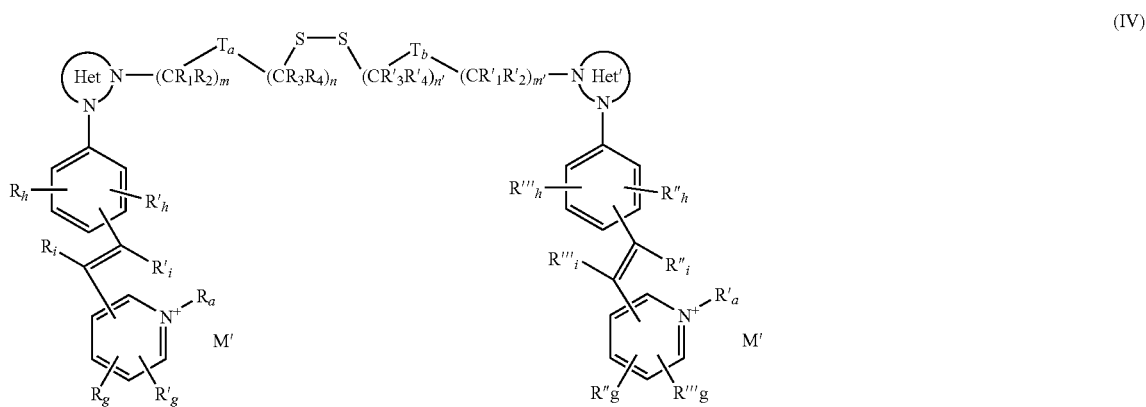
(IV)
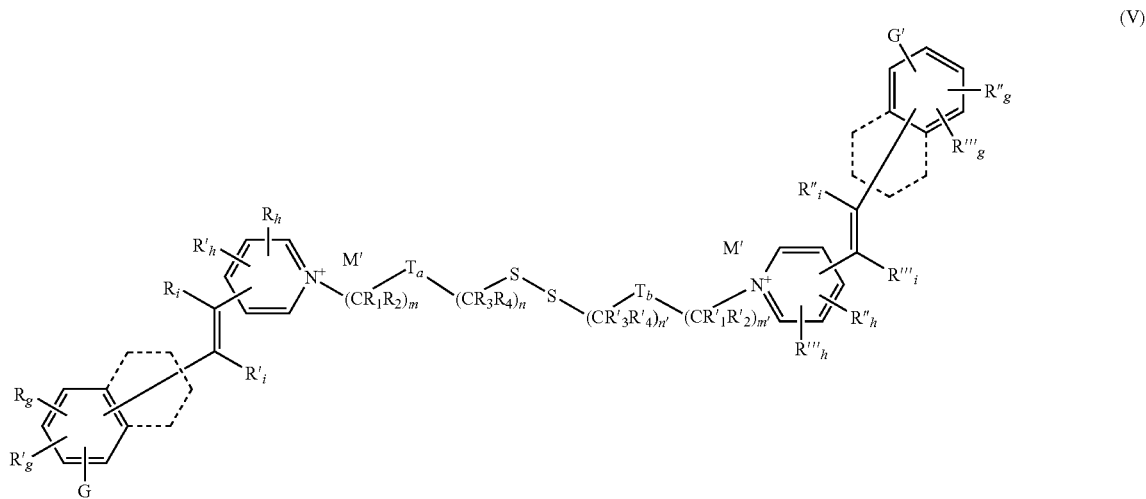
(V)
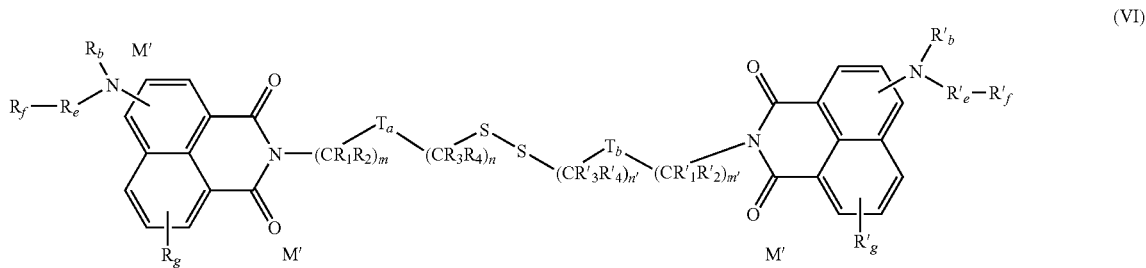
(VI)

(VII)
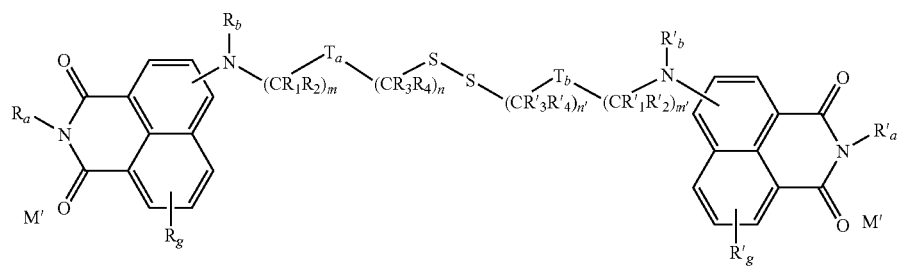
(VIII)
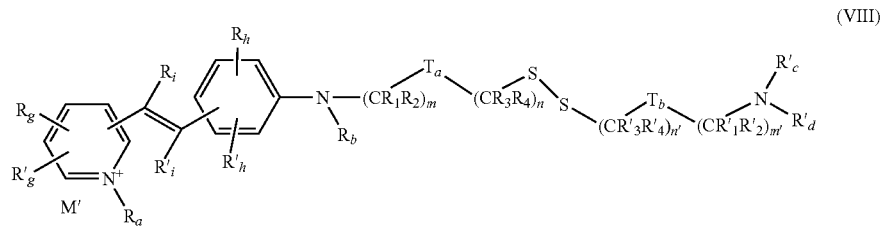
(IX)
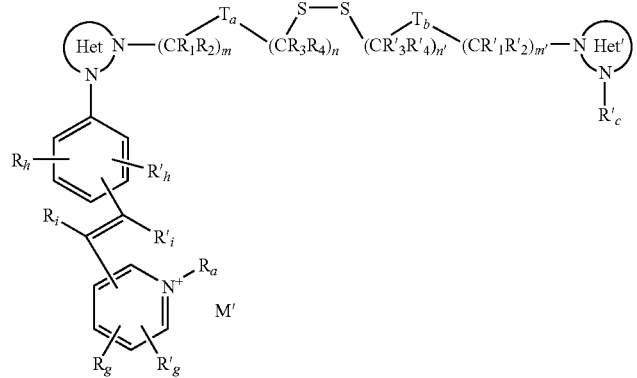
(X)
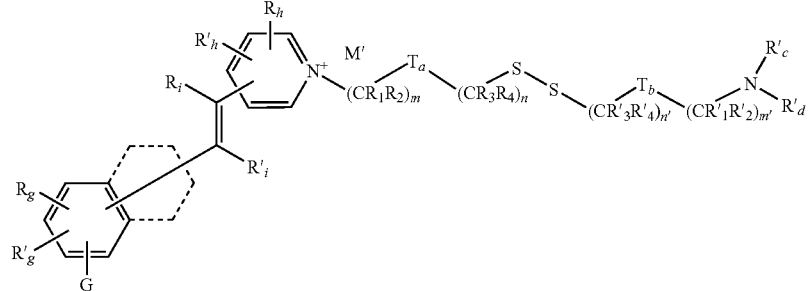
(XI)
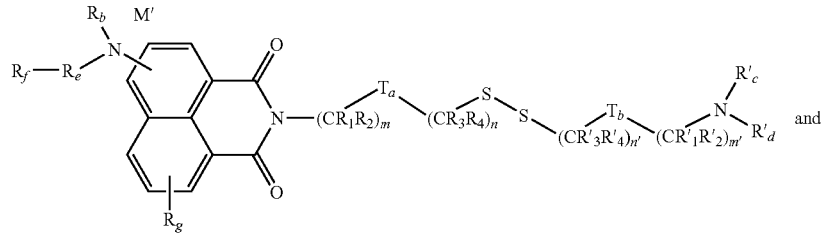
and -continued

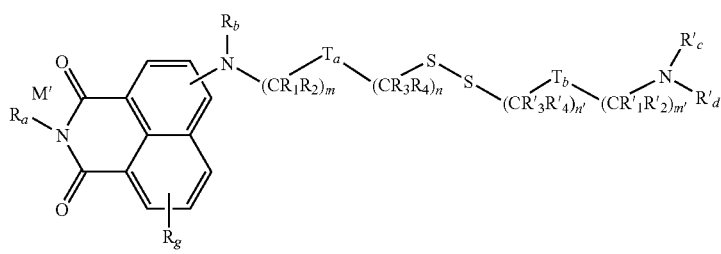

(XII)

wherein:
- G and G' are, independently of one another, chosen from optionally substituted —$NR_cR_d$—, —$NR'_cR_d$—, and $C_1$-$C_6$ alkoxy groups;
- $R_a$ and $R'_a$ are, independently of one another, chosen from aryl($C_1$-$C_4$)alkyl and $C_1$-$C_6$ alkyl groups optionally substituted with hydroxyl, amino, $C_1$-$C_4$ alkylamino, and $C_1$-$C_4$ dialkylamino groups, said alkyl radicals possibly forming, with the nitrogen atom which bears them, a heterocycle comprising from 5 to 7 ring members, optionally comprising another heteroatom;
- $R_b$, $R'_b$ are, independently of one another, chosen from hydrogen atoms, aryl($C_1$-$C_4$)alkyl groups, and $C_1$-$C_6$ alkyl groups which are optionally substituted;
- $R_c$, $R'_c$, $R_d$ and $R'_d$ are, independently of one another, chosen from hydrogen atoms, aryl($C_1$-$C_4$)alkyl, $C_1$-$C_6$ alkoxy, and optionally substituted $C_1$-$C_6$ alkyl groups;
- or else two adjacent radicals $R_c$ and $R_d$, or $R'_c$ and $R'_d$, borne by the same nitrogen atom together form a heterocyclic or heteroaryl group;
- $R_e$ and $R'_e$ are, independently of one another, chosen from optionally unsaturated, linear and branched, divalent $C_1$-$C_6$ alkylenyl hydrocarbon chains;
- $R_f$ and $R'_f$ are, independently of one another, chosen from quaternary ammonium groups (R")(R''')(R'''')$N^+$— where R", R''' and R'''' are, independently of one another, chosen from hydrogen atoms and $C_1$-$C_4$ alkyl groups, or else (R")(R''')(R'''')$N^+$— represents an optionally substituted cationic heteroaryl group;
- $R_g$, $R'_g$, $R''_g$, $R'''_g$, $R_h$, $R'_h$, $R''_h$, and $R'''_h$ are, independently of one another, chosen from hydrogen atoms, halogen atoms, amino, $C_1$-$C_4$ alkylamino, $C_1$-$C_4$ dialkylamino, cyano, carboxy, hydroxyl, and trifluoromethyl groups, acylamino, $C_1$-$C_4$ alkoxy, (poly)hydroxy($C_2$-$C_4$)alkoxy, alkylcarbonyloxy, alkoxycarbonyl, and alkylcarbonylamino radicals, acylamino, carbamoyl, and alkylsulfonylamino radicals, aminosulfonyl radicals, and $C_1$-$C_{16}$ alkyl radicals optionally substituted with a group chosen from $C_1$-$C_{12}$ alkoxy, hydroxy, cyano, carboxy, amino, $C_1$-$C_4$ alkylamino, and $C_1$-$C_4$ dialkylamino groups, or else the two alkyl radicals borne by the nitrogen atom of the amino group form a heterocycle comprising from 5 to 7 ring members and optionally comprising another heteroatom;
- or else two groups $R_g$ and $R'_g$; $R''_g$ and $R'''_g$; $R_h$ and $R'_h$; $R''_h$ and $R'''_h$; borne by two adjacent carbon atoms together form a benzo or indeno ring, or a fused heterocycloalkyl or fused heteroaryl group; the benzo, indeno, heterocycloalkyl or heteroaryl ring optionally being substituted with at least one group chosen from halogen atoms, amino, $C_1$-$C_4$ alkylamino, $C_1$-$C_4$ dialkylamino, nitro, cyano, carboxy, hydroxyl, and trifluoromethyl groups, acylamino, $C_1$-$C_4$ alkoxy, (poly)hydroxy($C_2$-$C_4$)alkoxy, alkylcarbonyloxy, alkoxycarbonyl, and alkylcarbonylamino radicals, acylamino, carbamoyl, and alkylsulfonylamino radicals, aminosulfonyl radicals, and $C_1$-$C_{16}$ alkyl radicals optionally substituted with a group chosen from $C_1$-$C_{12}$ alkoxy, hydroxy, cyano, carboxy, amino, $C_1$-$C_4$ alkylamino, and $C_1$-$C_4$ dialkylamino groups, or else the two alkyl radicals borne by the nitrogen atom of the amino group form a heterocycle comprising from 5 to 7 ring members and optionally comprising another heteroatom;
- or else when G is chosen from —$NR_cR_d$ groups and G' is chosen from —$NR'_cR'_d$ groups, two groups $R_c$ and $R'_g$; $R'_c$ and $R''_g$; $R_d$ and $R_g$; or $R'_d$ and $R'''_g$ together form a saturated heteroaryl or heterocycle, optionally substituted with a $C_1$-$C_6$ alkyl group;
- $R_i$, $R'_i$, $R''_i$, and $R'''_i$ are, independently of one another, chosen from hydrogen atoms and $C_1$-$C_4$ alkyl groups;
- $R_1$, $R_2$, $R_3$, $R_4$, $R'_1$, $R'_2$, $R'_3$ and $R'_4$ are, independently of one another, chosen from hydrogen atoms and $C_1$-$C_4$ alkyl, $C_1$-$C_{12}$ alkoxy, hydroxy, cyano, carboxy, amino, $C_1$-$C_4$ alkylamino, and $C_1$-$C_4$ dialkylamino groups, said alkyl radicals possibly forming with the nitrogen atom that bears them, a heterocycle comprising from 5 to 7 ring members, optionally comprising another heteroatom;
- $T_a$ and $T_b$ are, independently of one another, chosen from: i) a covalent bond a, ii) a group chosen from —$SO_2$—, —O—, —S—, —N(R)—, —$N^+$(R)($R^\circ$)—, and —CO— radicals, and combinations thereof, wherein R and $R^\circ$ are, independently of one another, chosen from hydrogen atoms, $C_1$-$C_4$ alkyl, $C_1$-$C_4$ hydroxyalkyl radical, and aryl($C_1$-$C_4$)alkyl radicals; and iii) cationic and non-cationic heterocycloalkyl and heteroaryl radicals;

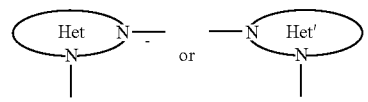

are, independently of one another, chosen from optionally substituted heterocyclic groups;

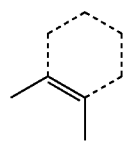

is chosen from aryl and heteroaryl groups fused to the phenyl ring; or else lacking the phenyl ring;

m, m', n and n' are, independently of one another, chosen from integers ranging from 0 to 6, wherein m+n and m'+n' are, independently of one another, chosen from integers ranging from 1 to 10; and M' is chosen from organic and mineral acid salts.

19. The composition according to claim 1, wherein the at least one disulfide direct dye is chosen from:

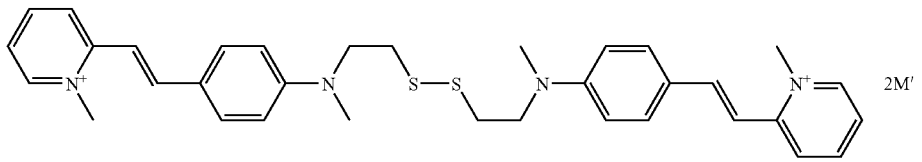

2M'

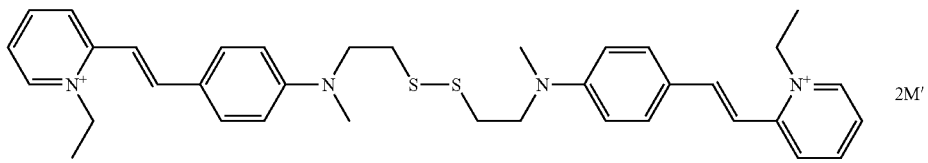

2M'

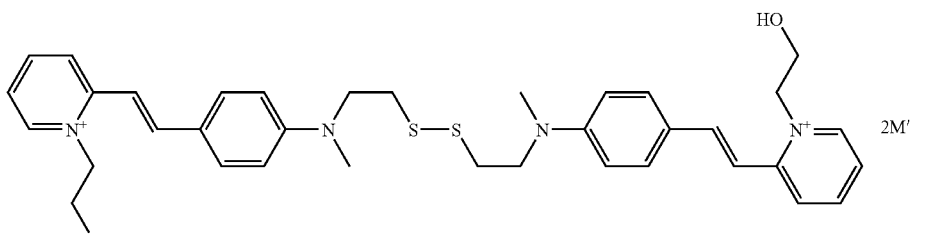

2M'

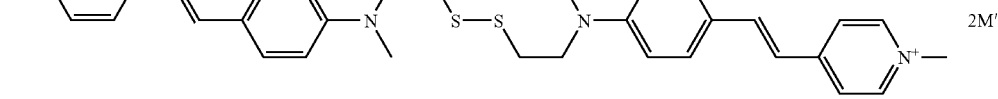

2M'

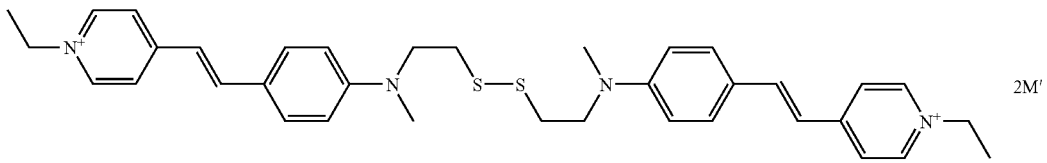

2M'

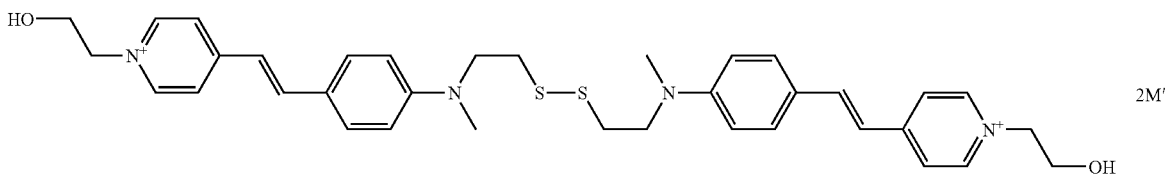

2M'

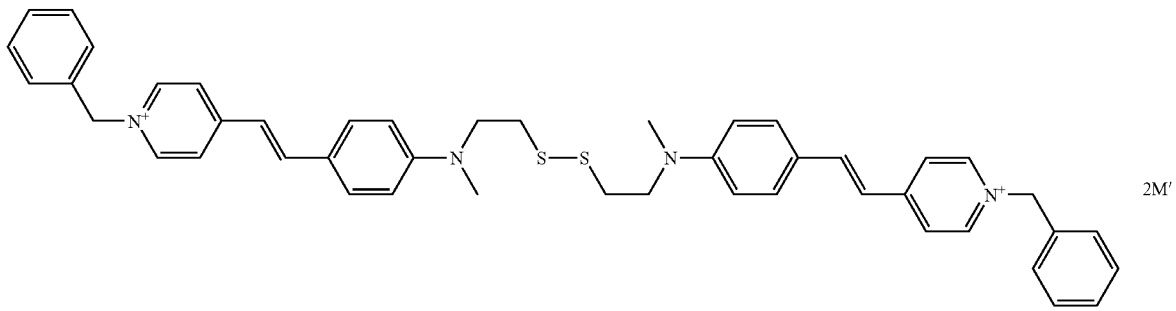

2M'

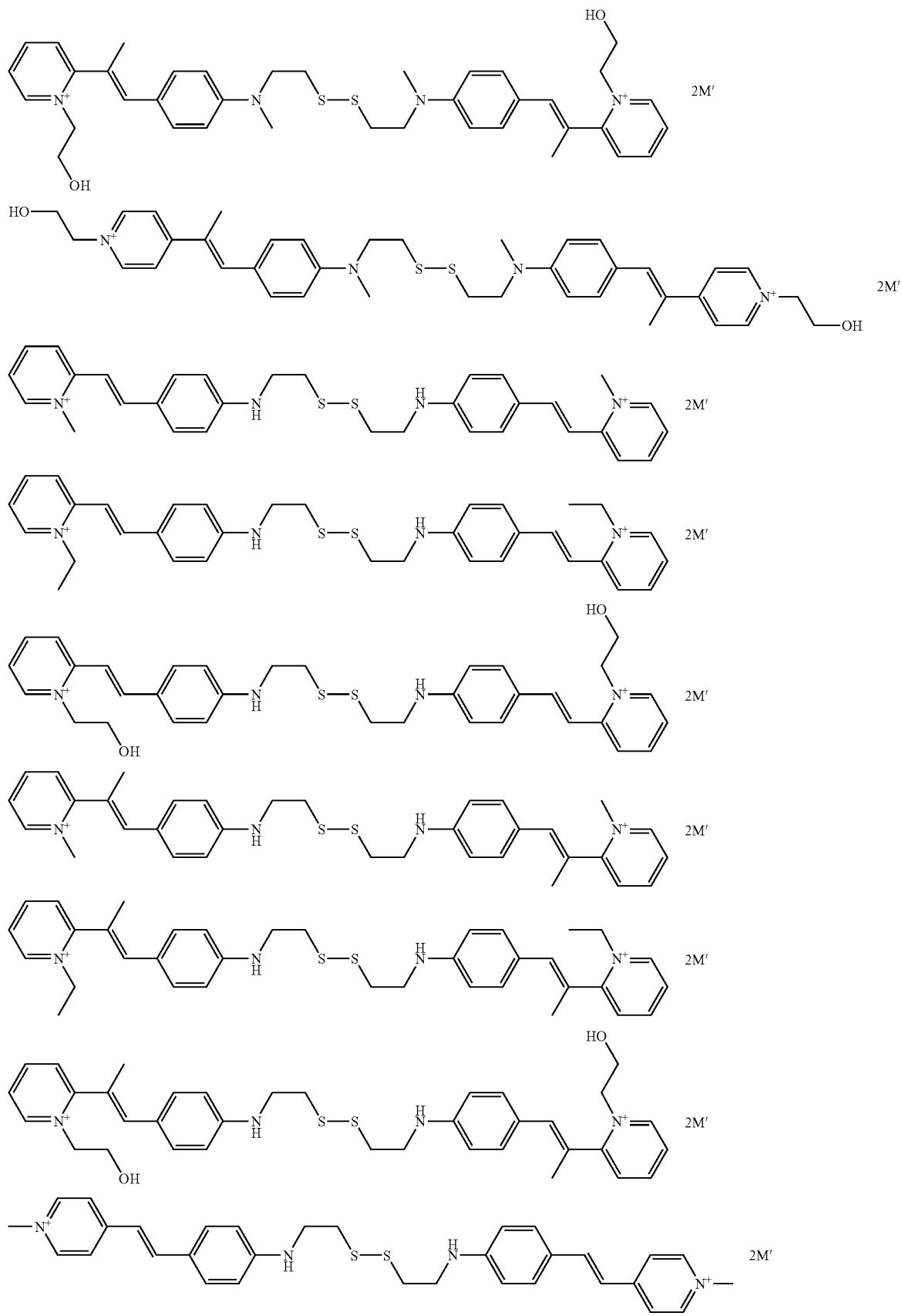

-continued
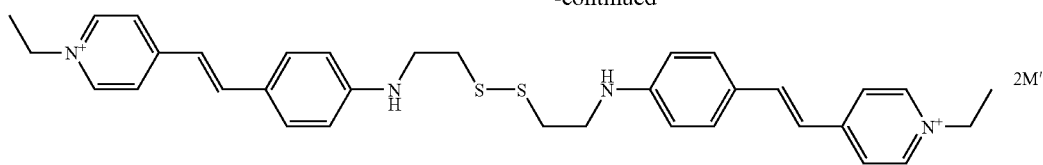
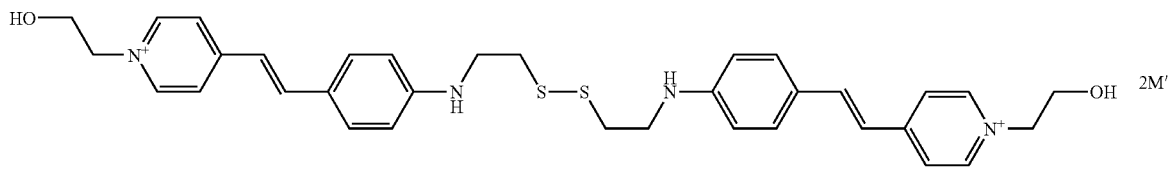
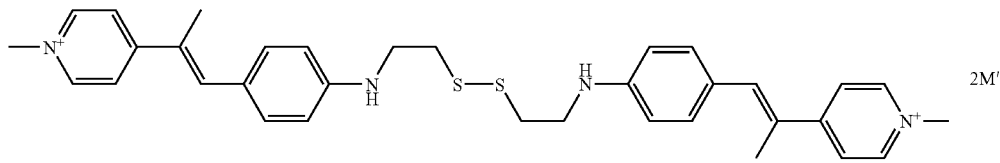
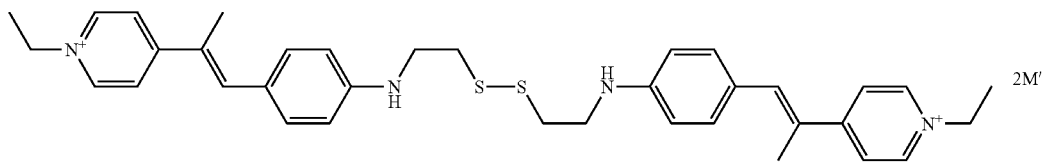
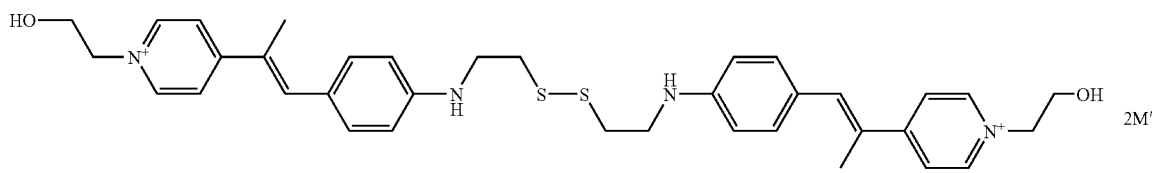
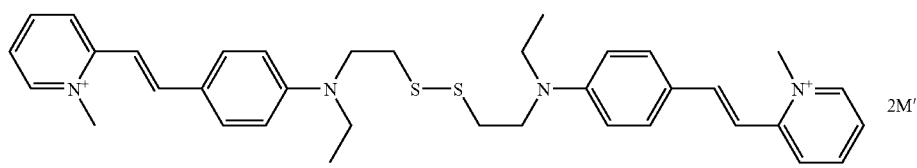
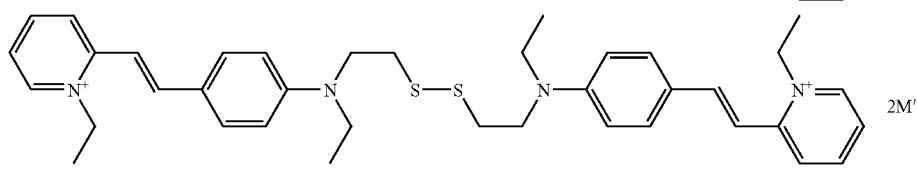
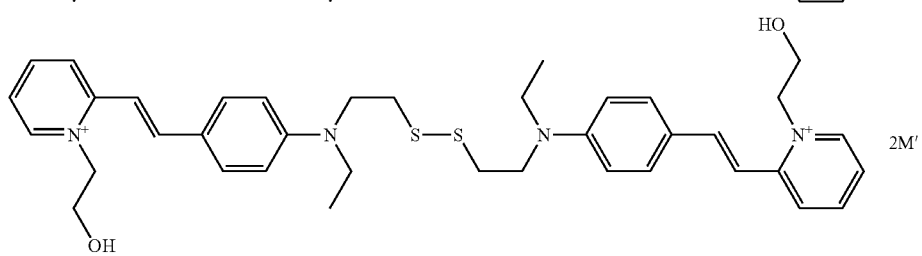
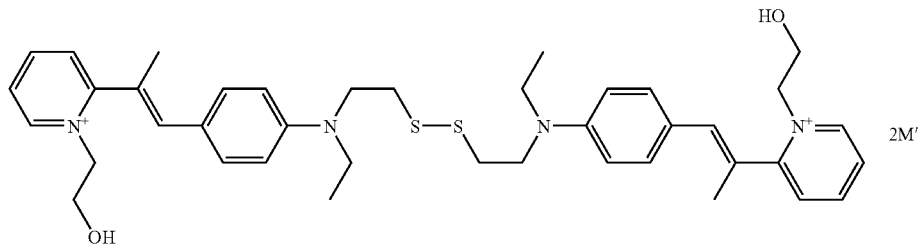

-continued
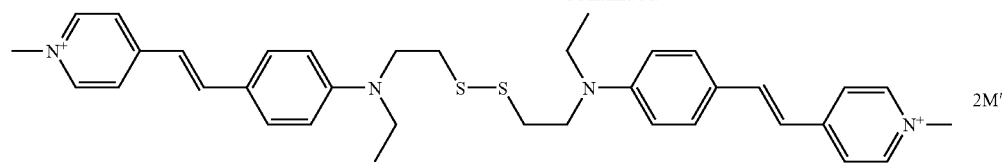 2M'
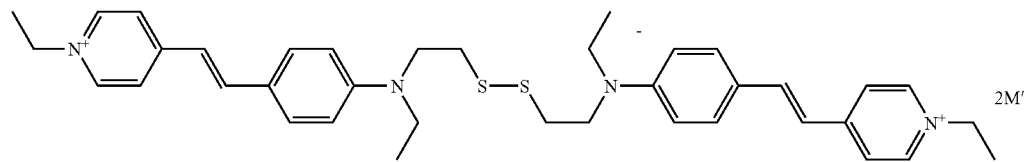 2M'
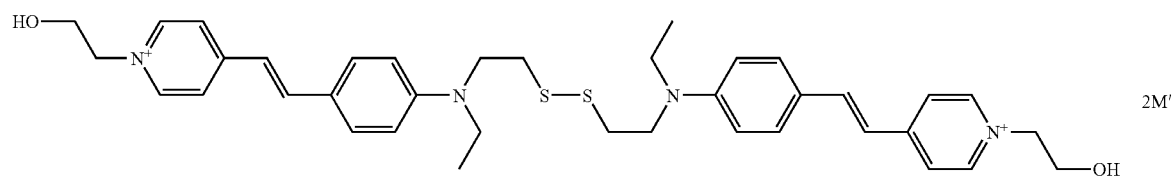 2M'
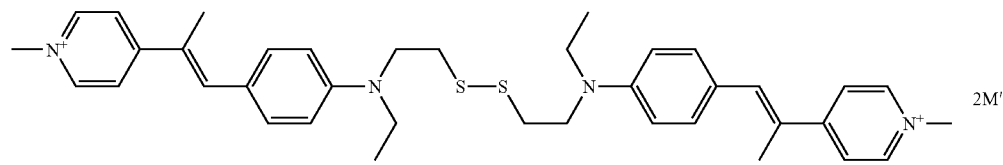 2M'
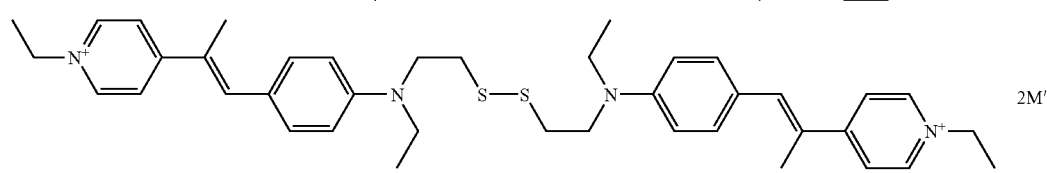 2M'
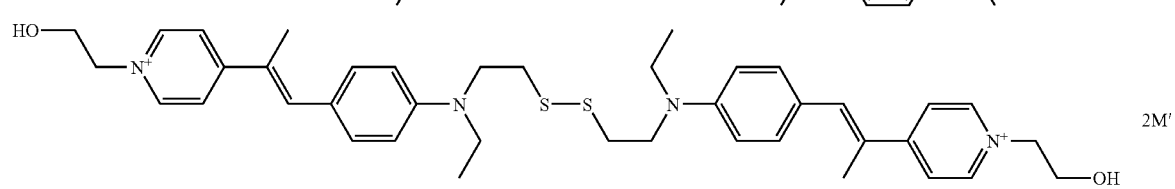 2M'
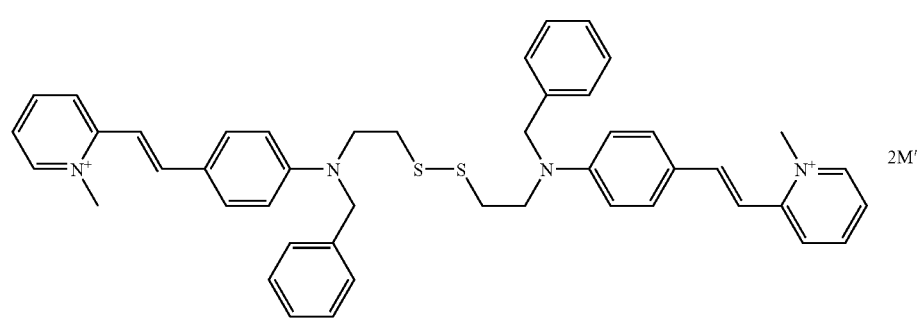 2M'
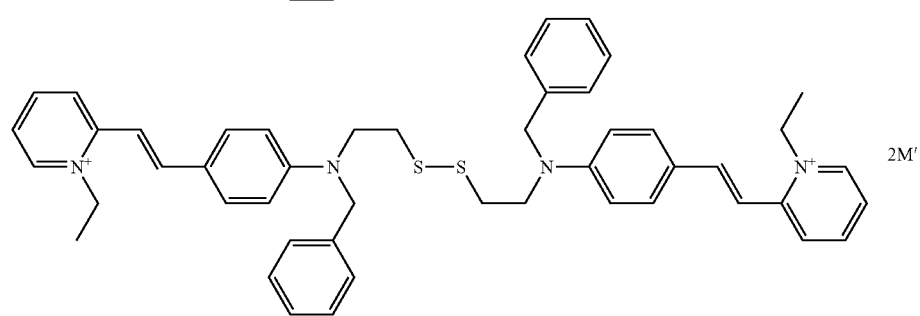 2M'

-continued
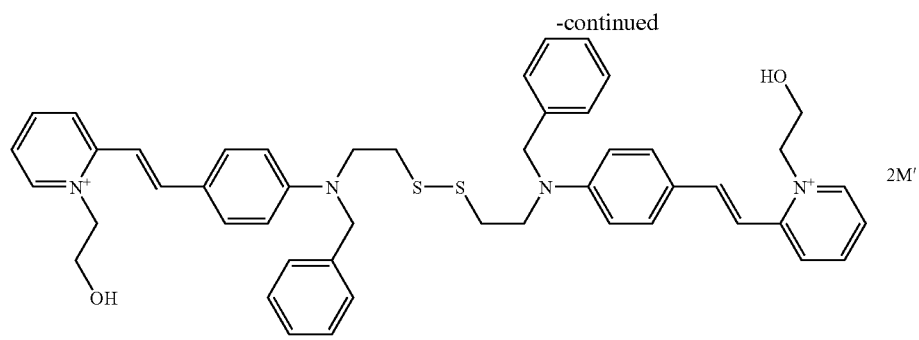
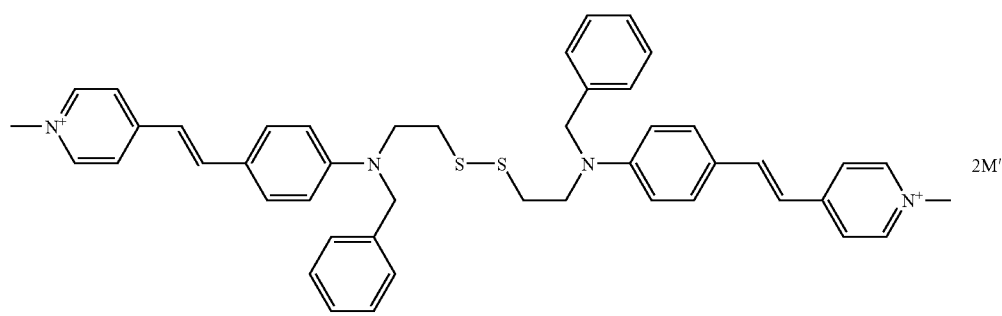
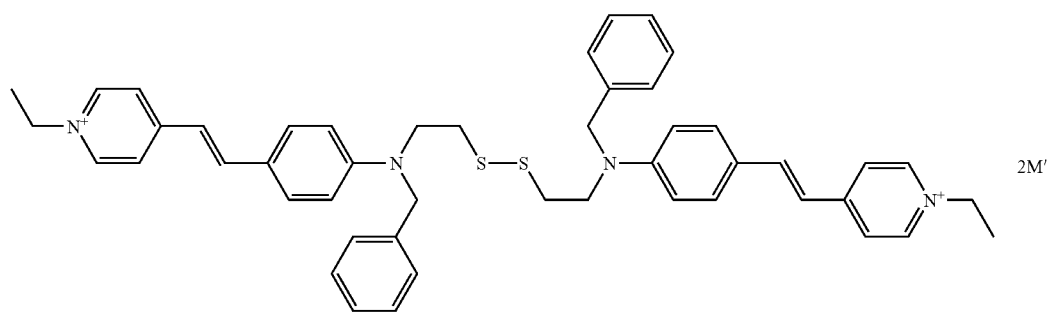
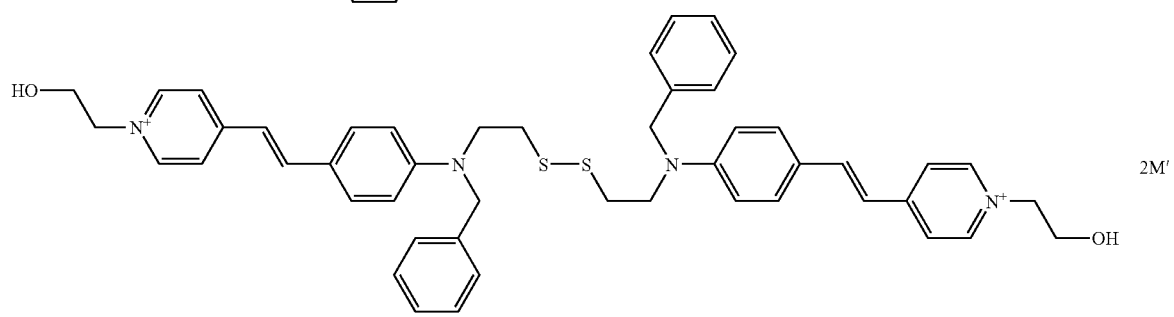
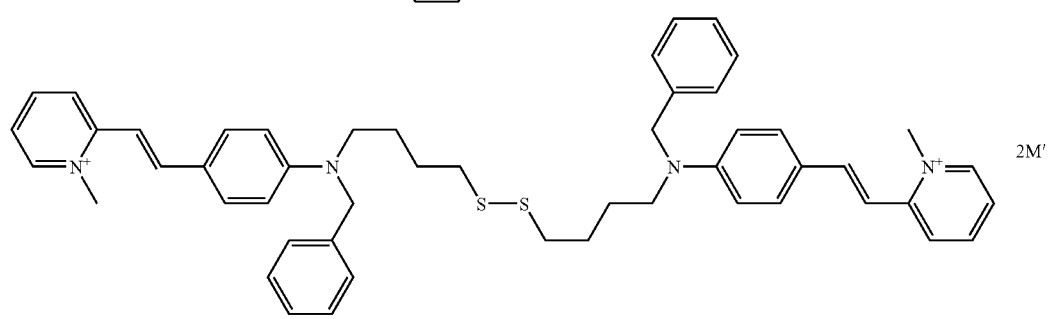

-continued
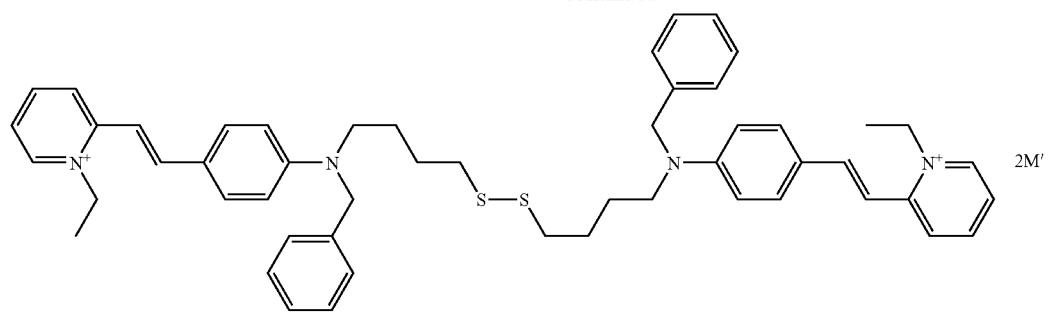
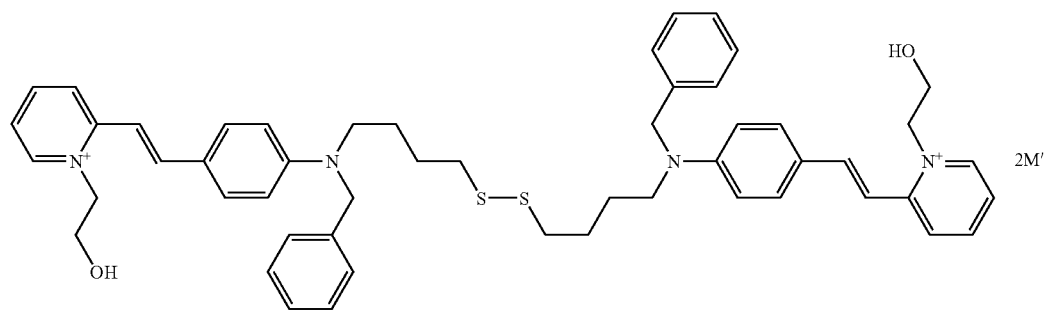
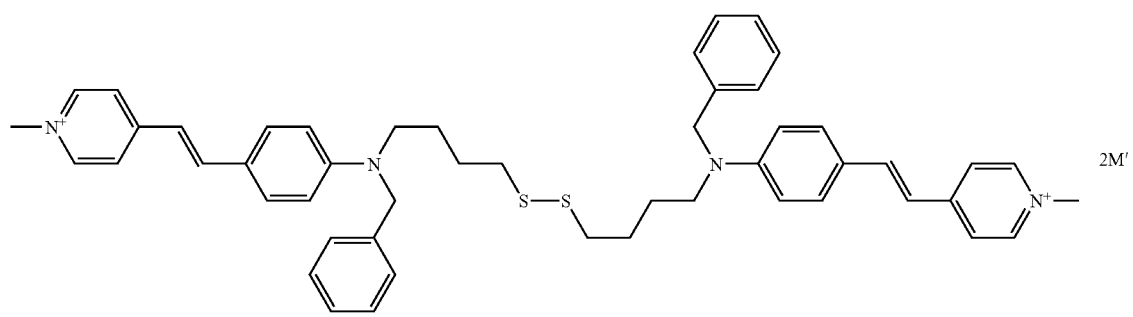
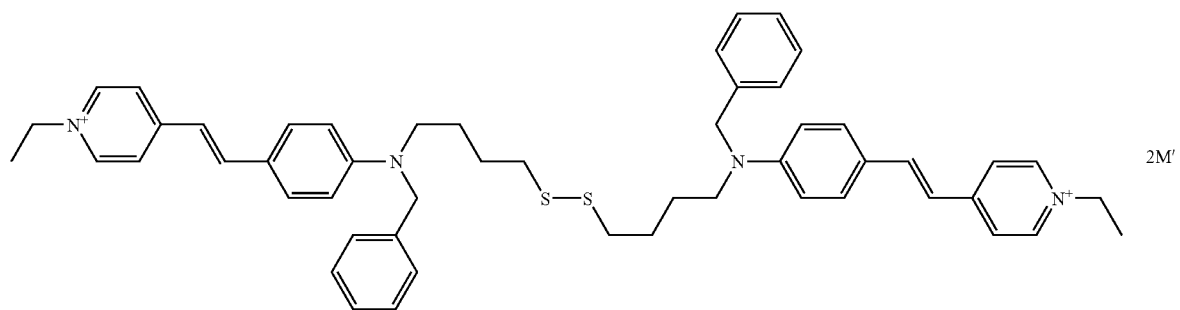
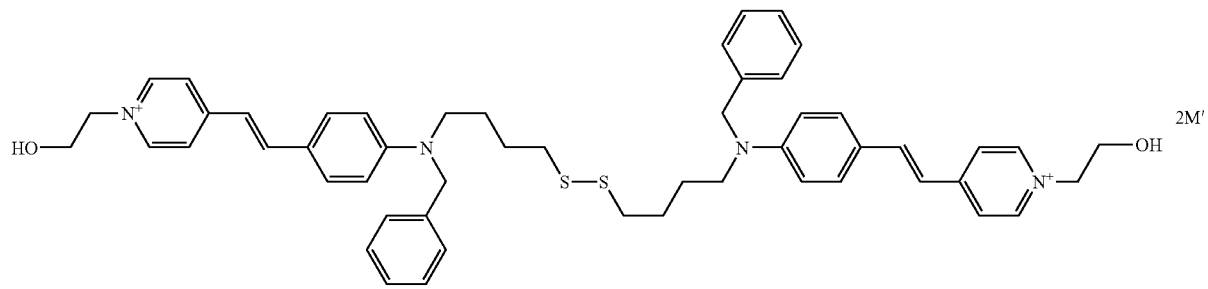
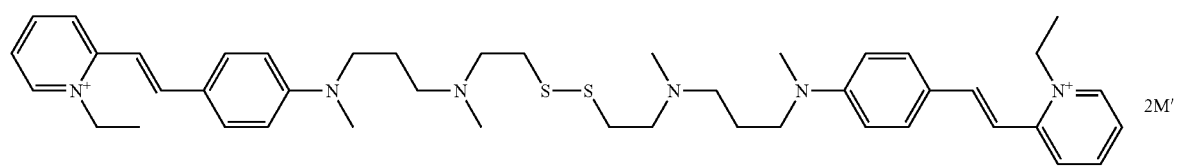

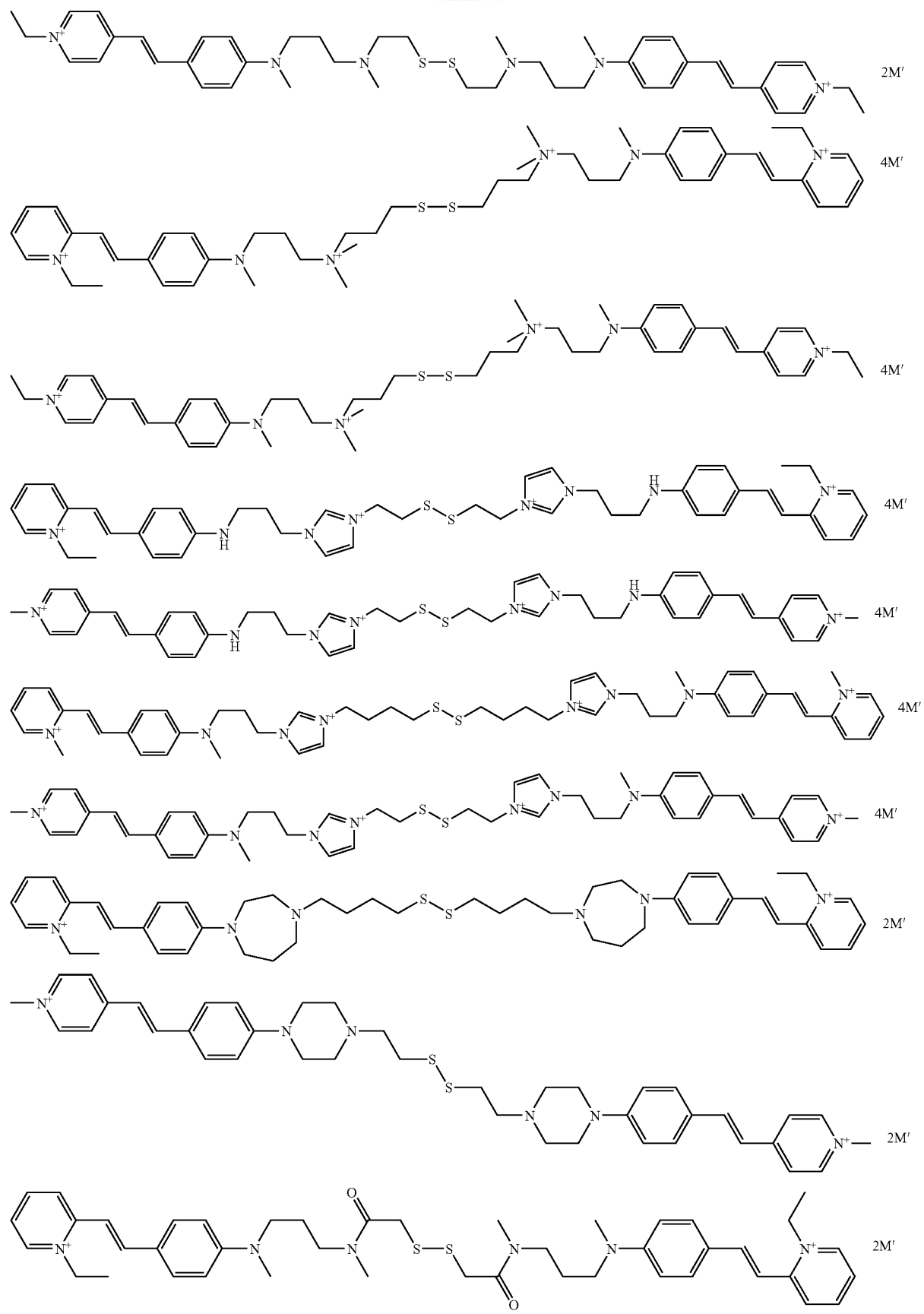

-continued
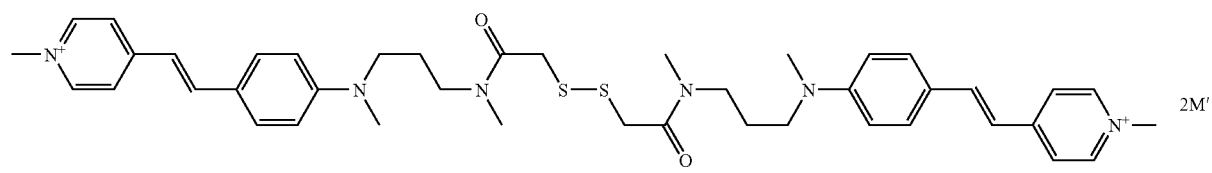
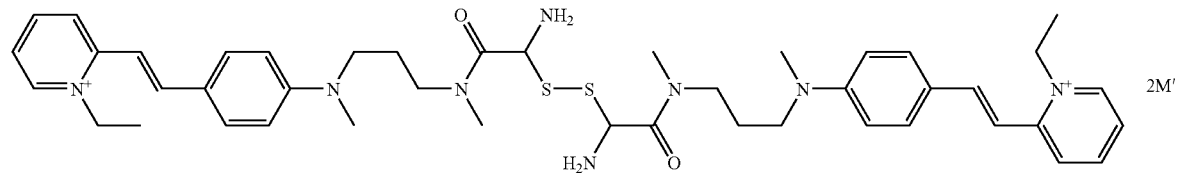
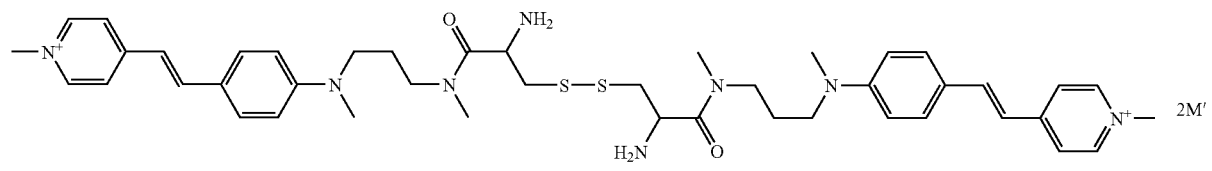
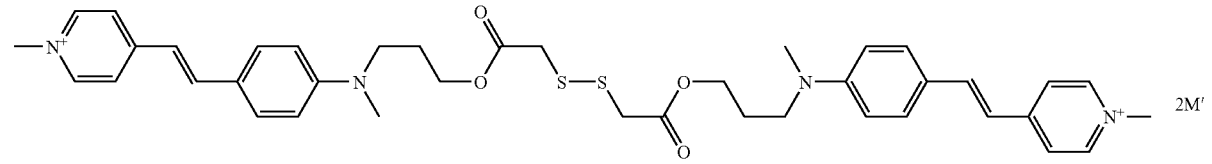
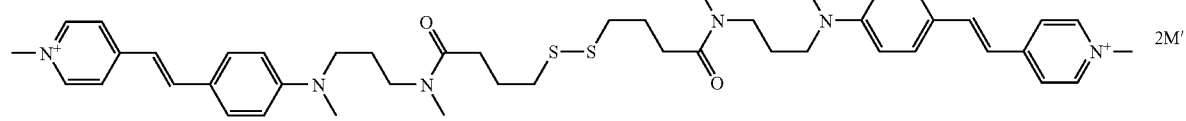
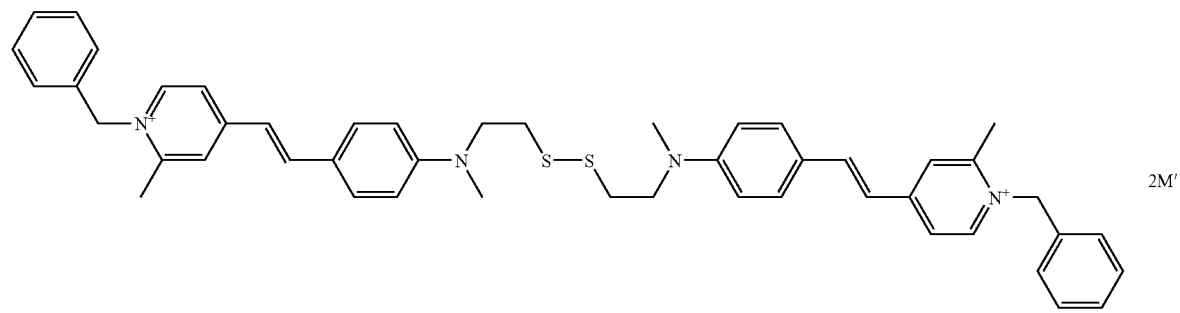
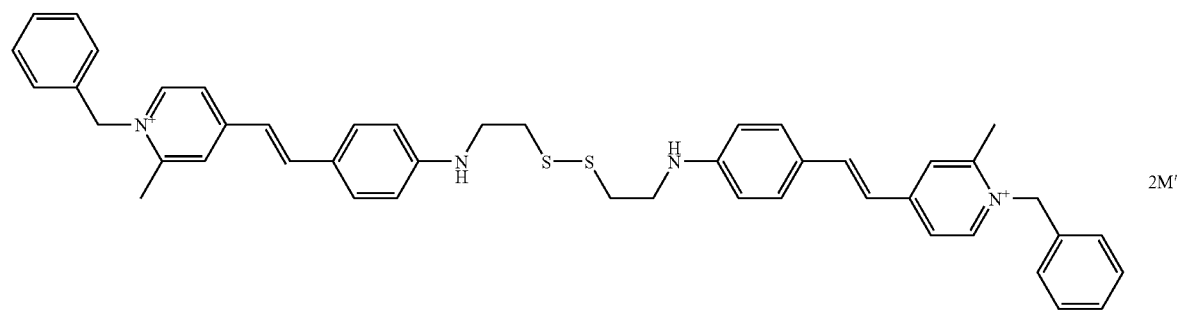
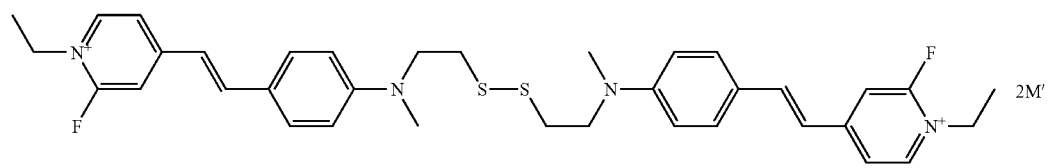

-continued
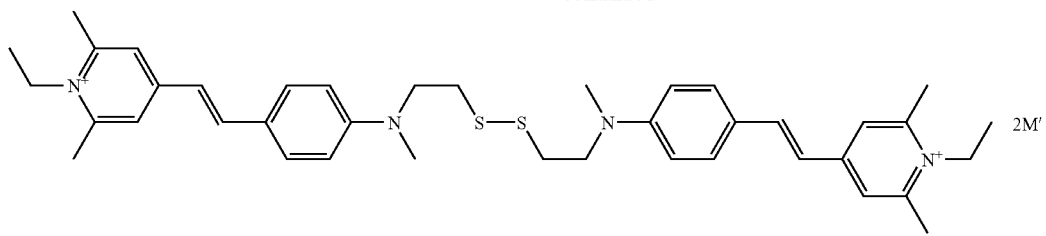
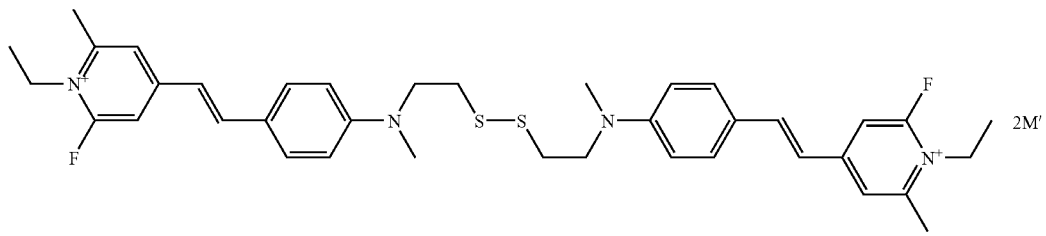
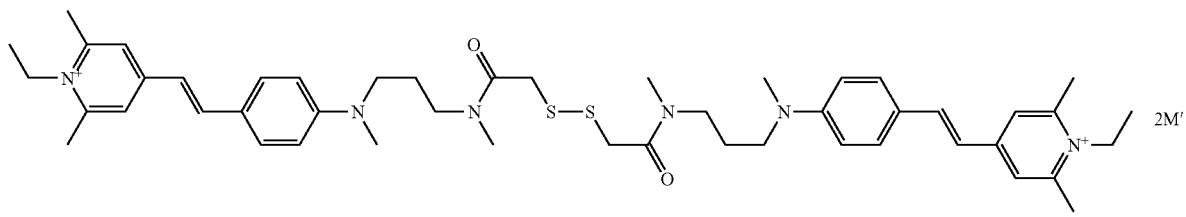
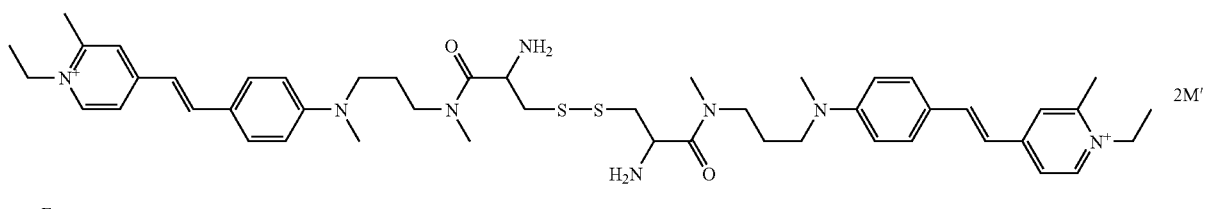
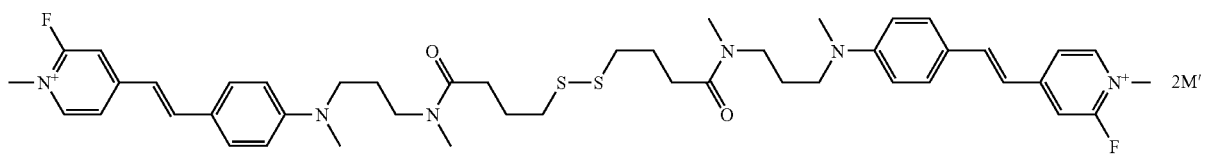
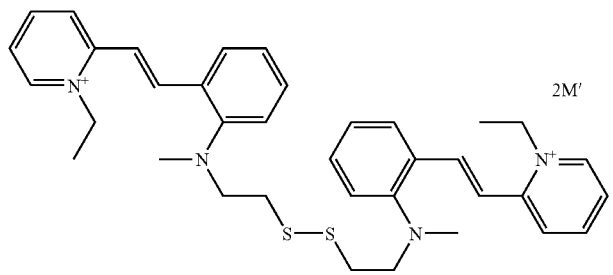
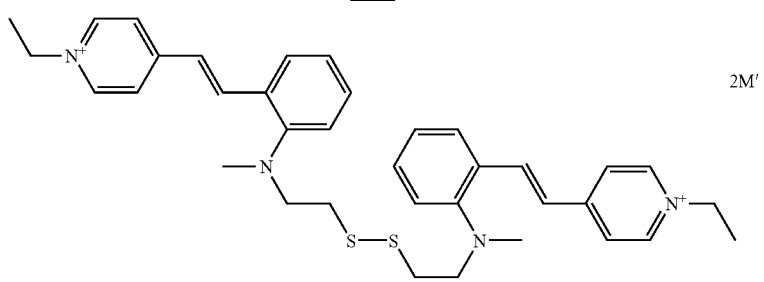

-continued
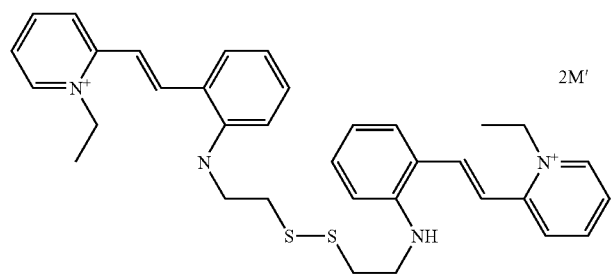
2M′
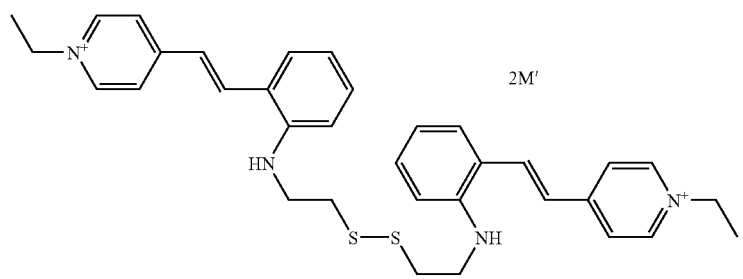
2M′
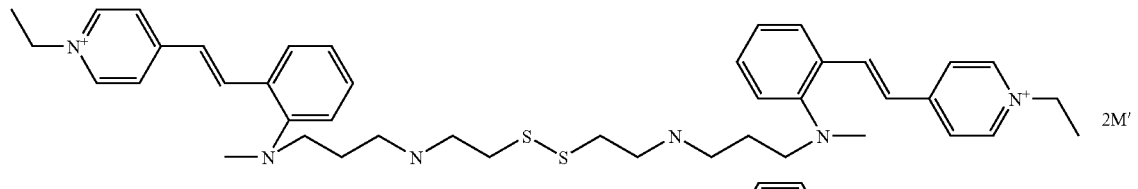
2M′
4M′
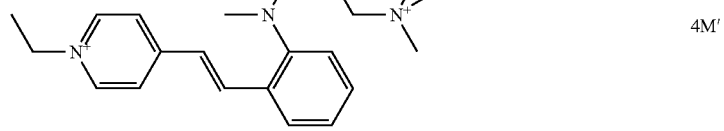
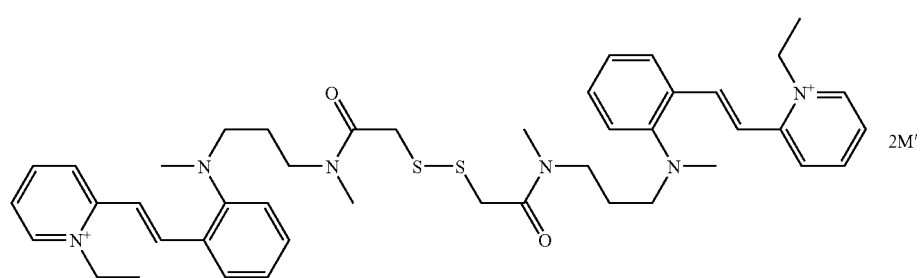
2M′
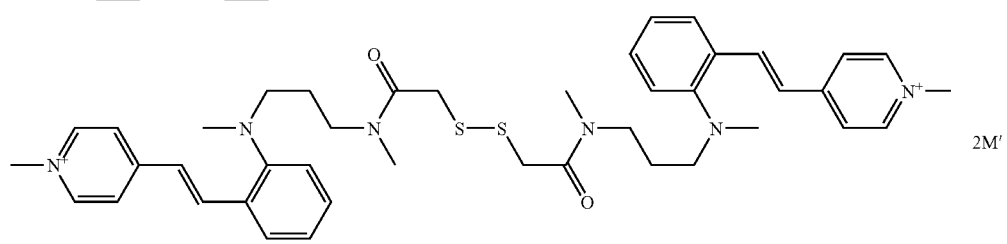
2M′

-continued
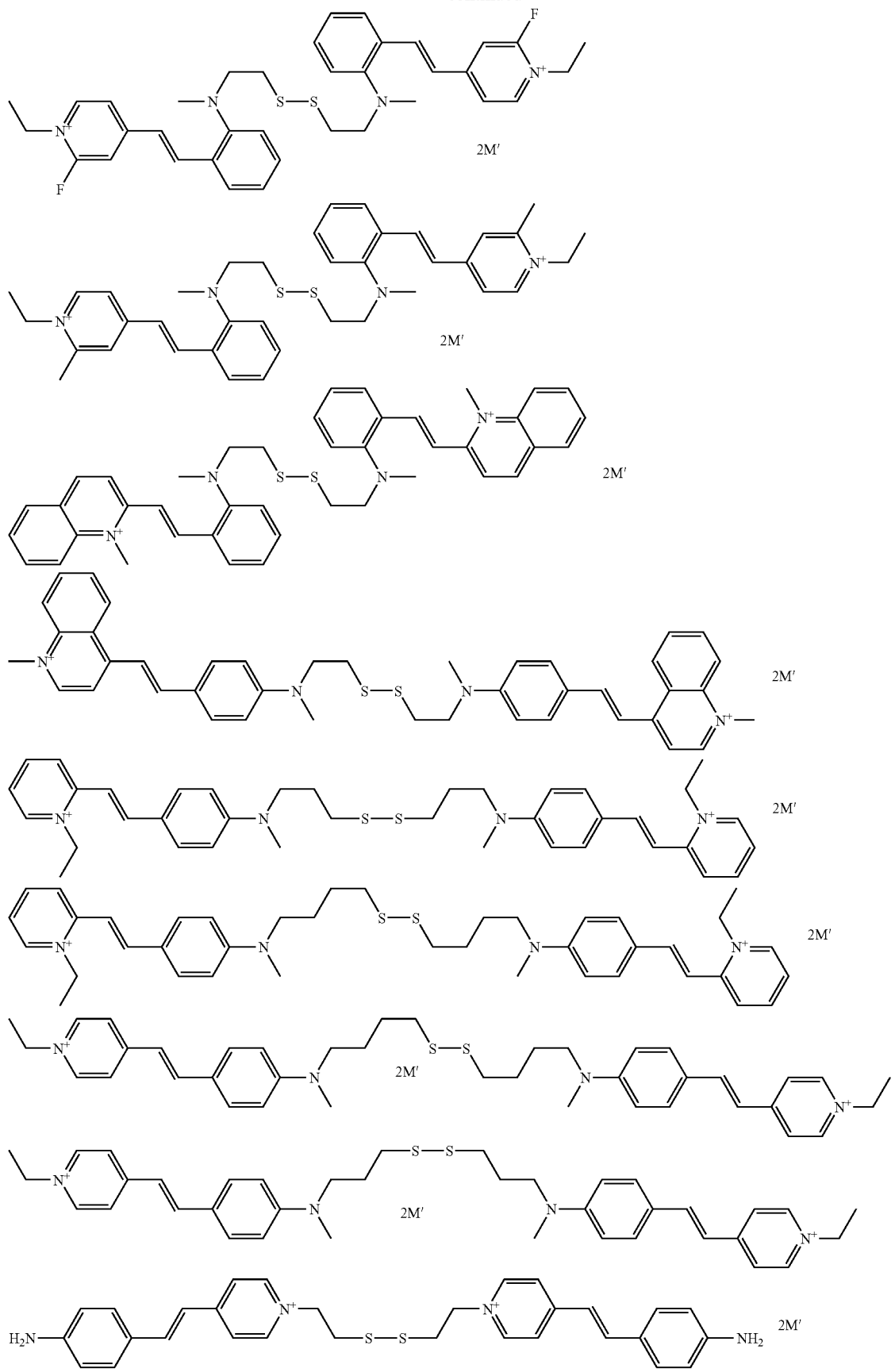

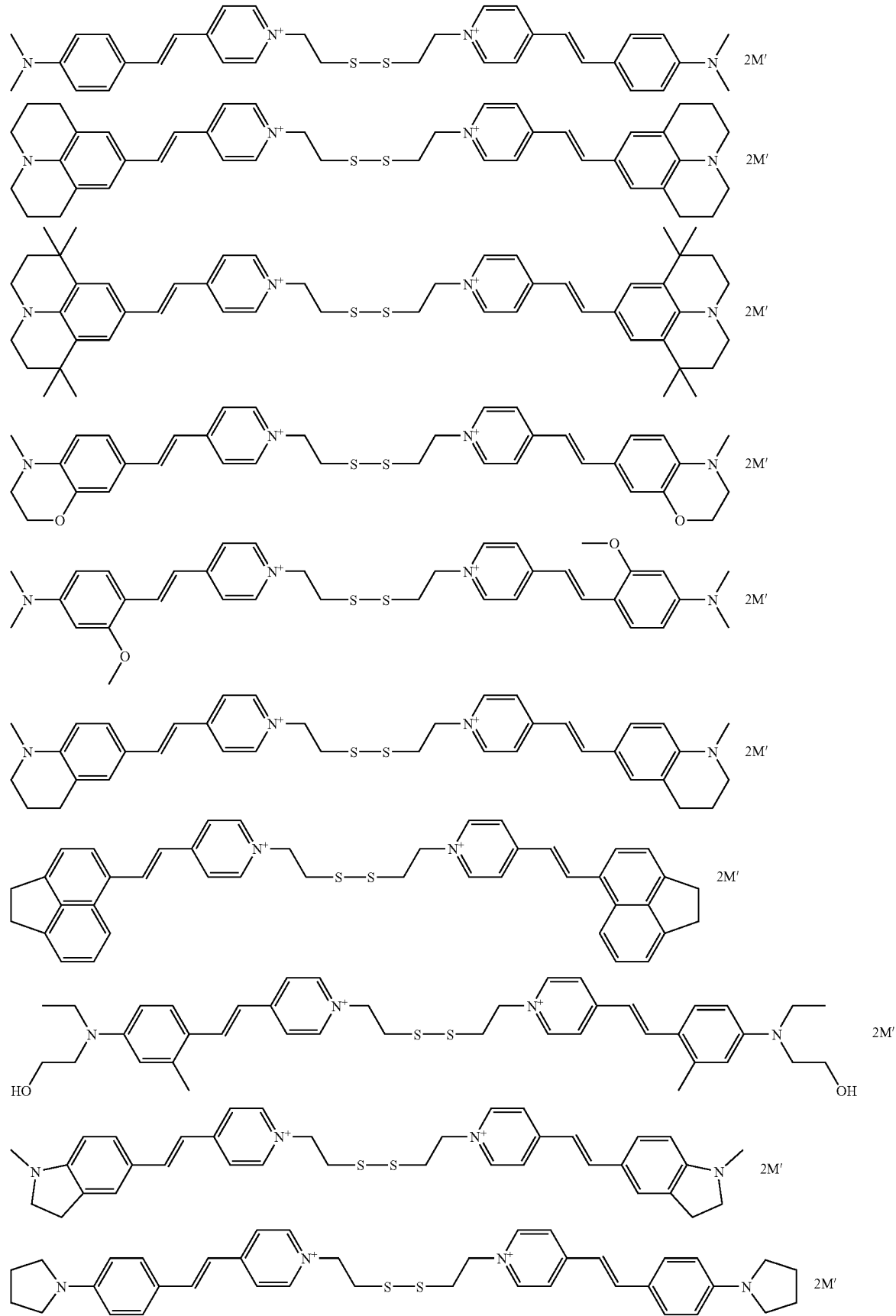

-continued
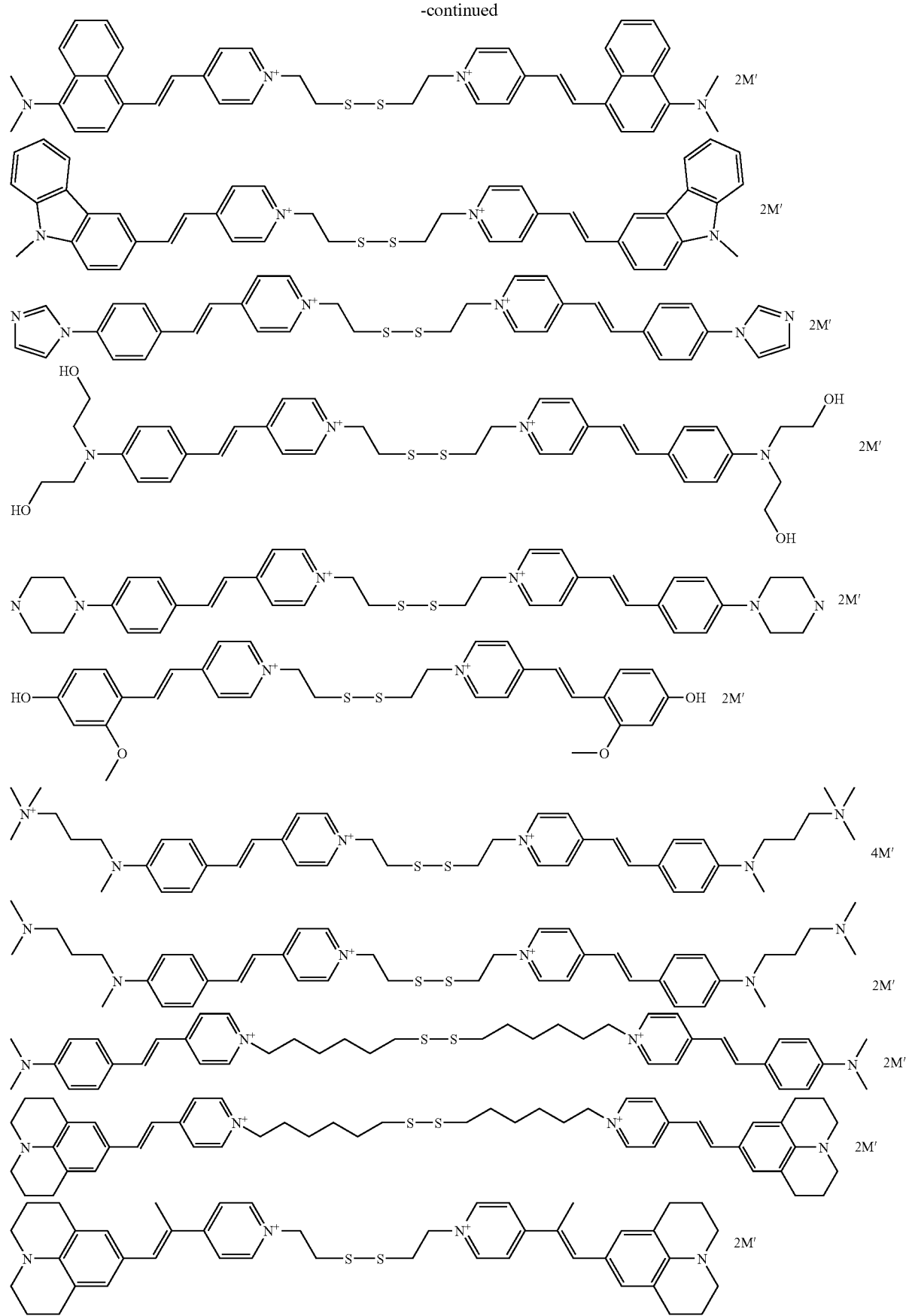

149 150
-continued
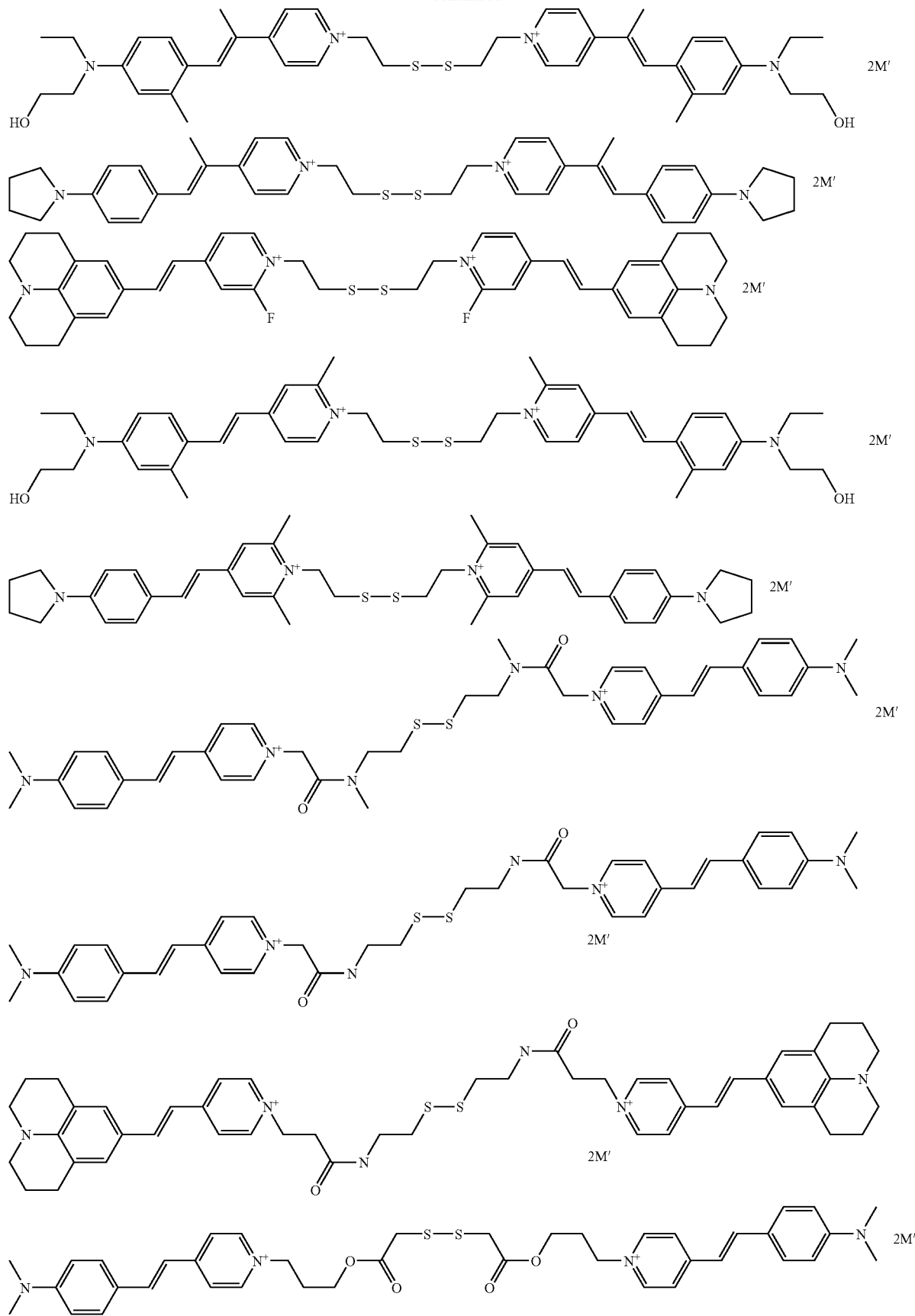

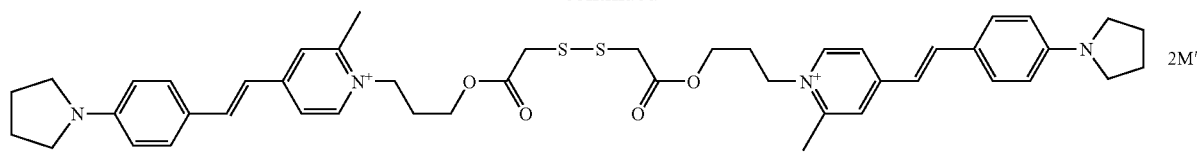
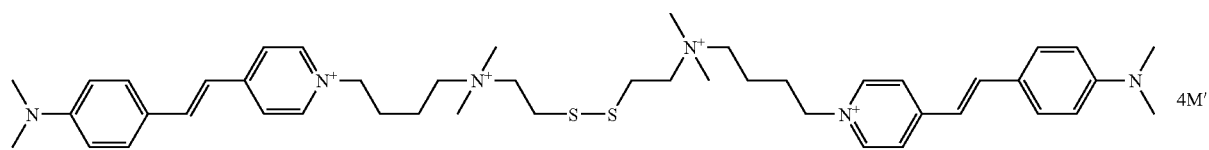
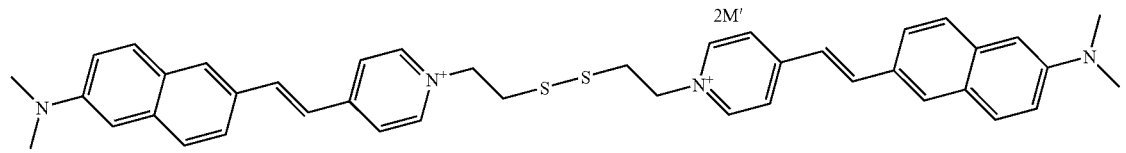
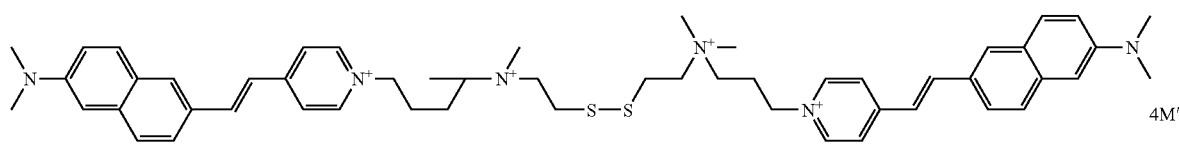
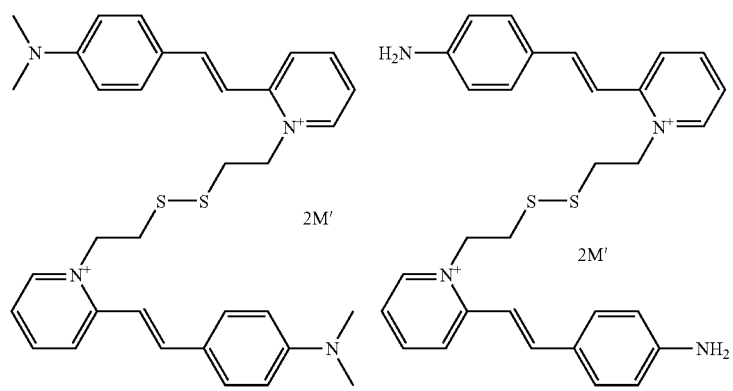
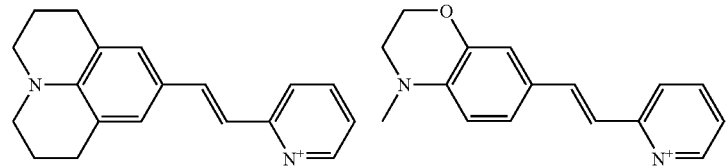
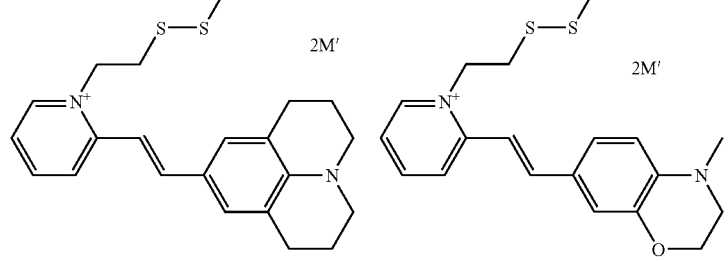

-continued
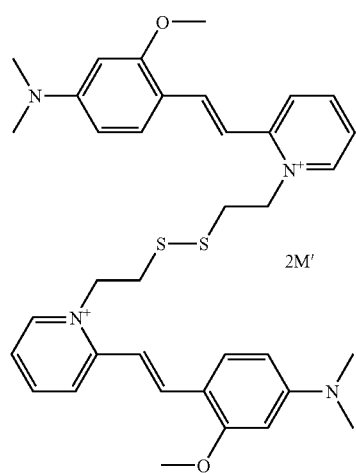 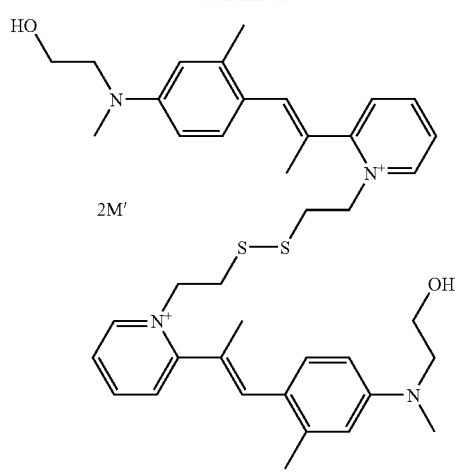
2M′
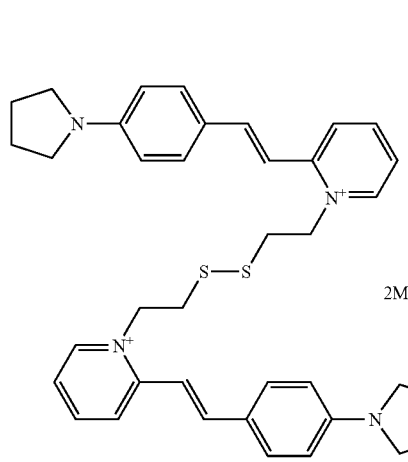 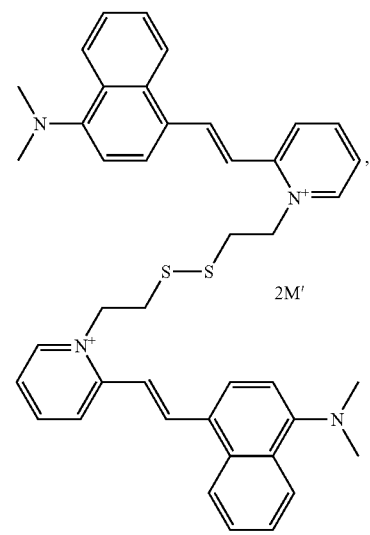
2M′ 2M′
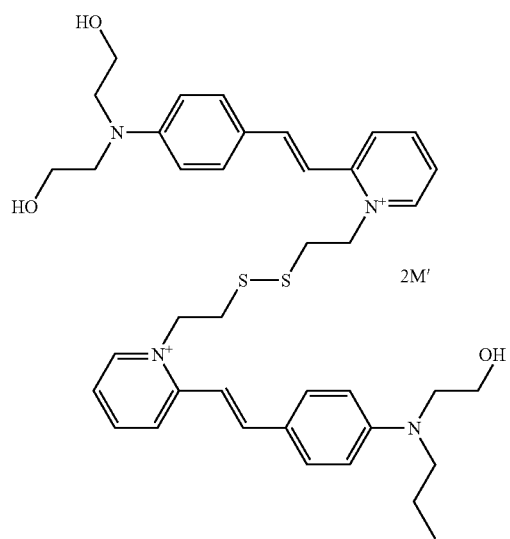
2M′

-continued
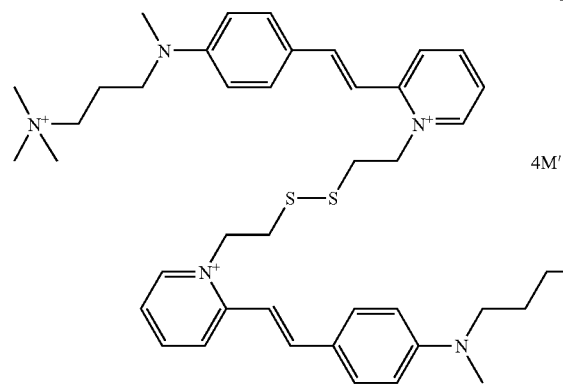
4M′
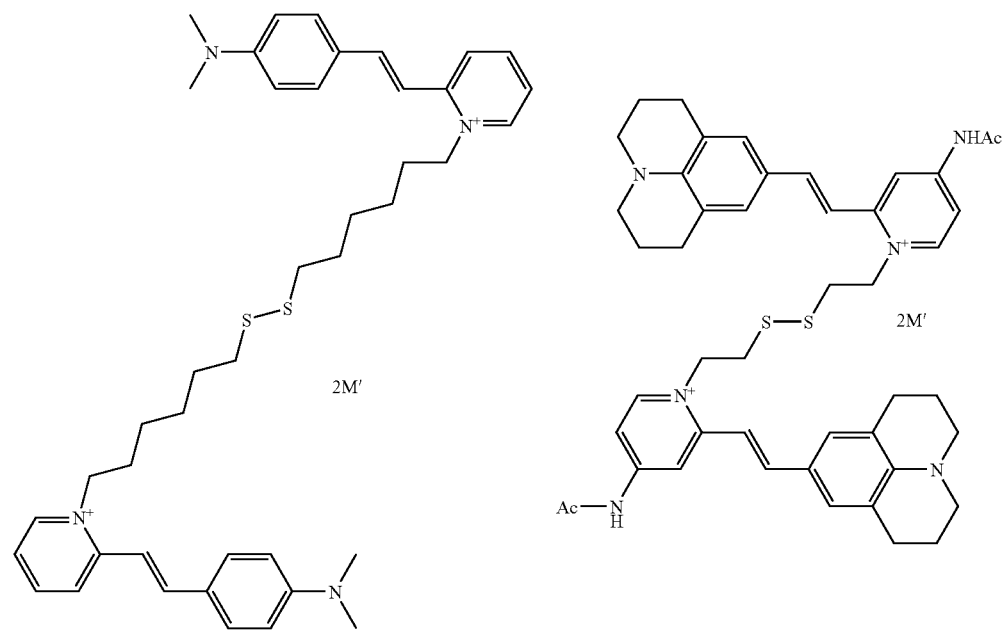
2M′
2M′
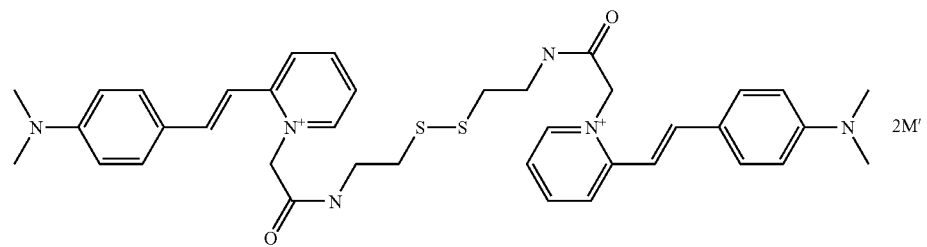
2M′
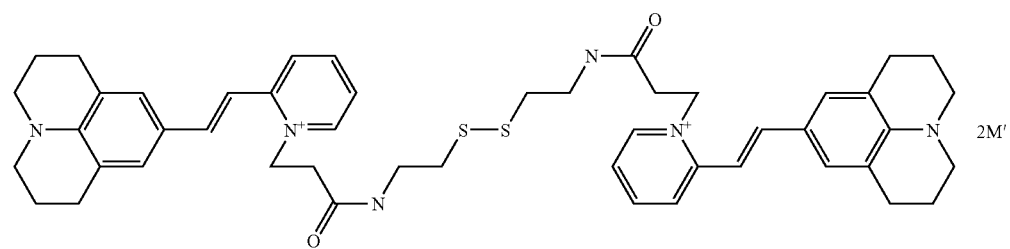
2M′

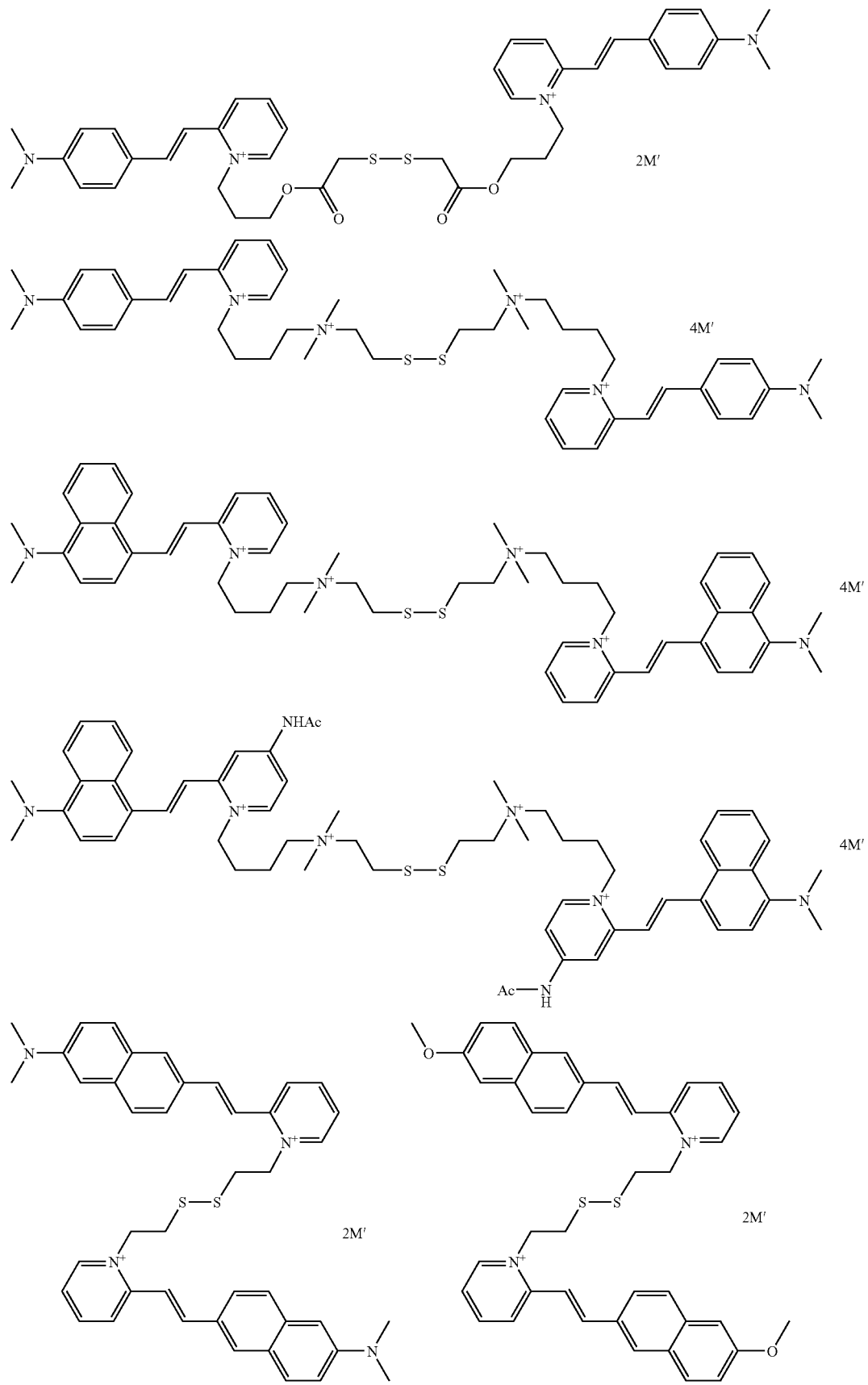

-continued
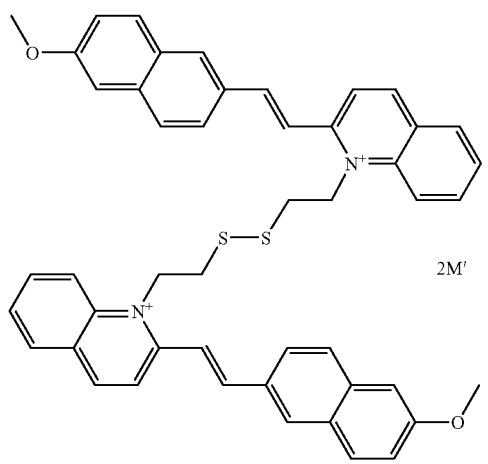
2M'
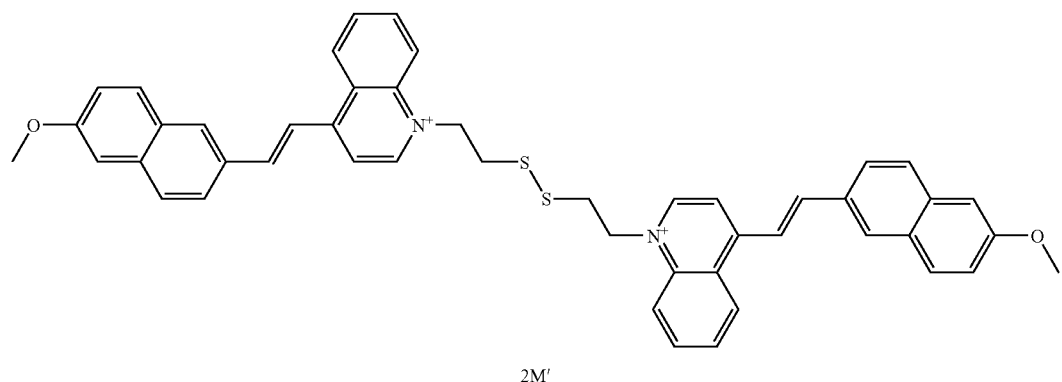
2M'
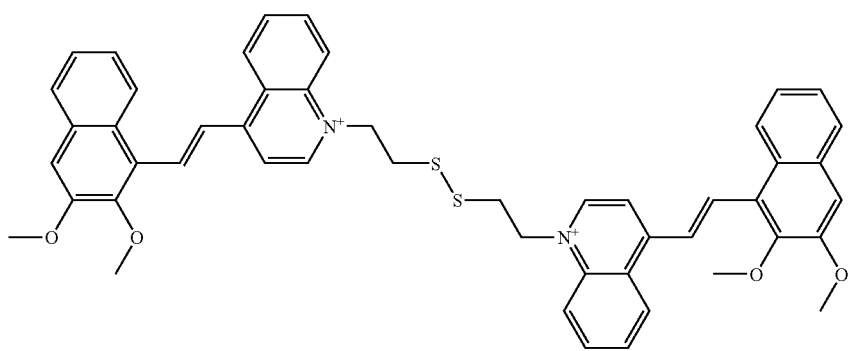
2M'
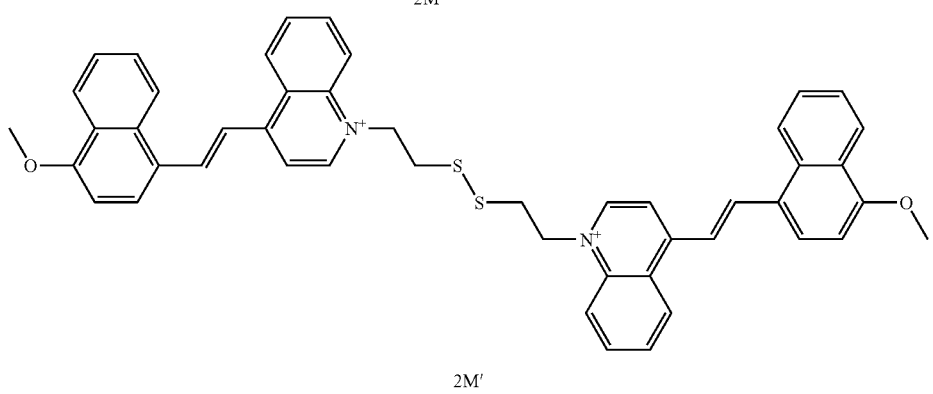
2M'

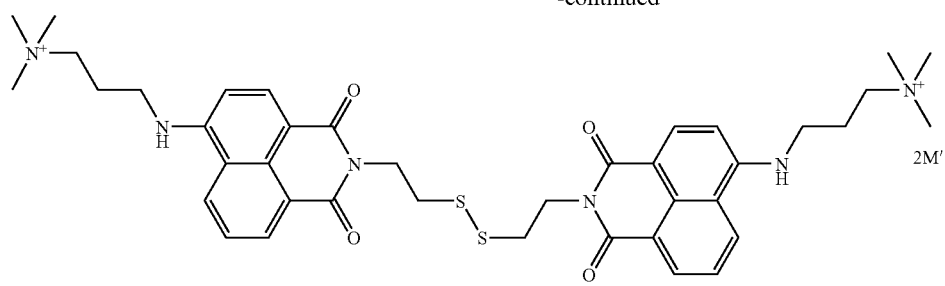
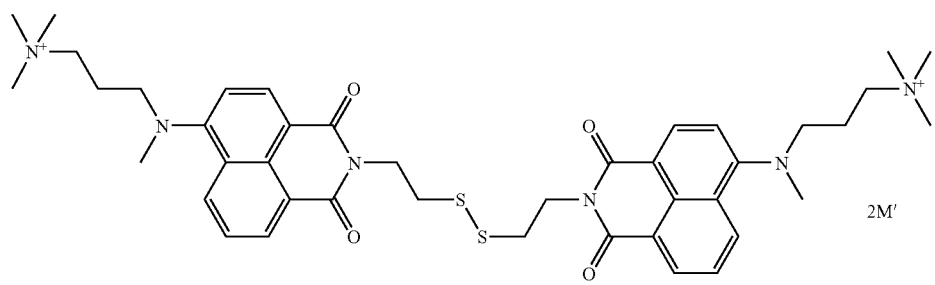
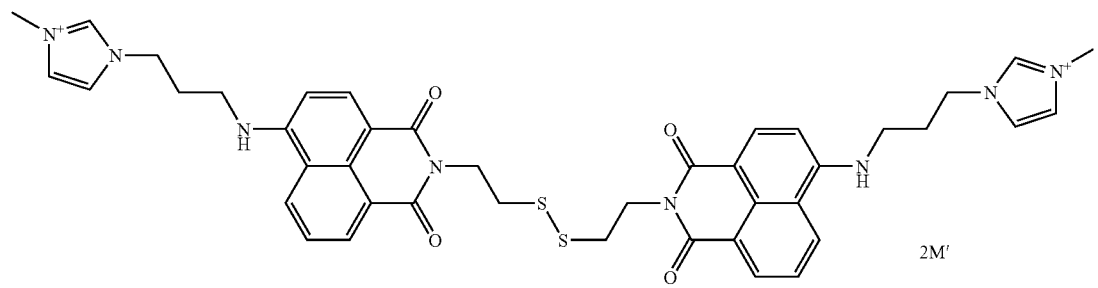
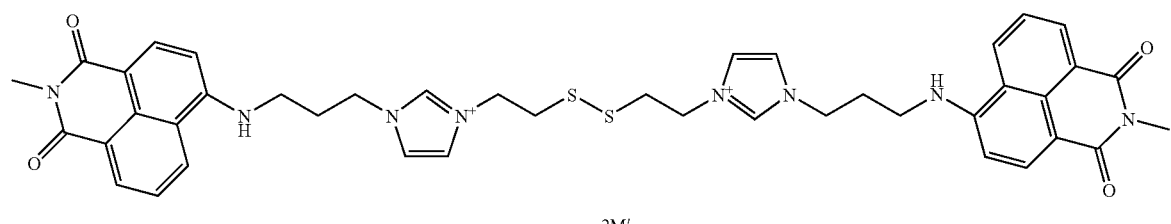
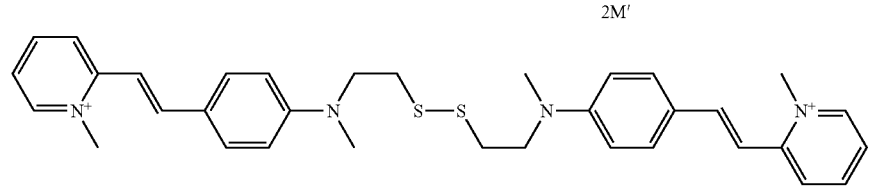
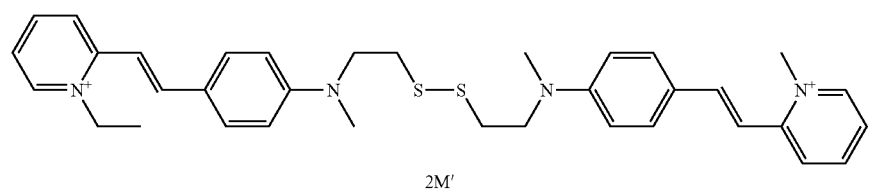

-continued
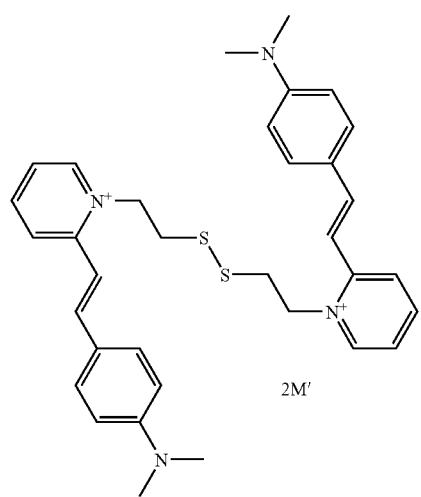
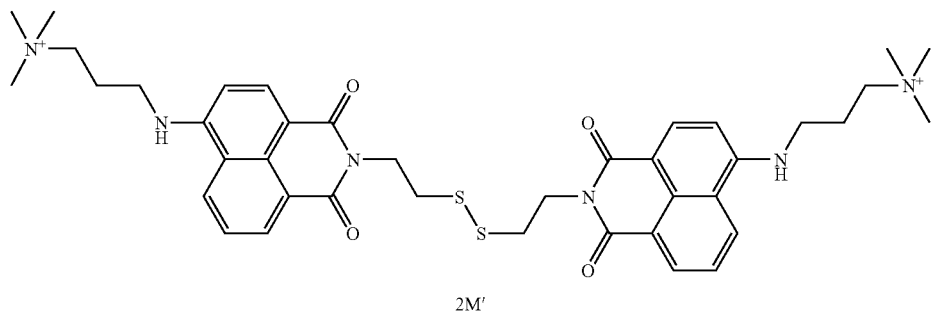
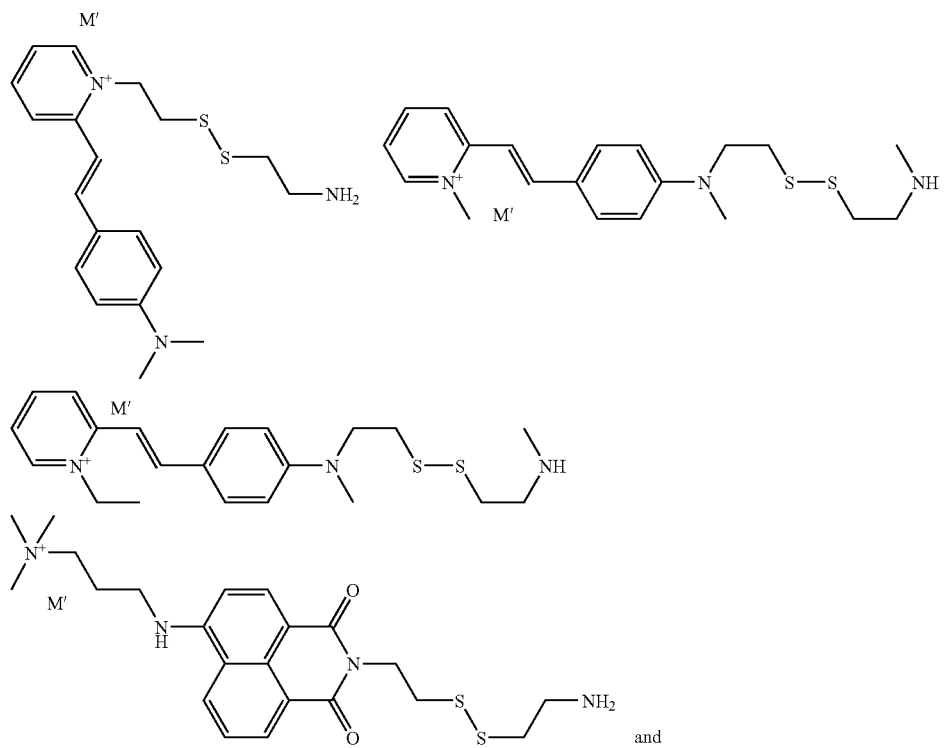
and

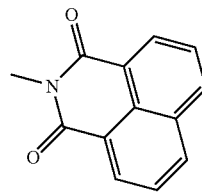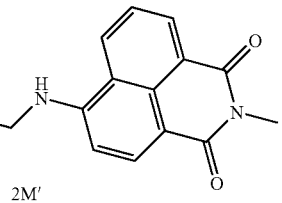

wherein M' is chosen from organic and mineral acid salts.

20. The composition according to claim 1, wherein the at least one alkaline agent chosen from mineral and organic hydroxides is chosen from the hydroxides of alkali metals, alkaline-earth-metals, transition metals, lanthanides, and actinides, ammonium and guanidine hydroxides, and mixtures thereof.

21. The composition according to claim 20, wherein the at least one alkaline agent is chosen from sodium, potassium, calcium, and guanidine hydroxides, and mixtures thereof.

22. The composition according to claim 1, the at least one alkaline agent is present in the composition in an amount ranging from 0.5 to 10% by weight relative to the weight of the composition.

23. The composition according to claim 1, comprising from 0.001 to 10% by weight of disulfide direct dye(s) relative to the total weight of the composition.

24. The composition according to claim 1, wherein the cosmetically acceptable medium is a medium comprising water and optionally at least one organic solvent.

25. The composition according to claim 24, wherein the at least one organic solvent is chosen from $C_1$-$C_4$ lower alkanols, polyols, polyol ethers, aromatic alcohols, and mixtures thereof.

26. The composition according to claim 24, comprising from 1 to 40% by weight of the at least one organic solvent, relative to the total weight of the composition.

27. The composition according to claim 1, further comprising at least one inert organic liquid phase.

28. The composition according to claim 27, wherein the at least one inert organic liquid phase is chosen from polydecenes of formula $C_{10n}H_{[(20n)+2]}$ wherein n varies from 3 to 9, esters, esters and diesters of sugars and of $C_{12}$-$C_{24}$ fatty acids, and cyclic esters, cyclic ethers, silicone oils, mineral oils, plant oils, and mixtures thereof.

29. The composition according to claim 27, wherein the at least one inert organic liquid phase is present in the composition in an amount ranging from 5 to 60% by weight, relative to the total weight of the composition.

30. The composition according to claim 1, further comprising at least one surfactant chosen from non-ionic, anionic, cationic, and amphoteric surfactants, and mixtures thereof.

31. The composition according to claim 30, wherein the at least one surfactant is present in an amount ranging from 0.5 to 30% by weight, relative to the total weight of the composition.

32. The composition according to claim 1, further comprising at least one additional direct dye of non-ionic, cationic, or anionic nature, wherein said additional direct dye does not comprise a disulfide bond.

33. The composition according to claim 32, comprising from 0.0005 to 12% by weight of additional direct dye(s), relative to the total weight of the composition.

34. A process for simultaneous shaping, dyeing, and/or lightening of keratin fibers, comprising:

applying a composition for treating keratin fibers to the keratin fibers for a sufficient time to obtain a desired shaping and dyeing, and/or lightening, and the optional rinsing and washing of the keratin fibers; wherein the composition for treating keratin fibers comprises, in a cosmetically acceptable medium:
at least one disulfide direct dye; and
at least one alkaline agent chosen from mineral and organic hydroxides and present in the composition in an amount such that the pH of the composition ranges from 10 to 14; and
shaping the keratin fibers.

35. The process according to claim 34, comprising the following steps:
a) the composition for treating keratin fiber is applied to the fibers;
b) the fibers are subjected to a mechanical shaping operation that makes it possible to give them a new shape;
c) the composition is left on for a time ranging from 10 to 30 minutes;
d) optionally, a smoothing operation is carried out; and
e) the hair is rinsed.

36. The process according to claim 34, wherein the composition for treating keratin fibers is applied to fibers having a tone level of less than or equal to 6.

37. The process according to claim 34, wherein the keratin fibers are artificially pigmented or colored.

38. A multi-compartment device, comprising at least one first compartment (i) comprising at least one alkaline agent chosen from mineral and organic hydroxides is chosen from the hydroxides of alkali metals, alkaline-earth-metals, transition metals, lanthanides, and actinides, ammonium and guanidine hydroxides, and mixtures thereof; and at least one second compartment (ii) comprising a composition comprising at least one disulfide direct dye; the pH of the mixture of the contents of the various compartments ranging from 10 to 14.

39. A multi-compartment device, comprising at least one first compartment (i) comprising guanidine carbonate and at least one disulfide direct dye; and at least one second compartment (ii) comprising at least one alkaline agent chosen from alkali metal and alkaline-earth metal hydroxides; the pH of the mixture of the contents of the various compartments ranging from 10 to 14.

40. A multi-compartment device, comprising at least one first compartment (i) comprising guanidine carbonate; at least one second compartment (ii) comprising at least one alkaline agent chosen from alkali metal and alkaline-earth metal hydroxides; and at least a third compartment (iii) comprising at least one disulfide direct dye; the pH of the mixture of the contents of the various compartments ranging from 10 to 14.

* * * * *

UNITED STATES PATENT AND TRADEMARK OFFICE
CERTIFICATE OF CORRECTION

PATENT NO. : 8,097,044 B2
APPLICATION NO. : 12/219616
DATED : January 17, 2012
INVENTOR(S) : Frédéric Guerin et al.

It is certified that error appears in the above-identified patent and that said Letters Patent is hereby corrected as shown below:

On the Title Page, Item (30), in the "Foreign Application Priority Data", "07 56706" should read --0756706--.

IN THE CLAIMS:
In column 99, claim 2, in the structure for formula (I) between lines 15-18, " 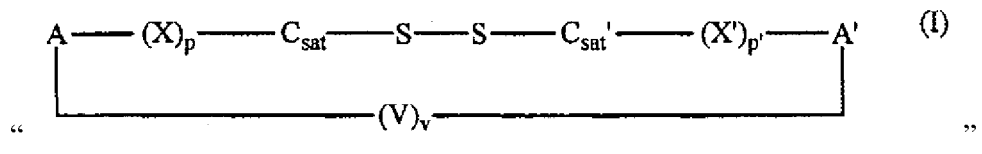 "

should read

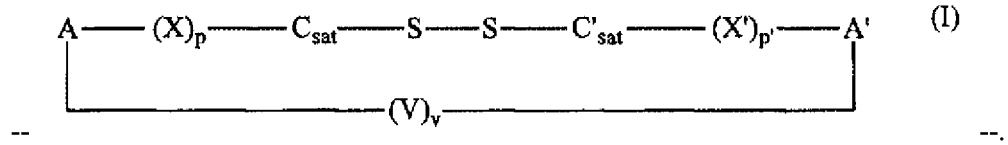

-- --.

In column 99, claim 2, in the structure for formula (II) between lines 19-21,

" 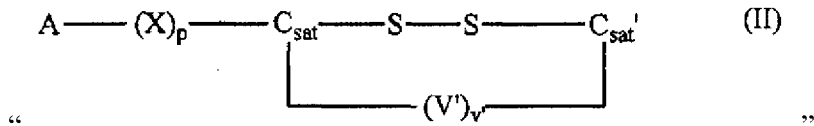 "

should read

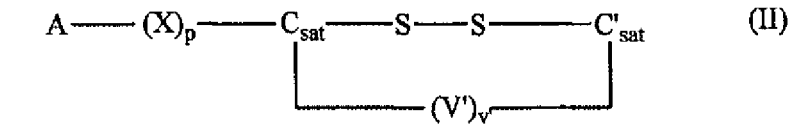

-- --.

Signed and Sealed this
First Day of May, 2012

David J. Kappos
*Director of the United States Patent and Trademark Office*

In column 99, claim 2, in the structure for formula (III) between lines 22-24,

" $A-(X)_p-C_{sat}-S-S-C_{sat}'-(X')_{p'}-A'$ (III) "

should read

-- $A-(X)_p-C_{sat}-S-S-C'_{sat}-(X')_{p'}-D$ (III) --.

In column 99, claim 2, line 34, "v and v are," should read --v and v' are,--.

In column 100, claim 2, line 60, "one hydroxyls)," should read --one hydroxyl),--.

In column 101, claim 2, line 42, "1 to 8" should read --1 to 8,--.

In column 101, claim 2, line 48, "-SOW" should read --$SO_3M$--.

In column 102, claim 3, line 1, "$A\text{-}(T)_t\text{-}(Y)_y\text{-}(Z)_z\text{-}C_{aat}$ or $C'_{sat}\text{-}(T)_t\text{-}(Y)_y\text{-}(Z)_z\text{-}K$," should read --$A\text{-}(T)_t\text{-}(Y)_y\text{-}(Z)_z\text{-}C_{sat}$ or $C'_{sat}\text{-}(T)_t\text{-}(Y)_y\text{-}(Z)_z\text{-}A'$,--.

In column 102, claim 3, line 43, "-$CR_a$-radicals," should read --$CR_a$- radicals,--.

In column 102, claim 3, line 44, "$R_l$ is chosen" should read --$R_a$ is chosen--.

In column 102, claim 3, line 54, "one hydroxyl groups;" should read
--one hydroxyl group;--.

In column 103, claim 3, line 46, "1 to 8" should read --1 to 8,--.

In column 103, claim 3, line 48, "1 to 15" should read --1 to 15,--.

In column 113-114, claim 9, in the structure for formula (22),

CERTIFICATE OF CORRECTION (continued)
U.S. Pat. No. 8,097,044 B2

Page 3 of 9

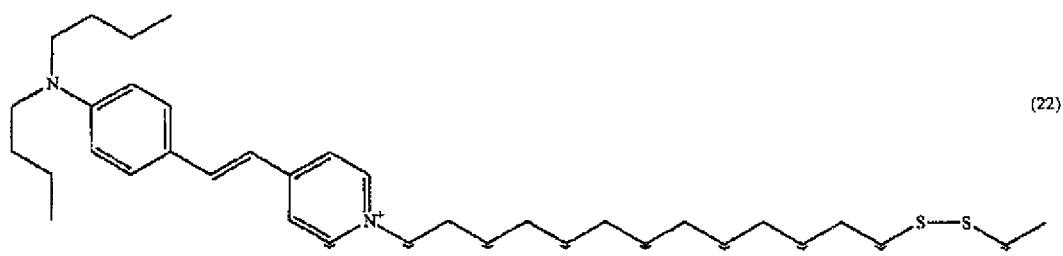

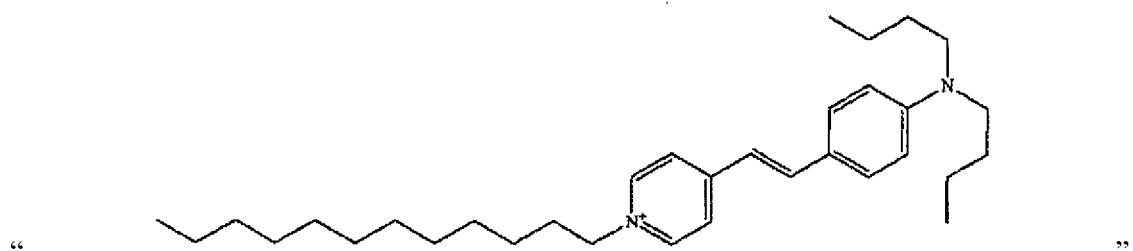

should read

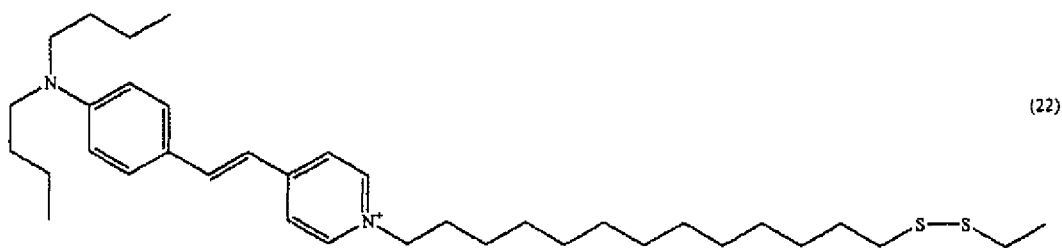

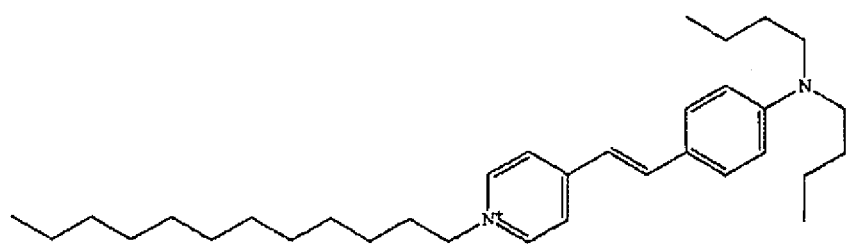

In columns 115-116, claim 17, in the ninth structure from the top,

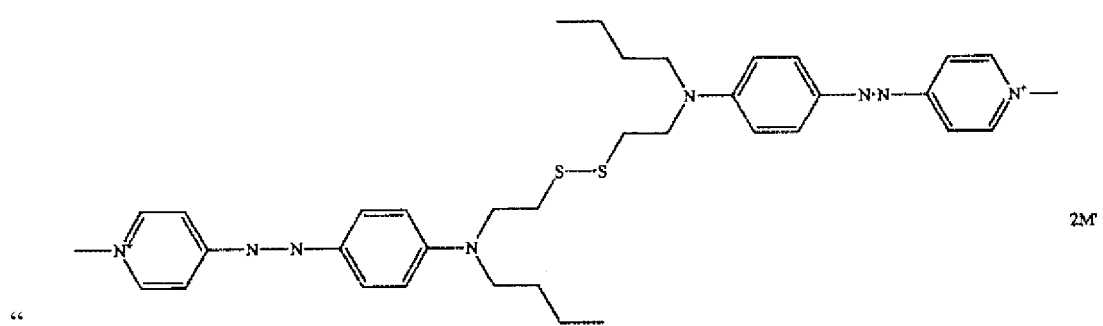

should read
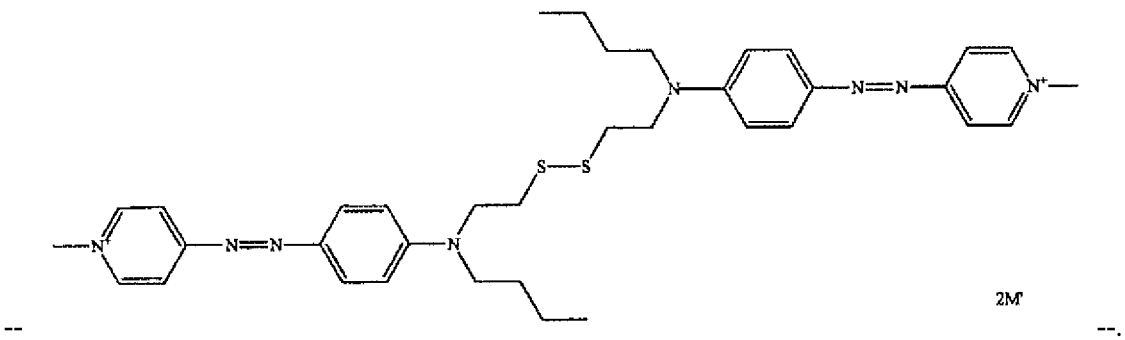
In columns 115-116, claim 17, in the tenth structure on the page,
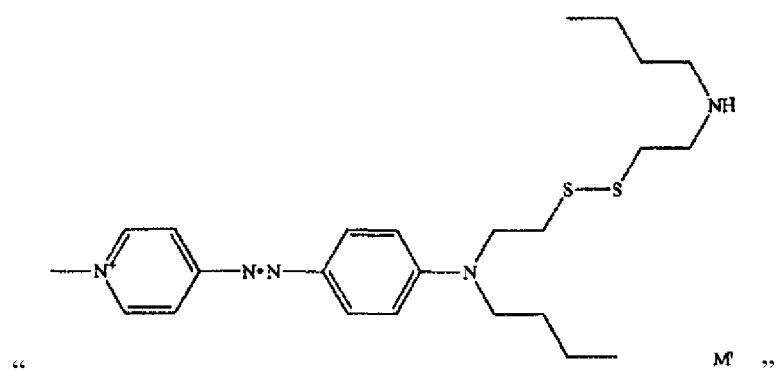
should read
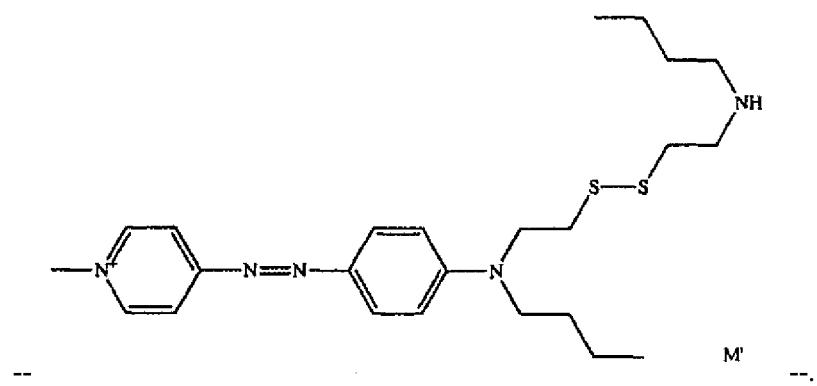
In columns 117-118, claim 18, in the structure for formula (III),

CERTIFICATE OF CORRECTION (continued)
U.S. Pat. No. 8,097,044 B2

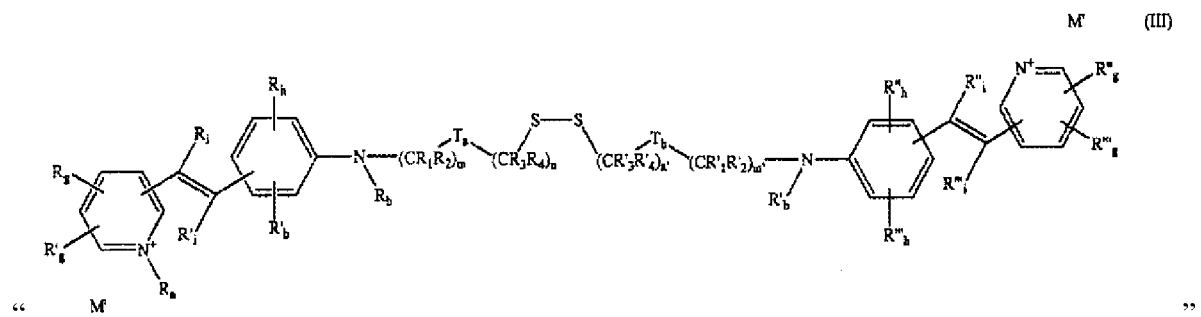

" M' should read

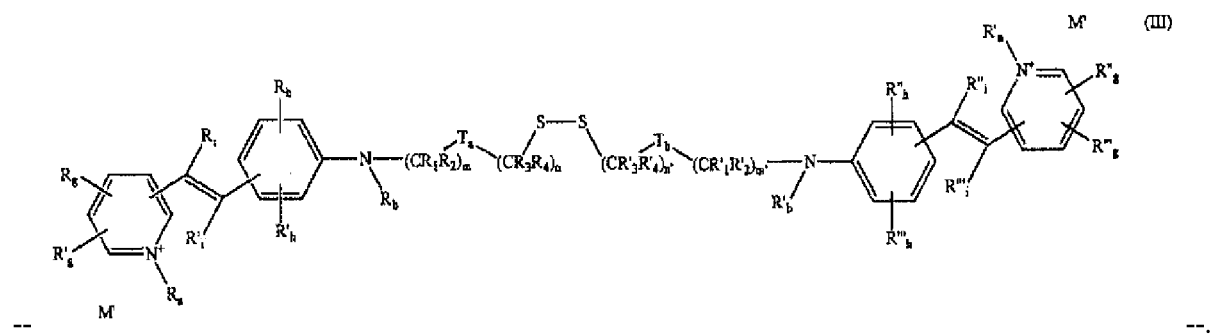

-- M' --.

In columns 117-118, claim 18, in the structure for formula (IV),

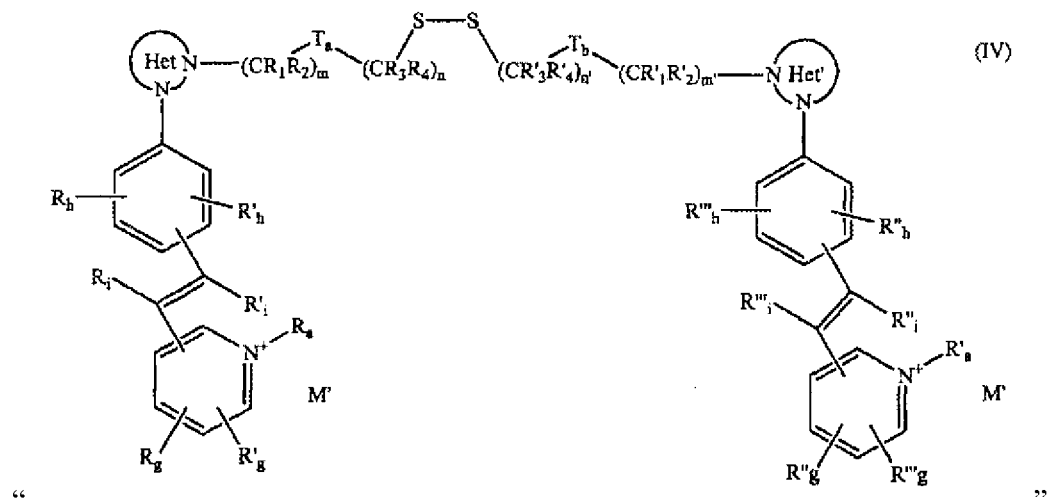

should read

CERTIFICATE OF CORRECTION (continued)
U.S. Pat. No. 8,097,044 B2

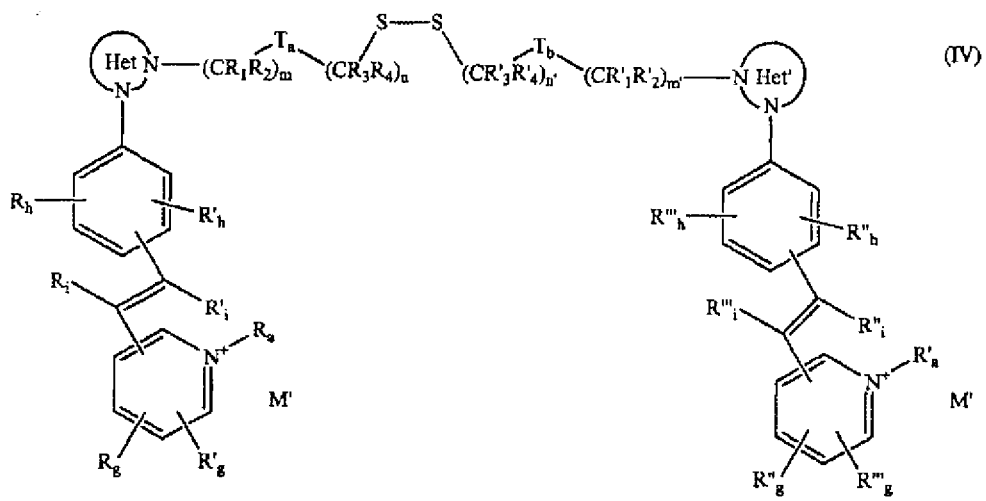

In columns 117-118, claim 18, in the structure for formula (VI),

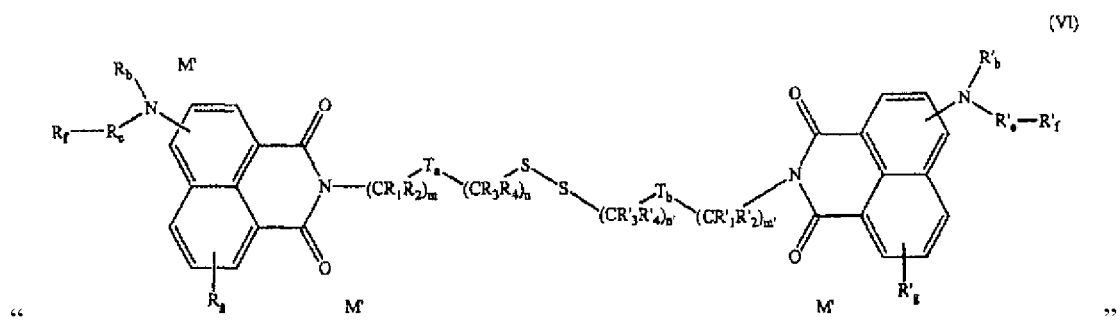

should read

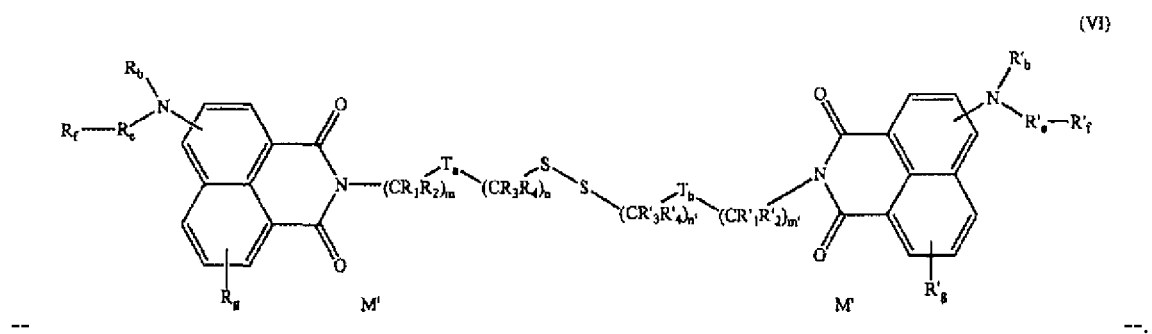

In column 121, claim 18, line 16, "-NR'$_c$R$_d$," should read -- -NR'$_c$R'$_d$,--.

In column 121, claim 18, line 59, "R$_h$, and R'$_h$;" should read --R$_h$ and R'$_h$;--.

In column 122, claim 18, line 42, "bond a," should read --bond σ,--.

CERTIFICATE OF CORRECTION (continued)
U.S. Pat. No. 8,097,044 B2

In column 122, claim 18, line 43, "-N⁺(R)(R°-," should read -- -N⁺(R)(R°)-,--.

In columns 145-146, claim 19, in the seventh structure from the top,

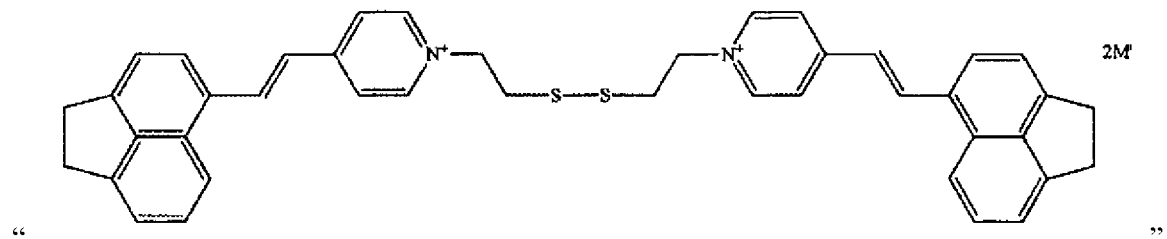

should read

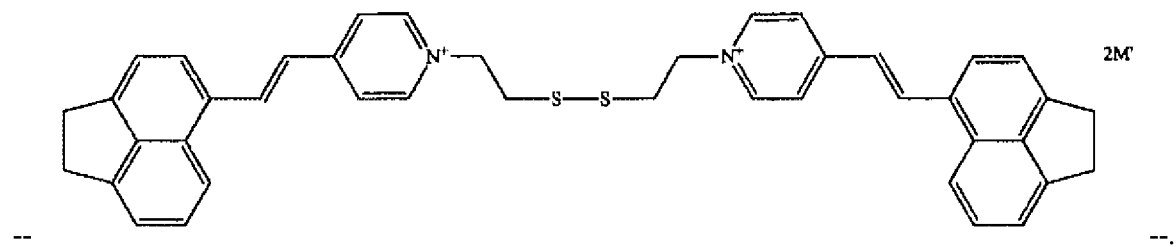

In columns 147-148, claim 19, in the seventh structure from the top,

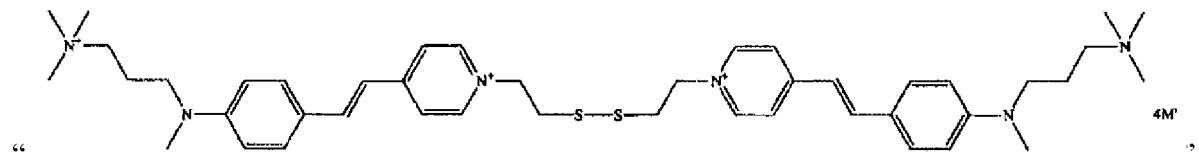

should read

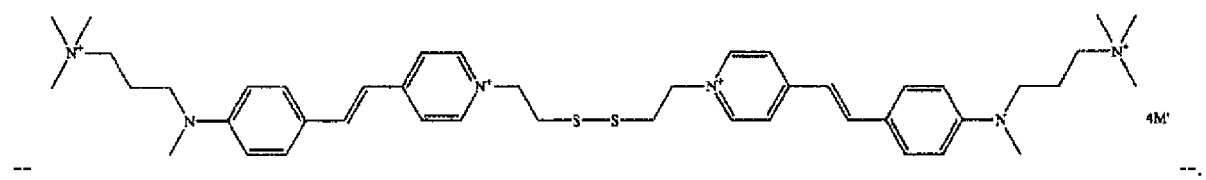

In columns 151-152, claim 19, in the fourth structure from the top,

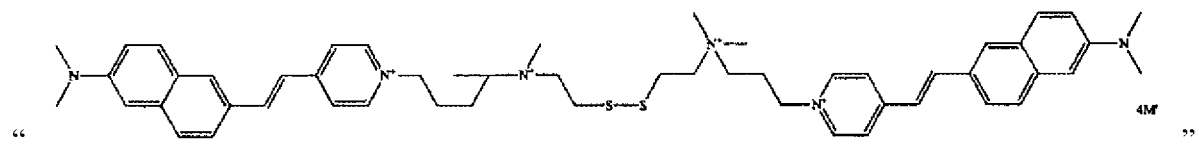

CERTIFICATE OF CORRECTION (continued)
U.S. Pat. No. 8,097,044 B2 should read

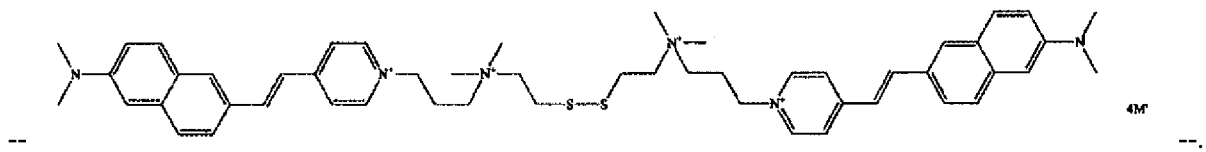

In columns 153-154, claim 19, in the fourth structure on the page,

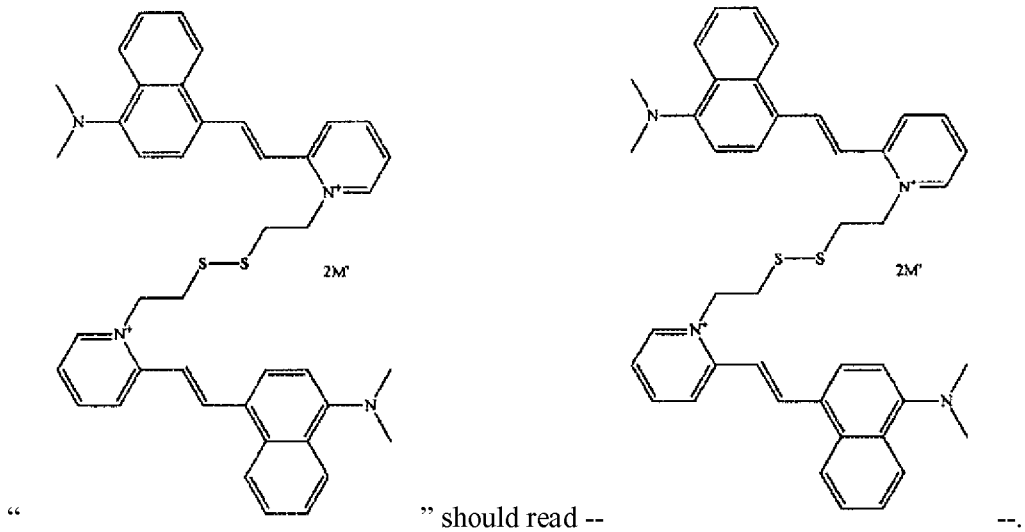

In columns 153-154, claim 19, in the fifth structure on the page,

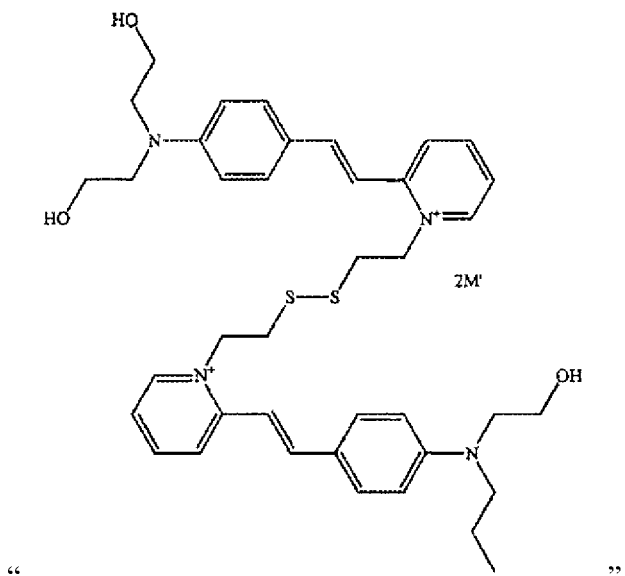

should read

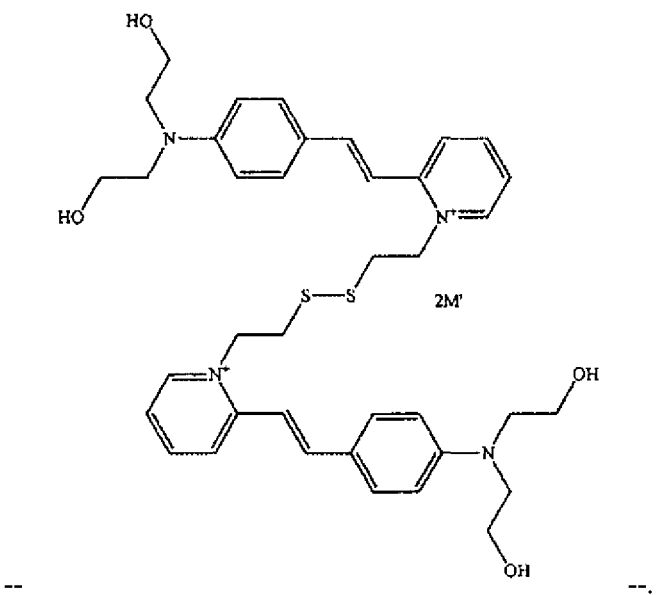
-- --.
In column 165, claim 22, line 25, "claim 1, the at least one" should read --claim 1, wherein the at least one--.